(12) United States Patent
Wu et al.

(10) Patent No.: US 11,760,751 B2
(45) Date of Patent: Sep. 19, 2023

(54) BENZO 2-AZASPIRO[4.4]NONANE COMPOUND AND USE THEREOF

(71) Applicants: HELIOEAST PHARMACEUTICAL CO., LTD., Nanchang (CN); HELIOEAST SCIENCE & TECHNOLOGY CO., LTD., Nanchang (CN)

(72) Inventors: Lingyun Wu, Shanghai (CN); Peng Yang, Shanghai (CN); Lele Zhao, Shanghai (CN); Xu You, Shanghai (CN); Jian Li, Shanghai (CN); Shuhui Chen, Shanghai (CN)

(73) Assignee: HELIOEAST SCIENCE & TECHNOLOGY CO., LTD., Nanchang (CN)

( * ) Notice: Subject to any disclaimer, the term of this patent is extended or adjusted under 35 U.S.C. 154(b) by 0 days.

(21) Appl. No.: 17/905,531

(22) PCT Filed: Mar. 2, 2021

(86) PCT No.: PCT/CN2021/078742
§ 371 (c)(1),
(2) Date: Sep. 2, 2022

(87) PCT Pub. No.: WO2021/175223
PCT Pub. Date: Sep. 10, 2021

(65) Prior Publication Data
US 2023/0126480 A1 Apr. 27, 2023

(30) Foreign Application Priority Data

| Mar. 4, 2020 | (CN) | 202010144397.7 |
| Mar. 4, 2020 | (CN) | 202010144413.2 |
| May 27, 2020 | (CN) | 202010464132.5 |
| May 27, 2020 | (CN) | 202010464155.6 |
| Sep. 1, 2020 | (CN) | 202010902712.8 |

(51) Int. Cl.
*C07D 413/04* (2006.01)
*C07D 417/04* (2006.01)
*C07D 403/04* (2006.01)

(52) U.S. Cl.
CPC .................. *C07D 413/04* (2013.01)

(58) Field of Classification Search
CPC ... C07D 413/04; C07D 417/04; C07D 403/04
See application file for complete search history.

(56) References Cited

U.S. PATENT DOCUMENTS

| 2012/0108638 A1 | 5/2012 | Bolli et al. |
| 2015/0299149 A1 | 10/2015 | Martinborough et al. |

FOREIGN PATENT DOCUMENTS

| CN | 102471328 A | 5/2012 |
| CN | 102762100 A | 10/2012 |
| EP | 3590929 A1 | 1/2020 |
| JP | 2012505920 A | 3/2012 |
| JP | 2013531002 A | 8/2013 |
| JP | 2018525429 A | 9/2018 |
| WO | 2010045580 A1 | 4/2010 |
| WO | 2012004373 A1 | 1/2012 |
| WO | 2012158550 A2 | 11/2012 |
| WO | 2017036978 A1 | 3/2017 |
| WO | 2018083171 A1 | 5/2018 |
| WO | 2018157813 A1 | 9/2018 |
| WO | 2019007696 A1 | 1/2019 |
| WO | 2019016112 A1 | 1/2019 |

OTHER PUBLICATIONS

International Search Report for International Application No. PCT/CN2021/078742 dated May 26, 2021, 10 pages including English translation.
Written Opinion of the International Searching Authority for International Application No. PCT/CN2021/078742 dated May 26, 2021, 8 pages including English translation.
Feb. 14, 2023 Notice of Reasons for Refusal issued in Japanese Patent Application No. 2022-553172.

*Primary Examiner* — Samira J Jean-Louis
(74) *Attorney, Agent, or Firm* — MH2 TECHNOLOGY LAW GROUP LLP

(57) ABSTRACT

Disclosed are a series of benzo 2-azaspiro[4.4]nonane compounds, and specifically disclosed are a compound as represented by formula (P) or a pharmaceutically acceptable salt thereof.

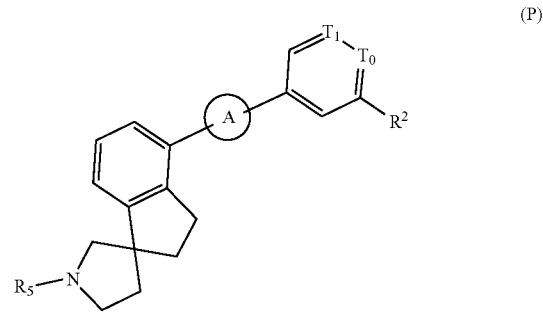

16 Claims, No Drawings

BENZO 2-AZASPIRO[4.4]NONANE COMPOUND AND USE THEREOF

CROSS-REFERENCE TO RELATED APPLICATIONS

The present application is a U.S. National Stage application of PCT/CN2021/078742 filed 2 Mar. 2021, which claims priority to Chinese Patent Application No. 202010144413.2 filed 4 Mar. 2020, Chinese Application No. 202010144397.7 filed 4 Mar. 2020, Chinese Application No. 202010464132.5 filed 27 May 2020, Chinese Patent Application No. 202010464155.6 filed 27 May 2020, and Chinese Application No. 202010902712.8 filed 1 Sep. 2020, the entire disclosures of which are hereby incorporated by reference in their entireties.

TECHNICAL FIELD

The present disclosure relates to a series of benzo 2-azaspiro[4.4]nonane compounds, in particular to a compound represented by formula (P) or a pharmaceutically acceptable salt thereof.

BACKGROUND

Sphingosine-1-phosphate (S1P) is a lysophospholipid signaling molecule derived from a cell membrane, which mainly exerts physiological functions by stimulating some members of the G protein-coupled receptor family, mainly sphingosine-1-phosphate receptors (S1PRs) family. At present, five different S1PR subtypes have been identified in mammals, including sphingosine-1-phosphate receptor 1 (S1PR1 or EDG1), sphingosine-1-phosphate receptor 2 (S1PR2 or EDG5), sphingosine-1-phosphate receptor 3 (S1PR3 or EDG3), sphingosine-1-phosphate receptor 4 (S1PR4 or EDG6) and sphingosine-1-phosphate receptor 5 (S1PR5 or EDG8). S1PR1-3 are widely expressed in various tissues, S1PR4 is mainly expressed in lymphatic system and blood system, and S1PR5 is mainly expressed in the central nervous system. Lymphocytes sense a S1P concentration gradient through S1PR1, thereby regulating the entry of lymphocytes from secondary lymphoid organs into the lymph and blood circulation. S1PR1 agonists can trigger the endocytosis of S1PR1 on the surface of lymphocytes, make the lymphocytes unable to sense the S1P concentration gradient, prevent the migration of lymphocytes to the lymph and blood circulation, trigger the homing of lymphocytes, reduce the number of lymphocytes in the peripheral circulatory system, and prevent the lymphocytes from reaching the position of inflammatory lesions or grafts, reduce excessive inflammation, and have immunomodulatory effect.

Autoimmune disease refers to a general term for a class of diseases caused by the body's immune response to autoantigen, causing the immune system to mistakenly attack its own tissues. At present, there are more than 80 kinds of autoimmune diseases that are precisely defined, and excessive inflammatory reaction is a common feature. S1PR1 agonists can effectively reduce excessive inflammation, and can be used to treat or prevent autoimmune diseases, including multiple sclerosis, inflammatory bowel disease (divided into Crohn's disease and ulcerative colitis), systemic lupus erythematosus and psoriasis, etc.

At present, the efficacy studies of S1PR1 agonists in vivo are used to treat or prevent autoimmune diseases. Fingolimod, the first-generation non-selective S1PRs agonist of Novartis, was approved by FDA for relapsing multiple sclerosis (RMS) in September 2010. Siponimod, the second-generation selective S1PR1 and S1PR5 agonist of Novartis, was also approved by FDA for relapsing multiple sclerosis (RMS) in March 2019. The discovery and application of novel S1PR agonists holds great promise.

CONTENT OF THE PRESENT INVENTION

The present disclosure provides a compound represented by formula (P) or a pharmaceutically acceptable salt thereof,

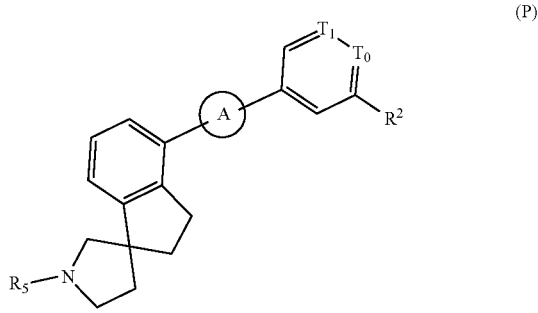

wherein,
$T_0$ is selected from CH-E-$R_3$ and N;
$T_1$ is selected from $CR_4$ and N;
E is absent, or is selected from O and NH;
ring A is selected from oxazolyl, 1,2,4-oxadiazolyl, thiazolyl, 1,3,4-thiadiazolyl, 1,2,4-thiadiazolyl, pyrimidinyl and pyrazinyl;
$R_2$ is selected from H, F, Cl, Br, CN, $Cl_{1-3}$ alkyl and $C_{1-3}$ alkoxy, and the $C_{1-3}$ alkyl and $C_{1-3}$ alkoxy are optionally substituted by 1, 2 or 3 $R_b$;
$R_3$ is selected from $C_{1-6}$ alkyl, cyclopentyl and cyclohexyl, and the $C_{1-6}$ alkyl, cyclopentyl and cyclohexyl are optionally substituted by 1, 2 or 3 $R_c$;
$R_4$ is selected from H and cyclopentyl;
$R_5$ is selected from

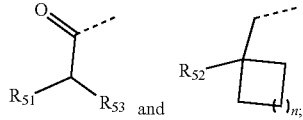

$R_{51}$ is selected from H, OH, $NH_2$, CN, COOH, $CH_2COOH$, $CH_2OH$, $C_{1-3}$ alkoxy and —S(O)$_2$—$C_{1-3}$ alkyl, and the $C_{1-3}$ alkoxy and $C_{1-3}$ alkyl are optionally substituted by 1, 2 or 3 $R_a$;
$R_{52}$ is selected from OH, CN, $NH_2$ and COOH;
$R_{53}$ is selected from H and OH;
$R_a$, $R_b$ and $R_c$ are each independently selected from F, Cl and Br;
n is selected from 0 and 1.

In some embodiments of the present disclosure, the ring A is selected from

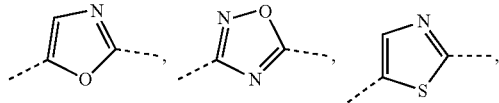

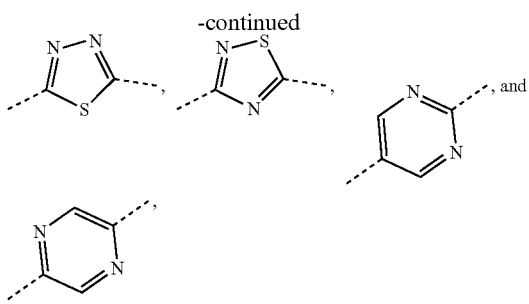

and other variables are defined in the present disclosure.

In some embodiments of the present disclosure, the $R_2$ is selected from H, F, Cl, Br, CN, $CH_3$ and $OCH_3$, and the $CH_3$ and $OCH_3$ are optionally substituted by 1, 2 or 3 $R_b$, and other variables are defined in the present disclosure.

In some embodiments of the present disclosure, the $R_2$ is selected from H, Br, Cl, CN, $CHF_2$, $CF_3$ and $OCH_3$, and other variables are defined in the present disclosure.

In some embodiments of the present disclosure, the $R_3$ is selected from $C_{1-4}$ alkyl,

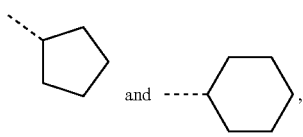

and the $C_{1-4}$ alkyl,

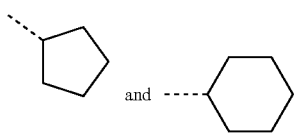

are optionally substituted by 1, 2 or 3 $R_c$, and other variables are defined in the present disclosure.

In some embodiments of the present disclosure, the $R_3$ is selected from $CH(CH_3)_2$, $CHF_2$, $CH_2CH(CH_3)_2$,

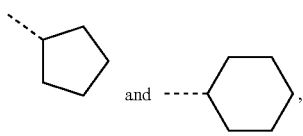

and other variables are defined in the present disclosure.

In some embodiments of the present disclosure, the structural moiety

is selected from

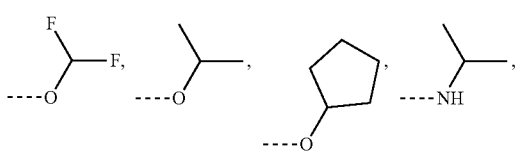

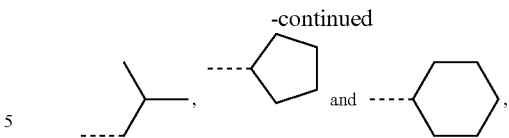

and other variables are defined in the present disclosure.

In some embodiments of the present disclosure, the $R_{51}$ is selected from H, OH, $NH_2$, CN, COOH, $CH_2COOH$, $CH_2OH$, $OCH_3$ and $-S(O)_2CH_3$, and the $OCH_3$ and $-S(O)_2CH_3$ are optionally substituted by 1, 2 or 3 $R_a$, and other variables are defined in the present disclosure.

In some embodiments of the present disclosure, the $R_{51}$ is selected from OH, $NH_2$, CN, $CH_2COOH$, $CH_2OH$, $OCH_3$ and $-S(O)_2CH_3$, and other variables are defined in the present disclosure.

In some embodiments of the present disclosure, the structural moiety

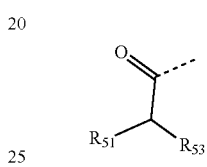

is selected from

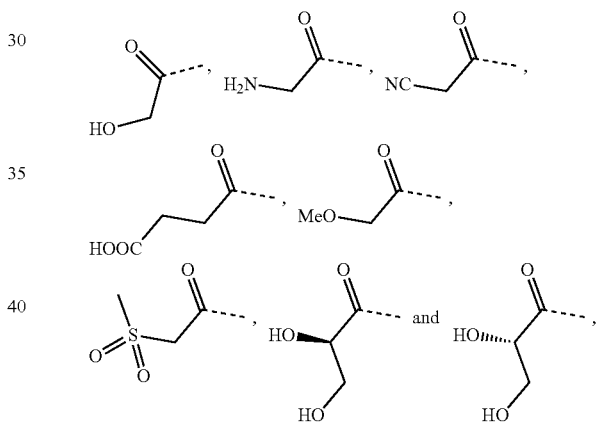

and other variables are defined in the present disclosure.

In some embodiments of the present disclosure, the $R_{52}$ is selected from CN, $NH_2$ and COOH, and other variables are defined in the present disclosure.

In some embodiments of the present disclosure, the structural moiety

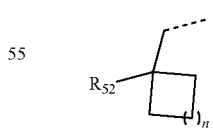

is selected from

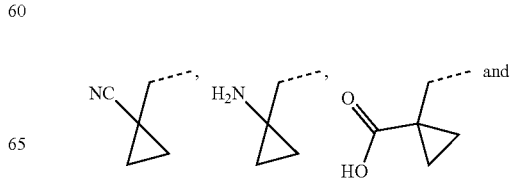

-continued

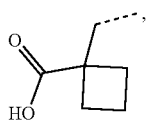

and other variables are defined in the present disclosure.

In some embodiments of the present disclosure, the compound or the pharmaceutically acceptable salt thereof is selected from:

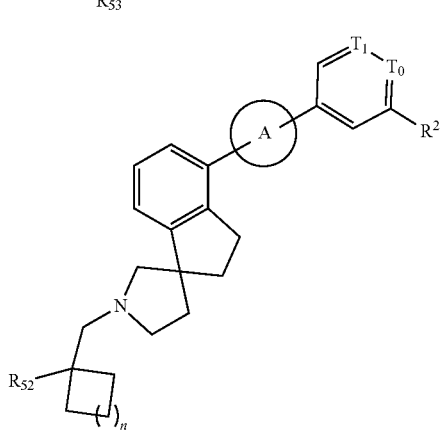
(P-1)

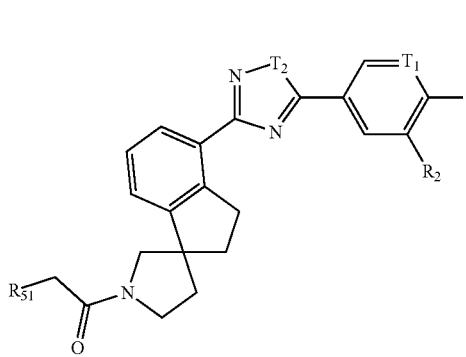
(P-2)

wherein, $T_0$, $T_1$, $R_{53}$, n, ring A, $R_2$, $R_{51}$ and $R_{52}$ are defined in the present disclosure.

In some embodiments of the present disclosure, the compound or the pharmaceutically acceptable salt thereof is selected from:

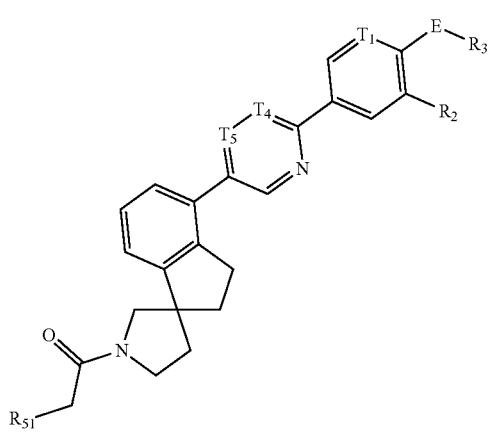
(I-1)

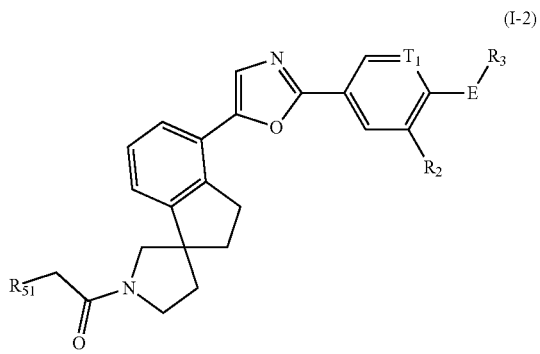
(I-2)

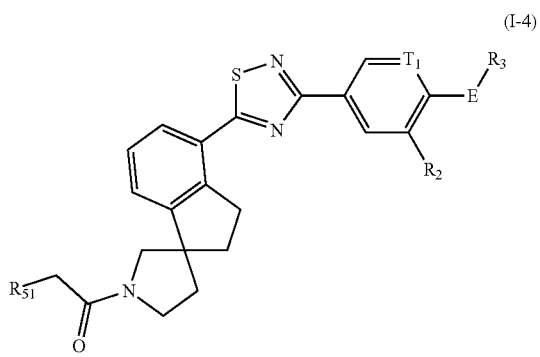
(I-3)

(I-4)

(I-5)

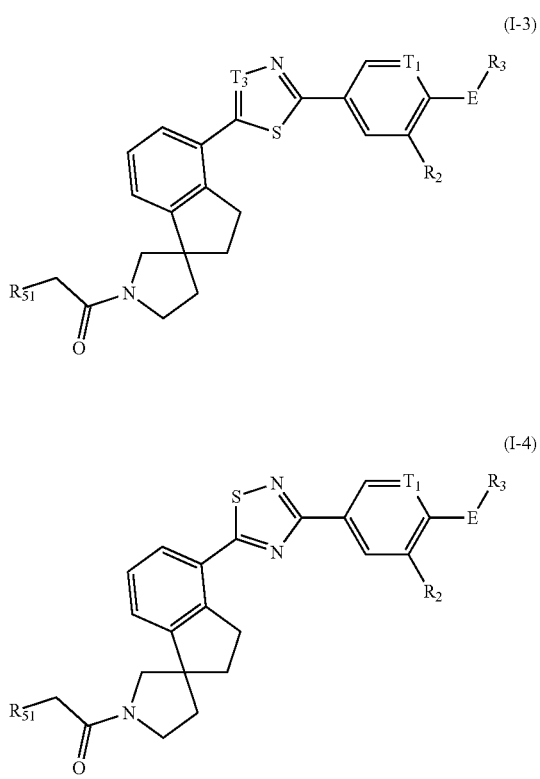

-continued
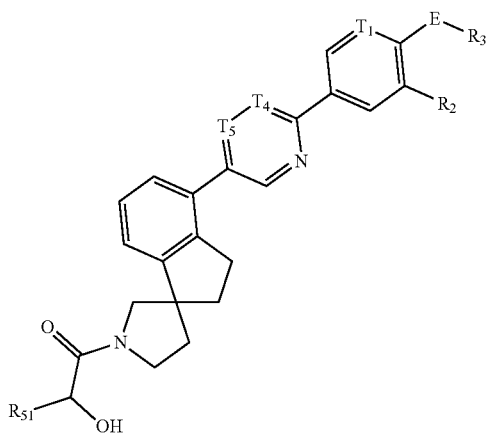
(P-1-1)
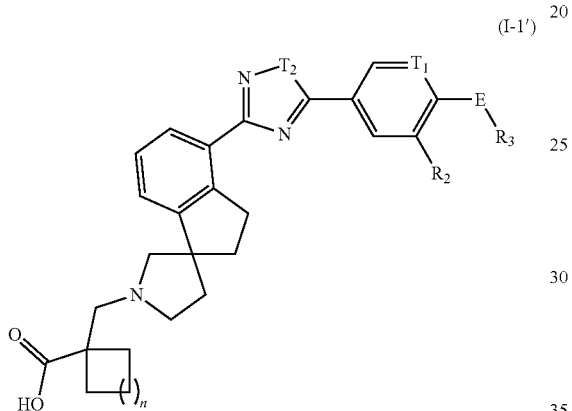
(I-1')
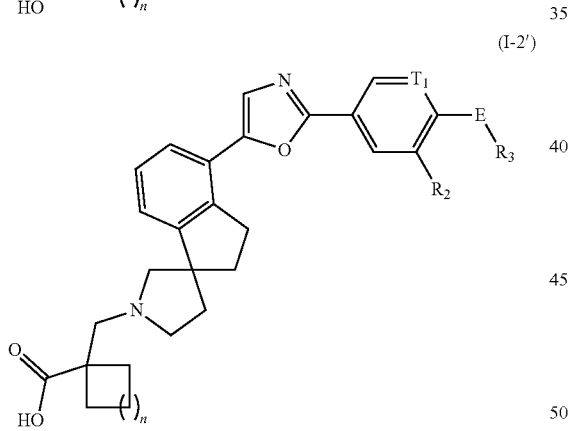
(I-2')
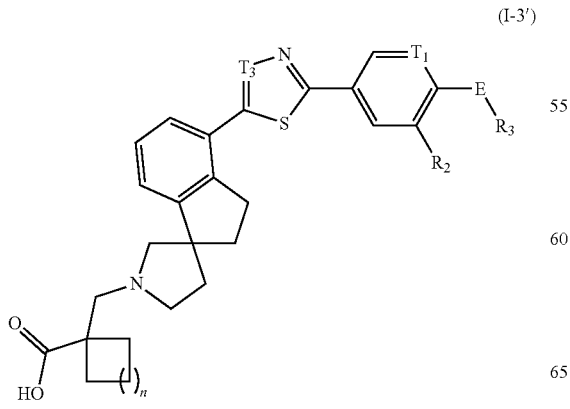
(I-3')
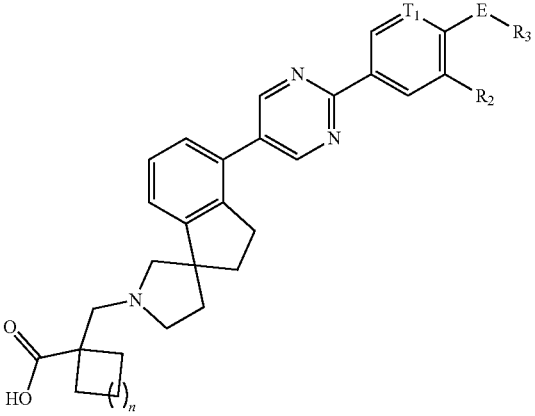
(I-4')
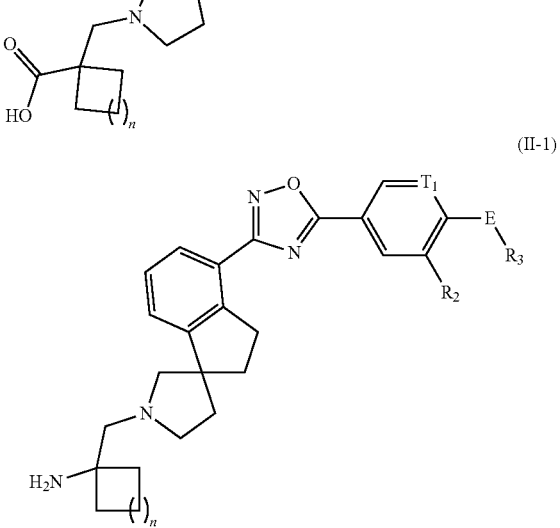
(II-1)
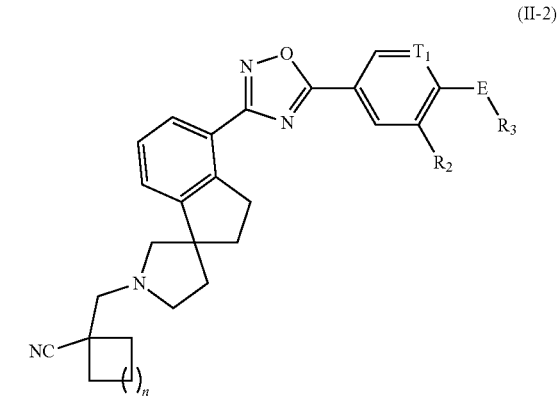
(II-2)
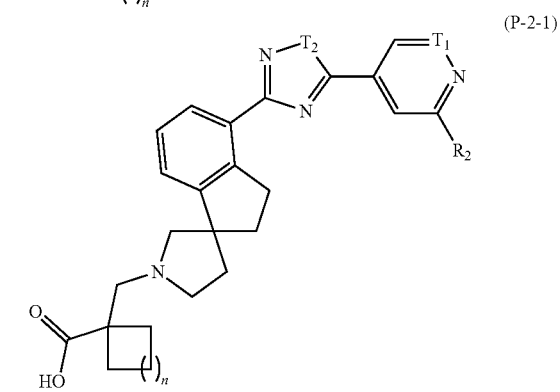
(P-2-1)
wherein,
$R_2$, $R_3$, $T_1$, E and n are defined in the present disclosure;
$T_2$ is selected from O and S;

$T_3$ is selected from CH and N;
$T_4$ is selected from CH and $T_5$ is selected from N, or $T_4$ is selected from N and $T_5$ is selected from CH.

There are also some embodiments of the present disclosure obtained by an arbitrary combination of the above variables.

The present disclosure provides a compound represented by the following formula or a pharmaceutically acceptable salt thereof,

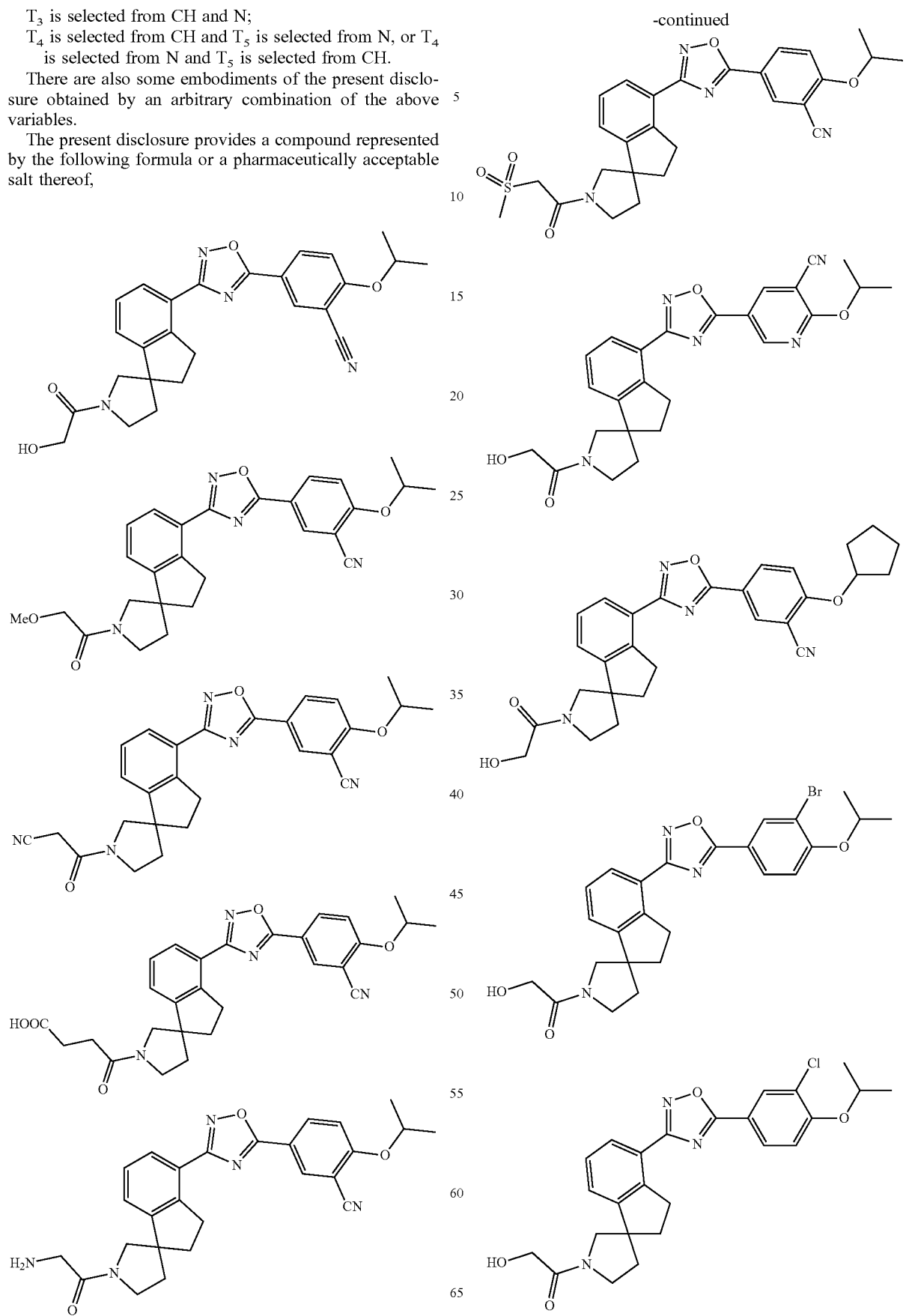

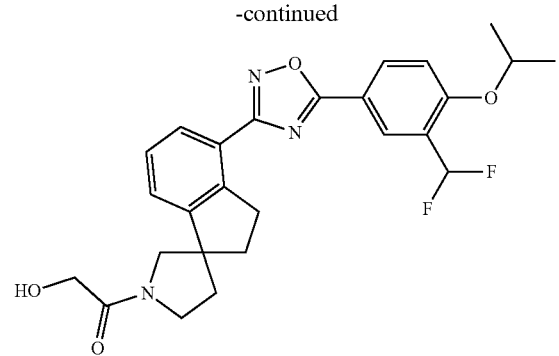
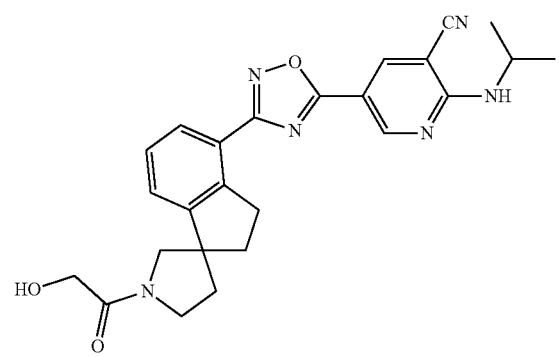
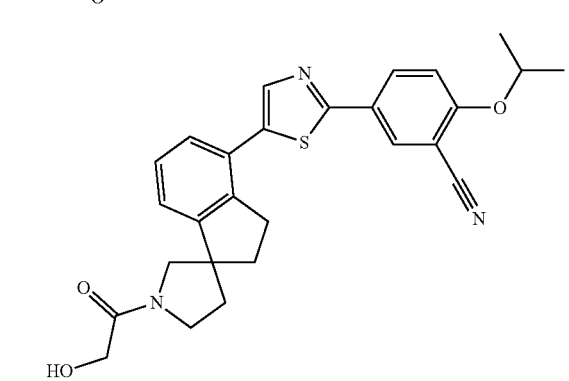
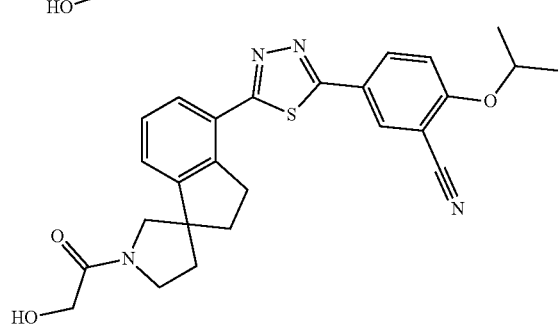
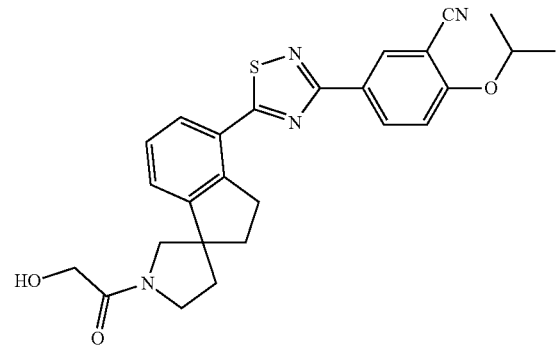
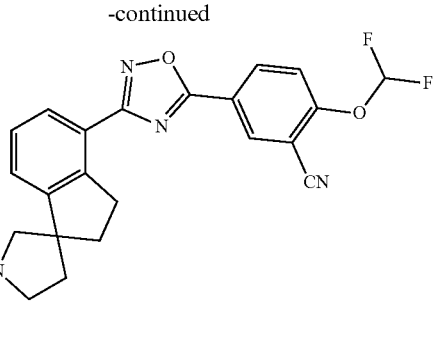
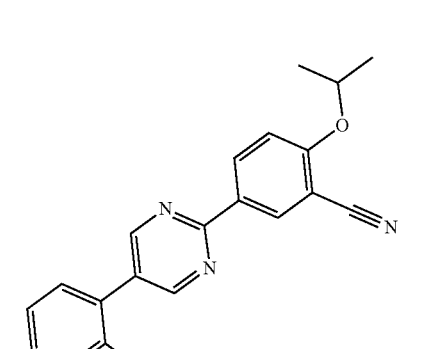
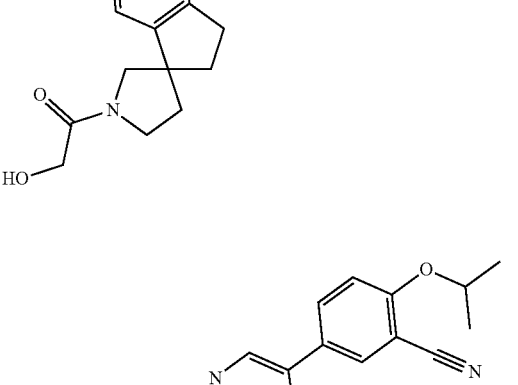
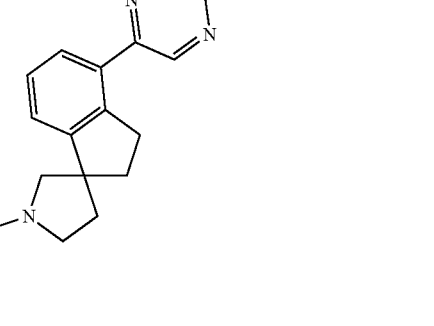
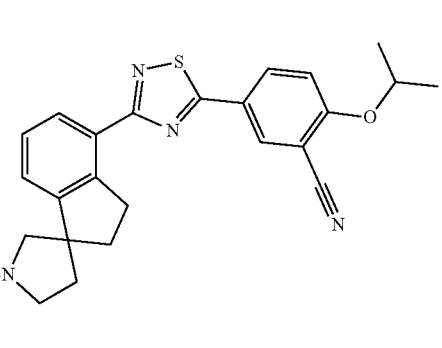

13
-continued
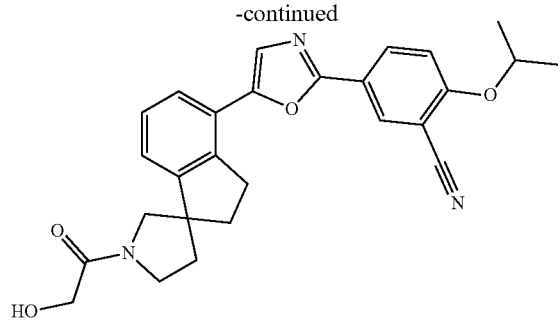
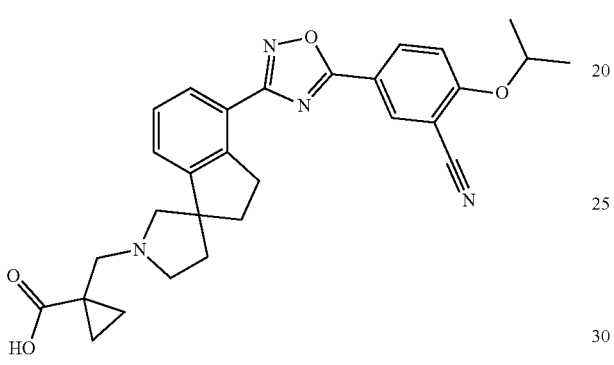
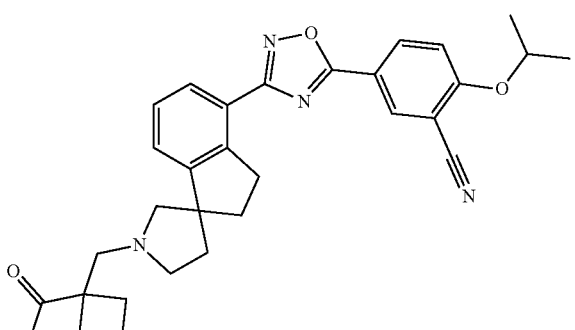
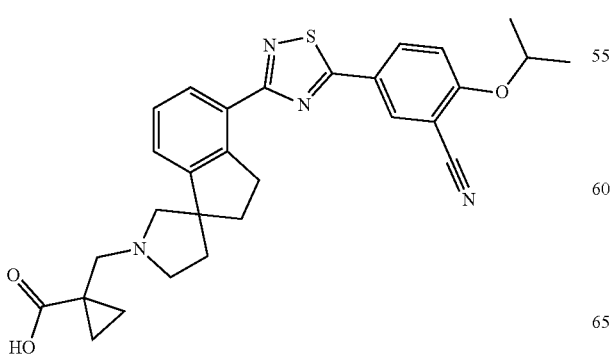
14
-continued
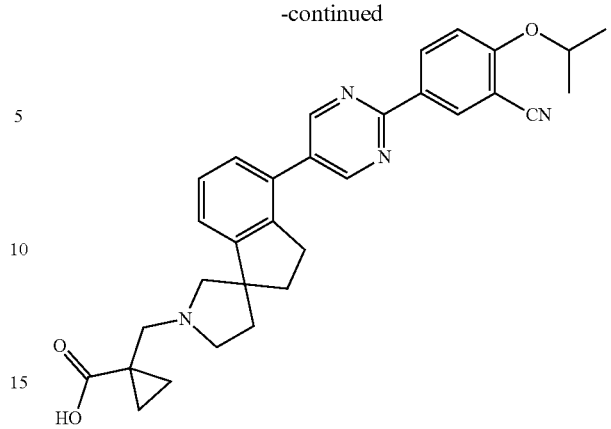

15
-continued
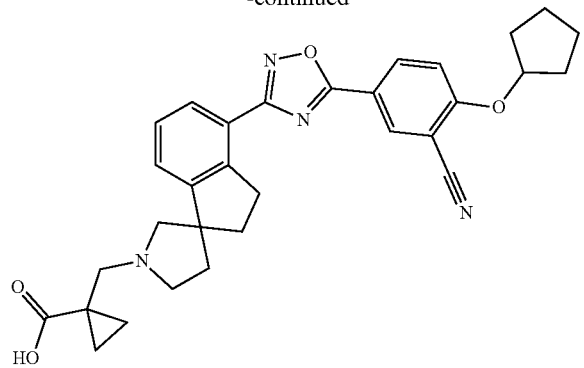
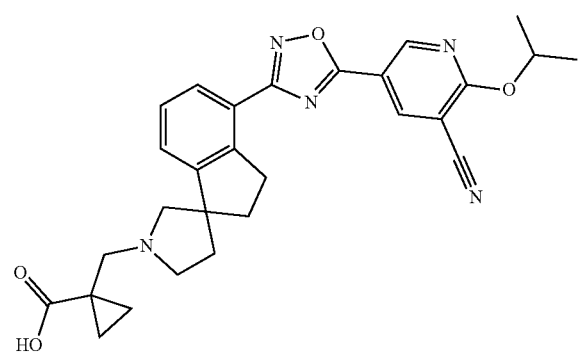
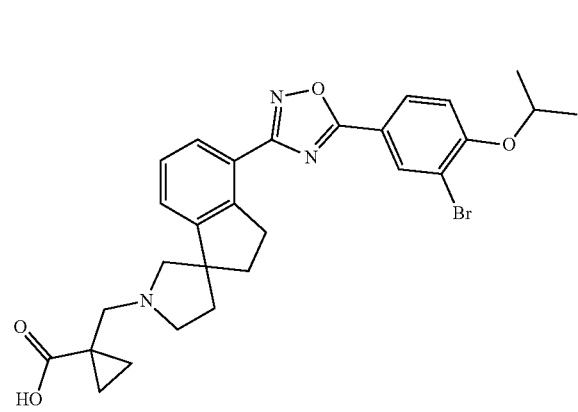
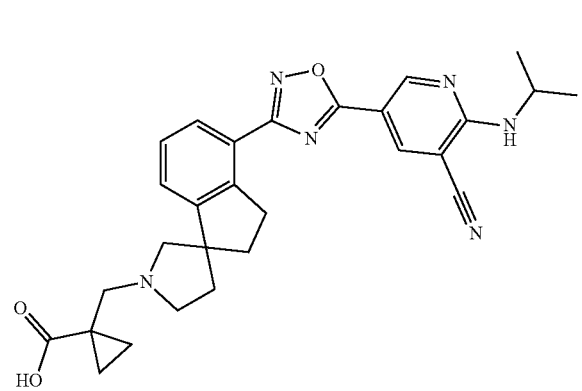
16
-continued
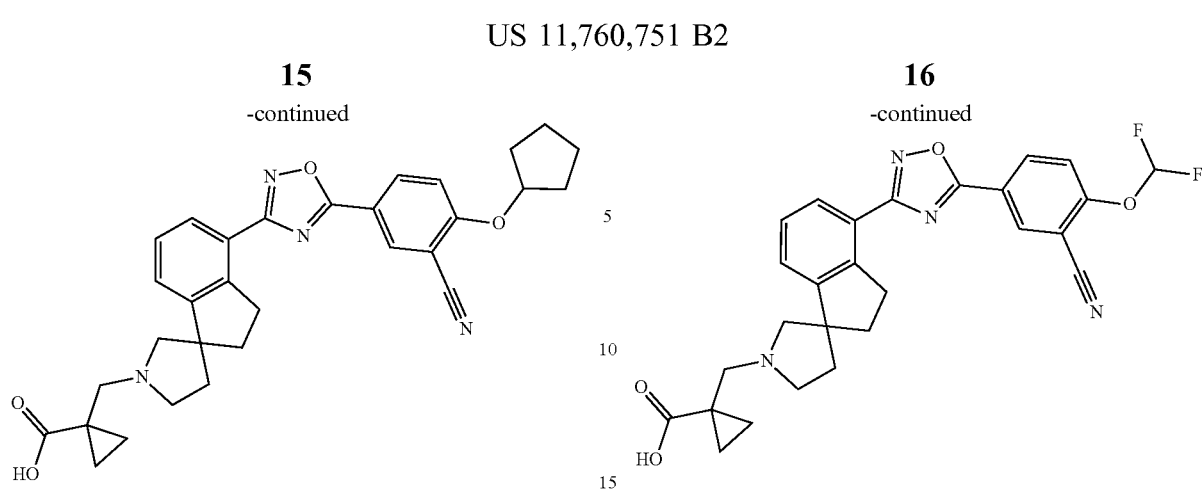
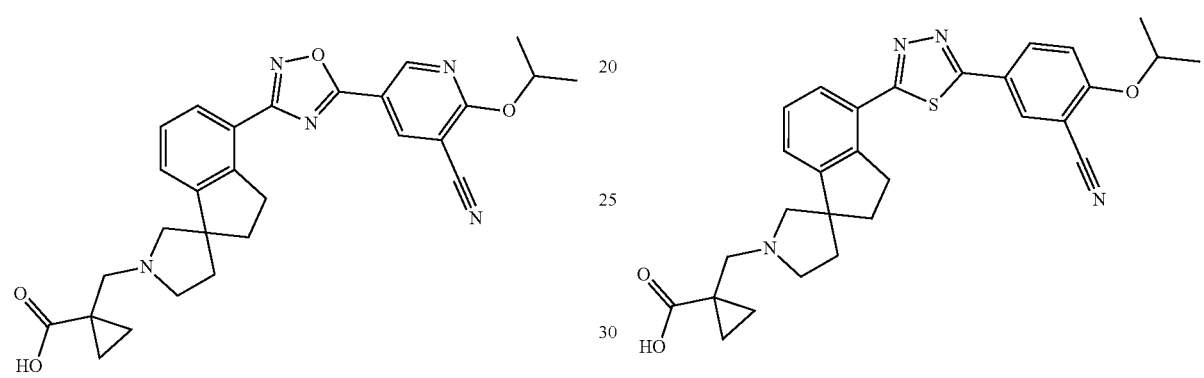
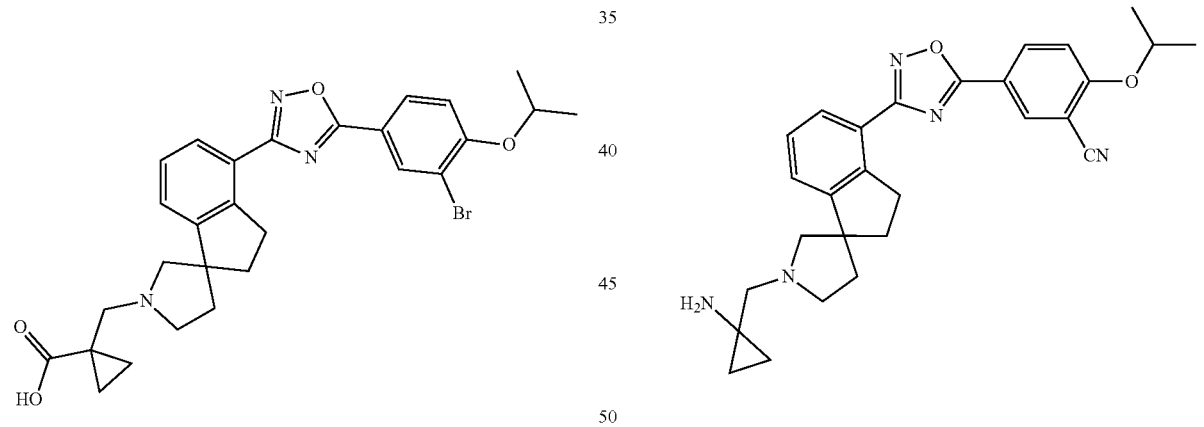
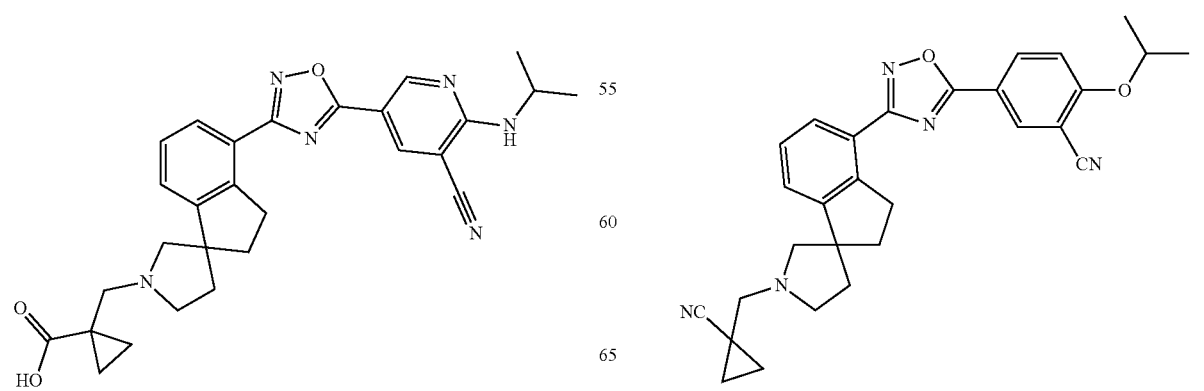

17
-continued
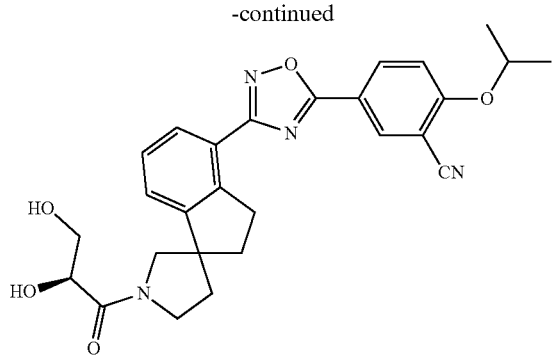
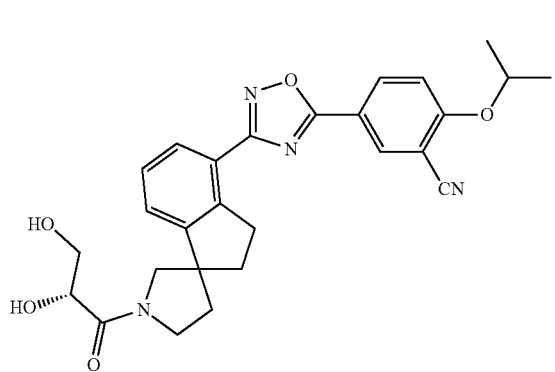
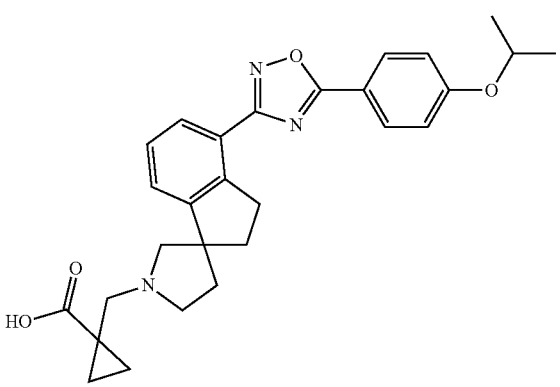
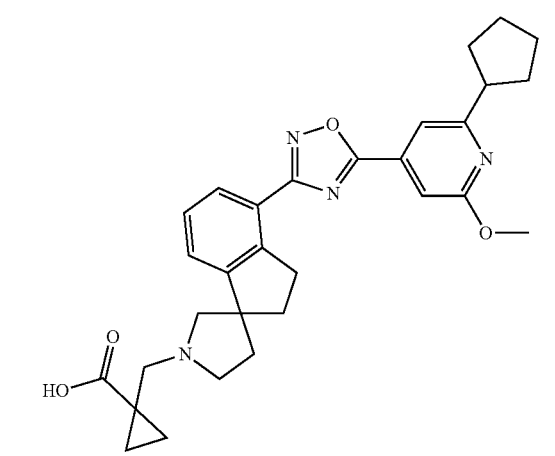
18
-continued
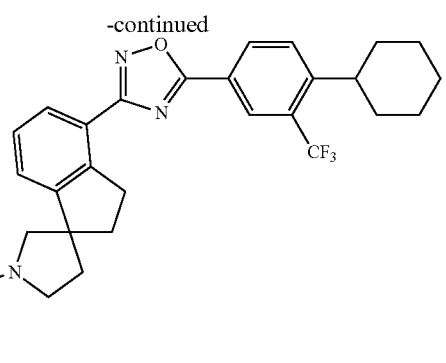
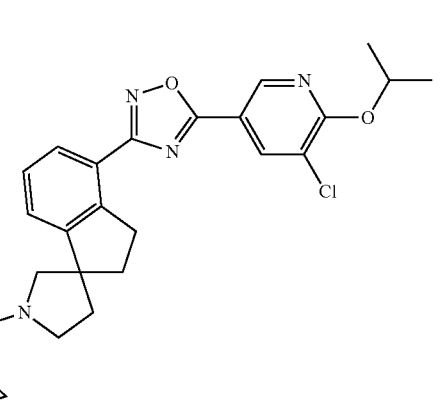
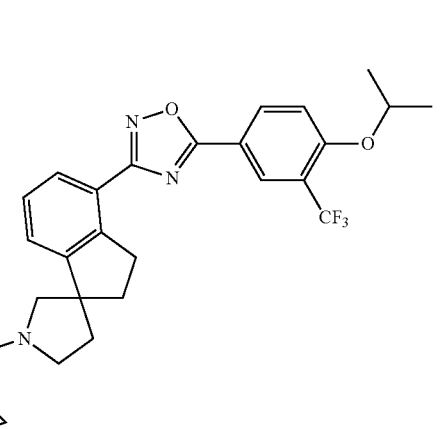
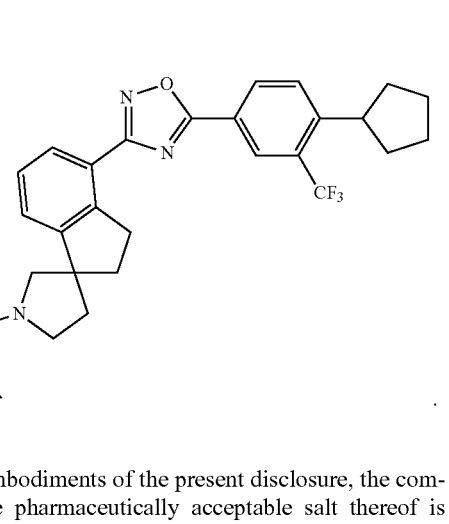
In some embodiments of the present disclosure, the compound or the pharmaceutically acceptable salt thereof is selected from:

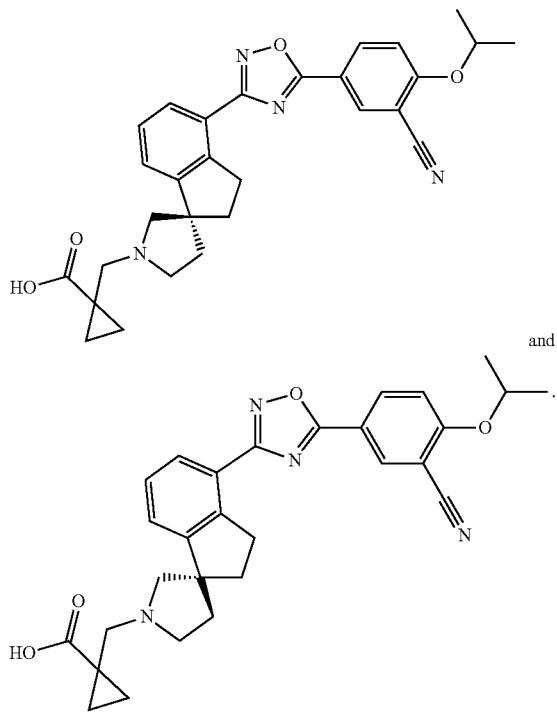

The present disclosure also provides use of the compound or the pharmaceutically acceptable salt thereof in the manufacture of a medicament for treating diseases related to S1PR1.

The present disclosure also provides the following solutions:

the present disclosure provides a compound represented by formula (I) or a pharmaceutically acceptable salt thereof,

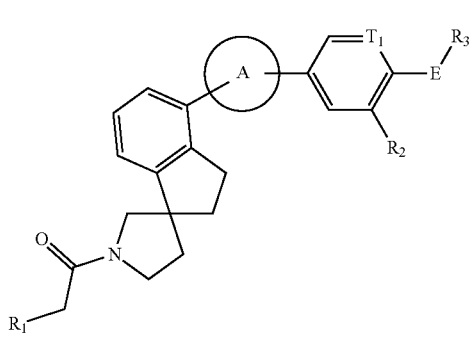

wherein,
$T_1$ is selected from CH and N;
E is selected from O and NH;
ring A is selected from oxazolyl, 1,2,4-oxadiazolyl, thiazolyl, 1,3,4-thiadiazolyl, 1,2,4-thiadiazolyl, pyrimidinyl and pyrazinyl;
$R_1$ is selected from H, OH, $NH_2$, CN, COOH, $CH_2COOH$, $C_{1-3}$ alkoxy and $-S(O)_2-C_{1-3}$ alkyl, and the $C_{1-3}$ alkoxy and $C_{1-3}$ alkyl are optionally substituted by 1, 2 or 3 $R_a$;
$R_2$ is selected from F, Cl, Br, CN and $C_{1-3}$ alkyl, and the $C_{1-3}$ alkyl is optionally substituted by 1, 2 or 3 $R_b$;
$R_3$ is selected from $C_{1-6}$ alkyl and cyclopentyl, and the $C_{1-6}$ alkyl and cyclopentyl are optionally substituted by 1, 2 or 3 $R_c$;

$R_a$, $R_b$ and $R_c$ are each independently selected from F, Cl and Br.

In some embodiments of the present disclosure, the ring A is selected from

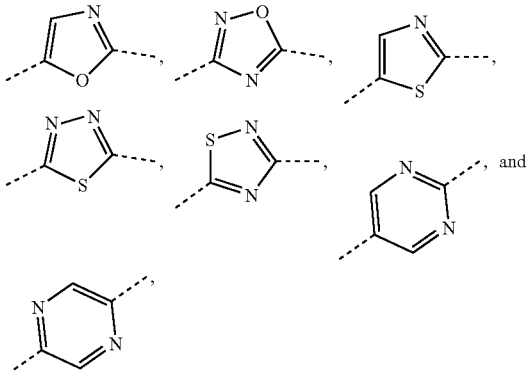

and other variables are defined in the present disclosure.

In some embodiments of the present disclosure, the $R_1$ is selected from H, OH, $NH_2$, CN, COOH, $CH_2COOH$, $OCH_3$ and $-S(O)_2CH_3$, and the $OCH_3$ and $-S(O)_2CH_3$ are optionally substituted by 1, 2 or 3 $R_a$, and other variables are defined in the present disclosure.

In some embodiments of the present disclosure, the $R_1$ is selected from OH, $NH_2$, CN, $CH_2COOH$, $OCH_3$ and $-S(O)_2CH_3$, and other variables are defined in the present disclosure.

In some embodiments of the present disclosure, the $R_2$ is selected from F, Cl, Br, CN and $CH_3$, and the $CH_3$ is optionally substituted by 1, 2 or 3 $R_b$, and other variables are defined in the present disclosure.

In some embodiments of the present disclosure, the $R_2$ is selected from Cl, Br, CN and $CHF_2$, and other variables are defined in the present disclosure.

In some embodiments of the present disclosure, the $R_3$ is selected from $C_{1-3}$ alkyl and

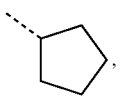

and the $C_{1-3}$ alkyl and

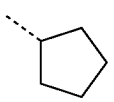

are optionally substituted by 1, 2 or 3 $R_c$, and other variables are defined in the present disclosure.

In some embodiments of the present disclosure, the $R_3$ is selected from $CHF_2$, $CH(CH_3)_2$ and

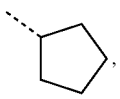

and other variables are defined in the present disclosure.

In some embodiments of the present disclosure, the structural moiety

is selected from

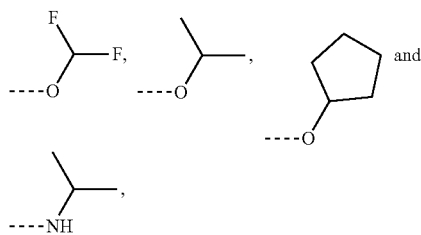

and other variables are defined in the present disclosure.

In some embodiments of the present disclosure, the compound or the pharmaceutically acceptable salt thereof is selected from:

(I-1)

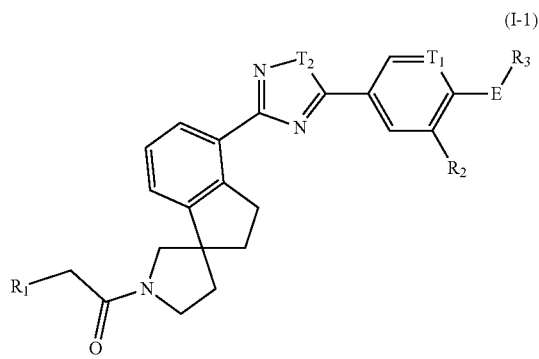

(I-2)

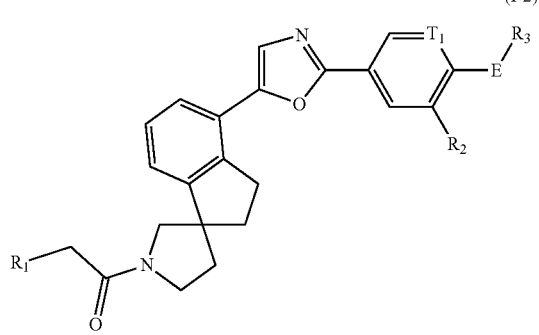

(I-3)

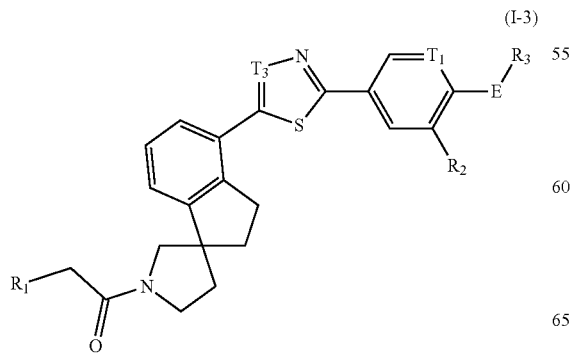

(I-4)

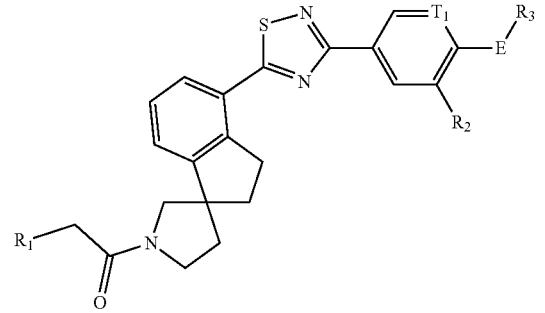

(I-5)

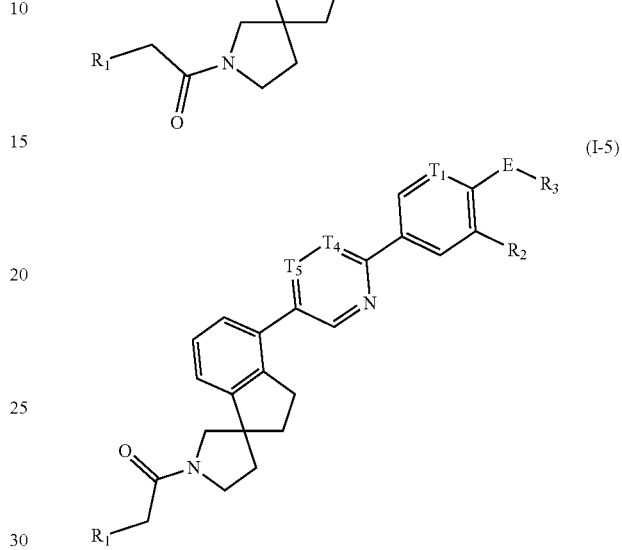

wherein,
$R_1$, $R_2$, $R_3$, $T_1$ and E are defined in the present disclosure;
$T_2$ is selected from O and S;
$T_3$ is selected from CH and N;
$T_4$ is selected from CH and $T_5$ is selected from N, or $T_4$ is selected from N and $T_5$ is selected from CH.

There are also some embodiments of the present disclosure obtained by an arbitrary combination of the above variables.

The present disclosure also provides the following solutions:

the present disclosure provides a compound represented by formula (I) or a pharmaceutically acceptable salt thereof, (I)

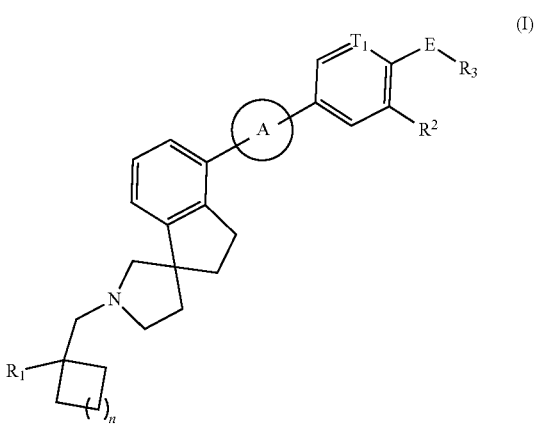

wherein,
$T_1$ is selected from CH and N;
E is selected from O and NH;

ring A is selected from oxazolyl, 1,2,4-oxadiazolyl, thiazolyl, 1,3,4-thiadiazolyl, 1,2,4-thiadiazolyl, pyrimidinyl and pyrazinyl;

$R_1$ is selected from OH, CN, $NH_2$ and COOH;

$R_2$ is selected from F, Cl, Br, CN and $C_{1-3}$ alkyl, and the $C_{1-3}$ alkyl is optionally substituted by 1, 2 or 3 $R_b$;

$R_3$ is selected from $C_{1-6}$ alkyl and cyclopentyl, and the $C_{1-6}$ alkyl and cyclopentyl are optionally substituted by 1, 2 or 3 $R_c$;

$R_b$ and $R_c$ are each independently selected from F, Cl and Br;

n is selected from 0 or 1;

In some embodiments of the present disclosure, the ring A is selected from

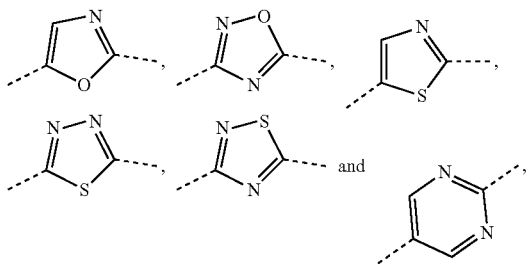

and other variables are defined in the present disclosure.

In some embodiments of the present disclosure, the $R_1$ is selected from CN, $NH_2$ and COOH, and other variables are defined in the present disclosure.

In some embodiments of the present disclosure, the $R_2$ is selected from F, Cl, Br, CN and $CH_3$, and the $CH_3$ is optionally substituted by 1, 2 or 3 $R_b$, and other variables are defined in the present disclosure.

In some embodiments of the present disclosure, the $R_2$ is selected from Br, CN and $CHF_2$, and other variables are defined in the present disclosure.

In some embodiments of the present disclosure, the $R_3$ is selected from $C_{1-3}$ alkyl and

and the $C_{1-3}$ alkyl and

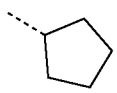

are optionally substituted by 1, 2 or 3 $R_c$, and other variables are defined in the present disclosure.

In some embodiments of the present disclosure, the $R_3$ is selected from $CH(CH_3)_2$, $CHF_2$ and

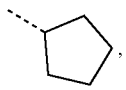

and other variables are defined in the present disclosure.

In some embodiments of the present disclosure, the structural moiety

is selected from

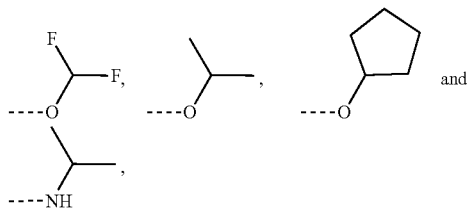

and other variables are defined in the present disclosure.

In some embodiments of the present disclosure, the compound or the pharmaceutically acceptable salt thereof is selected from:

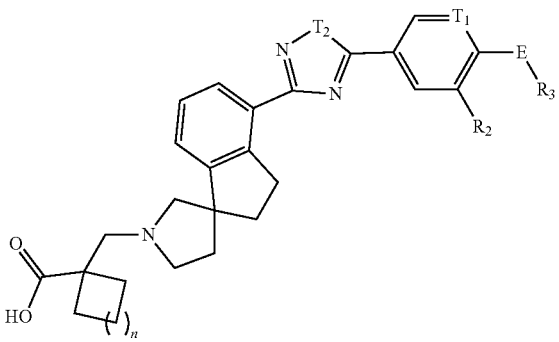

(I-1)

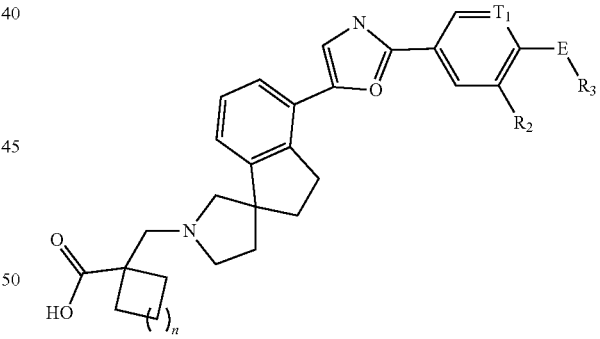

(I-2)

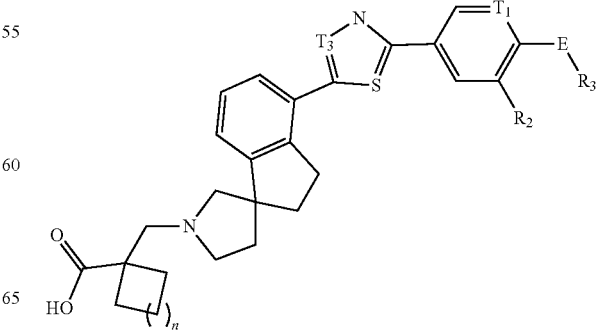

(I-3)

(I-4)

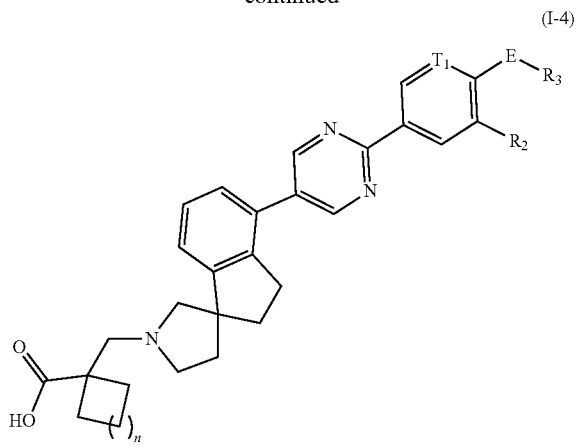

(II-1)

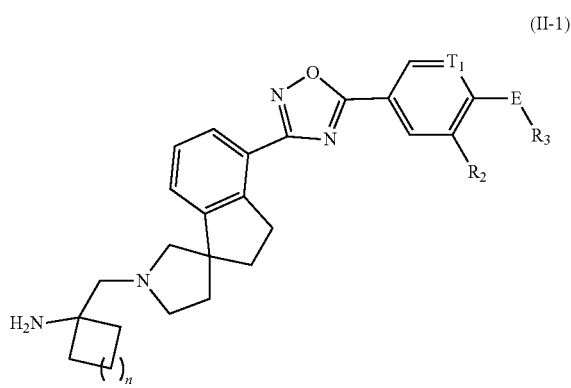

(II-2)

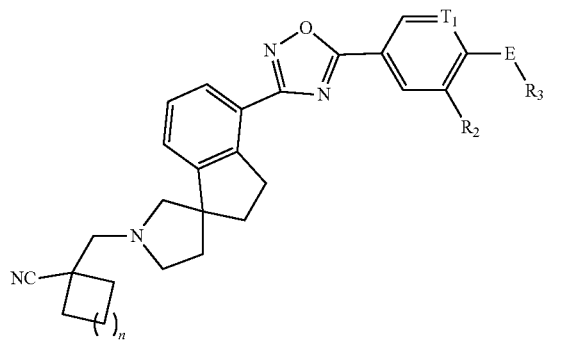

wherein,

R₂, R₃, T₁, E and n are defined in the present disclosure;

T₂ is selected from O and S;

T₃ is selected from CH and N.

There are also some embodiments of the present disclosure obtained by an arbitrary combination of the above variables.

The present disclosure also provides a compound represented by formula (I) or a pharmaceutically acceptable salt thereof, (I)

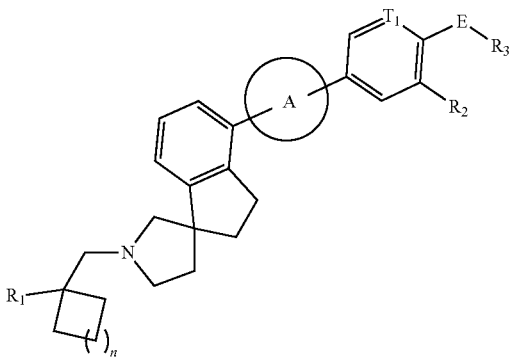

wherein, $T_1$ is selected from CH and N;

E is selected from O and NH;

ring A is selected from oxazolyl, 1,2,4-oxadiazolyl, thiazolyl, 1,3,4-thiadiazolyl, 1,2,4-thiadiazolyl, pyrimidinyl and pyrazinyl;

$R_1$ is selected from OH, CN, NH$_2$ and COOH;

$R_2$ is selected from F, Cl, Br, CN and $C_{1-3}$ alkyl, and the $C_{1-3}$ alkyl is optionally substituted by 1, 2 or 3 $R_b$;

$R_3$ is selected from $C_{1-6}$ alkyl and cyclopentyl, and the $C_{1-6}$ alkyl and cyclopentyl are optionally substituted by 1, 2 or 3 $R_c$;

$R_b$ and $R_c$ are each independently selected from F, Cl and Br;

n is selected from 0 or 1.

In some embodiments of the present disclosure, the ring A is selected from

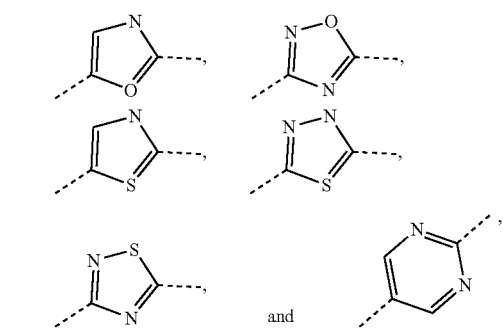

and other variables are defined in the present disclosure.

In some embodiments of the present disclosure, the $R_1$ is selected from COOH, and other variables are defined in the present disclosure.

In some embodiments of the present disclosure, the $R_2$ is selected from F, Cl, Br, CN and CH$_3$, and the CH$_3$ is optionally substituted by 1, 2 or 3 $R_b$, and other variables are defined in the present disclosure.

In some embodiments of the present disclosure, the $R_2$ is selected from Br, CN and CHF$_2$, and other variables are defined in the present disclosure.

In some embodiments of the present disclosure, the $R_3$ is selected from $C_{1-3}$ alkyl and

and the $C_{1-3}$ alkyl and

are optionally substituted by 1, 2 or 3 $R_c$, and other variables are defined in the present disclosure.

In some embodiments of the present disclosure, the $R_3$ is selected from $CH(CH_3)_2$, $CHF_2$ and

and other variables are defined in the present disclosure.

In some embodiments of the present disclosure, the structural moiety

is selected from

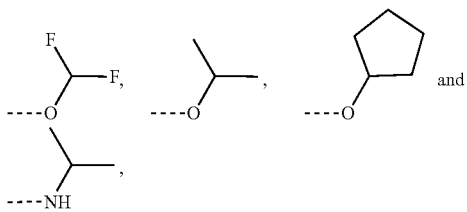

and other variables are defined in the present disclosure.

There are also some embodiments of the present disclosure obtained by an arbitrary combination of the above variables.

Technical Effect

The compounds of the present disclosure have significant or even unexpected S1PR1 agonistic activity and good bioavailability, and can significantly inhibit lymphocytes.

Related Definitions

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing such compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing such compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with deuterium, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond

a straight dashed bond

or a wavy line

For example, the straight solid bond in —OCH$_3$ means that it is linked to other groups through the oxygen atom in the group; the straight dashed bonds in

means that it is linked to other groups through the two ends of nitrogen atom in the group; the wave lines in

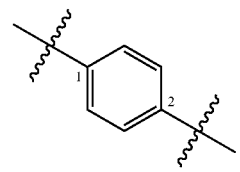 [SMILES: *c1ccc(*)cc1]

means that the phenyl group is linked to other groups through carbon atoms at position 1 and position 2;

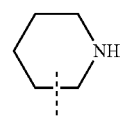

means that it can be linked to other groups through any linkable sites on the piperidinyl by one chemical bond, including at least four types of linkage, including

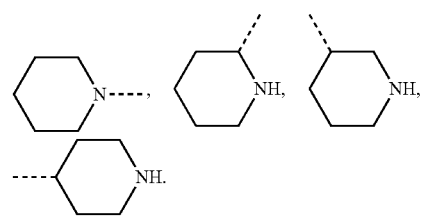

Even though the H atom is drawn on the —N—,

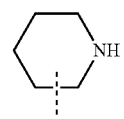

still includes the linkage of

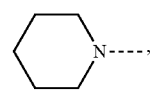

merely when one chemical bond is connected, the H of this site will be reduced by one to the corresponding monovalent piperidinyl.

Unless otherwise specified, the term "C$_{1-6}$ alkyl" refers to a linear or branched saturated hydrocarbon group consisting of 1 to 6 carbon atoms. The C$_{1-6}$ alkyl includes C$_{1-5}$, C$_{1-4}$, C$_{1-3}$, C$_{1-2}$, C$_{2-6}$, C$_{2-4}$, C$_6$ and C$_5$ alkyl and the like; it can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl and the like.

Unless otherwise specified, the term "$C_{1-4}$ alkyl" refers to a linear or branched saturated hydrocarbon group consisting of 1 to 4 carbon atoms. The $C_{1-4}$ alkyl includes $C_{1-2}$, $C_{1-3}$ and $C_{2-3}$ alkyl and the like. It can be monovalent (such as methyl), divalent (such as methylene) or multivalent (such as methine). Examples of $C_{1-4}$ alkyl include but are not limited to methyl (Me), ethyl (Et), propyl (including n-propyl and isopropyl), butyl (including n-butyl, isobutyl, s-butyl, and t-butyl) and the like.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl) and the like.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy) and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like; similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97).

The solvent used in the present disclosure is commercially available.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

The following embodiments further illustrate the present disclosure, but the present disclosure is not limited thereto. The present disclosure has been described in detail herein, and its specific embodiments have also been disclosed, for one skilled in the art, it is obvious to make various modifications and improvements to the embodiments of the present disclosure without departing from the spirit and scope of the present disclosure.

Embodiment 1

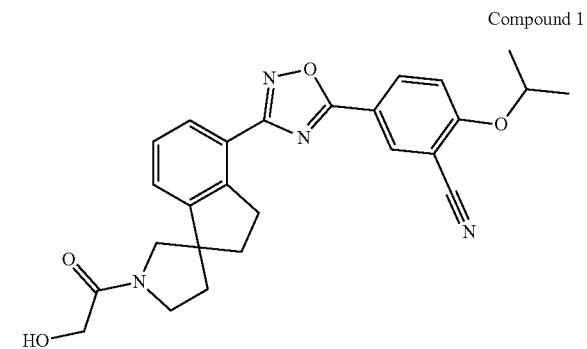 [SMILES: CC(C)Oc1ccc(-c2nc(-c3cccc4c3CCC43CCN(C(=O)CO)C3)no2)cc1C#N]

Compound 1

Synthetic Route:

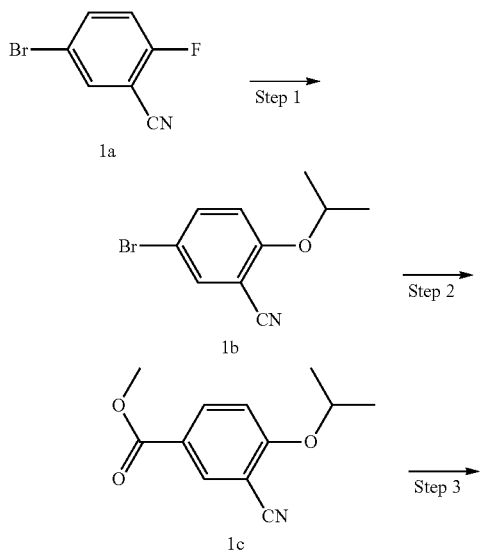

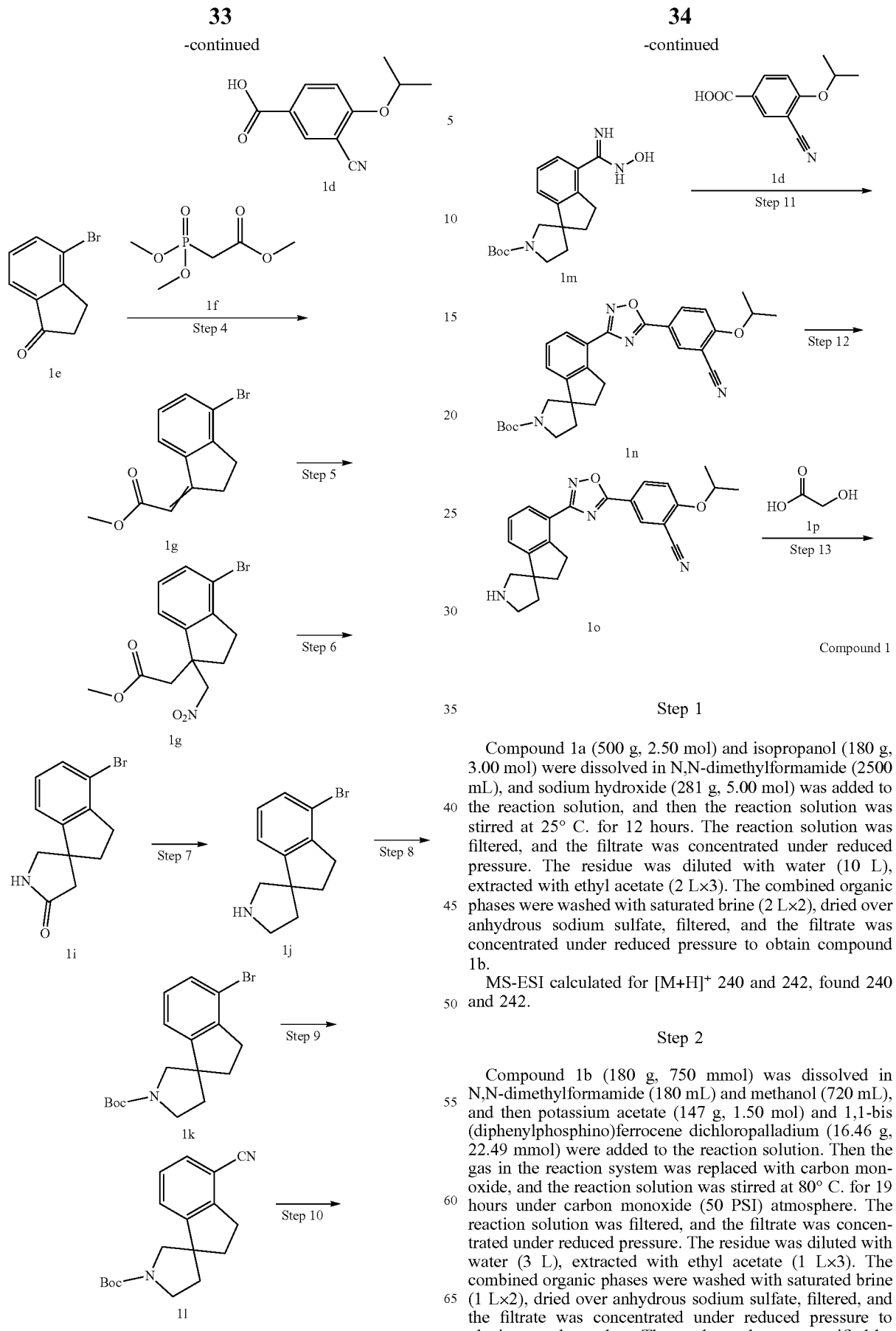

Step 1

Compound 1a (500 g, 2.50 mol) and isopropanol (180 g, 3.00 mol) were dissolved in N,N-dimethylformamide (2500 mL), and sodium hydroxide (281 g, 5.00 mol) was added to the reaction solution, and then the reaction solution was stirred at 25° C. for 12 hours. The reaction solution was filtered, and the filtrate was concentrated under reduced pressure. The residue was diluted with water (10 L), extracted with ethyl acetate (2 L×3). The combined organic phases were washed with saturated brine (2 L×2), dried over anhydrous sodium sulfate, filtered, and the filtrate was concentrated under reduced pressure to obtain compound 1b.

MS-ESI calculated for [M+H]$^+$ 240 and 242, found 240 and 242.

Step 2

Compound 1b (180 g, 750 mmol) was dissolved in N,N-dimethylformamide (180 mL) and methanol (720 mL), and then potassium acetate (147 g, 1.50 mol) and 1,1-bis(diphenylphosphino)ferrocene dichloropalladium (16.46 g, 22.49 mmol) were added to the reaction solution. Then the gas in the reaction system was replaced with carbon monoxide, and the reaction solution was stirred at 80° C. for 19 hours under carbon monoxide (50 PSI) atmosphere. The reaction solution was filtered, and the filtrate was concentrated under reduced pressure. The residue was diluted with water (3 L), extracted with ethyl acetate (1 L×3). The combined organic phases were washed with saturated brine (1 L×2), dried over anhydrous sodium sulfate, filtered, and the filtrate was concentrated under reduced pressure to obtain a crude product. The crude product was purified by silica gel column chromatography (5:1, petroleum ether/ethyl acetate, Rf=0.45) to obtain compound 1c.

$^1$H NMR (400 MHz, CDCl$_3$) δ=8.23 (d, J=1.7 Hz, 1H), 8.20-8.14 (m, 1H), 6.99 (d, J=9.0 Hz, 1H), 4.81-4.69 (m, 1H), 3.91 (s, 3H), 1.43 (d, J=6.0 Hz, 6H).

Step 3

Compound 1c (432 g, 1.91 mol) was dissolved in methanol (860 mL), and a solution of lithium hydroxide monohydrate (161 g, 3.83 mol) in water (860 mL) was added to the above reaction solution in batches. The reaction solution was stirred at 25° C. for 4 hours. The reaction solution was concentrated under reduced pressure to remove an organic solvent, and the residue was washed with ethyl acetate (800 mL×2). The pH value of an aqueous phase was adjusted to 3 with 1 M aqueous hydrochloric acid solution, and the mixture was extracted with ethyl acetate (1000 mL×3). The combined organic phases were washed with saturated brine (1000 mL×2), dried over anhydrous sodium sulfate, filtered, and concentrated under reduced pressure. The crude product was added to a mixed solution of ethyl acetate (160 mL) and n-heptane (960 mL), stirred at 20° C. for 16 hours, filtered, and the filter cake was dried under vacuum to obtain compound 1d.

$^1$H NMR (400 MHz, CDCl$_3$) δ=8.32 (d, J=2.2 Hz, 1H), 8.25 (dd, J=2.2, 8.9 Hz, 1H), 7.04 (d, J=9.2 Hz, 1H), 4.84-4.73 (m, 1H), 1.47 (d, J=6.1 Hz, 6H).

Step 4

Compound if (56.0 g, 308 mmol) was dissolved in N,N-dimethylformamide (200 mL), and then potassium tert-butoxide (34.6 g, 308 mmol) was added thereto. The reaction solution was stirred at 25° C. for 2 hours, then compound 1e (50.0 g, 237 mmol) was slowly added thereto, and the reaction solution was stirred at 25° C. for 12 hours. The reaction solution was added with water (800 mL), extracted with ethyl acetate (400 mL×3), and the organic phases were combined. The organic phases were washed with water (500 mL×1) and saturated brine (500 mL×1) respectively, dried over anhydrous sodium sulfate, concentrated, and the crude product was purified by column chromatography (10:1, petroleum ether/ethyl acetate, Rf=0.6, 0.7) to obtain compound 1 g.

MS-ESI calculated for [M+H]$^+$ 267 and 269, found 267 and 269.

$^1$H NMR (400 MHz, CDCl$_3$) δ=7.57-7.48 (m, 1H), 7.39-7.29 (m, 1H), 7.24-7.10 (m, 1H), 6.55-6.27 (m, 1H), 3.81-3.70 (m, 3H), 3.63-3.37 (m, 2H), 3.33-3.00 (m, 2H).

Step 5

Compound 1g (100 g, 374 mmol) was dissolved in dimethyl sulfoxide (400 mL), and then cesium carbonate (97.6 g, 299 mmol) was added thereto, and nitromethane (68.6 g, 1.12 mol) was slowly added dropwise. The reaction solution was stirred at 70° C. for 16 hours. The mixture was added with water (1600 mL) to quench the reaction, extracted with ethyl acetate (800 mL×3), and the combined organic phases were washed with water (1000 mL×1) and saturated brine (1000 mL×1) respectively, dried over anhydrous sodium sulfate, and concentrated to obtain compound 1h.

$^1$H NMR (400 MHz, CDCl$_3$) δ=7.41 (dd, J=7.2, 1.6 Hz, 1H), 7.12-7.04 (m, 2H), 4.89 (d, J=11.6 Hz, 1H), 4.81 (d, J=11.6 Hz, 1H), 3.86 (s, 3H), 3.04-2.96 (m, 3H), 2.78 (d, J=16.4 Hz, 1H), 2.44-2.35 (m, 1H), 2.26-2.16 (m, 1H).

Step 6

Compound 1h (100 g, 305 mmol) was dissolved in a mixed solvent of ethanol (300 mL) and water (100 mL), and then ammonium chloride (48.90 g, 914 mmol) and iron powder (51.1 g, 914 mmol) were added thereto. The reaction solution was stirred at 80° C. for 15 hours. The reaction solution was filtered with diatomite, and the filtrate was diluted with water (1000 mL), extracted with ethyl acetate (500 mL×3). The combined organic phases were washed with saturated brine (500 mL×1) respectively, dried over anhydrous sodium sulfate, and concentrated. The crude product was added to a mixed solution of ethyl acetate/n-heptane (1:6, 1180 mL), and the mixture was stirred at 25° C. for 3 days, filtered, and the filter cake was dried under vacuum to obtain compound 1i.

MS-ESI calculated for [M+H]$^+$ 266 and 268, found 266 and 268.

$^1$H NMR (400 MHz, CDCl$_3$) δ=7.52-7.32 (m, 1H), 7.25-7.06 (m, 2H), 7.06-6.87 (m, 1H), 3.63-3.32 (m, 2H), 3.08-2.83 (m, 2H), 2.69-2.41 (m, 2H), 2.36-2.10 (m, 2H).

Step 7

Compound 1i (2.00 g, 7.52 mmol) was dissolved in anhydrous tetrahydrofuran (20 mL), and then lithium aluminum hydride (570 mg, 15.0 mmol) was slowly added to the reaction solution in batches, and the reaction solution was stirred at 70° C. for 3 hours. The reaction solution was quenched by adding saturated ammonium chloride solution (50 mL), filtered, and the filtrate was collected and concentrated under reduced pressure. The residue was diluted with water (100 mL), and extracted with ethyl acetate (100 mL×2). The combined organic phases were washed with saturated brine (100 mL×2), dried over anhydrous sodium sulfate, filtered, and the filtrate was concentrated under reduced pressure to obtain the crude product of compound 1j.

MS-ESI calculated for [M+H]$^+$ 252 and 254, found 252 and 254.

Step 8

Compound 1j (1.22 g, 4.84 mmol) was dissolved in anhydrous dichloromethane (20 mL), and then di-tert-butyl dicarbonate (1.27 g, 5.81 mmol) and triethylamine (1.18 g, 11.6 mmol) were added to the mixture. The reaction solution was stirred at 25° C. for 2 hours. The reaction solution was concentrated, and the crude product was purified by silica gel column chromatography (5:1, petroleum ether/ethyl acetate, Rf=0.7) to obtain compound 1k.

MS-ESI calculated for [M+H–$^t$Bu]$^+$ 296 and 298, found 296 and 298.

Step 9

Compound 1k (1.44 g, 4.09 mmol), zinc cyanide (720 mg, 6.13 mmol) and 2-dicyclohexylphosphino-2,4,6-triisopropylbiphenyl (156 mg, 327 μmol) were dissolved in anhydrous N,N-dimethylformamide (20 mL), and tris(dibenzylideneacetone)dipalladium (150 mg, 164 μmol) was added to the mixture under nitrogen protection. The reaction solution was stirred at 90° C. for 12 hours. The reaction solution was diluted with water (100 mL), and then the mixture was extracted with ethyl acetate (100 mL×2). The combined organic phases were washed with saturated brine (100 mL×2), dried over anhydrous sodium sulfate, and filtered. The filtrate was concentrated under reduced pressure, and the crude product was purified by silica gel column chromatography (5:1, petroleum ether/ethyl acetate, Rf=0.25) to obtain compound 11.

MS-ESI calculated for [M+H–$^t$Bu]$^+$ 243, found 243.

Step 10

Compound 11 (720 mg, 2.41 mmol) was dissolved in anhydrous ethanol (10 mL), and then hydroxylamine hydrochloride (502 mg, 7.22 mmol) and triethylamine (731 mg, 7.22 mmol) were added to the mixture. The reaction solution was stirred at 80° C. for 3 hours. The reaction solution was concentrated under reduced pressure, diluted by adding water (25 mL) to the residue. The reaction solution became turbid, and then was filtered, and the filter cake was dried under vacuum to obtain the crude product of compound 1m.

MS-ESI calculated for [M+H]$^+$ 332, found 332.

Step 11

Compound 1d (495 mg, 2.41 mmol) was dissolved in anhydrous N,N-dimethylformamide (10 mL), and then 1-hydroxybenzotriazole (391 mg, 2.90 mmol) and N-(3-dimethylaminopropyl)-N-ethylcarbodiimide (555 mg, 2.90 mmol) were added to the mixture. The reaction solution was stirred at 25° C. for 1 hour. Compound 1m (800 mg, 2.41 mmol) was added to the mixture, and the reaction solution was stirred at 25° C. for 1 hour and stirred at 80° C. for 16 hours. The reaction solution was diluted with water (50 mL), and the mixture was extracted with ethyl acetate (500 mL×3). The combined organic phases were washed with saturated brine (50 mL×2), dried over anhydrous sodium sulfate, and filtered. The filtrate was concentrated under reduced pressure, and the crude product was purified by column chromatography (3:1, petroleum ether/ethyl acetate, Rf=0.4) to obtain compound 1n.

MS-ESI calculated for [M+H−$^t$Bu]$^+$ 445, found 445.

Step 12

Compound 1n (750 mg, 1.50 mmol) was dissolved in ethyl acetate (5 mL), and hydrochloric acid/ethyl acetate (4 M, 1.87 mL) was added to the mixture, and the reaction solution was stirred at 25° C. for 1 hour. The reaction solution was concentrated under reduced pressure to obtain the hydrochloride of the crude product of compound 1o.

MS-ESI calculated for [M+H]$^+$ 401, found 401.

$^1$H NMR (400 MHz, CDCl$_3$) δ=8.41 (d, J=2.1 Hz, 1H), 8.34 (dd, J=2.1, 8.9 Hz, 1H), 8.10 (d, J=7.7 Hz, 1H), 7.60-7.40 (m, 2H), 7.13 (d, J=9.0 Hz, 1H), 4.88-4.73 (m, 1H), 3.91-3.35 (m, 6H), 2.51-2.19 (m, 4H), 1.48 (d, J=6.1 Hz, 6H).

Step 13

Compound 1o (7.83 mg, 103 μmol) was dissolved in anhydrous dichloromethane (2 mL), and 2-(7-azabenzotriazole)-N,N,N,N-tetramethyluronium hexafluorophosphate (65.3 mg, 172 μmol) was added to the mixture, and the reaction solution was stirred at 25° C. for 0.5 hours. Hydrochloride of compound 1p (50 mg, 114 μmol) and triethylamine (34.7 mg, 343 μmol) were added to the mixture, and the reaction solution was stirred at 25° C. for 0.5 hours. The reaction solution was concentrated under reduced pressure, and the crude product was purified by high performance liquid chromatography { hydrochloric acid condition, column type: 3_Phenomenex Luna C18 75*30 mm*3 μm; mobile phase: [water (0.05% HCl)-acetonitrile]; acetonitrile %: 57%-77%, 6.5 minutes} to obtain compound 1.

MS-ESI calculated for [M+H]$^+$ 459, found 459.

$^1$H NMR (400 MHz, DMSO-d$_6$) δ=8.51 (d, J=2.4 Hz, 1H), 8.41 (dd, J=9.2, 2.4 Hz, 1H), 8.01-7.98 (m, 1H), 7.56 (d, J=8.8 Hz, 1H), 7.53-7.49 (m, 1H), 7.48-7.44 (m, 1H), 5.02-4.95 (m, 1H), 4.15-3.95 (m, 2H), 3.72-3.25 (m, 7H), 2.19-2.04 (m, 4H), 1.41-1.38 (m, 6H).

Embodiment 3

Compound 3

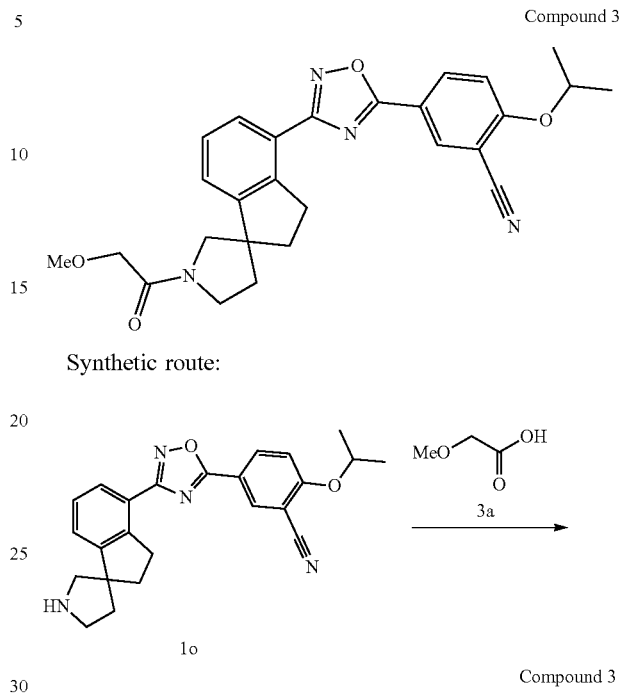

Synthetic route:

Compound 3

Compound 3a (9.28 mg, 103 μmol) was dissolved in anhydrous dichloromethane (2 mL), and 2-(7-azabenzotriazole)-N,N,N,N-tetramethyluronium hexafluorophosphate (65.3 mg, 172 μmol) was added to the mixture, and the reaction solution was stirred at 25° C. for 0.5 hours. Hydrochloride of compound 1o (50.0 mg, 114 μmol) and triethylamine (34.7 mg, 343 μmol) were added to the mixture, and the reaction solution was stirred at 25° C. for 0.5 hours. The reaction solution was concentrated, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 60%-80%, 7.5 minutes} to obtain compound 3.

MS-ESI calculated for [M+H]$^+$ 473, found 473.

$^1$H NMR (400 MHz, DMSO-d$_6$) δ=8.53 (d, J=2.2 Hz, 1H), 8.42 (dd, J=2.3, 8.9 Hz, 1H), 8.04-7.98 (m, 1H), 7.59-7.43 (m, 3H), 5.03-4.94 (m, 1H), 4.13-3.97 (m, 2H), 3.73-3.34 (m, 6H), 3.30 (s, 3H), 2.23-2.01 (m, 4H), 1.42-1.37 (m, 6H).

Embodiment 4

Compound 4

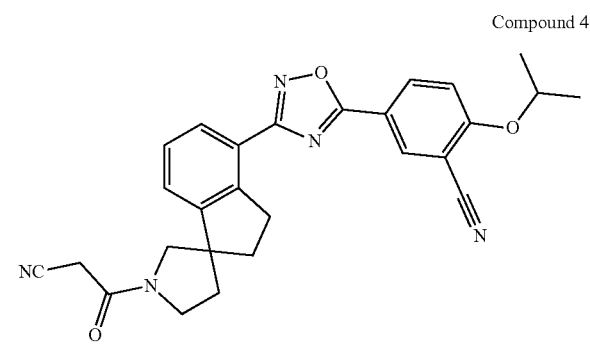 [SMILES: CC(C)Oc1ccc(-c2nc(-c3cccc4c3CCC43CCN(C(=O)CC#N)C3)no2)cc1C#N]

Synthetic route:

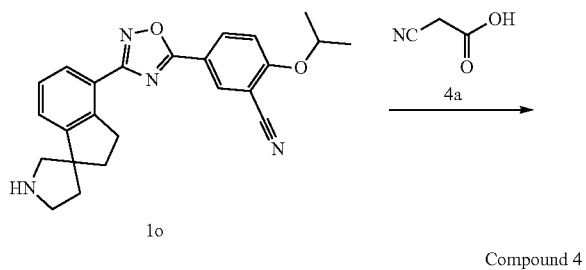

Compound 4

Compound 4a (8.76 mg, 103 μmol) was dissolved in anhydrous dichloromethane (2 mL), and 2-(7-azabenzotriazole)-N,N,N,N-tetramethyluronium hexafluorophosphate (65.3 mg, 172 μmol) was added to the mixture, and the reaction solution was stirred at 25° C. for 0.5 hours. Hydrochloride of compound 1o (50.0 mg, 114 μmol) and triethylamine (34.7 mg, 343 μmol) were added to the mixture, and the reaction solution was stirred at 25° C. for 0.5 hours. The reaction solution was concentrated, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 57%-77%, 7.5 minutes} to obtain compound 4.

MS-ESI calculated for [M+H]$^+$ 468, found 468.

$^1$H NMR (400 MHz, DMSO-d$_6$) δ=8.53 (d, J=2.2 Hz, 1H), 8.42 (dd, J=2.3, 9.0 Hz, 1H), 8.06-7.97 (m, 1H), 7.61-7.44 (m, 3H), 5.04-4.94 (m, 1H), 4.07-3.89 (m, 2H), 3.74-3.42 (m, 4H), 3.36-3.25 (m, 2H), 2.23-2.03 (m, 4H), 1.42-1.37 (m, 6H).

Embodiment 5

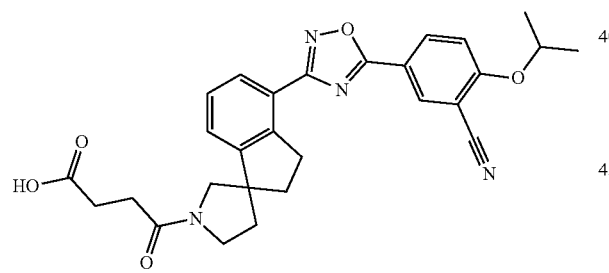

Compound 5

Synthetic route:

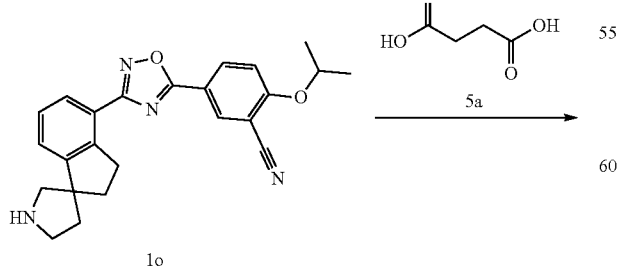

Compound 5

Compound 5a (13.5 mg, 103 μmol) was dissolved in anhydrous dichloromethane (2 mL), and 2-(7-azabenzotriazole)-N,N,N,N-tetramethyluronium hexafluorophosphate (65.3 mg, 172 μmol), hydrochloride of compound 1o (50.0 mg, 114 μmol) and triethylamine (34.7 mg, 343 μmol) were added to the mixture, and the reaction solution was stirred at 25° C. for 1 hour. The reaction solution was concentrated, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 52%-72%, 6.5 minutes} to obtain compound 5.

MS-ESI calculated for [M+H]$^+$ 501, found 501.

$^1$H NMR (400 MHz, DMSO-d$_6$) δ=8.55-8.51 (m, 1H), 8.45-8.40 (m, 1H), 8.03-7.98 (m, 1H), 7.59-7.43 (m, 3H), 5.04-4.95 (m, 1H), 3.79-3.25 (m, 6H), 2.59-2.42 (m, 4H), 2.25-2.04 (m, 4H), 1.42-1.37 (m, 6H).

Embodiment 6

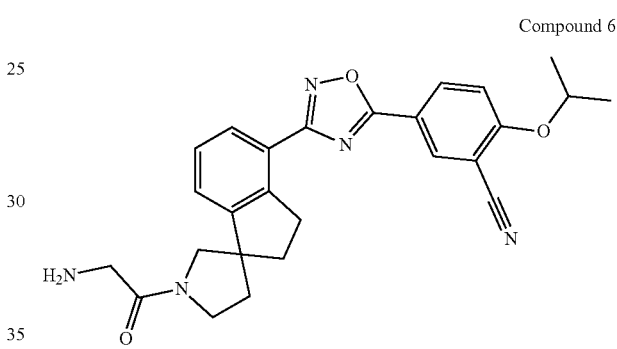

Compound 6

Synthetic route:

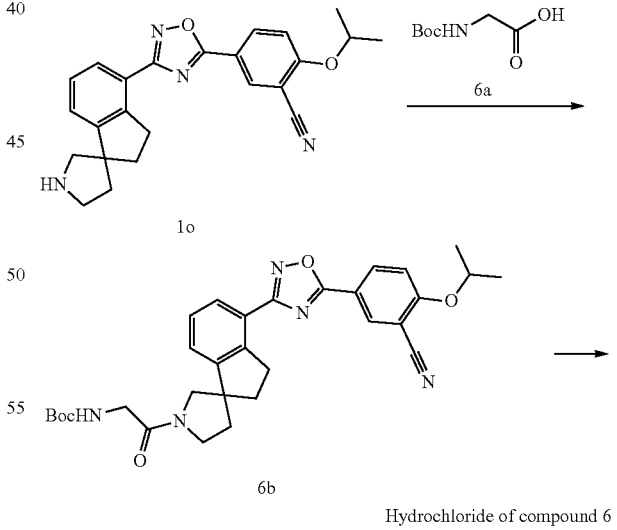

Hydrochloride of compound 6

Step 1

Compound 6a (18.0 mg, 103 μmol) was dissolved in anhydrous dichloromethane (2 mL), and 2-(7-azabenzotriazole)-N,N,N,N-tetramethyluronium hexafluorophosphate (65.3 mg, 172 μmol) was added to the mixture, and the reaction solution was stirred at 25° C. for 0.5 hours. Hydrochloride of compound 1o (50.0 mg, 114 μmol) and triethylamine (34.7 mg, 343 μmol) were added to the mixture. Water (20 mL) was added to the reaction solution, and the mixture was extracted with dichloromethane (10 mL×3). The organic phases were combined, and the organic phases were washed with water (10 mL) and saturated brine (10 mL) successively, and dried over anhydrous sodium sulfate. The mixture was concentrated under reduced pressure to obtain compound 6b, and the crude product was directly used in the next reaction without purification.

MS-ESI calculated for [M+H]$^+$ 558, found 558.

Step 2

Compound 6b (81.0 mg, 145 μmol) was dissolved in anhydrous methanol (2 mL), and methanol hydrochloride (4 M, 363 μL) was added to the mixture. The reaction solution was stirred at 25° C. for 1 hour. The reaction solution was concentrated, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 29%-49%, 7.5 minutes} to obtain the hydrochloride of compound 6.

MS-ESI calculated for [M+H]$^+$ 458, found 458.

$^1$H NMR (400 MHz, DMSO-d$_6$) δ=8.53 (d, J=2.2 Hz, 1H), 8.42 (dd, J=2.2, 8.9 Hz, 1H), 8.14 (br s, 3H), 8.06-9.00 (m, 1H), 7.61-7.44 (m, 3H), 5.05-4.93 (m, 1H), 3.92-3.25 (m, 8H), 2.26-1.98 (m, 4H), 1.42-1.37 (m, 6H).

Embodiment 7

Compound 7

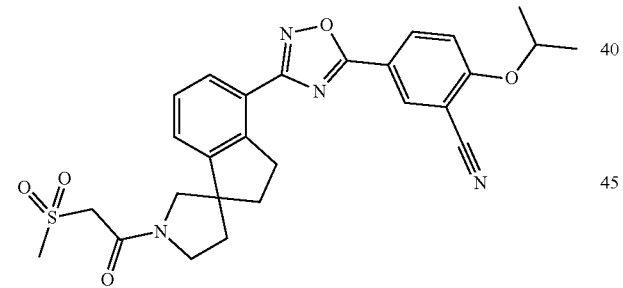

Synthetic route:

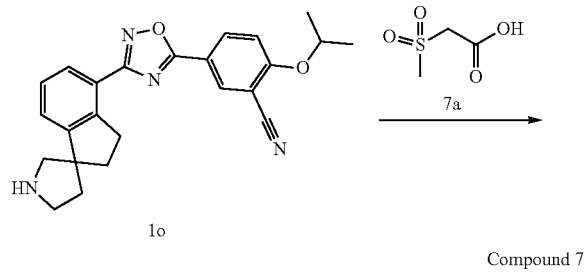

Compound 7

Compound 7a (15.8 mg, 114 μmol) was dissolved in anhydrous dichloromethane (2 mL), and 2-(7-azabenzotriazole)-N,N,N,N-tetramethyluronium hexafluorophosphate (65.3 mg, 172 μmol) was added to the mixture, and the reaction solution was stirred at 25° C. for 0.5 hours. Hydrochloride of compound 1o (50.0 mg, 114 μmol) and triethylamine (34.7 mg, 343 μmol) were added to the mixture, and the reaction solution was stirred at 25° C. for 0.5 hours. The reaction solution was concentrated, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 32%-52%, 6.5 minutes} to obtain compound 7.

MS-ESI calculated for [M+H]$^+$ 521, found 521.

$^1$H NMR (400 MHz, DMSO-d$_6$) δ=8.56-8.52 (m, 1H), 8.46-8.40 (m, 1H), 8.04-7.99 (m, 1H), 7.61-7.44 (m, 3H), 5.05-4.94 (m, 1H), 4.45-4.35 (m, 2H), 3.92-3.44 (m, 4H), 3.34-3.28 (m, 2H), 3.18-3.11 (m, 3H), 2.26-1.96 (m, 4H), 1.42-1.37 (m, 6H).

Embodiment 8

Compound 8

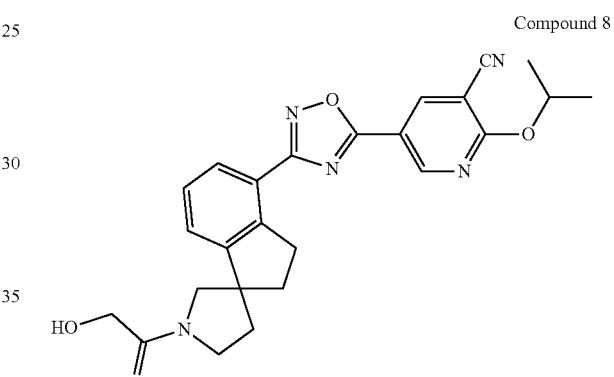

Synthetic route:

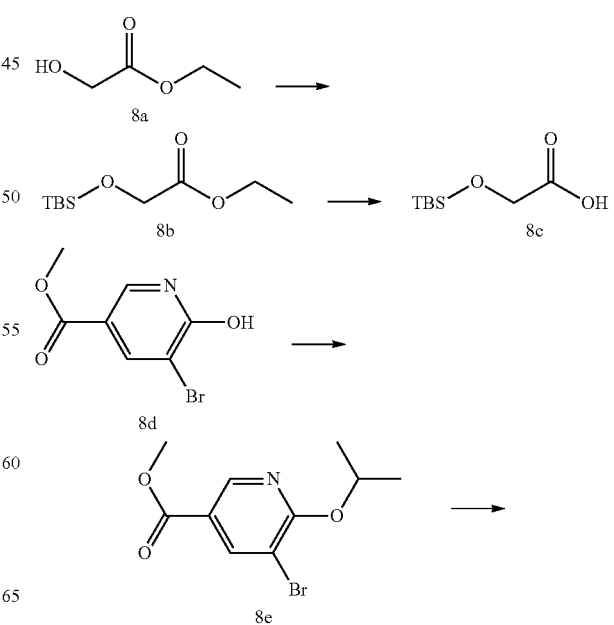

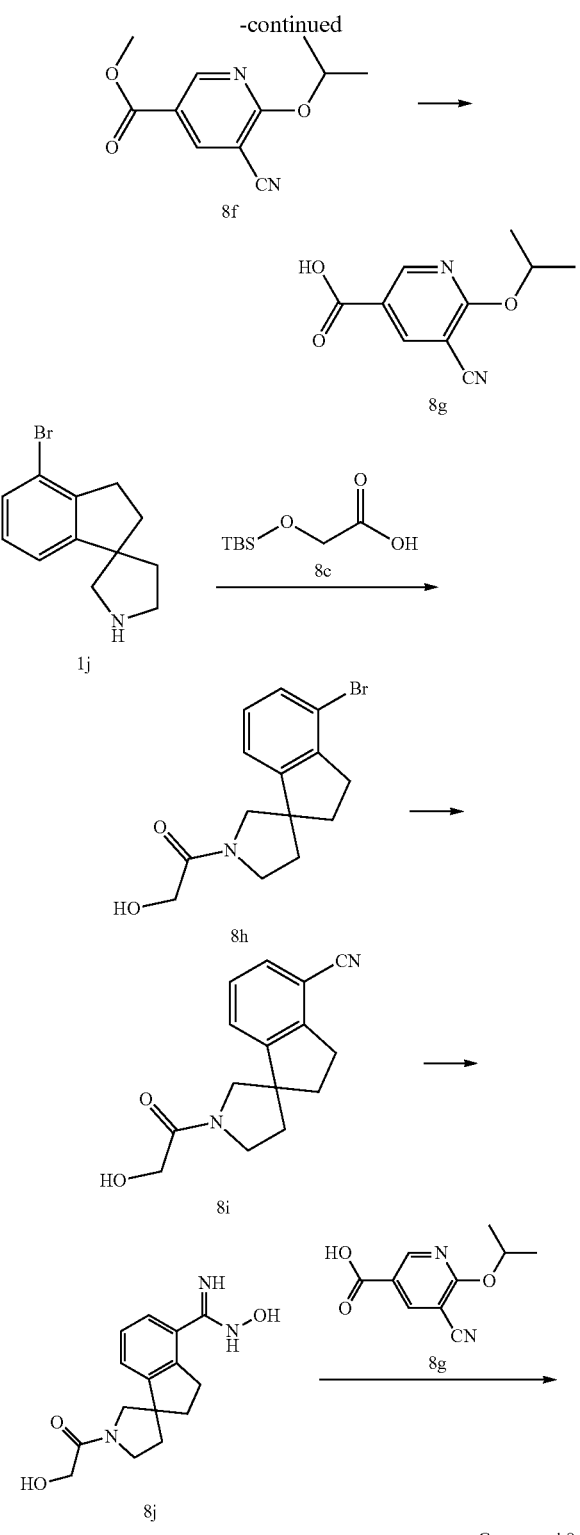

Step 1

Compound 8a (68.0 g, 653 mmol) and imidazole (200 mL) were dissolved in dichloromethane (500 mL) and cooled to 0° C. tert-Butyldimethylsilyl chloride (103 g, 686 mmol) was dissolved in dichloromethane (200 mL), and the mixture was added to the above reaction solution. The reaction solution was stirred at 0° C. for 3 hours under nitrogen protection. The reaction solution was concentrated under reduced pressure, diluted with petroleum ether (1500 mL), washed with water (300 mL×3), dried over anhydrous sodium sulfate, and concentrated under reduced pressure to obtain compound 8b.

$^1$H NMR (400 MHz, CDCl$_3$) δ=4.24 (s, 2H), 4.20 (q, J=7.2 Hz, 2H), 1.28 (t, J=7.2 Hz, 3H), 0.93 (s, 9H), 0.11 (s, 6H).

Step 2

Compound 8b (12.0 g, 55.0 mmol) was dissolved in ethanol (120 mL) and cooled to 0° C. A solution of potassium hydroxide (4.62 g, 82.4 mmol) in ethanol (120 mL) was added to the above reaction solution, and the reaction solution was stirred at 25° C. for 12 hours. The reaction solution was concentrated under reduced pressure, and the residue was dissolved in water (100 mL), and 1 M hydrochloric acid was slowly added dropwise thereto at 0° C. to adjust the pH to 4. The mixture was extracted with ethyl acetate (50 mL×4). The organic phases were combined, and the organic phases were washed with water (30 mL×1) and saturated brine (30 mL×2) respectively, dried over anhydrous sodium sulfate, and concentrated to obtain compound 8c.

$^1$H NMR (400 MHz, CDCl$_3$) δ=4.24 (s, 2H), 0.94 (s, 9H), 0.15 (s, 6H)

Step 3

Compound 8d (1.00 g, 4.31 mmol) and 2-iodopropane (1.47 g, 8.62 mmol) were dissolved in toluene (8 mL), then silver carbonate (3.57 g, 12.9 mmol) was added thereto, and the reaction solution was stirred at 50° C. for 16 hours. The reaction solution was concentrated under reduced pressure, and the residue was diluted with water (100 mL), extracted with ethyl acetate (100 mL×3). The combined organic phases were washed with saturated brine (100 mL), dried over anhydrous sodium sulfate, filtered, and the filtrate was concentrated under reduced pressure to obtain compound 8e.

MS-ESI calculated for [M+H]$^+$ 274 and 276, found 274 and 276.

$^1$H NMR (400 MHz, CDCl$_3$) δ=8.72 (d, J=2.1 Hz, 1H), 8.38 (d, J=2.1 Hz, 1H), 5.48-5.37 (m, 1H), 3.92 (s, 3H), 1.42 (d, J=6.2 Hz, 6H).

Step 4

Compound 8e (1.00 g, 3.65 mmol) was dissolved in anhydrous N,N-dimethylformamide (15 mL), and zinc cyanide (857 mg, 7.30 mmol), tris(dibenzylideneacetone)dipalladium (334 mg, 365 μmol) and 2-di-tert-butylphosphino-2',4',6'-triisopropylbiphenyl (348 mg, 730 μmol) were added thereto. The reaction solution was stirred at 90° C. for 12 hours under nitrogen protection. The reaction solution was concentrated, and the residue was diluted with water (50 mL), extracted with ethyl acetate (30 mL×3). The combined organic phases were washed with saturated brine (40 mL×1), dried over anhydrous sodium sulfate, concentrated, and the crude product was purified by silica gel column chromatography (10:1, petroleum ether/ethyl acetate, Rf=0.4) to obtain compound 8f.

MS-ESI calculated for [M+H−$^i$Pr]$^+$ 179, found 179.

Step 5

Compound 8f (100 mg, 454 μmol) was dissolved in tetrahydrofuran (1 mL) and methanol (0.5 mL), and a solution of lithium hydroxide monohydrate (57.2 mg, 1.36 mmol) in water (0.5 mL) was added dropwise to the reaction solution, and the reaction solution was stirred at 25° C. for 1 hour. The reaction solution was concentrated under reduced pressure to remove the organic solvent. The pH of the residue was adjusted to about 6 with 1 N aqueous hydrochloric acid solution, then the mixture was diluted with water (50 mL) and extracted with ethyl acetate (50 mL×3). The combined organic phases were dried over anhydrous sodium sulfate, filtered and concentrated to obtain a crude product. The crude product was purified by thin-layer silica gel chromatography (10:1, dichloromethane/methanol, Rf=0.21) to obtain compound 8g.

$^1$H NMR (400 MHz, CDCl$_3$) δ=9.18-8.74 (m, 1H), 8.70-8.23 (m, 1H), 5.60-5.38 (m, 1H), 1.43 (d, J=6.1 Hz, 6H).

Step 6

Compound 1j (8.20 g, 32.5 mmol), compound 8c (7.43 g, 39.0 mmol) and diisopropylethylamine (12.6 g, 97.6 mmol) were dissolved in N,N-dimethylformamide (80 mL), and then 2-(7-azabenzotriazole)-N,N,N,N-tetramethyluronium hexafluorophosphate (14.8 g, 39.0 mmol) was added thereto. The reaction solution was stirred at 25° C. for 12 hours. The reaction solution was concentrated under reduced pressure, diluted with water (200 mL), and extracted with ethyl acetate (100 mL×3). The combined organic phases were washed with saturated brine (100 mL), dried over anhydrous sodium sulfate, concentrated, and the crude product was purified by column chromatography (2:1, petroleum ether/ethyl acetate, Rf=0.3) to obtain compound 8h.

MS-ESI calculated for [M+H]$^+$ 310 and 312, found 310 and 312.

Step 7

Compound 8h (5.00 g, 16.1 mmol) was dissolved in anhydrous N,N-dimethylformamide (50 mL), and zinc cyanide (3.79 g, 32.2 mmol), tris(dibenzylideneacetone)dipalladium (738 mg, 806 μmol) and 2-di-tert-butylphosphino-2',4',6'-triisopropylbiphenyl (768 mg, 1.66 mmol) were added thereto, and the reaction system was replaced with nitrogen for three times. Under nitrogen protection, the reaction solution was stirred at 90° C. for 12 hours, and the reaction solution was concentrated after completion of the reaction. The residue was diluted with water (200 mL), extracted with ethyl acetate (100 mL×3), and the combined organic phases were washed with saturated brine (100 mL), dried over anhydrous sodium sulfate, concentrated, and purified by silica gel column chromatography (2:1, petroleum ether/ethyl acetate, Rf=0.3) to obtain a crude product. The crude product was purified by high performance liquid chromatography {hydrochloric acid condition, column type: Phenomenex luna C18 250*50 mm*10 μm; mobile phase: [water (0.05% HCl)-acetonitrile]; acetonitrile %: 10%-40%, 20 minutes} to obtain compound 8i.

MS-ESI calculated for [M+H]$^+$ 257, found 257.

Step 8

Compound 8i (700 mg, 2.73 mmol) and diisopropylethylamine (706 mg, 5.46 mmol) were dissolved in ethanol (15 mL), and then hydroxylamine hydrochloride (380 mg, 5.46 mmol) was added thereto, and the reaction solution was stirred at 60° C. for 12 hours. The reaction solution was cooled to room temperature, and concentrated. The residue was diluted with ethanol (10 mL), stirred at 25° C. for 12 hours, filtered, and the filter cake was washed with ethanol (5 mL×2), and dried under vacuum to obtain compound 8j.

MS-ESI calculated for [M+H]$^+$ 290, found 290.

Step 9

Compound 8g (43.9 mg, 213 μmol) was dissolved in N,N-dimethylformamide (2 mL), and 1-(3-dimethylaminopropyl)-3-ethylcarbodiimide hydrochloride (44.5 mg, 232 μmol) and 1-hydroxybenzotriazole (31.4 mg, 232 μmol) were added to the reaction solution, and the reaction solution was stirred at 25° C. for 15 minutes. Then compound 8j (56.0 mg, 194 μmol) was added thereto, and the reaction solution was stirred at 25° C. for 1 hour, then stirred at 80° C. for 12 hours. The reaction solution was concentrated under reduced pressure, diluted with water (50 mL), extracted with ethyl acetate (20 mL×3). The combined organic phases were dried over anhydrous sodium sulfate, filtered, and the filtrate was concentrated under reduced pressure. The crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 57%-77%, 7 minutes} to obtain compound 8.

MS-ESI calculated for [M+H]$^+$ 460, found 460.

$^1$H NMR (400 MHz, CDCl$_3$) δ=9.16 (d, J=2.3 Hz, 1H), 8.65 (d, J=2.3 Hz, 1H), 8.14-8.07 (m, 1H), 7.42 (t, J=8.0 Hz, 1H), 7.32 (d, J=8.0 Hz, 1H), 5.62-5.51 (m, 1H), 4.25-4.06 (m, 2H), 3.97-3.33 (m, 6H), 2.32-2.01 (m, 4H), 1.48 (d, J=6.0 Hz, 1H).

Embodiment 9

Compound 9

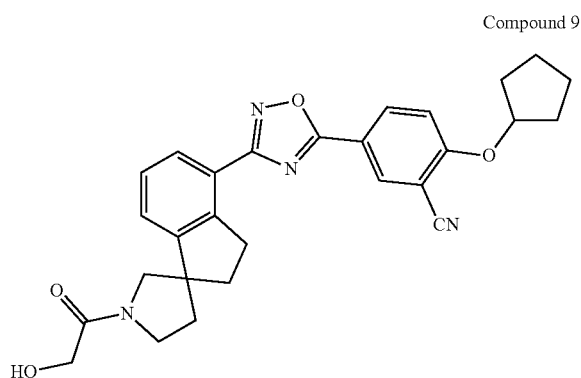 [SMILES: N#Cc1cc(-c2nc(-c3cccc4c3CCC43CCN(C(=O)CO)C3)no2)ccc1OC1CCCC1]

Synthetic route:

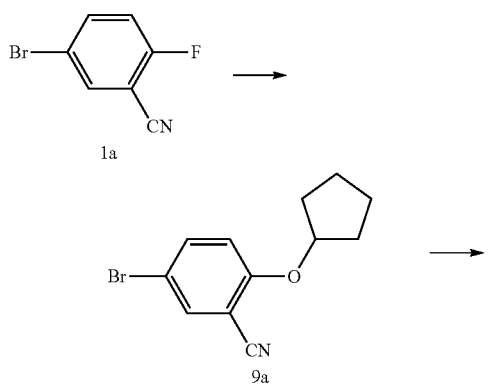

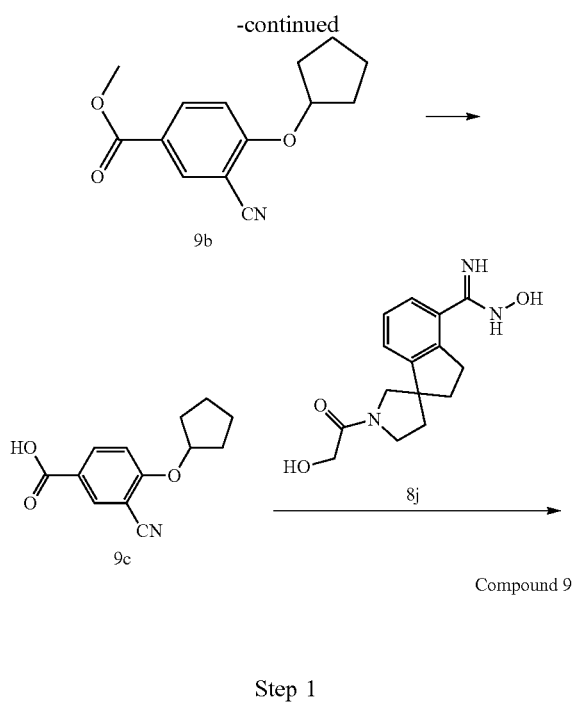

Compound 9

Step 1

Compound 1a (1.00 g, 5.00 mmol) and cyclopentanol (517 mg, 6.00 mmol) were dissolved in N,N-dimethylformamide (10 mL) at 0° C.; after stirring for 15 minutes, sodium hydride (600 mg, 15.0 mmol, 60% purity) was added to the reaction solution, and then the reaction solution was stirred at 25° C. for 12 hours. The reaction solution was concentrated, and the residue was diluted with water (50 mL), extracted with ethyl acetate (50 mL×3). The combined organic phases were washed with saturated brine (30 mL×3), dried over anhydrous sodium sulfate, filtered, and the filtrate was concentrated under reduced pressure to obtain compound 9a.

MS-ESI calculated for [M+H]$^+$ 266 and 268, found 266 and 268.

Step 2

Compound 9a (1.30 g, 4.88 mmol) was dissolved in N,N-dimethylformamide (3 mL) and methanol (9 mL), and potassium acetate (1.44 g, 14.7 mmol) and 1,1-bis(diphenylphosphino)ferrocene dichloropalladium (357 mg, 488 μmol) were added to the reaction solution. Then the gas in the reaction system was replaced with argon and carbon monoxide in turn, and the reaction solution was stirred at 80° C. for 19 hours under carbon monoxide (50 PSI) atmosphere. The reaction solution was concentrated under reduced pressure, and the residue was diluted with water (200 mL), extracted with ethyl acetate (200 mL×2). The combined organic phases were dried over anhydrous sodium sulfate, filtered, and the filtrate was concentrated under reduced pressure to obtain a crude product. The crude product was purified by silica gel column chromatography (10:1, petroleum ether/ethyl acetate, Rf=0.20) to obtain compound 9b.

MS-ESI calculated for [M+H]$^+$ 246, found 246.

Step 3

Compound 9b (1.00 g, 4.08 mmol) was dissolved in tetrahydrofuran (10 mL) and methanol (2 mL), and a solution of lithium hydroxide monohydrate (513 mg, 12.2 mmol) in water (1 mL) was added dropwise to the reaction solution, and the reaction solution was stirred at 25° C. for 2 hours. The reaction solution was concentrated under reduced pressure, diluted with water (100 mL), washed with ethyl acetate (100 mL×3), and the pH of the aqueous phase was adjusted to less than 6 with 1 N aqueous hydrochloric acid solution. The mixture was extracted with ethyl acetate (50 mL×3). The combined organic phases were dried over anhydrous sodium sulfate, filtered, and the filtrate was concentrated under reduced pressure to obtain compound 9c.

MS-ESI calculated for [M+H]$^+$ 232, found 232.

$^1$H NMR (400 MHz, CDCl$_3$) δ=8.32 (d, J=2.1 Hz, 1H), 8.25 (dd, J=9.0, 2.1 Hz, 1H), 7.04 (d, J=9.0 Hz, 1H), 5.00-4.92 (m, 1H), 2.07-1.94 (m, 4H), 1.92-1.83 (m, 2H), 1.75-1.63 (m, 2H).

Step 4

Compound 9c (52.8 mg, 228 μmol) was dissolved in N,N-dimethylformamide (2 mL), and 1-(3-dimethylaminopropyl)-3-ethylcarbodiimide hydrochloride (47.7 mg, 249 μmol) and 1-hydroxybenzotriazole (33.6 mg, 249 μmol) were added to the reaction solution, and the reaction solution was stirred at 25° C. for 15 minutes. Then compound 8j (60.0 mg, 207 μmol) was added thereto, and the reaction solution was stirred at 25° C. for 1 hour, then stirred at 80° C. for 12 hours. After the reaction was completed, the reaction solution was diluted with water (50 mL), extracted with ethyl acetate (30 mL×3). The combined organic phases were dried over anhydrous sodium sulfate, filtered, and the filtrate was concentrated under reduced pressure. The crude product was purified by high performance liquid chromatography {hydrochloric acid condition, column type: Phenomenex luna C18 150*25 mm*10 μm; mobile phase: [water (0.05% HCl)-acetonitrile]; acetonitrile %: 53%-83%, 10 minutes} to obtain compound 9.

MS-ESI calculated for [M+H]$^+$ 485, found 485.

$^1$H NMR (400 MHz, CDCl$_3$) δ=8.45-8.41 (m, 1H), 8.37-8.32 (m, 1H), 8.13-8.07 (m, 1H), 7.45 7.38 (m, 1H), 7.34-7.29 (m, 1H), 7.18-7.11 (m, 1H), 5.06-4.93 (m, 1H), 4.30-4.20 (m, 1H), 4.20-4.03 (m, 1H), 3.96-3.52 (m, 4H), 3.47-3.33 (m, 3H), 2.34-1.98 (m, 8H), 1.94-1.69 (m, 4H).

Embodiment 10

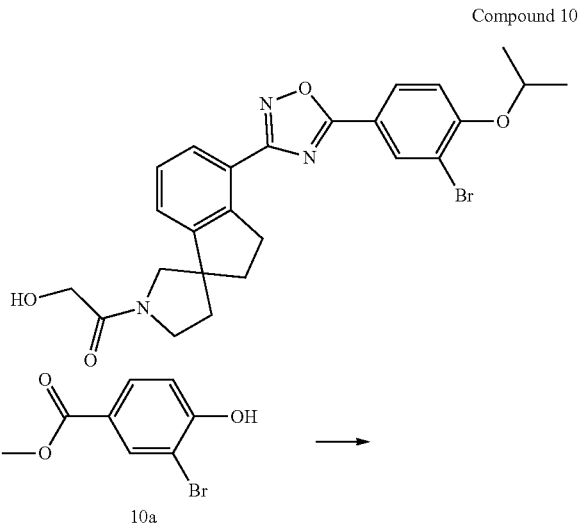

Compound 10

49

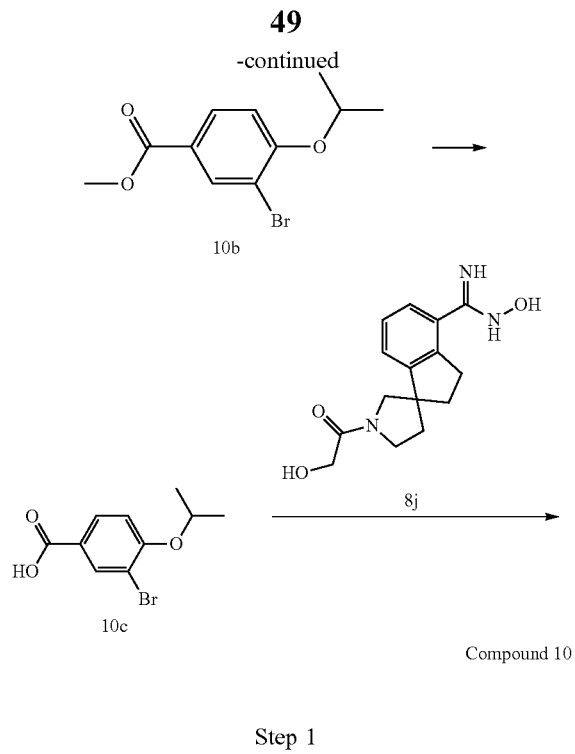

Compound 10

Step 1

Compound 10a (2.00 g, 8.66 mmol) was dissolved in N,N-dimethylformamide (20 mL), and 2-bromopropane (1.60 g, 13.0 mmol) and potassium carbonate (2.39 g, 17.3 mmol) were added thereto, and the reaction solution was stirred at 80° C. for 12 hours. The reaction solution was diluted with water (200 mL), extracted with ethyl acetate (200 mL×2), and the combined organic phases were dried over anhydrous sodium sulfate, filtered and concentrated. The crude product was separated by silica gel column chromatography (3:1, petroleum ether/ethyl acetate, Rf=0.74) to obtain compound 10b.

MS-ESI calculated for [M+H]$^+$ 273 and 275, found 273 and 275.

Step 2

Compound 10b (900 mg, 3.30 mmol) was dissolved in tetrahydrofuran (10 mL) and methanol (2 mL), and a solution of lithium hydroxide monohydrate (415 mg, 9.89 mmol) in water (3 mL) was added dropwise to the reaction solution, and the reaction solution was stirred at 25° C. for 12 hours. The reaction solution was concentrated, and the pH was adjusted to about 6 with 1 N hydrochloric acid solution. Then the reaction solution was diluted with water (50 mL), extracted with ethyl acetate (50 mL×3). The combined organic phases were dried over anhydrous sodium sulfate, filtered, and the filtrate was concentrated to obtain compound 10c.

MS-ESI calculated for [M+H]$^+$ 259 and 261, found 259 and 261.

$^1$H NMR (400 MHz, CDCl$_3$) δ=8.30 (d, J=2.0 Hz, 1H), 8.02 (dd, J=8.8, 2.0 Hz, 1H), 6.94 (d, J=8.8 Hz, 1H), 4.76-4.64 (m, 1H), 1.44 (d, J=6.0 Hz, 6H).

Step 3

Compound 10c (64.5 mg, 249 μmol) was dissolved in N,N-dimethylformamide (2 mL), and 1-(3-dimethylaminopropyl)-3-ethylcarbodiimide hydrochloride (55.7 mg, 290 μmol) and 1-hydroxybenzotriazole (39.2 mg, 290 μmol) were added to the reaction solution, and the reaction solution was stirred at 25° C. for 15 minutes. Then compound 8j

50

(60.0 mg, 207 μmol) was added thereto, and the reaction solution was stirred at 25° C. for 1 hour, then stirred at 80° C. for 16 hours. The reaction solution was concentrated under reduced pressure, diluted with water (100 mL), extracted with ethyl acetate (50 mL×3). The combined organic phases were washed with water (30 mL×2), dried over anhydrous sodium sulfate, filtered, and the filtrate was concentrated under reduced pressure. The crude product was purified by high performance liquid chromatography {hydrochloric acid condition, column type: Phenomenex luna C18 150*25 mm*10 μm; mobile phase: [water (0.05% HCl)-acetonitrile]; acetonitrile %: 60%-90%, 10 minutes} to obtain compound 10.

MS-ESI calculated for [M+H]$^+$ 512 and 514, found 512 and 514.

$^1$H NMR (400 MHz, CDCl$_3$) δ=8.43 (d, J=2.1 Hz, 1H), 8.14-8.08 (m, 2H), 7.44-7.37 (m, 1H), 7.32-7.28 (m, 1H), 7.07-7.01 (m, 1H), 4.77-4.68 (m, 1H), 4.23-4.17 (m, 1H), 4.14-4.08 (m, 1H), 3.95-3.49 (m, 3H), 3.47-3.37 (m, 3H), 2.32-1.98 (m, 4H), 1.49-1.44 (m, 6H).

Embodiment 11

Compound 11

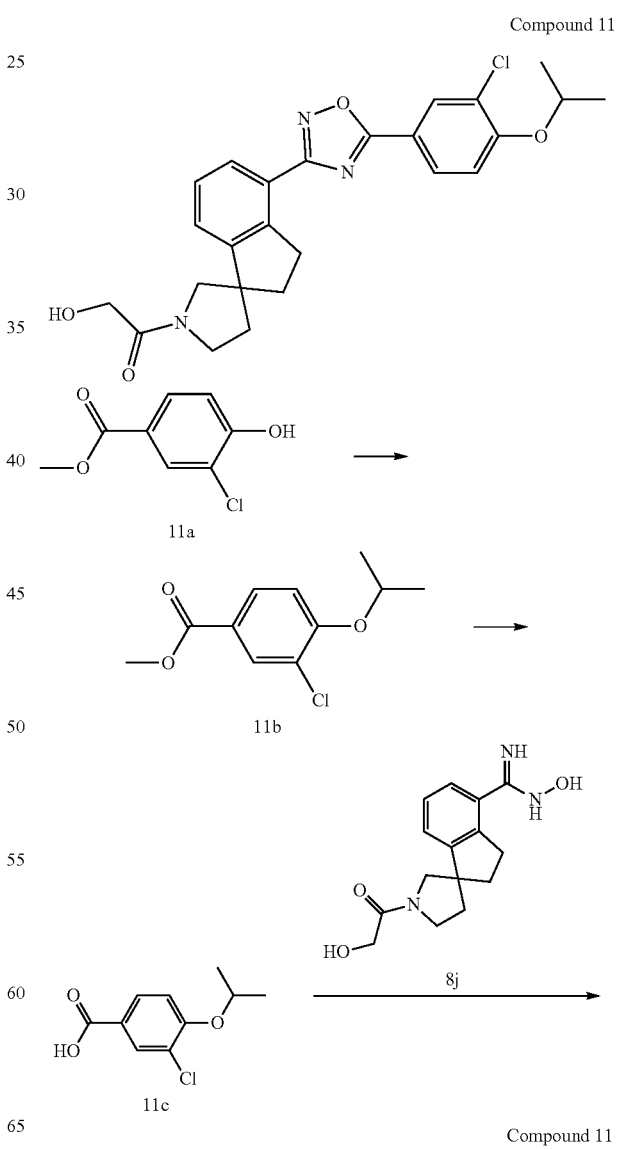

Compound 11

Step 1

Compound 11a (0.500 g, 2.68 mmol) was dissolved in N,N-dimethylformamide (10 mL), and 2-bromopropane (494 mg, 4.02 mmol) and potassium carbonate (741 mg, 5.36 mmol) were added thereto, and the reaction solution was stirred at 80° C. for 12 hours. The reaction solution was diluted with water (200 mL), extracted with ethyl acetate (200 mL×2), and the combined organic phases were dried over anhydrous sodium sulfate, filtered and concentrated. The crude product was separated by column chromatography (3:1, petroleum ether/ethyl acetate, Rf=0.62) to obtain compound 11b.

MS-ESI calculated for [M+H]$^+$ 229, found 229.

Step 2

Compound 11b (500 mg, 2.19 mmol) was dissolved in tetrahydrofuran (5 mL) and methanol (1 mL), and a solution of lithium hydroxide monohydrate (275 mg, 6.56 mmol) in water (1 mL) was added dropwise to the reaction solution, and the reaction solution was stirred at 25° C. for 12 hours. The reaction solution was concentrated to remove the organic solvent, and the pH was adjusted to about 6 with 1 N hydrochloric acid solution. Then the reaction solution was diluted with water (50 mL), extracted with ethyl acetate (50 mL×3). The combined organic phases were dried over anhydrous sodium sulfate, filtered, and the filtrate was concentrated under reduced pressure to obtain compound 11c.

MS-ESI calculated for [M+H]$^+$ 215, found 215.

$^1$H NMR (400 MHz, CDCl$_3$) δ=8.13 (d, J=2.0 Hz, 1H), 7.98 (dd, J=8.8, 2.0 Hz, 1H), 6.97 (d, J=8.8 Hz, 1H), 4.83-4.59 (m, 1H), 1.44 (d, J=6.1 Hz, 6H).

Step 3

Compound 11c (44.5 mg, 207 μmol) was dissolved in N,N-dimethylformamide (2 mL), and 1-(3-dimethylaminopropyl)-3-ethylcarbodiimide hydrochloride (47.7 mg, 249 μmol) and 1-hydroxybenzotriazole (33.6 mg, 249 μmol) were added to the reaction solution, and the reaction solution was stirred at 25° C. for 15 minutes. Then compound 8j (60.0 mg, 207 μmol) was added thereto, and the reaction solution was stirred at 25° C. for 1 hour, then stirred at 80° C. for 12 hours. The reaction solution was concentrated under reduced pressure, diluted with water (50 mL), extracted with ethyl acetate (30 mL×3). The combined organic phases were washed with water (20 mL×2) and saturated brine (20 mL×2) respectively, dried over anhydrous sodium sulfate, filtered, and the filtrate was concentrated under reduced pressure. The crude product was purified by high performance liquid chromatography {hydrochloric acid condition, column type: Phenomenex luna C18 150*25 mm*10 μm; mobile phase: [water (0.05% HCl)-acetonitrile]; B %: 52%-82%, 10 minutes} to obtain compound 11.

MS-ESI calculated for [M+H]$^+$ 468, found 468.

$^1$H NMR (400 MHz, CDCl$_3$) δ=8.25 (d, J=2.1 Hz, 1H), 8.13-8.04 (m, 2H), 7.45-7.37 (m, 1H), 7.32-7.28 (m, 1H), 7.07 (d, J=8.7 Hz, 1H), 4.78-4.66 (m, 1H), 4.25-4.17 (m, 1H), 4.16-4.04 (m, 1H), 3.98-3.50 (m, 3H), 3.46-3.37 (m, 3H), 2.33-2.04 (m, 4H), 1.49-1.44 (m, 6H).

Embodiment 12

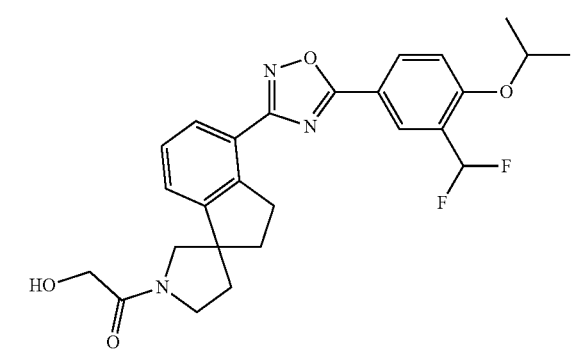

Compound 12

Synthetic route:

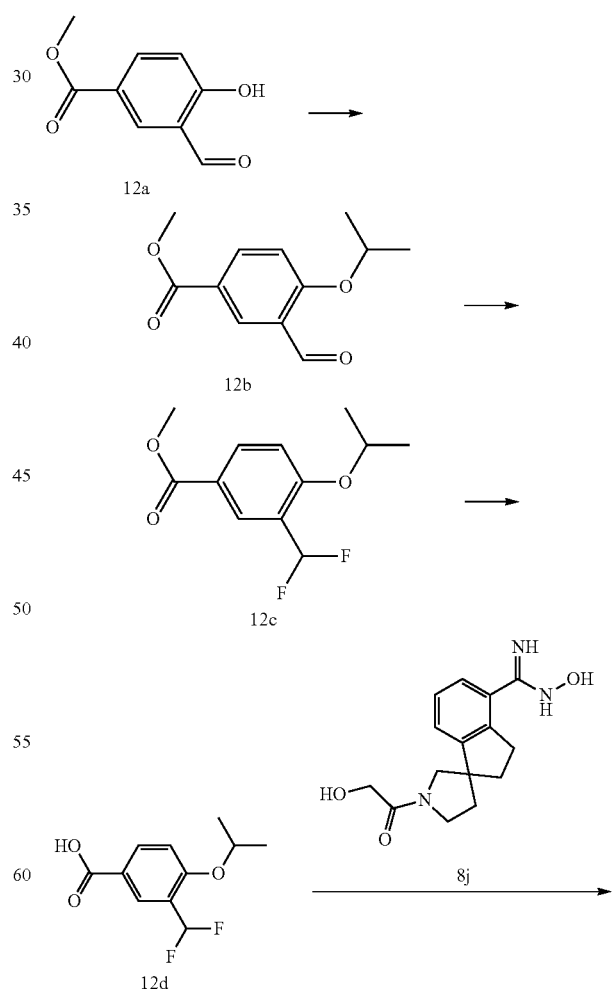

Compound 12

Step 1

Compound 12a (100 mg, 555 μmol) was dissolved in anhydrous N,N-dimethylformamide (1 mL), and anhydrous potassium carbonate (307 mg, 2.22 mmol) and 2-iodopropane (189 mg, 111 μmol) were added to the mixture. The reaction solution was stirred at 60° C. for 18 hours, and 10 mL of water was added to the reaction solution, and the mixture was extracted with ethyl acetate (20 mL×2). The organic phases were combined, and the organic phases were washed with 10 mL of water and 10 mL of saturated brine, dried over anhydrous sodium sulfate, and concentrated to obtain compound 12b.

MS-ESI calculated for [M+H-$^i$Pr]$^+$ 181, found 181.

$^1$H NMR (400 MHz, CDCl$_3$) δ=10.40 (s, 1H), 8.42 (d, J=2.3 Hz, 1H), 8.13 (dd, J=8.9, 2.3, Hz, 1H), 6.96 (d, J=8.9 Hz, 1H), 4.71 (p, J=6.1 Hz, 1H), 3.83 (s, 3H), 1.37 (d, J=6.1 Hz, 6H).

Step 2

Compound 12b (140 mg, 630 μmol) was dissolved in anhydrous dichloromethane (4 mL), and (diethylamino)sulfur trifluoride (609 mg, 3.78 mmol) was added dropwise to the mixture. The reaction solution was stirred at 25° C. for 15 hours, and 20 mL of water was added to the reaction solution, extracted with dichloromethane (10 mL×2). The organic phases were combined, and the organic phases were washed with 10 mL of water and 10 mL of saturated brine, dried over anhydrous sodium sulfate, concentrated, and the crude product was purified by thin-layer silica gel chromatography (petroleum ether:ethyl acetate=10:1) to obtain compound 12c.

MS-ESI calculated for [M+H]$^+$ 245, found 245.

$^1$H NMR (400 MHz, CDCl$_3$) δ=8.18 (d, J=2.0 Hz, 1H), 8.03 (dd, J=8.8, 2.0 Hz, 1H), 6.88 (d, J=8.8 Hz, 1H), 8.50 (t, J=55.4 Hz, 1H), 4.63 (p, J=6.1 Hz, 1H), 3.83 (s, 3H), 1.32 (d, J=6.1 Hz, 6H).

Step 3

Compound 12c (89.0 mg, 440 μmol) was dissolved in anhydrous tetrahydrofuran (3 mL) and anhydrous methanol (1.5 mL), and a solution of lithium hydroxide monohydrate (45.9 mg, 1.09 mmol) in water (0.75 mL) was added to the reaction solution. The reaction solution was stirred at 25° C. for 12 hours, and the organic solvent was removed under reduced pressure. The pH was adjusted to 1 by added 1 N aqueous hydrochloric acid solution, and the mixture was filtered under reduced pressure, and the filter cake was dried to obtain compound 12d.

MS-ESI calculated for [M+H]$^+$ 231, found 231.

Step 4

Compound 12d (47.7 mg, 207 μmol) was dissolved in N,N-dimethylformamide (2 mL), and 1-(3-dimethylaminopropyl)-3-ethylcarbodiimide hydrochloride (47.7 mg, 249 μmol) and 1-hydroxybenzotriazole (33.6 mg, 249 μmol) were added to the reaction solution, and the reaction solution was stirred at 25° C. for 15 minutes. Then compound 8j (60.0 mg, 207 μmol) was added thereto, and the reaction solution was stirred at 25° C. for 1 hour, then stirred at 80° C. for 12 hours. The reaction solution was concentrated under reduced pressure, diluted with water (50 mL), extracted with ethyl acetate (30 mL×3). The combined organic phases were washed with water (20 mL×2) and saturated brine (40 mL×1) respectively, dried over anhydrous sodium sulfate, filtered, and the filtrate was concentrated under reduced pressure. The crude product was purified by high performance liquid chromatography {hydrochloric acid condition, column type: Phenomenex luna C18 150*25 mm*10 μm; mobile phase: [water (0.05% HCl)-acetonitrile]; acetonitrile %: 50%-80%, 10 minutes} to obtain compound 12.

MS-ESI calculated for [M+H]$^+$ 484, found 484.

$^1$H NMR (400 MHz, CDCl$_3$) δ=8.44 (s, 1H), 8.31-8.24 (m, 1H), 8.17 8.08 (m, 1H), 7.46-7.37 (m, 1H), 7.33-7.28 (m, 1H), 7.14-6.84 (m, 2H), 4.83-4.69 (m, 1H), 4.24-4.17 (m, 1H), 4.16-4.05 (m, 1H), 3.99-3.50 (m, 3H), 3.46-3.37 (m, 3H), 2.38-2.07 (m, 4H), 1.49-1.39 (m, 6H).

Embodiment 13

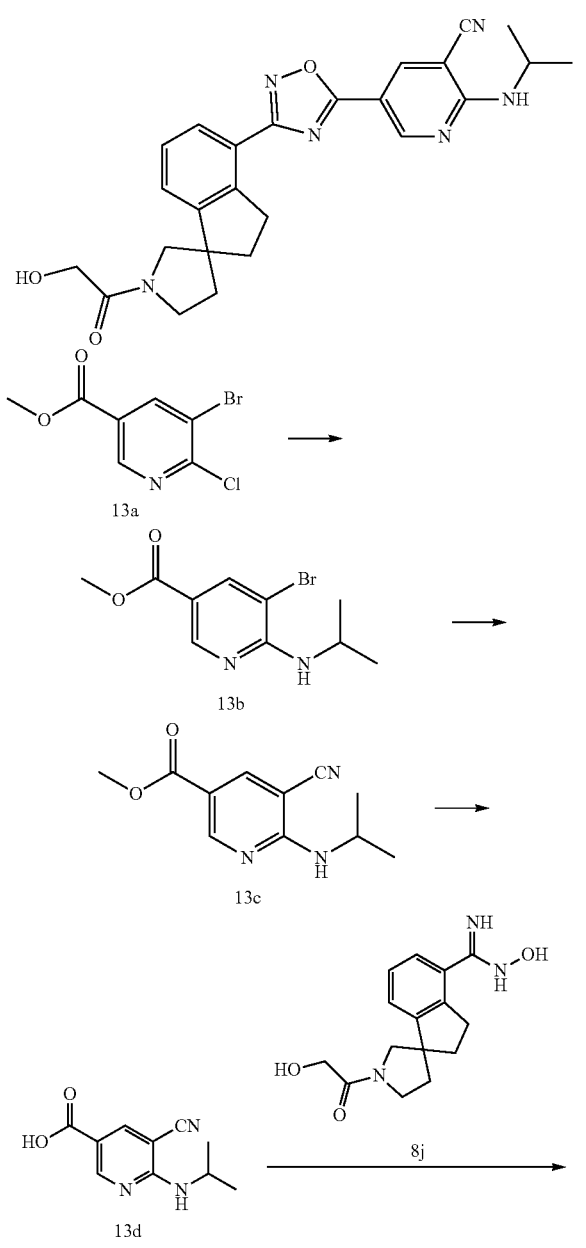

Compound 13

Step 1

Compound 13a (3.00 g, 12.0 mmol) was dissolved in isopropylamine (10 mL), and triethylamine (1.31 g, 12.9 mmol) was added to the mixture. The reaction solution was stirred at 90° C. for 12 hours, added with water (30 mL), and extracted with ethyl acetate (20 mL×2). The organic phases were combined, and the organic phases were washed with water (20 mL×1) and saturated brine (20 mL×1), dried over anhydrous sodium sulfate, concentrated, and the crude product was purified by silica gel column chromatography (10:1, petroleum ether/ethyl acetate, Rf=0.50) to obtain compound 13b.

MS-ESI calculated for [M+H]$^+$ 273 and 275, found 273 and 275.

NMR (400 MHz, CDCl$_3$) δ=8.62 (d, J=1.9 Hz, 1H), 8.09 (d, J=1.9 Hz, 1H), 4.35-4.19 (m, 1H), 3.79 (s, 3H), 1.20 (d, J=6.5 Hz, 6H).

Step 2

Compound 13b (1.53 g, 5.60 mmol) was dissolved in anhydrous N,N-dimethylformamide (20 mL), and zinc cyanide (1.32 g, 11.2 mmol), tris(dibenzylideneacetone)dipalladium (513 mg, 560 μmol) and 2-di-tert-butylphosphino-2',4',6'-triisopropylbiphenyl (534 mg, 1.12 mmol) were added to the mixture. Under nitrogen protection, the reaction solution was stirred at 90° C. for 12 hours. The reaction solution was concentrated and the residue was added with water (100 mL) and extracted with ethyl acetate (50 mL×2). The organic phases were combined, and the organic phases were washed with water (50 mL×1) and saturated brine (50 mL×1) respectively, dried over anhydrous sodium sulfate, and concentrated. The crude product was purified by silica gel column chromatography (10:1, petroleum ether/ethyl acetate, Rf=0.35) to obtain compound 13c.

MS-ESI calculated for [M+H]$^+$ 220, found 220.

$^1$H NMR (400 MHz, CDCl$_3$) δ=8.89 (d, J=2.3 Hz, 1H), 8.25 (d, J=2.3 Hz, 1H), 4.49-4.38 (m, 1H), 3.90 (s, 3H), 1.30 (d, J=6.6 Hz, 6H).

Step 3

Compound 13c (100 mg, 456 μmol) was dissolved in anhydrous tetrahydrofuran (4 mL) and anhydrous methanol (2 mL), and a solution of lithium hydroxide monohydrate (55.4 mg, 1.32 mmol) in water (2 mL) was added to the reaction solution. The reaction solution was stirred at 25° C. for 12 hours, concentrated under reduced pressure to remove the organic solvent. The residue was diluted with water (10 mL), adjusted to pH=1 with 1 N hydrochloric acid, filtered, and the filter cake was dried to obtain compound 13d.

MS-ESI calculated for [M+H]$^+$ 206, found 206.

Step 4

Compound 13d (35.5 mg, 173 μmol) was dissolved in N,N-dimethylformamide (2 mL), and 1-(3-dimethylaminopropyl)-3-ethylcarbodiimide hydrochloride (39.8 mg, 207 μmol) and 1-hydroxybenzotriazole (28.0 mg, 207 μmol) were added to the reaction solution, and the reaction solution was stirred at 25° C. for 15 minutes. Then compound 8j (50.0 mg, 173 μmol) was added thereto, and the reaction solution was stirred at 25° C. for 1 hour, then stirred at 80° C. for 12 hours. The reaction solution was diluted with water (50 mL), extracted with ethyl acetate (20 mL×3). The combined organic phases were dried over anhydrous sodium sulfate respectively, filtered, and the filtrate was concentrated under reduced pressure. The crude product was purified by high performance liquid chromatography {hydrochloric acid condition, column type: 3_Phenomenex luna C18 75*30 mm*3 μm; mobile phase: [water (0.05% HCl)-acetonitrile]; acetonitrile %: 50%-70%, 7 minutes} to obtain compound 13.

MS-ESI calculated for [M+H]$^+$ 459, found 459.

$^1$H NMR (400 MHz, CDCl$_3$) δ=9.10 (d, J=2.3 Hz, 1H), 8.42 (d, J=2.3 Hz, 1H), 8.14-8.04 (m, 1H), 7.45-7.38 (m, 1H), 7.34-7.28 (m, 1H), 5.54-5.39 (m, 1H), 4.54-4.04 (m, 2H), 3.97-3.34 (m, 6H), 2.33-1.99 (m, 4H), 1.39-1.31 (m, 6H).

Embodiment 14

Compound 14

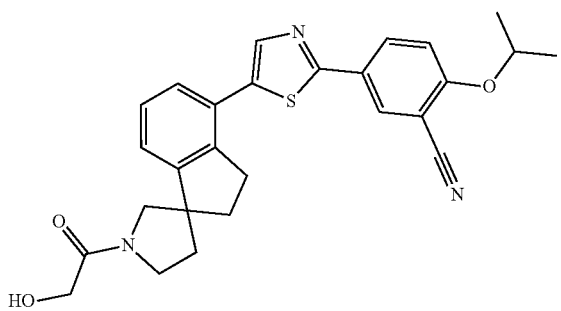

Synthetic route:

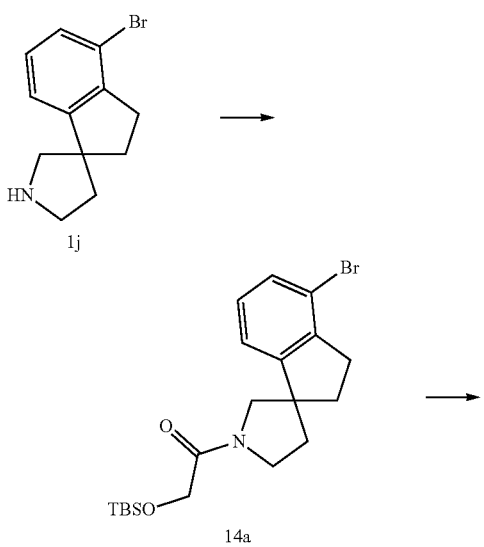

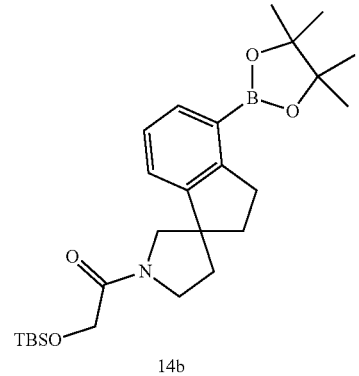

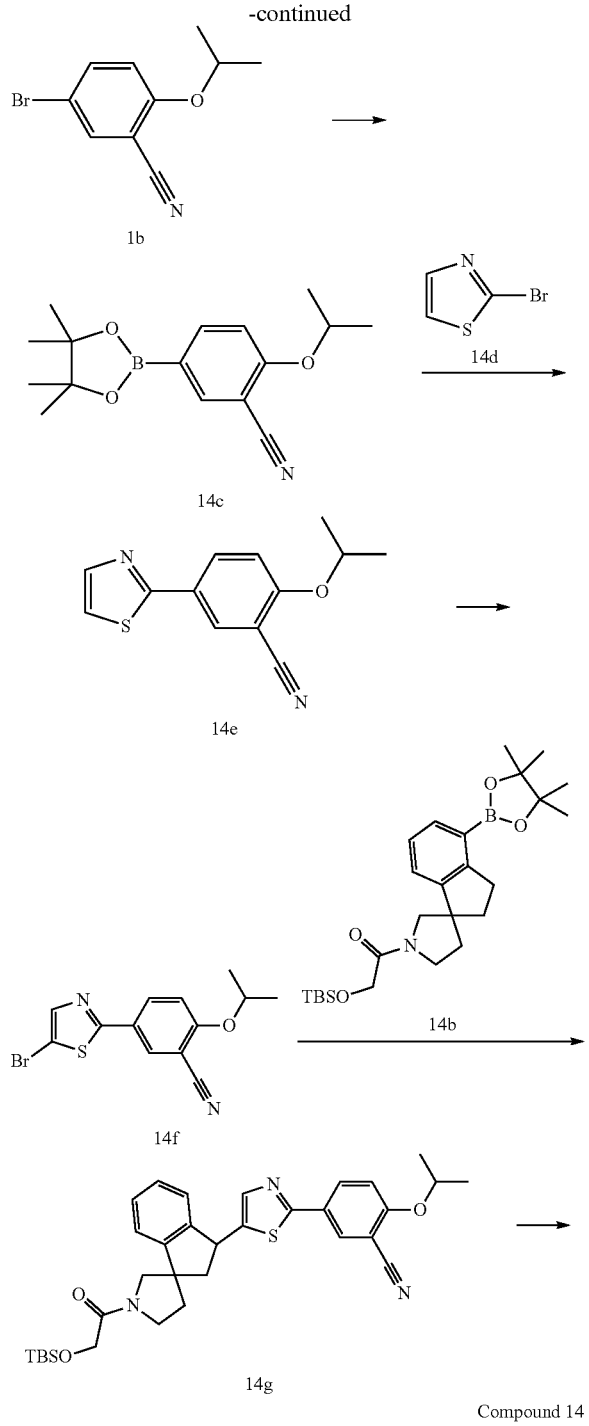

sodium sulfate, and concentrated under reduced pressure. The crude product was purified by silica gel column chromatography (10:1, petroleum ether/ethyl acetate, Rf=0.5) to obtain compound 14a.

MS-ESI calculated for [M+H]$^+$ 424 and 426, found 424 and 426.

Step 2

Compound 14a (1.50 g, 3.53 mmol) and bis(pinacolato) diboron (987 mg, 3.89 mmol) were dissolved in 1,4-dioxane (20 mL), and then 1,1-bis(diphenylphosphino)ferrocene dichloropalladium (259 mg, 353 μmol) and potassium acetate (1.04 g, 10.6 mmol) were added thereto. The reaction solution was stirred at 80° C. for 15 hours under nitrogen protection. The reaction solution was concentrated under reduced pressure, diluted with water (200 mL), and extracted with ethyl acetate (100 mL×3). The combined organic phases were washed with saturated brine (200 mL×1), dried over anhydrous sodium sulfate, and filtered. The filtrate was concentrated under reduced pressure, and the crude product was purified by silica gel column chromatography (5:1, petroleum ether/ethyl acetate, Rf=0.70) to obtain compound 14b.

MS-ESI calculated for [M+H]$^+$ 472, found 472.

Step 3

Compound 1b (10.0 g, 41.7 mmol), bis(pinacolato)diboron (12.7 g, 50.0 mmol) and potassium acetate (8.18 g, 83.3 mmol) were dissolved in anhydrous N,N-dimethylformamide (100 mL). Under nitrogen protection, 1,1-bis(diphenylphosphino)ferrocene dichloropalladium (1.83 g, 2.50 mmol) was added to the reaction solution, and the reaction solution was stirred at 120° C. for 3 hours. The reaction solution was concentrated under reduced pressure, and the residue was diluted with water (500 mL), extracted with ethyl acetate (300 mL×2). The combined organic phases were washed with saturated brine (300 mL×2), dried over anhydrous sodium sulfate, and filtered. The filtrate was concentrated under reduced pressure, and the obtained crude product was purified by silica gel column chromatography (5:1, petroleum ether/ethyl acetate, Rf=0.49) to obtain compound 14c.

MS-ESI calculated for [M+H]$^+$ 288, found 288.

Step 4

Compound 14c (1.00 g, 3.48 mmol), compound 14d (685 mg, 4.18 mmol) and sodium carbonate (738 mg, 6.96 mmol) were dissolved in ethylene glycol dimethyl ether (10 mL) and water (10 mL). Under nitrogen protection, 1,1-bis (diphenylphosphino)ferrocene dichloropalladium (255 mg, 348 μmol) was added to the reaction solution, and the reaction solution was stirred at 100° C. for 12 hours. The reaction solution was diluted with water (100 mL), and extracted with ethyl acetate (50 mL×2). The combined organic phases were washed with saturated brine (50 mL×2), dried over anhydrous sodium sulfate, and filtered. The filtrate was concentrated under reduced pressure, and the obtained crude product was purified by silica gel column chromatography (5:1, petroleum ether/ethyl acetate, Rf=0.53) to obtain compound 14e.

MS-ESI calculated for [M+H]$^+$ 245, found 245.

Step 5

Compound 14e (480 mg, 1.96 mmol) was dissolved in anhydrous N,N-dimethylformamide (5 mL), and N-bromo- Step 1

Compound 1j (3.00 g, 9.67 mmol) and imidazole (856 mg, 12.6 mmol) were dissolved in dichloromethane (100 mL). A solution of tert-butyldimethylsilyl chloride (856 mg, 12.6 mmol) in dichloromethane (20 mL) was added to the above reaction solution at 0° C. The reaction solution was stirred at 25° C. for 3 hours under nitrogen protection. The mixture was diluted with dichloromethane (200 mL), washed with water (100 mL×3), dried over anhydrous succinimide (699 mg, 3.93 mmol) was added to the reaction solution at 0° C., and the reaction solution was stirred at 20° C. for 3 hours. The reaction solution was diluted with water (30 mL), and extracted with ethyl acetate (30 mL×2). The combined organic phases were washed with saturated brine (30 mL×2), dried over anhydrous sodium sulfate, and filtered. The filtrate was concentrated under reduced pressure, and the obtained crude product was purified by silica gel column chromatography (5:1, petroleum ether/ethyl acetate, Rf=0.64) to obtain compound 14f.

MS-ESI calculated for [M+H]$^+$ 323 and 325, found 323 and 325.

Step 6

Compound 14f (50.0 mg, 155 μmol), compound 14b (72.9 mg, 155 μmol) and potassium phosphate (65.7 mg, 309 μmol) were dissolved in anhydrous dioxane (1.5 mL) and water (0.5 mL). Under nitrogen protection, 1,1-bis(diphenylphosphino)ferrocene dichloropalladium (11.3 mg, 15.5 μmol) was added to the reaction solution, and the reaction solution was stirred at 80° C. for 12 hours. The reaction solution was concentrated under reduced pressure, and the residue was diluted with water (15 mL), and extracted with ethyl acetate (15 mL×2). The combined organic phases were washed with saturated brine (20 mL×2), dried over anhydrous sodium sulfate, filtered, and the filtrate was concentrated under reduced pressure to obtain the crude product of compound 14g.

MS-ESI calculated for [M+H]$^+$ 588, found 588.

Step 7

Compound 14g (69.0 mg, 117 μmol) was dissolved in ethyl acetate (1 mL), and hydrochloric acid/ethyl acetate (4 M, 1 mL) was added to the mixture, and the reaction solution was stirred at 20° C. for 1 hour. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 52%-72%, 7 minutes} to obtain compound 14.

MS-ESI calculated for [M+H]$^+$ 474, found 474.

$^1$H NMR (400 MHz, CDCl$_3$) δ=8.26-8.09 (m, 2H), 8.05-7.85 (m, 1H), 7.54-7.40 (m, 1H), 7.39-7.29 (m, 1H), 7.25-6.98 (m, 2H), 4.82-4.69 (m, 1H), 4.30-4.07 (m, 2H), 3.93-3.08 (m, 6H), 2.26-2.07 (m, 4H), 1.56-1.37 (m, 6H).

Embodiment 15

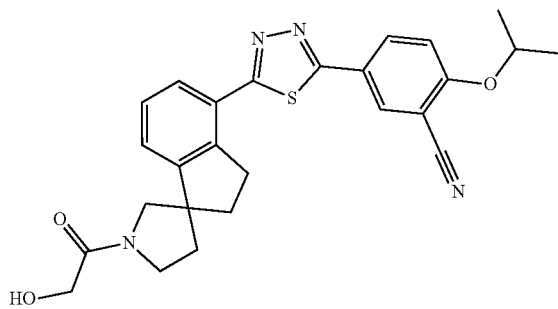

Compound 15

Synthetic route:

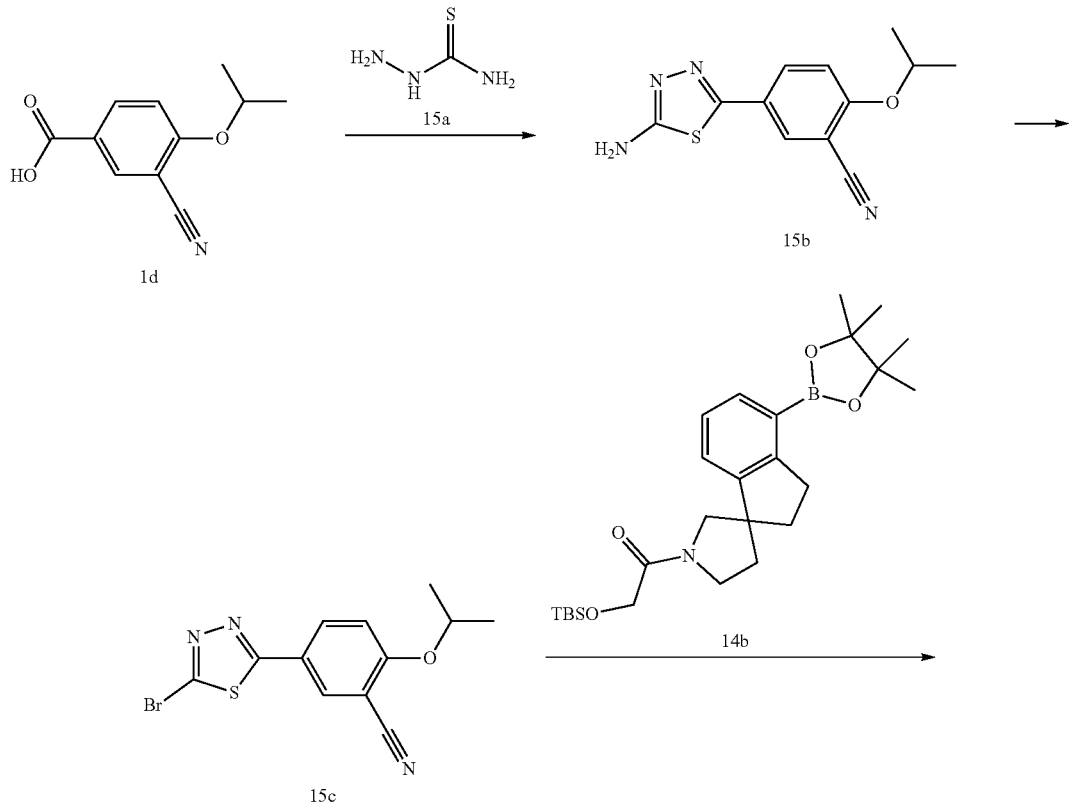

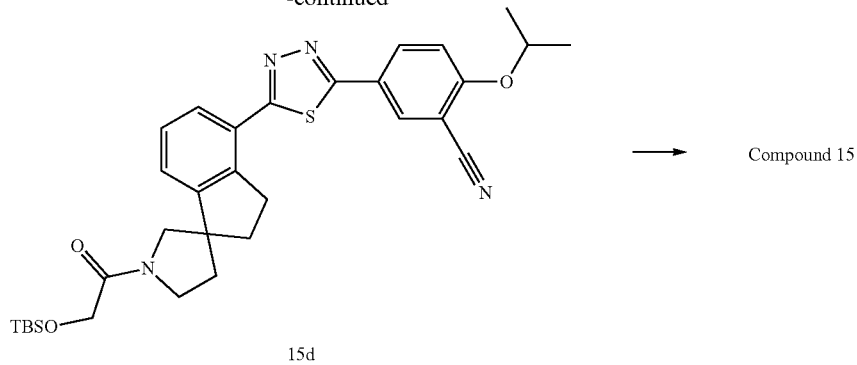

15d

→ Compound 15

Step 1

Compound 1d (1.00 g, 4.87 mmol) and compound 15a (666 mg, 7.31 mmol) were slowly dissolved in phosphorus oxychloride (5 mL), and the reaction solution was stirred at 90° C. for 3 hours. The reaction solution was slowly quenched with 5 M NaOH aqueous solution, and adjusted to pH=10. The reaction solution was stirred at 25° C. for 30 minutes, and the reaction solution became turbid, and was filtered. The filter cake was dissolved with dichloromethane (100 mL) and methanol (10 mL), and the organic phase was washed with water (100 mL×2), dried over anhydrous sodium sulfate, filtered, and the filtrate was concentrated under reduced pressure to obtain the crude product of compound 15b.

MS-ESI calculated for $[M+H]^+$ 261, found 261.

Step 2

Copper bromide (601 mg, 2.69 mmol) and tert-butyl nitrite (277 mg, 2.69 mmol) were dissolved in acetonitrile (10 mL), and the reaction solution was stirred at 25° C. for 30 minutes. Compound 15b (350 mg, 1.34 mmol) was slowly added to the reaction solution, and the reaction solution was stirred at 25° C. for 1 hour and stirred at 70° C. for 2 hours. The reaction solution was filtered, and the filter cake was washed with ethyl acetate (20 mL). The filtrate was washed with 1 M hydrochloric acid aqueous solution (30 mL), and concentrated under reduced pressure. The residue was diluted with water (20 mL), extracted with dichloromethane (30 mL×2), and the combined organic phases were washed with water (30 mL×2), dried over anhydrous sodium sulfate, and filtered. The filtrate was concentrated under reduced pressure, and the obtained crude product was purified by silica gel column chromatography (3:1, petroleum ether/ethyl acetate, Rf=0.53) to obtain compound 15c.

MS-ESI calculated for $[M+H]^+$ 324 and 326, found 324 and 326.

Step 3

Compound 15c (50.0 mg, 154 µmol), compound 14b (72.7 mg, 154 µmol) and potassium phosphate (65.5 mg, 308 µmol) were dissolved in anhydrous dioxane (1.5 mL) and water (0.5 mL). Under nitrogen protection, 1,1-bis(diphenylphosphino)ferrocene dichloropalladium (11.3 mg, 15.4 µmol) was added to the reaction solution, and the reaction solution was stirred at 80° C. for 12 hours. The reaction solution was concentrated under reduced pressure, and the crude product was diluted with water (15 mL), and the mixture was extracted with ethyl acetate (15 mL×2). The combined organic phases were washed with saturated brine (20 mL×2), dried over anhydrous sodium sulfate, filtered, and the filtrate was concentrated under reduced pressure to obtain the crude product of compound 15d.

MS-ESI calculated for $[M+H]^+$ 589, found 589.

Step 4

Compound 15d (86.0 mg, 146 µmol) was dissolved in ethyl acetate (1 mL), and hydrochloric acid/ethyl acetate (4 M, 1 mL) was added to the mixture, and the reaction solution was stirred at 20° C. for 1 hour. The reaction solution was concentrated under reduced pressure, and the crude product was purified by high performance liquid chromatography {hydrochloric acid condition, column type: 3_Phenomenex Luna C18 75*30 mm*3 µm; mobile phase: [water (0.05% HCl)-acetonitrile]; acetonitrile %: 45%-65%, 8 minutes} to obtain compound 15.

MS-ESI calculated for $[M+H]^+$ 475, found 475.

$^1$H NMR (400 MHz, CDCl$_3$) δ=8.24 (d, J=8.0 Hz, 1H), 8.17 (s, 1H), 7.81 (d, J=7.2 Hz, 1H), 7.42-7.36 (m, 1H), 7.33-7.28 (m, 1H), 7.11 (d, J=8.4 Hz, 1H), 4.82-4.73 (m, 1H), 4.25-4.06 (m, 2H), 3.96-3.38 (m, 6H), 2.25-2.06 (m, 4H), 1.49-1.45 (m, 6H).

Embodiment 16

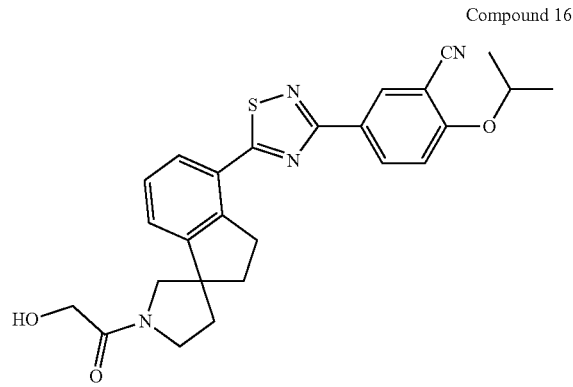 [SMILES: CC(C)Oc1ccc(-c2nsc(-c3cccc4c3CCC43CCN(C(=O)CO)C3)n2)cc1C#N]

Compound 16

Synthetic route:

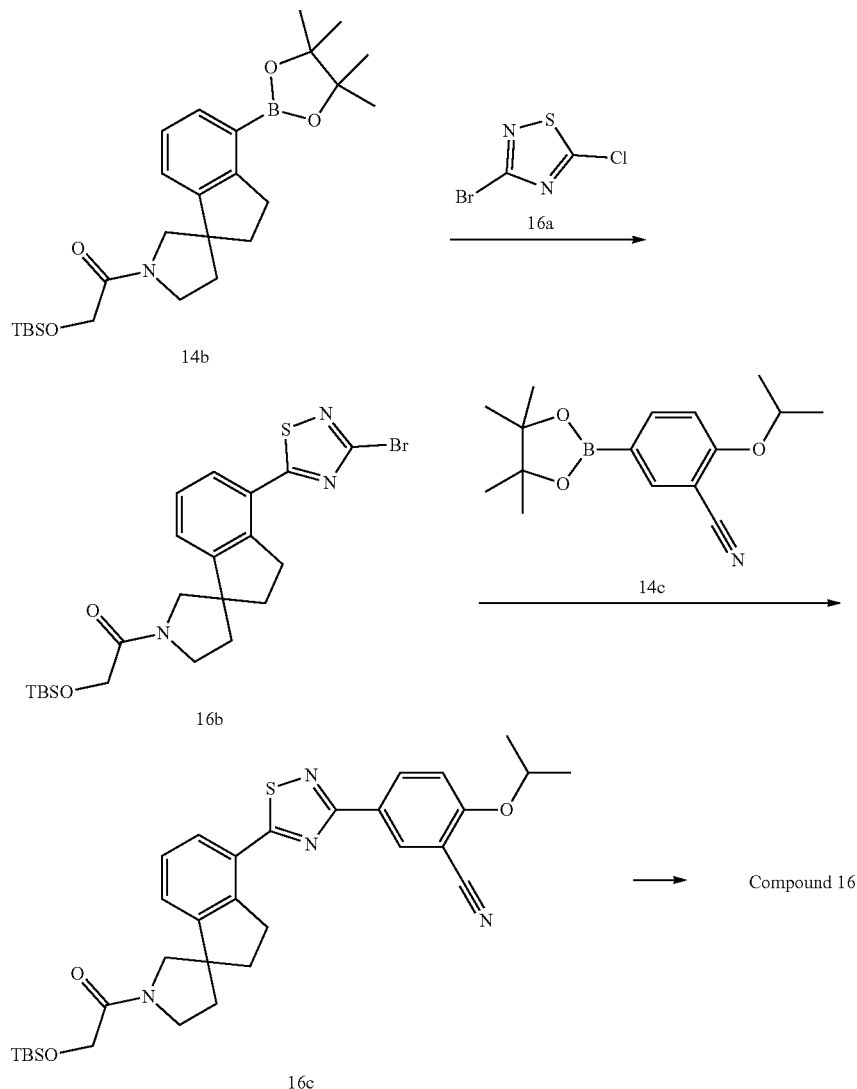

Step 1

Compound 14b (150 mg, 318 μmol) and compound 16a (63.5 mg, 318 μmol) were dissolved in 1,4-dioxane (3 mL), and then 1,1-bis(diphenylphosphino)ferrocene dichloropalladium (23.3 mg, 31.8 μmol), potassium phosphate (135 mg, 636 μmol) and water (0.6 mL) were added thereto. The reaction solution was stirred at 100° C. for 12 hours under nitrogen protection. The reaction solution was concentrated under reduced pressure, diluted with water (80 mL), and extracted with ethyl acetate (50 mL×3). The combined organic phases were dried over anhydrous sodium sulfate, and filtered. The filtrate was concentrated under reduced pressure, and the crude product was purified by thin-layer silica gel column chromatography (1:1, petroleum ether/ethyl acetate, Rf=0.50) to obtain compound 16b.

MS-ESI calculated for [M+H]$^+$ 508 and 510, found 508 and 510.

Step 2

Compound 16b (96.0 mg, 189 μmol) and compound 14c (65.1 mg, 227 μmol) were dissolved in 1,4-dioxane (1 mL), and then 1,1-bis(diphenylphosphino)ferrocene dichloropalladium (13.8 mg, 18.9 μmol), potassium phosphate (160 mg, 755 μmol) and water (0.2 mL) were added thereto. The reaction solution was stirred at 80° C. for 12 hours under nitrogen protection. The reaction solution was concentrated under reduced pressure, diluted with water (80 mL), extracted with ethyl acetate (40 mL×4). The combined organic phases were dried over anhydrous sodium sulfate, filtered, and the filtrate was concentrated under reduced pressure to obtain the crude product of compound 16c.

MS-ESI calculated for [M+H]$^+$ 589, found 589.

Step 3

Compound 16c (123 mg, 209 μmol) was dissolved in hydrochloric acid/methanol (4 M, 3 mL), and the reaction solution was stirred at 25° C. for 1 hour. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 60%-80%, 7 minutes} to obtain compound 16.

MS-ESI calculated for [M+H]⁺ 475, found 475.

¹H NMR (400 MHz, CDCl₃) δ=8.62 (d, J=2.1 Hz, 1H), 8.53 (dd, J=8.8, 2.1 Hz, 1H), 8.05 (d, J=7.6 Hz, 1H), 7.44 (t, J=7.6 Hz, 1H), 7.34 (d, J=8.0 Hz, 1H), 7.09 (d, J=9.0 Hz, 1H), 4.84-4.71 (m, 1H), 4.25-4.05 (m, 2H), 3.98-3.50 (m, 3H), 3.49-3.33 (m, 3H), 2.39-2.05 (m, 4H), 1.47 (d, J=6.0 Hz, 6H).

Embodiment 17

Compound 17

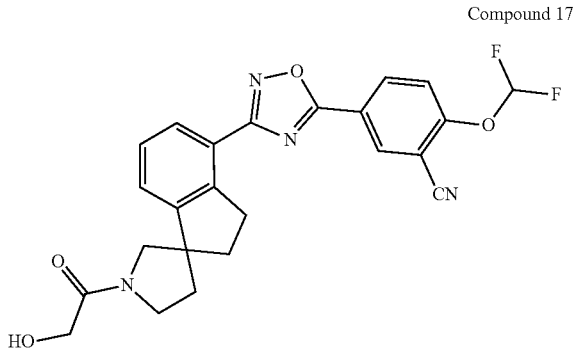 [SMILES: N#Cc1cc(-c2nc(-c3cccc4c3CCC43CCN(C(=O)CO)C3)no2)ccc1OC(F)F]

Synthetic route:

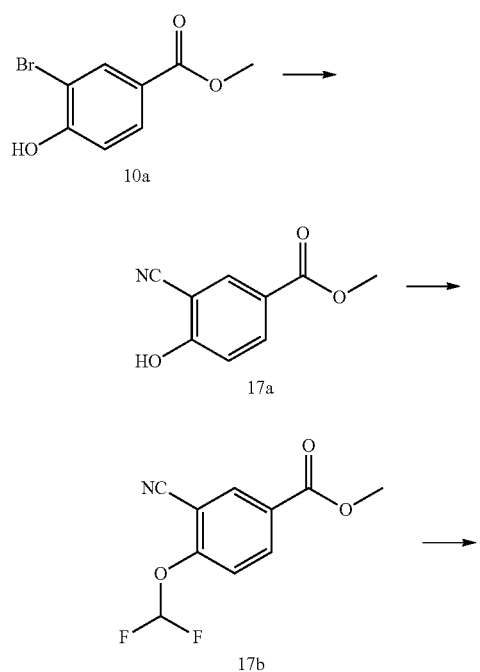

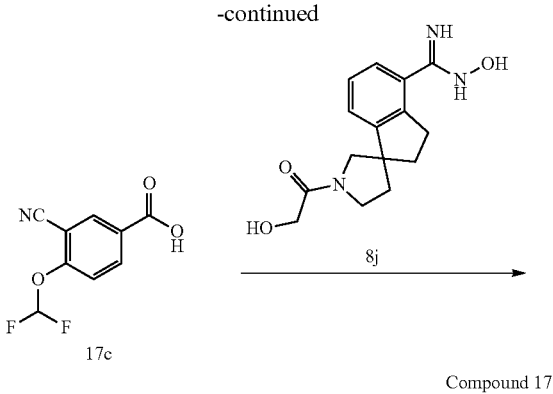

Compound 17

Step 1

Compound 10a (1.00 g, 4.33 mmol) was dissolved in anhydrous N,N-dimethylformamide (15 mL), and zinc cyanide (1.02 g, 8.66 mmol), tris(dibenzylideneacetone)dipalladium (396 mg, 433 μmol) and 2-di-tert-butylphosphino-2',4',6'-triisopropylbiphenyl (412 mg, 866 μmol) were added to the mixture. Under nitrogen protection, the reaction solution was stirred at 90° C. for 12 hours, and the reaction solution was concentrated to remove the N,N-dimethylformamide solvent. The crude product was purified by silica gel column chromatography (2:1, petroleum ether/ethyl acetate, Rf=0.24) to obtain compound 17a.

¹H NMR (400 MHz, CDCl₃) δ=8.16 (d, J=2.0 Hz, 1H), 8.08 (dd, J=2.0, 8.7 Hz, 1H), 6.97 (d, J=8.7 Hz, 1H), 3.85 (s, 3H).

Step 2

Compound 17a (523 mg, 2.80 mmol) was dissolved in N,N-dimethylformamide (15 mL) and water (1.5 mL), and potassium carbonate (969 mg, 7.01 mmol) and sodium chlorodifluoroacetate (2.21 g, 11.2 mmol) were added to the mixture. The reaction solution was stirred at 100° C. for 2 hours, and the reaction solution was cooled to 25° C. 1.6 mL of concentrated hydrochloric acid and 3.2 mL of water were added to the mixture. The reaction solution was stirred at 25° C. for 12 hours, added with 30 mL of water, and extracted with ethyl acetate (20 mL×2). The organic phases were combined, and the organic phases were washed with 20 mL of water and 20 mL of saturated brine, dried over anhydrous sodium sulfate, and concentrated to obtain the compound 17b.

Step 3

Compound 17b (100 mg, 440 μmol) was dissolved in anhydrous tetrahydrofuran (4 mL) and anhydrous methanol (2 mL), and a solution of lithium hydroxide monohydrate (55.4 mg, 1.32 mmol) in water (2 mL) was added to the mixture. The reaction solution was stirred at 25° C. for 12 hours, and the organic solvent was removed under reduced pressure. The pH was adjusted to 1 by adding 1 N aqueous hydrochloric acid solution. The mixture became turbid, and was filtered under reduced pressure, and the filter residue was dried under vacuum to obtain compound 17c.

$^1$H NMR (400 MHz, CDCl$_3$) δ=8.35 (d, J=2.1 Hz, 1H), 8.26 (dd, J=2.1, 8.7 Hz, 1H), 7.38 (d, J=8.8 Hz, 1H), 6.76 (t, J=70.4 Hz, 1H).

Step 4

Compound 17c (44.2 mg, 207 μmol) was dissolved in N,N-dimethylformamide (2 mL), and 1-(3-dimethylaminopropyl)-3-ethylcarbodiimide hydrochloride (47.7 mg, 249 μmol) and 1-hydroxybenzotriazole (33.6 mg, 249 μmol) were added to the reaction solution, and the reaction solution was stirred at 25° C. for 15 minutes. Then compound 8j (60.0 mg, 207 μmol) was added thereto, and the reaction solution was stirred at 25° C. for 1 hour, then stirred at 80° C. for 12 hours. The reaction solution was diluted with water (50 mL), extracted with ethyl acetate (30 mL×3). The combined organic phases were dried over anhydrous sodium sulfate respectively, filtered, and the filtrate was concentrated under reduced pressure. The crude product was purified by high performance liquid chromatography (hydrochloric acid condition, column type: Phenomenex luna C18 150*25 mm*10 μm; mobile phase: [water (0.05% HCl)-acetonitrile]; acetonitrile %: 44%-74%, 10 minutes} to obtain compound 17.

MS-ESI calculated for [M+H]$^+$ 467, found 467.

$^1$H NMR (400 MHz, CDCl$_3$) δ=8.60-8.54 (m, 1H), 8.48-8.43 (m, 1H), 8.15-8.07 (m, 1H), 7.56 (d, J=8.8 Hz, 1H), 7.43 (t, J=7.6 Hz, 1H), 7.33 (d, J=7.6 Hz, 1H), 6.78 (t, J=70.8 Hz, 1H), 4.33-4.08 (m, 2H), 3.99-3.51 (m, 4H), 3.48-3.39 (m, 3H), 2.31-2.04 (m, 4H).

Embodiment 18

Compound 18

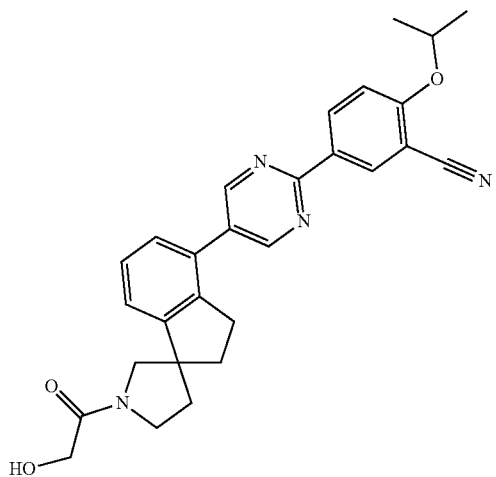

Synthetic route:

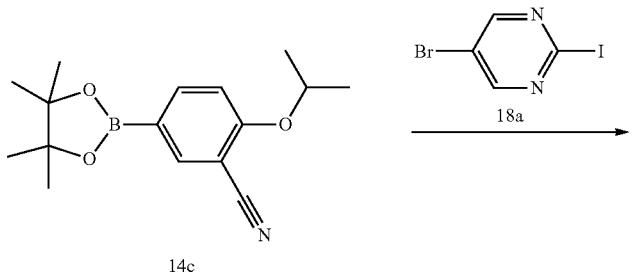

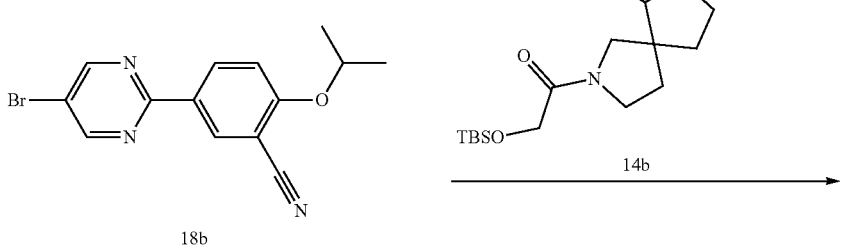

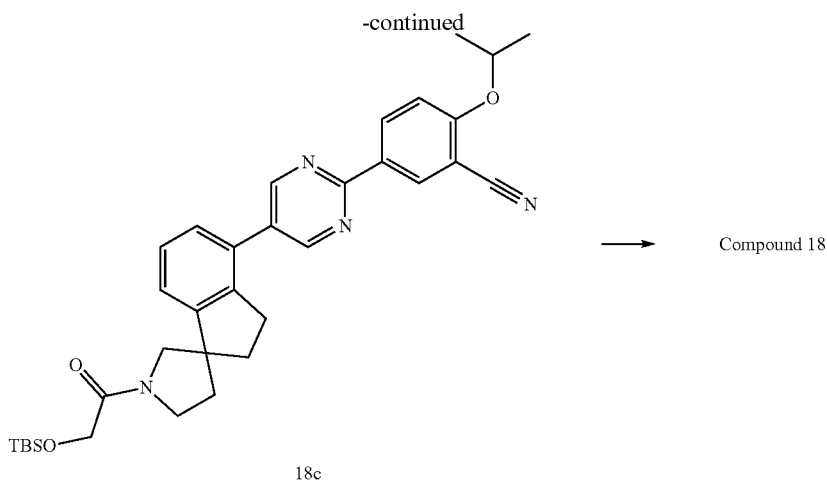

18c

Step 1

Compound 14c (200 mg, 696 μmol), compound 18a (198 mg, 696 μmol) and potassium phosphate (296 mg, 1.39 mmol) were dissolved in anhydrous dioxane (4 mL) and water (1 mL). Under nitrogen protection, 1,1-bis(diphenylphosphino)ferrocene dichloropalladium (51.0 mg, 70 μmol) was added to the reaction solution, and the reaction solution was stirred at 80° C. for 12 hours. The reaction solution was concentrated under reduced pressure, and the crude product was diluted with water (30 mL), and the mixture was extracted with ethyl acetate (30 mL×2). The combined organic phases were washed with saturated brine (30 mL×1), dried over anhydrous sodium sulfate, and filtered. The filtrate was concentrated under reduced pressure, and the crude product was separated by thin-layer silica gel chromatography (5:1, petroleum ether/ethyl acetate, Rf=0.31) to obtain compound 18b.

MS-ESI calculated for [M+H]$^+$ 318 and 320, found 318 and 320.

Step 2

Compound 18b (50.0 mg, 157 μmol), compound 14b (74.1 mg, 157 μmol) and potassium phosphate (66.7 mg, 314 μmol) were dissolved in anhydrous dioxane (1.5 mL) and water (0.5 mL). Under nitrogen protection, 1,1-bis(diphenylphosphino)ferrocene dichloropalladium (11.5 mg, 15.7 μmol) was added to the reaction solution, and the reaction solution was stirred at 80° C. for 12 hours. The reaction solution was concentrated under reduced pressure, and the crude product was diluted with water (10 mL), and the mixture was extracted with ethyl acetate (10 mL×2). The combined organic phases were washed with saturated brine (10 mL×2), dried over anhydrous sodium sulfate, filtered, and the filtrate was concentrated under reduced pressure to obtain the crude product of compound 18c.

MS-ESI calculated for [M+H]$^+$ 583, found 583.

Step 3

Compound 18c (78.0 mg, 134 μmol) was dissolved in ethyl acetate (1 mL), and hydrochloric acid/ethyl acetate (4 M, 1 mL) was added to the mixture, and the reaction solution was stirred at 20° C. for 1 hour. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 51%-71%, 7 minutes} to obtain compound 18.

MS-ESI calculated for [M+H]$^+$ 469, found 469.

$^1$H NMR (400 MHz, CDCl$_3$) δ=8.88 (s, 2H), 8.76 (br s, 1H), 8.68 (d, J=8.9 Hz, 1H), 7.44-7.38 (m, 1H), 7.36-7.32 (m, 1H), 7.26-7.22 (m, 1H), 7.10 (d, J=8.9 Hz, 1H), 4.82-4.75 (m, 1H), 4.27-4.08 (m, 2H), 3.99-3.42 (m, 4H), 3.14-3.03 (m, 2H), 2.24-2.09 (m, 4H), 1.49-1.46 (m, 6H).

Embodiment 19

Compound 19

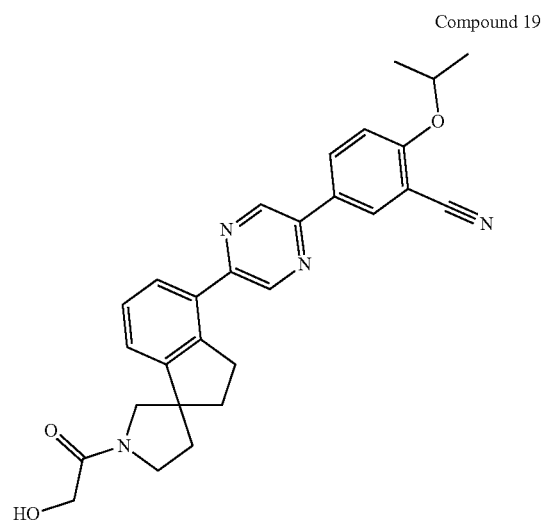 [SMILES: CC(C)Oc1ccc(-c2cnc(-c3cccc4c3CCC43CCN(C(=O)CO)C3)cn2)cc1C#N]

Synthetic route:

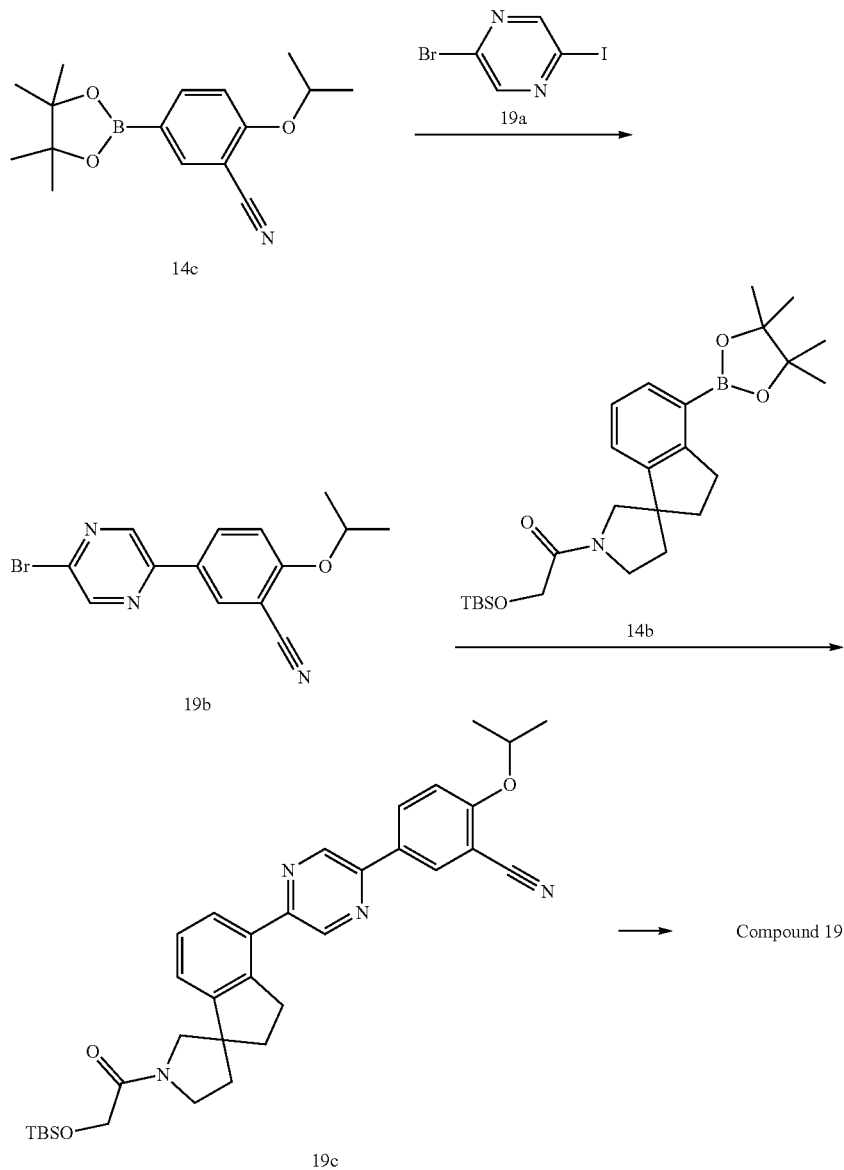

Step 1

Compound 14c (200 mg, 696 μmol), compound 19a (198 mg, 696 μmol) and potassium phosphate (296 mg, 1.39 mmol) were dissolved in anhydrous dioxane (4 mL) and water (1 mL). Under nitrogen protection, 1,1-bis(diphenylphosphino)ferrocene dichloropalladium (51.0 mg, 69.7 μmol) was added to the reaction solution, and the reaction solution was stirred at 60° C. for 12 hours. The reaction solution was concentrated under reduced pressure, and the crude product was diluted with water (30 mL), and the mixture was extracted with ethyl acetate (30 mL×2). The combined organic phases were washed with saturated brine (30 mL×1), dried over anhydrous sodium sulfate, and filtered. The filtrate was concentrated under reduced pressure, and the crude product was separated by thin-layer silica gel chromatography (5:1, petroleum ether/ethyl acetate, Rf=0.09) to obtain compound 19b.

MS-ESI calculated for [M+H]$^+$ 318 and 320, found 318 and 320.

Step 2

Compound 19b (61.0 mg, 192 μmol), compound 14b (90.4 mg, 192 μmol) and potassium phosphate (81.4 mg, 383 μmol) were dissolved in anhydrous dioxane (1.5 mL) and water (0.5 mL). Under nitrogen protection, 1,1-bis(diphenylphosphino)ferrocene dichloropalladium (14.0 mg, 19.2 μmol) was added to the reaction solution, and the reaction solution was stirred at 80° C. for 12 hours. The reaction solution was concentrated under reduced pressure, and the crude product was diluted with water (15 mL), and the mixture was extracted with ethyl acetate (10 mL×2). The combined organic phases were washed with saturated brine (10 mL×2), dried over anhydrous sodium sulfate, filtered, and the filtrate was concentrated under reduced pressure to obtain the crude product of compound 19c.

MS-ESI calculated for [M+H]$^+$ 583, found 583.

Step 3

Compound 19c (90.0 mg, 154 μmol) was dissolved in ethyl acetate (1 mL), and hydrochloric acid/ethyl acetate (4 M, 1 mL) was added to the mixture, and the reaction solution was stirred at 20° C. for 1 hour. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 51%-71%, 7 minutes} to obtain compound 19.

MS-ESI calculated for [M+H]$^+$ 469, found 469.

$^1$H NMR (400 MHz, CDCl$_3$) δ=9.13 (br s, 1H), 8.99 (br s, 1H), 8.39-8.30 (m, 2H), 7.70 (d, J=7.2 Hz, 1H), 7.45 (t, J=7.4 Hz, 1H), 7.31 (d, J=7.6 Hz, 1H), 7.16 (d, J=8.4 Hz, 1H), 4.83-4.75 (m, 1H), 4.23-4.10 (m, 2H), 3.97-3.18 (m, 6H), 2.36-2.04 (m, 4H), 1.51-1.45 (m, 6H).

Embodiment 20

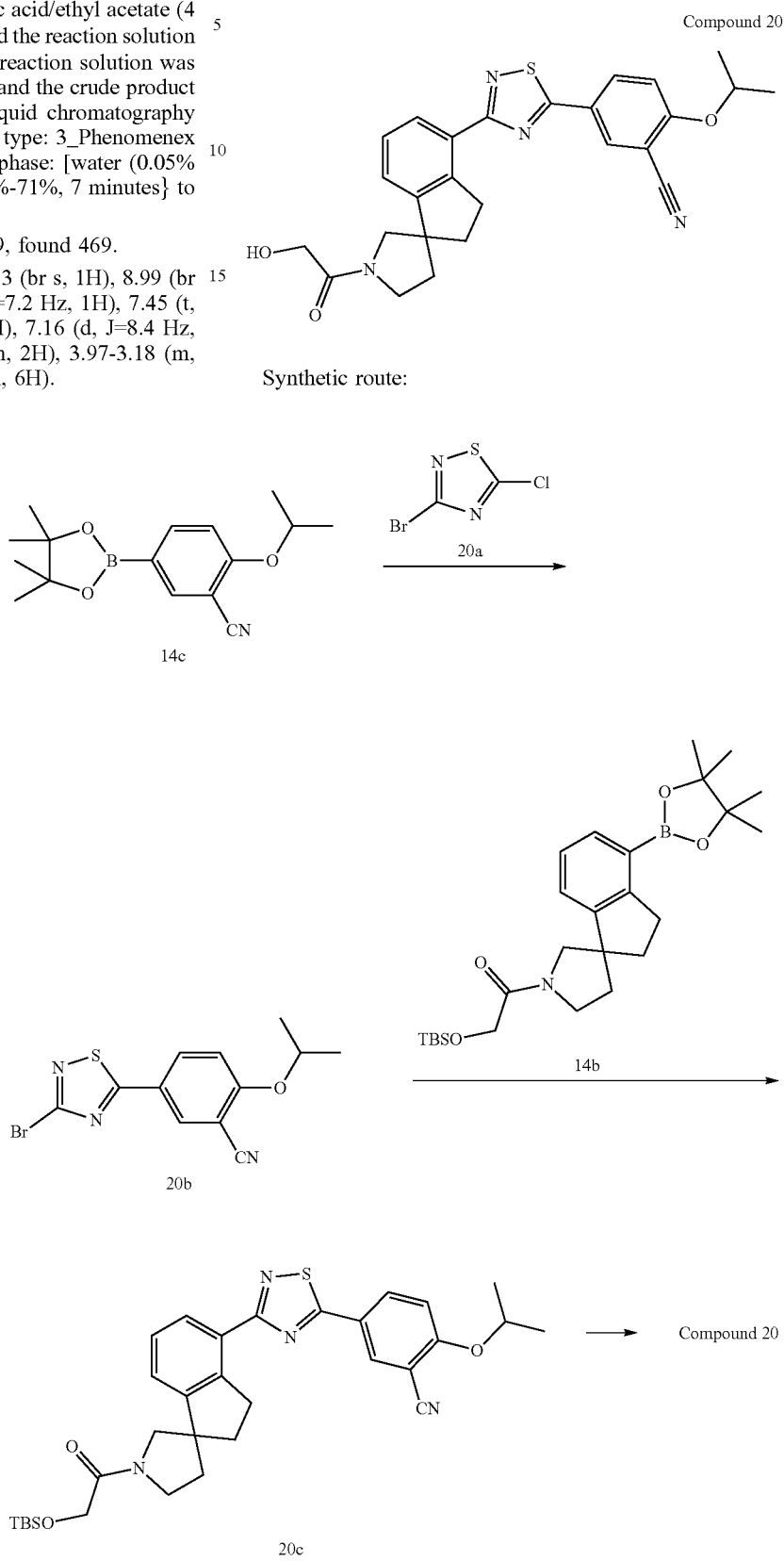

Synthetic route:

Step 1

Compound 14c (300 mg, 1.04 mmol), compound 20a (208 mg, 1.04 mmol) and potassium phosphate (554 mg, 2.61 mmol) were dissolved in ethylene glycol dimethyl ether (4 mL) and water (1 mL). Under nitrogen protection, tetrakis (triphenylphosphine)palladium (121 mg, 104 μmol) was added to the mixture. The reaction solution was stirred at 120° C. under microwave irradiation for 1 hour, added with 30 mL of water, and extracted with ethyl acetate (30 mL×2). The organic phases were combined, and the organic phases were washed with saturated brine (30 mL), dried over anhydrous sodium sulfate, concentrated, and the crude product was purified by silica gel column chromatography (5:1, petroleum ether/ethyl acetate, Rf=0.30) to obtain compound 20b.

MS-ESI calculated for [M+H]$^+$ 324 and 326, found 324 and 326.

Step 2

Compound 20b (50.0 mg, 154 μmol), compound 14b (72.7 mg, 154 μmol), potassium phosphate (65.5 mg, 308 μmol) and 1,1-bis(diphenylphosphino)ferrocene dichloropalladium (11.3 mg, 154 μmol) were dissolved in dioxane (1.5 mL) and water (0.5 mL). Under nitrogen protection, the reaction solution was stirred at 80° C. for 12 hours, and the reaction solution was concentrated. 20 mL of water was added to the residue, extracted with ethyl acetate (30 mL×2). The organic phases were combined, and the organic phases were washed with saturated brine (30 mL), and concentrated to obtain compound 20c.

MS-ESI calculated for [M+H]$^+$ 589, found 589.

Step 3

Compound 20c (83.0 mg, 141 μmol) was dissolved in ethyl acetate (2 mL), and hydrochloric acid/ethyl acetate (4 M, 353 μL) was added to the mixture, and the reaction solution was stirred at 25° C. for 2 hours. The reaction solution was diluted with water (10 mL), extracted with ethyl acetate (10 mL×2), and the combined organic phases were washed with water (10 mL) and saturated brine (10 mL) successively. The crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 58%-78%, 7 minutes} to obtain compound 20.

MS-ESI calculated for [M+H]$^+$ 475, found 475.

$^1$H NMR (400 MHz, DMSO-d$_6$) δ=8.52 (d, J=2.2 Hz, 1H), 8.38 (dd, J=8.8, 2.2 Hz, 1H), 8.20 (d, J=7.2 Hz, 1H), 7.54-7.41 (m, 3H), 5.02-4.91 (m, 1H), 4.61-4.52 (m, 1H), 4.12-3.94 (m, 2H), 3.73-3.38 (m, 6H), 2.19-1.97 (m, 4H), 1.42-1.37 (m, 6H).

Embodiment 21

Compound 21

Synthetic route:

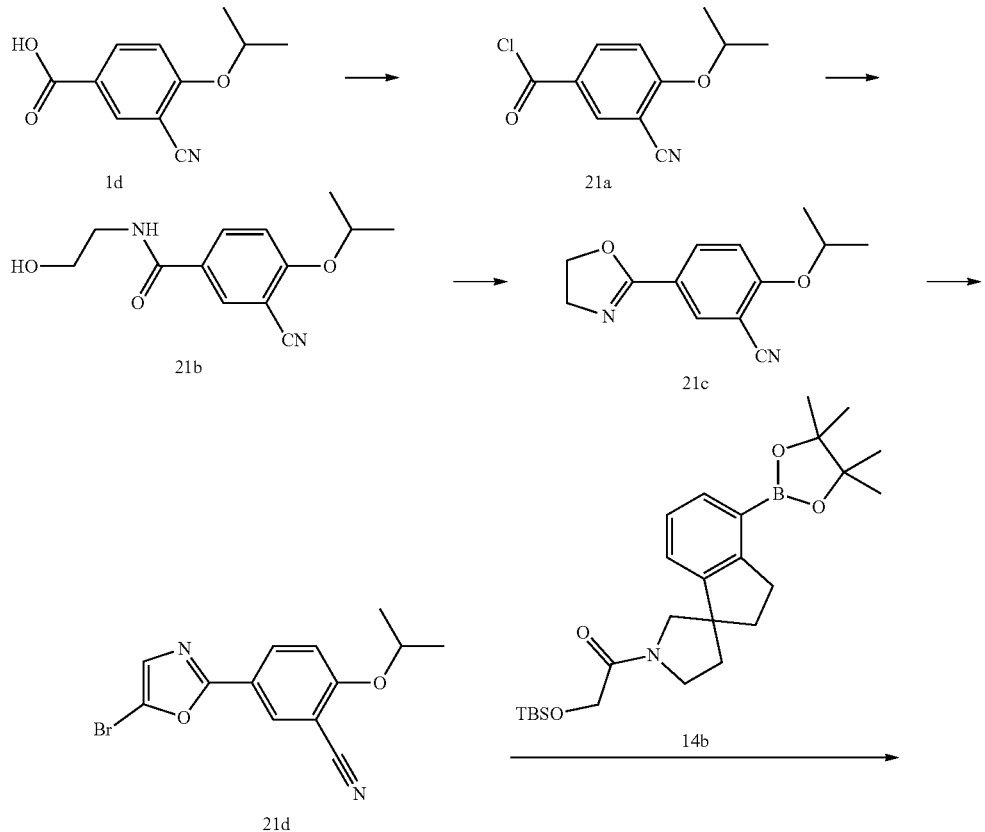

-continued

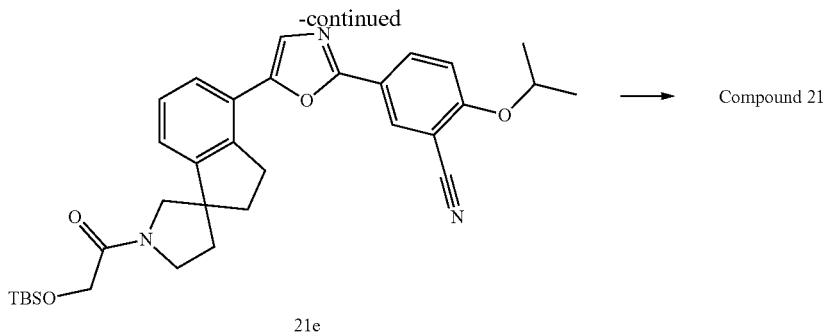

21e

→ Compound 21

Step 1

Compound 1d (100 g, 487 mmol) was dissolved in dichloromethane (500 mL), then thionyl chloride (116 g, 975 mmol, 70.7 mL) was slowly added, and then N,N-dimethylformamide (35.6 mg, 487 μmol) was added. The reaction solution was stirred at 25° C. for 16 hours. The reaction solution was concentrated under reduced pressure, and the crude product was added to a mixed solution of n-heptane/ethyl acetate (1:10, 220 mL), and the mixture was stirred at 25° C. for 3 hours. The mixture was filtered, and the filter cake was washed with n-heptane (50 mL×2) and dried under reduced pressure to obtain compound 21a.

Step 2

Compound 21a (2.00 g, 8.94 mmol), triethylamine (2.71 g, 26.8 mmol) and 2-aminoethanol (1.09 g, 17.88 mmol) were dissolved in dichloromethane (30 mL), and the reaction system was replaced with nitrogen for three times, and then the reaction solution was stirred at 25° C. for 12 hours under nitrogen protection. The reaction solution was concentrated under reduced pressure, and the residue was diluted with water (200 mL), extracted with ethyl acetate (200 mL×2). The combined organic phases were washed with 1 N aqueous hydrochloric acid solution (50 mL×2), dried over anhydrous sodium sulfate, filtered, and the filtrate was concentrated under reduced pressure to obtain compound 21b.

MS-ESI calculated for [M+H]$^+$ 249, found 249.

Step 3

Compound 21b (2.00 g, 8.06 mmol) was dissolved in dichloromethane (60 mL), and thionyl chloride (2.88 g, 24.2 mmol) was added dropwise to the reaction solution, and the reaction solution was stirred at 25° C. for 12 hours under nitrogen protection. The reaction solution was concentrated under reduced pressure, and the residue was diluted with water (50 mL), extracted with dichloromethane (50 mL×3). The combined organic phases were washed with saturated brine (30 mL×3), dried over anhydrous sodium sulfate, and filtered. The filtrate was concentrated under reduced pressure to obtain compound 21c.

MS-ESI calculated for [M+H]$^+$ 231, found 231.

Step 4

Compound 21c (1.20 g, 5.21 mmol), N-bromosuccinimide (1.86 g, 10.4 mmol) and azobisisobutyronitrile (42.8 mg, 261 μmol) were dissolved in carbon tetrachloride (30 mL), and the reaction system was replaced with nitrogen for three times, and the reaction solution was stirred at 80° C. for 16 hours under nitrogen protection. The reaction solution was concentrated under reduced pressure, and the residue was diluted with water (100 mL), extracted with dichloromethane (100 mL×3). The combined organic phases were washed with saturated brine (30 mL×3), dried over anhydrous sodium sulfate, and filtered. The filtrate was concentrated under reduced pressure to obtain a crude product. The crude product was separated by silica gel column chromatography (10:1, petroleum ether/ethyl acetate, Rf=0.14) to obtain compound 21d.

MS-ESI calculated for [M+H]$^+$ 307 and 309, found 307 and 309.

$^1$H NMR (400 MHz, CDCl$_3$) δ=8.18 (d, J=2.0 Hz, 1H), 8.13 (dd, J=8.8, 2.0 Hz, 1H), 7.09 (s, 1H), 7.04 (d, J=8.8 Hz, 1H), 4.74 (p, J=6.1, 1H), 1.45 (d, J=6.1 Hz, 6H).

Step 5

Compound 21d (50.0 mg, 162 μmol), compound 14b (76.8 mg, 163 μmol), potassium carbonate (67.5 mg, 488 μmol) and tetrakis(triphenylphosphine)palladium (18.8 mg, 16.3 μmol) were accurately weighed into microwave tube, then water (0.5 mL) and ethylene glycol dimethyl ether (1.5 mL) were added to the microwave tube. The reaction solution was heated to 100° C. and stirred for 40 minutes under microwave irradiation. The reaction solution was concentrated under reduced pressure, and the residue was diluted with water (50 mL), extracted with dichloromethane (50 mL×3). The combined organic phases were washed with saturated brine (30 mL×3), dried over anhydrous sodium sulfate, and filtered. The filtrate was concentrated under reduced pressure to obtain compound 21e.

MS-ESI calculated for [M+H]$^+$ 572, found 572.

Step 6

Compound 21e (50.0 mg, 87.5 mmol) was dissolved in ethyl acetate (2 mL) and hydrochloric acid/ethyl acetate (4 M, 2 mL), and the reaction system was replaced with nitrogen for three times, and the reaction solution was stirred at 25° C. for 1 hour under nitrogen protection. The reaction solution was concentrated under reduced pressure, and the residue was diluted with water (50 mL), extracted with dichloromethane (50 mL×3). The combined organic phases were washed with saturated brine (50 mL×3), dried over anhydrous sodium sulfate, and filtered. The filtrate was concentrated under reduced pressure to obtain a crude product. The crude product was then purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 48%-68%, 7 minutes} to obtain compound 21.

MS-ESI calculated for [M+H]$^+$ 458, found 458.

$^1$H NMR (400 MHz, DMSO-d$_6$) δ=8.41-8.36 (m, 1H), 8.33-8.27 (m, 1H), 7.84-7.79 (m, 1H), 7.66 (d, J=2.4 Hz, 1H), 7.48 (d, J=9.0 Hz, 1H), 7.41-7.34 (m, 1H), 7.33-7.27 (m, 1H), 4.96-4.87 (m, 1H), 4.12-3.94 (m, 2H), 3.72-3.49 (m, 5H), 3.21-3.13 (m, 2H), 2.20-1.91 (m, 4H), 1.38 (d, J=6.4 Hz, 6H).

Embodiment 22

Compound 22

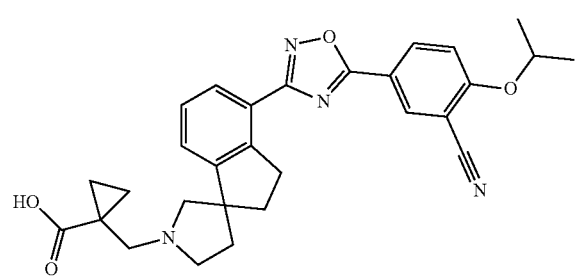

Synthetic route:

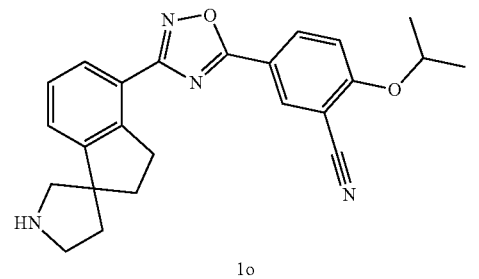

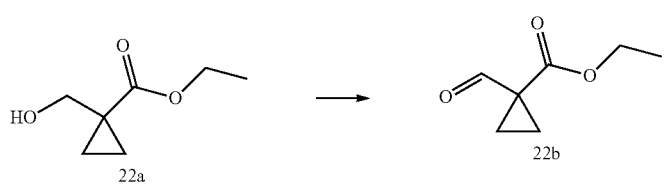

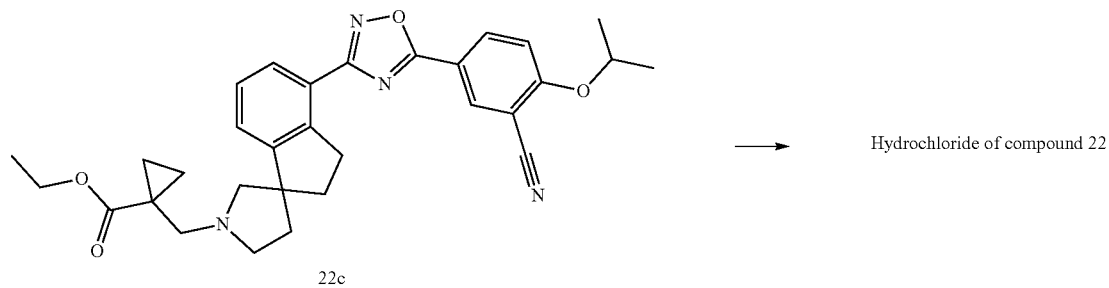

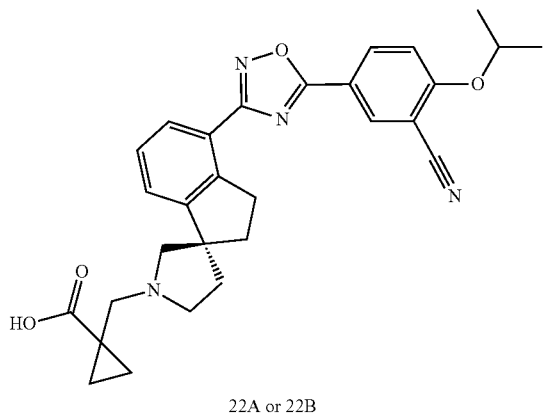

22A or 22B

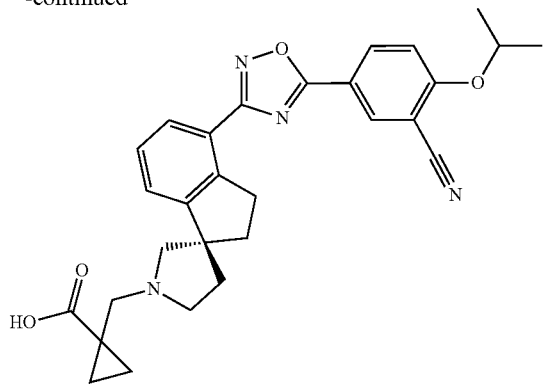

22B or 22A

Step 1

Compound 22a (200 mg, 1.39 mol) was dissolved in dichloromethane (2 mL), and Dess-Martin periodinane (1.30 g, 3.07 mmol) was added to the reaction solution, and the reaction solution was stirred at 25° C. for 1 hour. Saturated aqueous sodium bicarbonate solution (50 mL) was added to the reaction solution, and the mixture was extracted with dichloromethane (20 mL×4). The combined organic phases were dried over anhydrous sodium sulfate, filtered, and the filtrate was concentrated under reduced pressure. The crude product was separated by silica gel column chromatography (10/1, petroleum ether/ethyl acetate) to obtain compound 22b.

Step 2

Compound 1o (100 mg, 229 μmol) and compound 22b (97.6 mg, 687 μmol) were dissolved in dichloromethane (20 mL), and acetic acid (27.5 mg, 458 μmol) was added to the reaction solution, and then sodium triacetoxyborohydride (97.0 mg, 457 μmol) was added thereto, and the reaction solution was stirred at 25° C. for 12 hours. The reaction solution was concentrated under reduced pressure, diluted with water (50 mL), and extracted with ethyl acetate (30 mL×3). The combined organic phases were dried over anhydrous sodium sulfate, and filtered. The filtrate was concentrated under reduced pressure, and the crude product was purified by thin-layer silica gel column chromatography (15/1, dichloromethane/methanol) to obtain compound 22c.

MS-ESI calculated for [M+H]$^+$ 527, found 527.

Step 3

Compound 22c (110 mg, 209 μmol) was dissolved in a mixed solvent of tetrahydrofuran (4 mL) and methanol (2 mL), and a solution of lithium hydroxide monohydrate (26.3 mg, 627 μmol) in water (1 mL) was added to the above reaction solution, and the reaction solution was stirred at 25° C. for 12 hours. The reaction solution was concentrated under reduced pressure, and the residue was diluted with water (15 mL), adjusted to pH=5 with 1 M aqueous hydrochloric acid solution, extracted with ethyl acetate (10 mL×3). The combined organic phases were dried over anhydrous sodium sulfate, filtered, and the filtrate was concentrated under reduced pressure. The crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 33%-53%, 6.5 minutes} to obtain the hydrochloride of compound 22.

MS-ESI calculated for [M+H]$^+$ 499, found 499.

$^1$H NMR (400 MHz, DMSO-d$_6$) δ=8.52 (d, J=2.2 Hz, 1H), 8.45-8.37 (m, 1H), 8.06-8.00 (m, 1H), 7.76-7.70 (m, 1H), 7.60-7.49 (m, 2H), 5.06-4.85 (m, 1H), 3.88-3.46 (m, 4H), 3.29-3.20 (m, 2H), 2.57-2.52 (m, 4H), 2.27-2.18 (m, 2H), 1.41-1.36 (m, 6H), 1.35-1.28 (m, 2H), 1.25-1.19 (m, 2H).

Step 4

The hydrochloride of compound 22 was chiral separated. Chromatographic column: CHIRALPAK IG 50×4.6 mm×3 μm; mobile phase A: CO$_2$, mobile phase B: ethanol (0.05% diethylamine); gradient B %: 40%-40%, 9 minutes. Compound 22A (ee %=99.62%, SFC retention time: 6.567 minutes) and compound 22B (ee %=99.4%, SFC retention time: 5.084 minutes) were obtained.

Compound 22A: MS-ESI calculated for [M+H]$^+$ 499, found 499.

$^1$H NMR (400 MHz, CD$_3$OD) δ=8.47-8.41 (m, 2H), 8.11 (d, J=7.6 Hz, 1H), 7.60 (d, J=7.6 Hz, 1H), 7.52-7.43 (m, 2H), 5.00-4.92 (m, 2H), 3.76-3.57 (m, 3H), 3.45-3.36 (m, 4H), 2.50-2.41 (m, 1H), 2.40-2.32 (m, 3H), 1.48 (d, J=6.0 Hz, 6H), 1.32-1.29 (m, 2H), 0.88-0.84 (m, 2H).

Compound 22B: MS-ESI calculated for [M+H]$^+$ 499, found 499.

$^1$H NMR (400 MHz, CD$_3$OD) δ=8.39-8.33 (m, 2H), 8.04 (dd, J=0.8, 7.6 Hz, 1H), 7.55 (d, J=6.8 Hz, 1H), 7.47-7.37 (m, 2H), 4.96-4.85 (m, 2H), 3.74-3.52 (m, 3H), 3.39-3.33 (m, 3H), 3.32-3.31 (m, 1H), 3.32-3.30 (m, 1H), 2.47-2.37 (m, 1H), 2.36-2.28 (m, 3H), 1.44 (d, J=6.0 Hz, 6H), 1.26-1.21 (m, 2H), 0.81-0.74 (m, 2H).

Embodiment 23

Compound 23

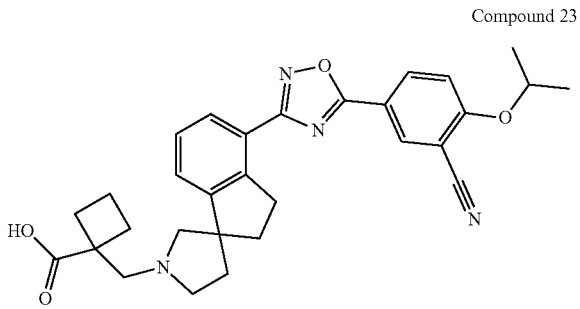 [SMILES: CC(C)Oc1ccc(-c2nc(-c3cccc4c3CCC43CCN(CC4(C(=O)O)CCC4)C3)no2)cc1C#N]

Synthetic route:

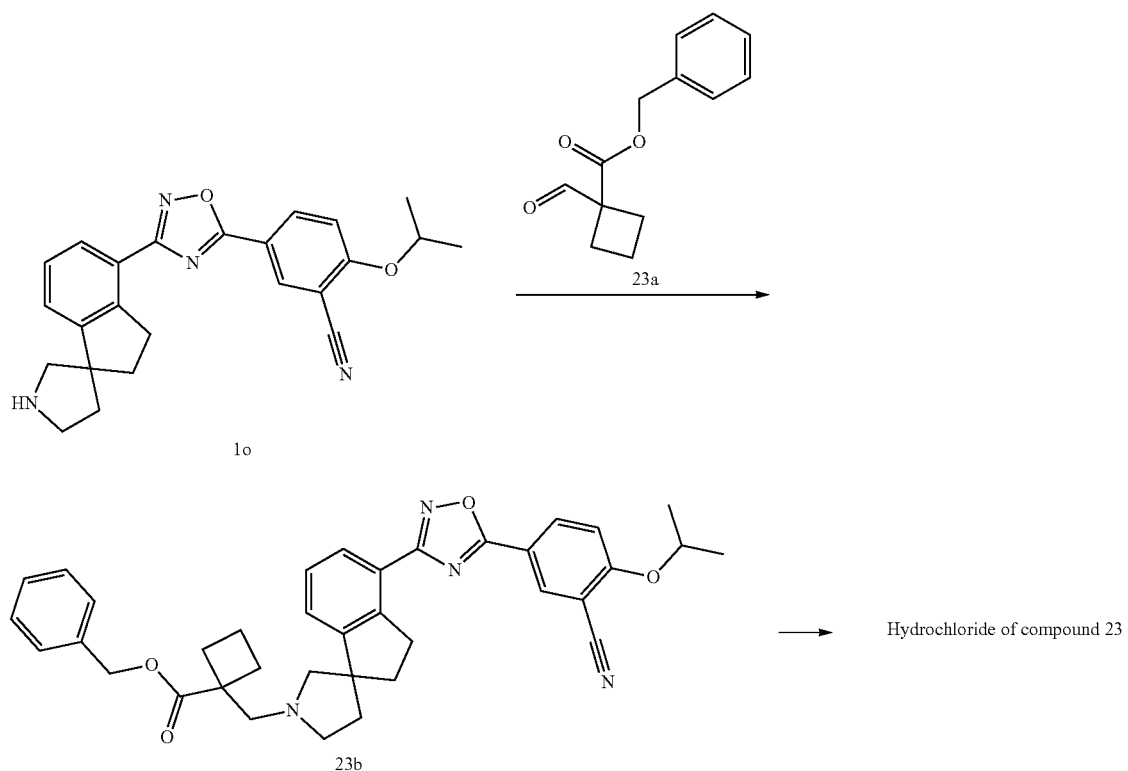

Step 1

Compound 1o (100 mg, 229 μmol) and compound 23a (99.9 mg, 458 μmol) were dissolved in dichloromethane (8 mL), and acetic acid (27.5 mg, 458 μmol) was added to the reaction solution. After the reaction solution was stirred at 25° C. for 12 hours, sodium triacetoxyborohydride (97.0 mg, 458 μmol) was added thereto. The reaction solution was stirred at 25° C. for 2 hours. The reaction solution was concentrated under reduced pressure, diluted with water (50 mL), and extracted with ethyl acetate (30 mL×3). The combined organic phases were dried over anhydrous sodium sulfate, filtered, and the filtrate was concentrated under reduced pressure to obtain the crude product of compound 23b.

MS-ESI calculated for [M+H]$^+$ 603, found 603.

Step 2

Compound 23b (120 mg, 199 μmol) was dissolved in a mixed solvent of tetrahydrofuran (2 mL) and ethanol (1 mL), and a solution of lithium hydroxide monohydrate (25.1 mg, 597 μmol) in water (1 mL) was added to the above reaction solution, and the reaction solution was stirred at 15° C. for 48 hours. The mixture was concentrated under reduced pressure, and the residue was diluted with 0.5 M aqueous hydrochloric acid solution (30 mL), and stirred at 15° C. for 10 minutes. The mixture was extracted with ethyl acetate (20 mL×3). The combined organic phases were dried over anhydrous sodium sulfate, filtered, and the filtrate was concentrated under reduced pressure. The crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 35%-55%, 7 minutes} to obtain the hydrochloride of compound 23.

MS-ESI calculated for [M+H]$^+$ 513, found 513.

$^1$H NMR (400 MHz, CDCl$_3$) δ=8.38-8.26 (m, 2H), 8.03 (d, J=7.4 Hz, 1H), 7.77 (br s, 1H), 7.41 (t, J=6.8 Hz, 1H), 7.13 (d, J=9.0 Hz, 1H), 4.87-4.75 (m, 1H), 4.09-3.09 (m, 8H), 2.80-1.95 (m, 10H), 1.49 (d, J=6.0 Hz, 6H).

Embodiment 24
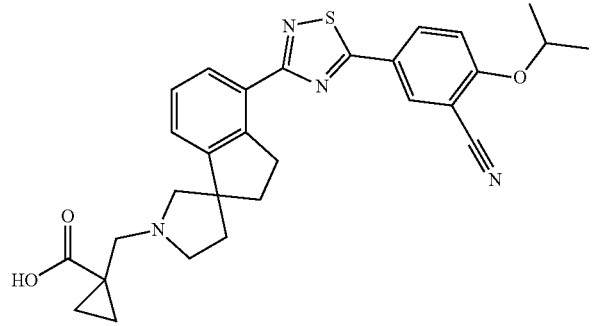
Compound 24
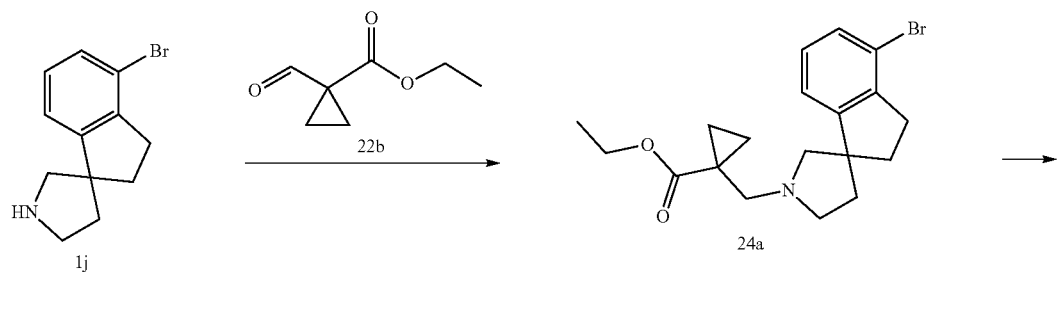
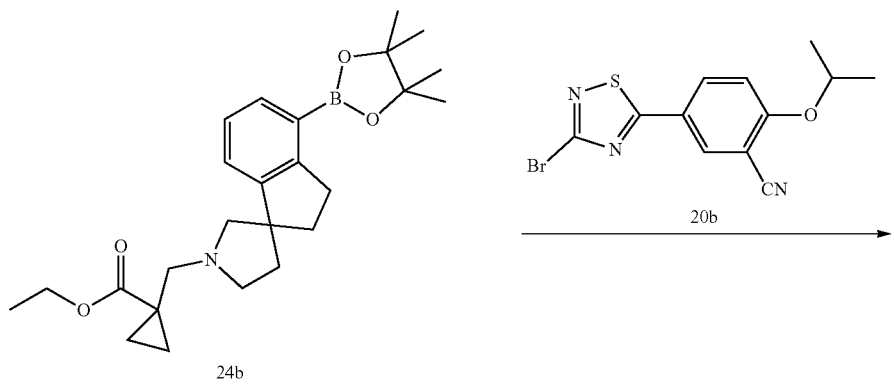
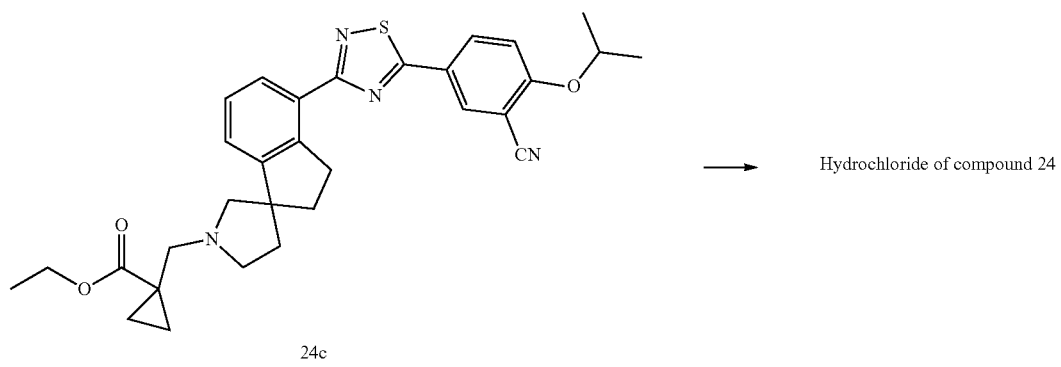
→ Hydrochloride of compound 24

Step 1

Compound 1j (4.0 g, 15.9 mmol) and compound 22b (2.93 g, 20.6 mmol) were dissolved in dichloromethane (100 mL), and acetic acid (953 mg, 15.9 mmol) was added to the reaction solution. After the reaction solution was stirred at 15° C. for 13 hours, sodium triacetoxyborohydride (6.72 g, 31.7 mmol) was added thereto. The reaction solution was stirred at 15° C. for 1 hour. The reaction solution was concentrated under reduced pressure, diluted with water (200 mL), and extracted with ethyl acetate (100 mL×3). The combined organic phases were dried over anhydrous sodium sulfate, and filtered. The filtrate was concentrated under reduced pressure, and the crude product was purified by silica gel column chromatography (1:1, petroleum ether/ethyl acetate) to obtain compound 24a.

MS-ESI calculated for [M+H]$^+$ 378 and 380, found 378 and 380.

Step 2

Compound 24a (2.35 g, 6.21 mmol), bis(pinacolato)diboron (2.37 g, 9.32 mmol) and potassium acetate (1.22 g, 12.42 mmol), 1,1-bis(diphenylphosphino)ferrocene dichloropalladium (454 mg, 621 μmol) were dissolved in dioxane (20 mL). Under nitrogen protection, the reaction solution was stirred at 80° C. for 12 hours, concentrated under reduced pressure. 50 mL of water was added to the residue, and the mixture was extracted with ethyl acetate (50 mL*3). The organic phases were combined, and the organic phases were washed with saturated brine (30 mL*2), dries over anhydrous sodium sulfate. The crude product was purified by column chromatography (5:1, petroleum ether/ethyl acetate) to obtain compound 24b.

MS-ESI calculated for [M+H]$^+$ 426, found 426.

Step 3

Compound 20b (195 mg, 601 μmol), compound 24b (256 mg, 601 μmol), potassium phosphate (255 mg, 1.20 μmol) and 1,1-bis(diphenylphosphino)ferrocene dichloropalladium (44.0 mg, 60.1 μmol) were dissolved in dioxane (6 mL) and water (3 mL). Under nitrogen protection, the reaction solution was stirred at 80° C. for 12 hours, and the reaction solution was concentrated under reduced pressure. 20 mL of water was added to the residue, and the mixture was extracted with ethyl acetate (50 mL×2). The organic phases were combined, and the organic phases were washed with 30 mL of water and 30 mL of saturated brine, dried over anhydrous sodium sulfate, concentrated. The crude product was purified by thin-layer chromatography (1:1, petroleum ether/ethyl acetate) to obtain compound 24c.

MS-ESI calculated for [M+H]$^+$ 543, found 543.

Step 4

Compound 24c (140 mg, 258 μmol) was dissolved in tetrahydrofuran (4 mL) and methanol (2 mL). A solution of lithium hydroxide monohydrate (43.3 mg, 1.03 mmol) in water (1 mL) was added to the mixture, and the reaction solution was stirred at 20° C. for 12 hours. 1 M aqueous hydrochloric acid solution was added to the reaction solution to adjust the pH value to about 5. The mixture was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 38%-58%, 7 minutes} to obtain the hydrochloride of compound 24.

MS-ESI calculated for [M+H]$^+$ 515, found 515.

1H NMR (400 MHz, MeOH-d$_4$) δ=8.39-8.21 (m, 3H), 7.56 (d, J=7.5 Hz, 1H), 7.50-7.41 (m, 1H), 7.41-7.33 (m, 1H), 4.98-4.89 (m, 1H), 4.09-3.77 (m, 2H), 3.74-3.43 (m, 6H), 2.61-2.22 (m, 4H), 1.57-1.48 (m, 2H), 1.47-1.43 (m, 6H), 1.22 (br s, 2H).

Embodiment 25

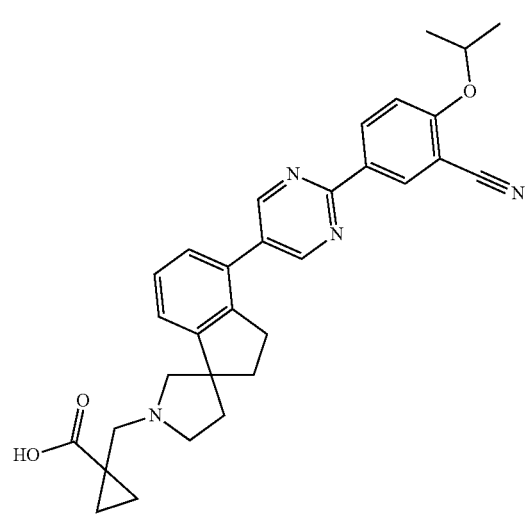

Synthetic route:

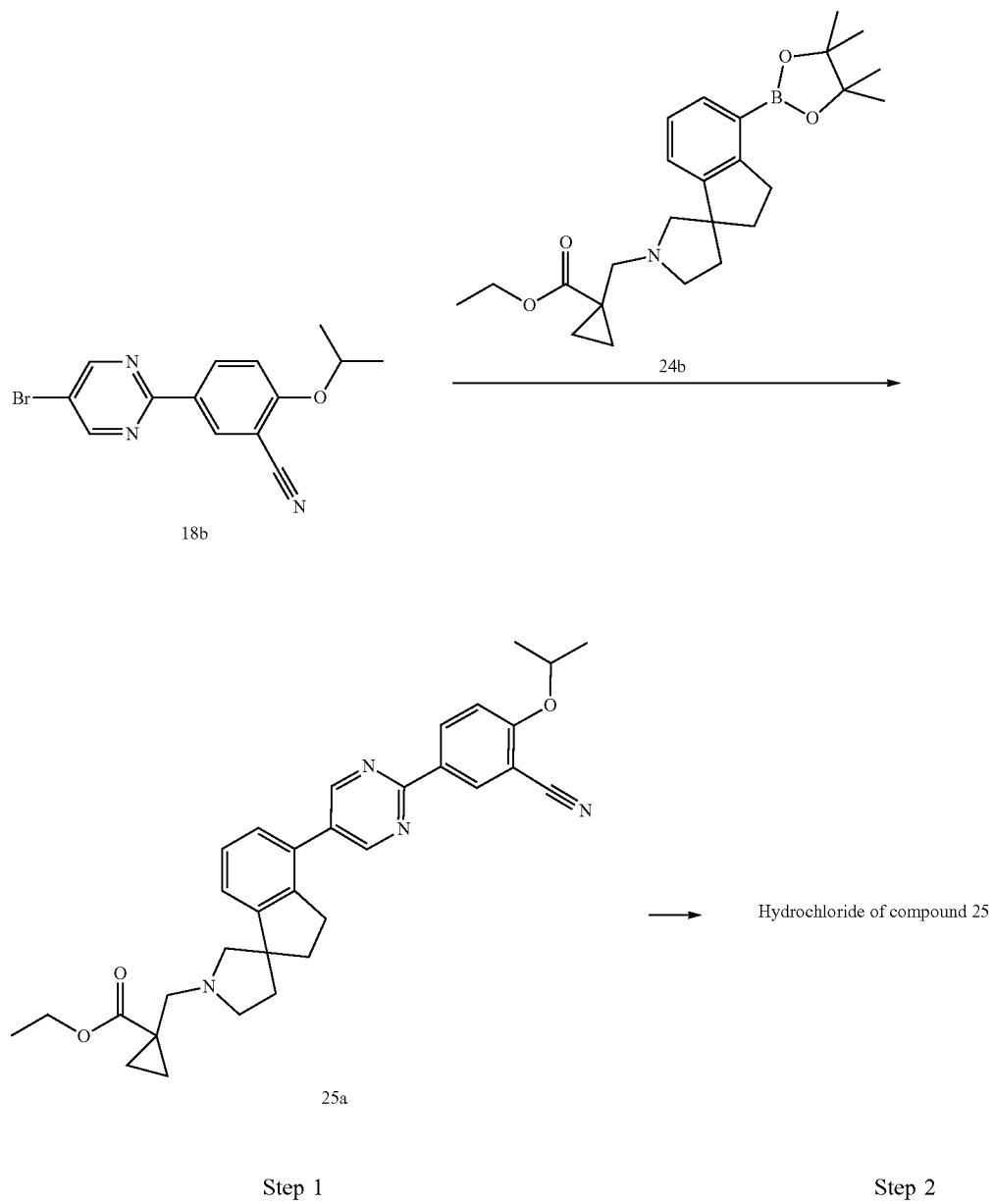

Step 1

Compound 18b (66.9 mg, 157 μmol), compound 24b (50 mg, 157 μmol) and potassium phosphate (66.7 mg, 314 μmol) were dissolved in anhydrous dioxane (3 mL) and water (1 mL). Under nitrogen atmosphere, 1,1-bis(diphenylphosphino)ferrocene dichloropalladium (11.5 mg, 15.7 μmol) was added to the reaction solution, and the reaction solution was stirred at 80° C. for 12 hours. The reaction solution was diluted with water (15 mL), extracted with ethyl acetate (15 mL×2), and the combined organic phases were washed with saturated sodium chloride (20 mL×2), dried over anhydrous sodium sulfate, filtered, and the filtrate was concentrated under reduced pressure to obtain compound 25a.

MS-ESI calculated for [M+H]$^+$ 537, found 537.

Step 2

Compound 25a (75 mg, 140 μmol) was dissolved in anhydrous tetrahydrofuran (3 mL), methanol (1 mL) and water (1 mL). Lithium hydroxide monohydrate (11.7 mg, 280 μmol) was added to the mixture, and the reaction solution was stirred at 50° C. for 3 hours. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 34%-54%, 7 minutes} to obtain the hydrochloride of compound 25.

MS-ESI calculated for [M+H]$^+$ 509, found 509.

$^1$H NMR (400 MHz, MeOH-d$_4$) δ=8.96-8.94 (m, 2H), 8.73-8.69 (m, 2H), 7.55-7.47 (m, 2H), 7.45-7.42 (m, 1H), 7.34 (d, J=8.7 Hz, 1H), 4.92-4.90 (m, 1H), 4.04-3.91 (m,

2H), 3.71-3.59 (m, 2H), 3.57-3.44 (m, 2H), 3.17-3.07 (m, 2H), 2.42-2.35 (m, 2H), 2.34-2.20 (m, 2H), 1.55-1.49 (m, 2H), 1.45 (d, J=6.0 Hz, 6H), 1.24-1.19 (m, 2H).

Embodiment 26

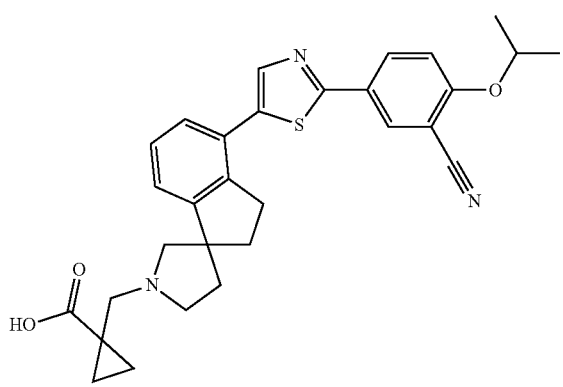

Synthetic route:

Step 1

Compound 24b (184 mg, 433 μmol), compound 14f (140 mg, 433 μmol) and potassium phosphate (184 mg, 866 μmol) were dissolved in anhydrous dioxane (3 mL) and water (1 mL). Under nitrogen protection, 1,1-bis(diphenylphosphino)ferrocene dichloropalladium (31.7 mg, 43.3 μmol) was added to the reaction solution, and the reaction solution was stirred at 80° C. for 12 hours. The reaction solution was diluted with water (20 mL), and extracted with ethyl acetate (15 mL×2). The combined organic phases were washed with saturated brine (20 mL×1), dried over anhydrous sodium sulfate, and filtered. The filtrate was concentrated under reduced pressure, and the crude product was purified by silica gel column chromatography (10:1, dichloromethane/methanol) to obtain compound 26a.

MS-ESI calculated for [M+H]$^+$ 542, found 542.

Step 2

Compound 26a (160 mg, 295 μmol) was dissolved in anhydrous tetrahydrofuran (3 mL), methanol (1 mL) and

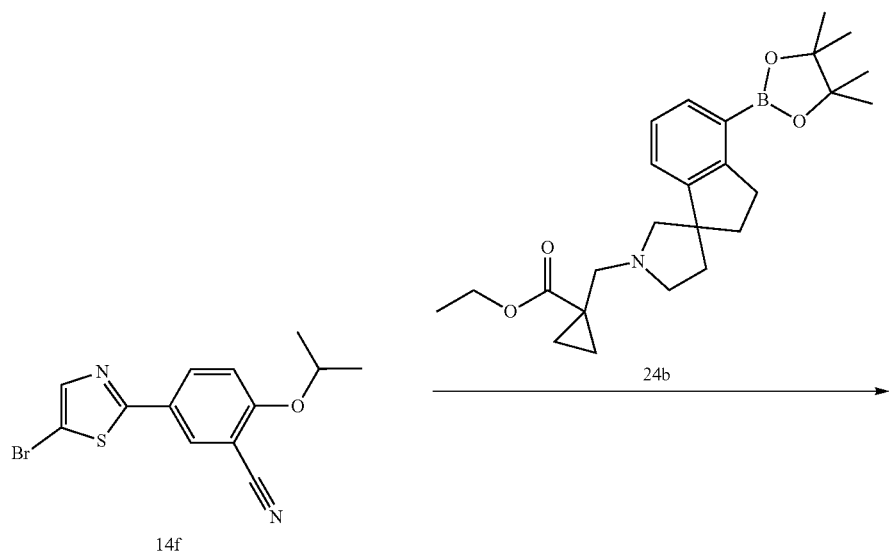

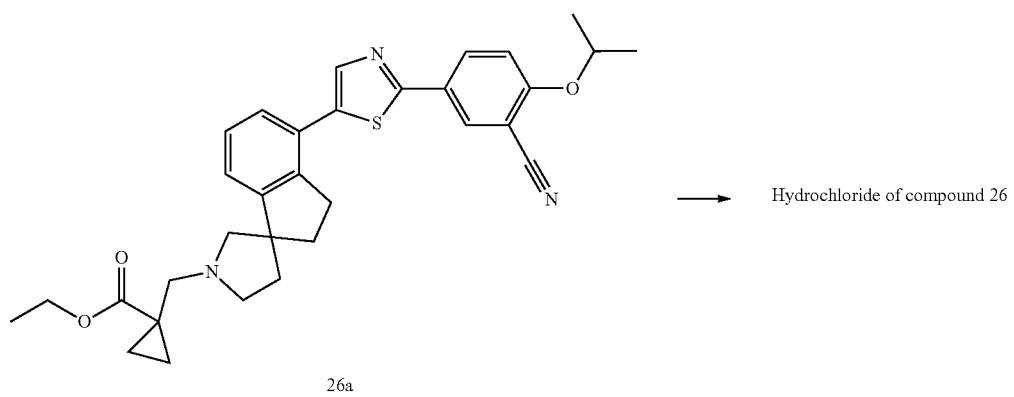

water (1 mL). Lithium hydroxide monohydrate (24.8 mg, 591 μmol) was added to the mixture, and the reaction solution was stirred at 50° C. for 3 hours. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 34%-54%, 7 minutes} to obtain the hydrochloride of compound 26.

MS-ESI calculated for [M+H]$^+$ 514, found 514.

$^1$H NMR (400 MHz, MeOH-d4) δ=8.24 (d, J=2.3 Hz, 1H), 8.21 (dd, J=8.9, 2.4 Hz, 1H), 8.10 (s, 1H), 7.59-7.55 (m, 1H), 7.52-7.47 (m, 1H), 7.45-7.40 (m, 1H), 7.36 (d, J=8.9 Hz, 1H), 4.93-4.90 (m, 1H), 4.03-3.89 (m, 2H), 3.70-3.60 (m, 2H), 3.59-3.44 (m, 2H), 3.25-3.20 (m, 2H), 2.56-2.37 (m, 2H), 2.35-2.23 (m, 2H), 1.54-1.50 (m, 2H), 1.44 (d, J=6.1 Hz, 6H), 1.26-1.22 (m, 2H).

Embodiment 27

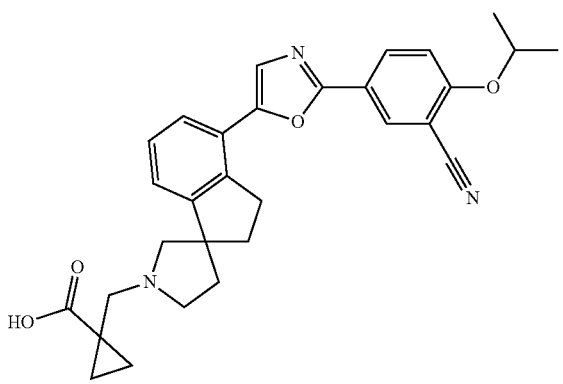

Synthetic route:

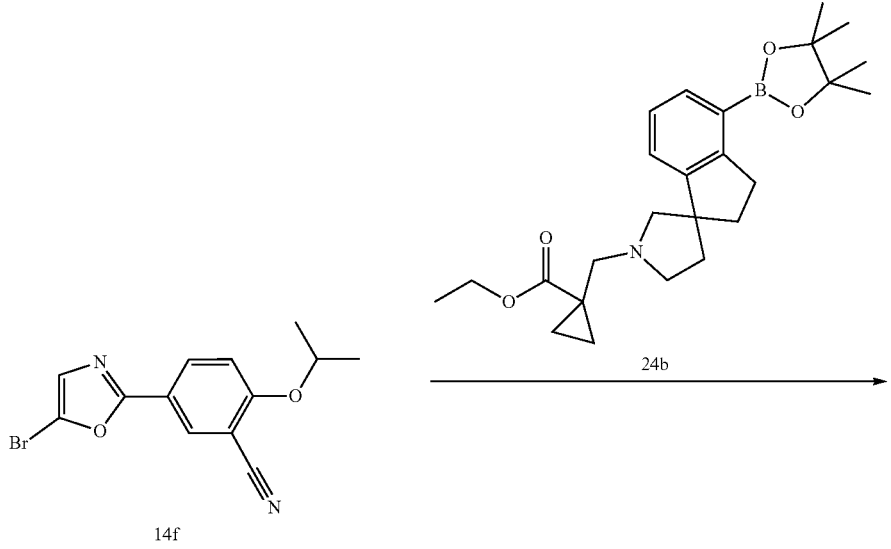

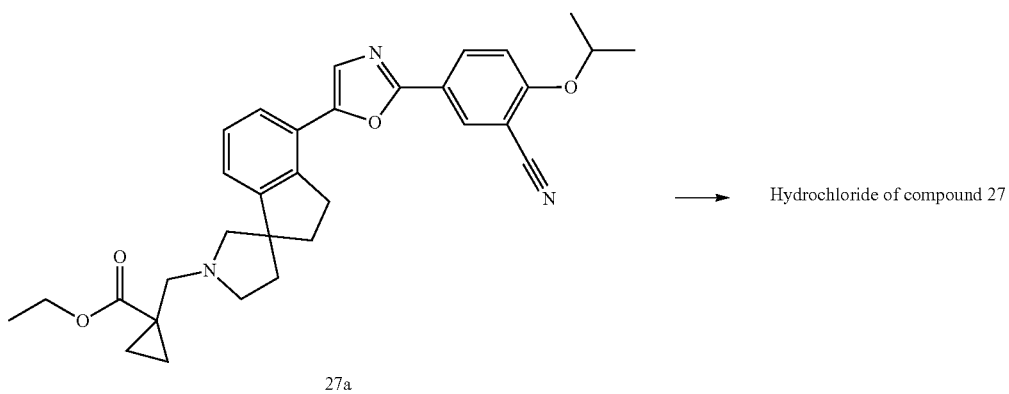

Step 1

Compound 24b (138 mg, 326 μmol), compound 21d (100 mg, 326 μmol) and potassium phosphate (138 mg, 651 μmol) were dissolved in anhydrous dioxane (3 mL) and water (1 mL). Under nitrogen protection, 1,1-bis(diphenylphosphino)ferrocene dichloropalladium (23.8 mg, 43.3 μmol) was added to the reaction solution, and the reaction solution was stirred at 80° C. for 12 hours. The reaction solution was diluted with water (20 mL), and extracted with ethyl acetate (15 mL×2). The combined organic phases were washed with saturated brine (20 mL×1), dried over anhydrous sodium sulfate, and filtered. The filtrate was concentrated under reduced pressure, and the crude product was purified by silica gel column chromatography (1:1, petroleum ether/ethyl acetate) to obtain compound 27a.

MS-ESI calculated for [M+H]$^+$ 526, found 526.

Step 2

Compound 27a (150 mg, 285 μmol) was dissolved in anhydrous tetrahydrofuran (3 mL), methanol (1 mL) and water (1 mL). Lithium hydroxide monohydrate (24.0 mg, 570 μmol) was added to the mixture, and the reaction solution was stirred at 50° C. for 3 hours. The reaction solution was concentrated under reduced pressure, and the crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 31%-51%, 7 minutes} to obtain the hydrochloride of compound 27.

MS-ESI calculated for [M+H]$^+$ 498, found 498.

$^1$H NMR (400 MHz, MeOH-d$_4$) δ=8.30-8.24 (m, 2H), 7.80-7.75 (m, 1H), 7.51-7.49 (m, 1H), 7.47-7.41 (m, 2H), 7.36 (d, J=8.9 Hz, 1H), 4.92-4.89 (m, 1H), 4.02-3.88 (m, 2H), 3.70-3.60 (m, 2H), 3.58-3.43 (m, 2H), 3.27-3.20 (m, 2H), 2.56-2.38 (m, 2H), 2.37-2.26 (m, 2H), 1.54-1.50 (m, 2H), 1.44 (d, J=6.0 Hz, 6H), 1.27-1.21 (m, 2H).

Embodiment 28

Compound 28

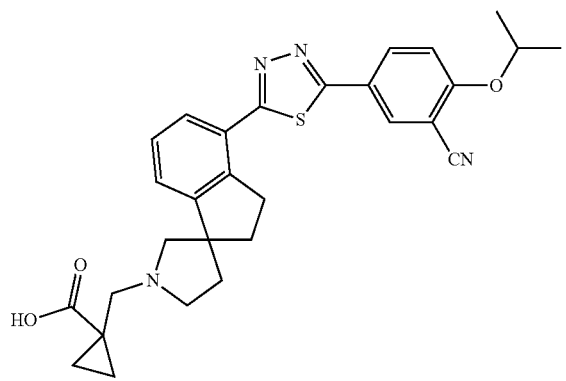

Synthetic route:

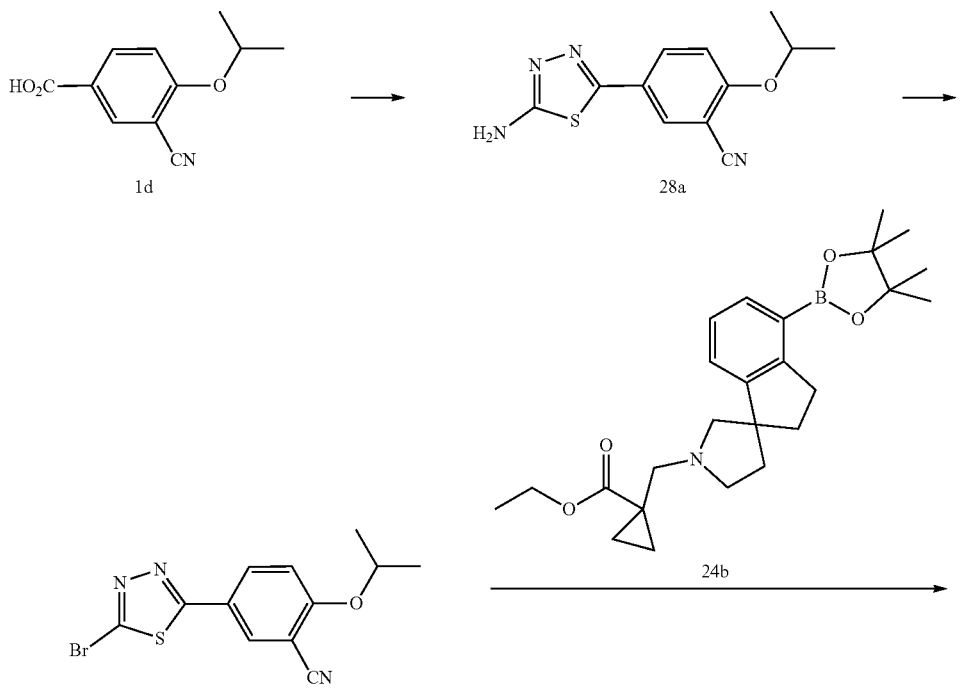

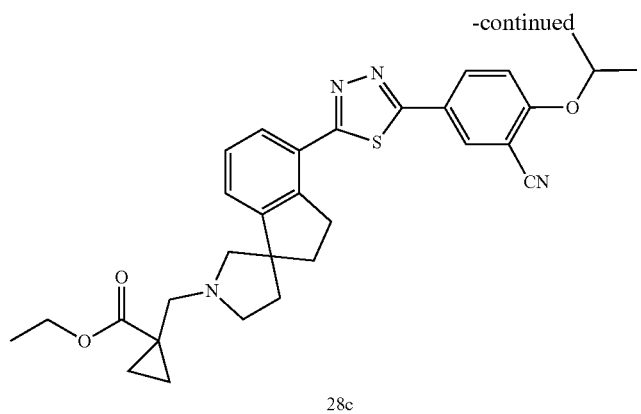

28c

→ Hydrochloride of compound 28

Step 1

Compound 1d (1.00 g, 4.87 mmol) was dissolved in phosphorus oxychloride (6 mL), and thiosemicarbazide hydrochloride (666 mg, 7.31 mmol) was added to the mixture. The reaction solution was stirred at 90° C. for 8 hours. The reaction solution was slowly dropped into 6 M NaOH (40 mL) aqueous solution, extracted with ethyl acetate (30 mL×2). The organic phases were combined, and the organic phases were washed with water (30 mL) and saturated brine (30 mL), dried over anhydrous sodium sulfate and concentrated to obtain compound 28a.

MS-ESI calculated for [M+H]$^+$ 261, found 261.

Step 2

Compound 28a (210 mg, 807 mmol) was dissolved in acetonitrile (5 mL), and tert-butyl nitrite (166 mg, 1.61 mmol) and copper bromide (360 mg, 1.61 mmol) were added to the mixture at 0° C. The reaction solution was stirred at 20° C. for 1 hour, and the reaction solution was stirred at 70° C. for 2 hours. The reaction solution was added with 1 M aqueous hydrochloric acid solution (10 mL), extracted with ethyl acetate (30 mL×2). The organic phases were combined, and the organic phases were washed with 20 mL of water and 20 mL of saturated brine, and dried over anhydrous sodium sulfate. The crude product was purified by silica gel thin-layer chromatography (3/1, petroleum ether/ethyl acetate) to obtain compound 28b.

MS-ESI calculated for [M+H]$^+$ 324 and 326, found 324 and 326.

Step 3

Compound 24b (87.9 mg, 207 μmol), compound 28b (67.0 mg, 207 μmol), potassium phosphate (87.7 mg, 413 μmol) and 1,1-bis(diphenylphosphino)ferrocene dichloropalladium (15.1 mg, 20.7 μmol) were dissolved in dioxane (3 mL) and water (1.5 mL). Under nitrogen protection, the reaction solution was stirred at 80° C. for 12 hours, and the reaction solution was concentrated under reduced pressure. 20 mL of water was added to the crude product, and the mixture was extracted with ethyl acetate (50 mL×2). The organic phases were combined, and the organic phases were washed with 30 mL of water and 30 mL of saturated brine, dried over anhydrous sodium sulfate, and concentrated to obtain compound 28c.

MS-ESI calculated for [M+H]$^+$ 543, found 543.

Step 4

Compound 28c (124 mg, 228 μmol) was dissolved in tetrahydrofuran (4 mL) and methanol (2 mL). A solution of lithium hydroxide monohydrate (28.8 mg, 685 μmol) in water (1 mL) was added to the mixture, and the reaction solution was stirred at 20° C. for 12 hours. 1M aqueous hydrochloric acid solution was added to the reaction solution to adjust the pH to about 5. The reaction solution was concentrated under reduced pressure, and the crude product was purified by high performance liquid chromatography {hydrochloric acid condition, column type: 3_Phenomenex Luna C18 75×30 mm×3 μm; mobile phase: [water (0.05% HCl)-acetonitrile]; acetonitrile %: 30%-50%, 7 minutes} to obtain the hydrochloride of compound 28.

MS-ESI calculated for [M+H]$^+$ 515, found 515.

$^1$H NMR (400 MHz, MeOH-d$_4$) δ=8.32-8.25 (m, 2H), 7.92-7.87 (m, 1H), 7.61 (d, J=7.2 Hz, 1H), 7.50 (t, J=7.7 Hz, 1H), 7.39 (d, J=8.9 Hz, 1H), 4.95-4.91 (m, 1H), 4.13-3.80 (m, 2H), 3.71-3.46 (m, 4H), 3.44-3.37 (m, 2H), 2.55-2.25 (m, 4H), 1.55-1.49 (m, 2H), 1.45 (d, J=6.0 Hz, 6H), 1.22-1.19 (m, 2H).

Embodiment 29

Compound 29

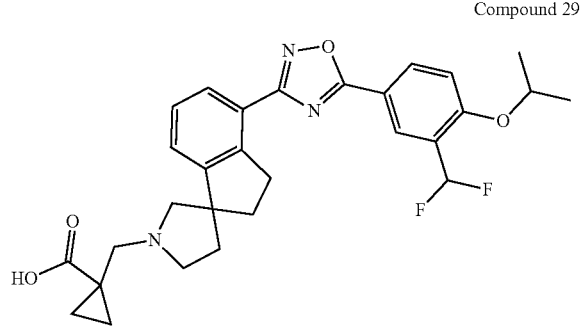 [SMILES: CC(C)Oc1ccc(-c2nc(-c3cccc4c3CCC43CCN(CC4(C(=O)O)CC4)C3)no2)cc1C(F)F]

Synthetic route:

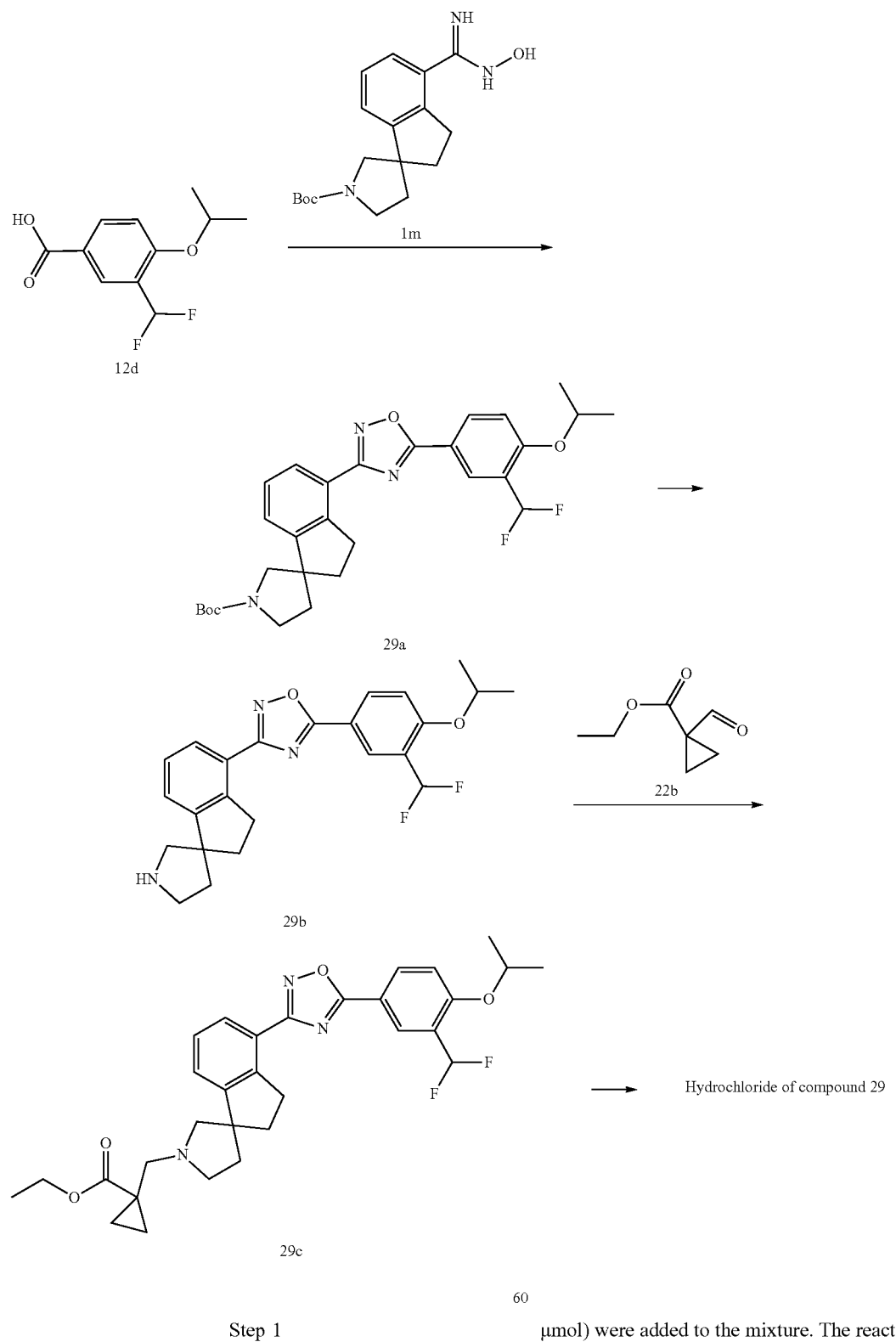

Step 1

Compound 12d (139 mg, 603 μmol) was dissolved in anhydrous N,N-dimethylformamide (3 mL), and 1-hydroxybenzotriazole (97.9 mg, 724 μmol) and 1-(3-dimethylaminopropyl)-3-ethylcarbodiimide hydrochloride (138 mg, 724 μmol) were added to the mixture. The reaction solution was stirred at 25° C. for 1 hour, and compound 1m (200 mg, 603 μmol) was added to the reaction solution. The reaction solution was stirred at 25° C. for 1 hour, and the reaction solution was further stirred at 80° C. for 12 hours. The reaction solution was concentrated under reduced pressure, and the residue was added with water (100 mL), extracted with dichloromethane (50 mL×3). The organic phases were combined, and the combined organic phases were washed with saturated brine (30 mL×3), and dried over anhydrous sodium sulfate. The crude product was purified by thin-layer chromatography (1:1, petroleum ether/ethyl acetate) to obtain compound 29a.

MS-ESI calculated for [M+H−$^t$Bu]$^+$ 470, found 470.

$^1$H NMR (400 MHz, CDCl$_3$) δ=8.44 (s, 1H), 8.27 (dd, J=8.8, 2.2 Hz, 1H), 8.09 (dd, J=7.6, 1.2 Hz, 1H), 7.39 (t, J=7.6 Hz, 1H), 7.33 (d, J=7.2 Hz, 1H), 7.09 (d, J=8.8 Hz, 1H), 6.99 (t, J=55.4 Hz, 1H), 4.84-4.71 (m, 1H), 3.74-3.36 (m, 6H), 2.28-2.09 (m, 3H), 2.02-1.94 (m, 1H), 1.54-1.47 (m, 9H), 1.44 (d, J=5.9 Hz, 6H).

Step 2

Compound 29a (200 mg, 380 μmol) was dissolved in dioxane (1 mL), and dioxane hydrochloride solution (4 M, 2.85 mL) was added to the mixture. The reaction solution was stirred at 25° C. for 1 hour, concentrated under reduced pressure and dried under reduced pressure to obtain the hydrochloride of compound 29b.

MS-ESI calculated for [M+H]$^+$ 426, found 426.

Step 3

The hydrochloride of compound 29b (156 mg, 367 μmol) and compound 22b (78.3 mg, 551 μmol) were dissolved in dichloromethane (2 mL). Glacial acetic acid (22.1 mg, 367 μmol) was added to the mixture, and the reaction solution was stirred at 15° C. for 13 hours. Sodium triacetoxyborohydride (156 mg, 735 μmol) was added to the reaction solution, and the reaction solution was stirred at 15° C. for 1 hour. The pH was adjusted to about 9 using 10% sodium bicarbonate solution, and the reaction solution was diluted with water (100 mL), then extracted with dichloromethane (50 mL×3). The organic phases were combined, and the organic phases were washed with saturated brine (30 mL×3), dried over anhydrous sodium sulfate, and concentrated to obtain compound 29c.

MS-ESI calculated for [M+H]$^+$ 552, found 552.

Step 4

Compound 29c (137 mg, 248 μmol) was dissolved in anhydrous tetrahydrofuran (2 mL), and a solution of sodium hydroxide (39.7 mg, 993 μmol) in water (0.5 mL) was added to the mixture, and the reaction solution was stirred at 20° C. for 12 hours. The pH of the reaction solution was adjusted to about 5 with 1 N hydrochloric acid solution, and the mixture was concentrated under reduced pressure. The crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 37%-57%, 7 minutes} to obtain the hydrochloride of compound 29.

MS-ESI calculated for [M+H]$^+$ 524, found 524.

$^1$H NMR (400 MHz, CDCl$_3$) δ=8.38 (s, 1H), 8.22 (d, J=8.6 Hz, 1H), 8.08 (d, J=7.1 Hz, 1H), 7.88 (br s, 1H), 7.42 (br s, 1H), 7.07 (d, J=8.8 Hz, 1H), 6.96 (t, J=55.5 Hz, 1H), 4.82-4.67 (m, 1H), 4.36-3.15 (m, 10H), 2.83-2.06 (m, 4H), 1.77-1.48 (m, 2H), 1.43 (d, J=8.6 Hz, 6H).

Embodiment 30

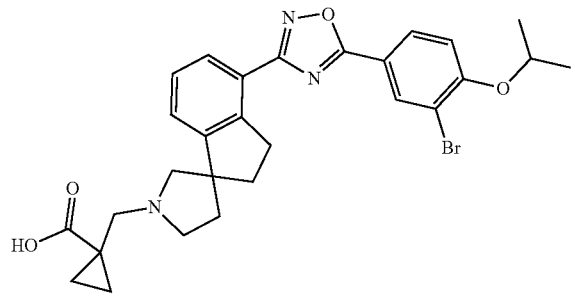

Compound 30

Synthetic route:

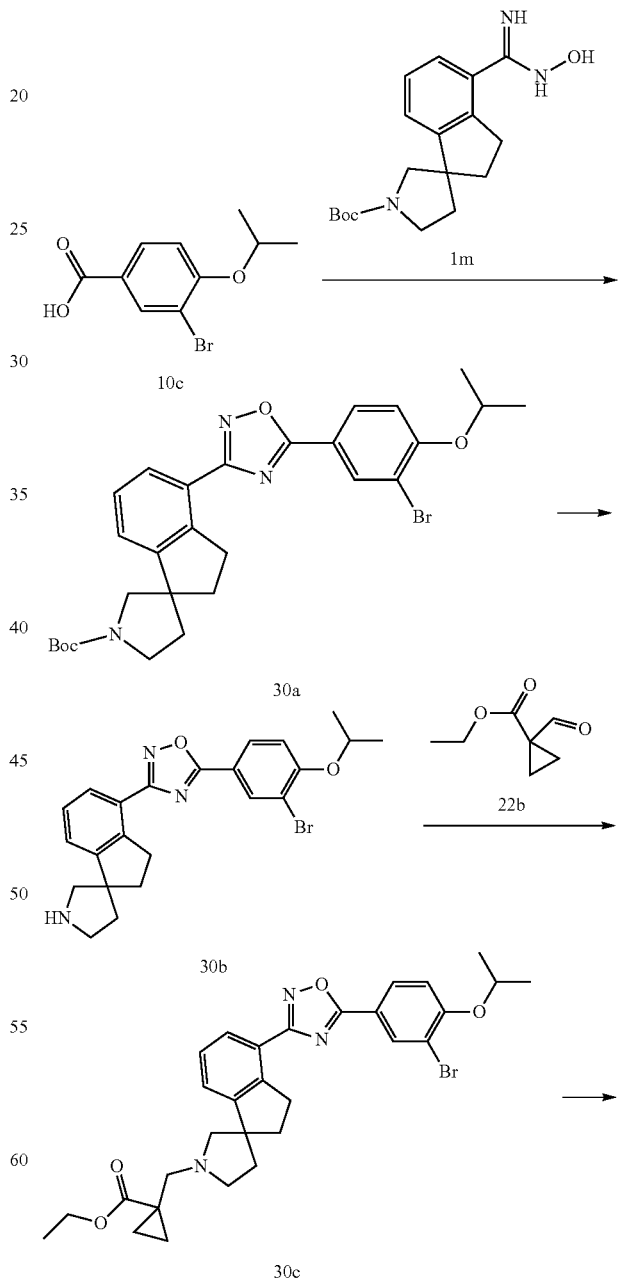

Hydrochloride of compound 30

Step 1

Compound 10c (156 mg, 603 μmol) was dissolved in anhydrous N,N-dimethylformamide (3 mL), and 1-hydroxybenzotriazole (97.9 mg, 724 μmol) and 1-(3-dimethylaminopropyl)-3-ethylcarbodiimide hydrochloride (138 mg, 724 μmol) were added to the mixture. The reaction solution was stirred at 25° C. for 1 hour, and compound 1m (200 mg, 603 μmol) was added to the reaction solution. The reaction solution was stirred at 25° C. for 1 hour, and the reaction solution was further stirred at 80° C. for 12 hours. The reaction solution was concentrated under reduced pressure, and the reaction solution was added with water (100 mL), extracted with dichloromethane (50 mL×3). The organic phases were combined, and the combined organic phases were washed with saturated brine (30 mL×3), and dried over anhydrous sodium sulfate. The crude product was purified by thin-layer chromatography (1:1, petroleum ether/ethyl acetate) to obtain compound 30a.

MS-ESI calculated for [M+H−$^t$Bu]$^+$ 498 and 500, found 498 and 500.

$^1$H NMR (400 MHz, CDCl$_3$) δ=8.43 (d, J=2.0 Hz, 1H), 8.16-8.01 (m, 2H), 7.44-7.30 (m, 2H), 7.03 (d, J=8.8 Hz, 1H), 4.78-4.68 (m, 1H), 3.75-3.31 (m, 6H), 2.31-1.94 (m, 4H), 1.58-1.41 (m, 15H).

Step 2

Compound 30a (100 mg, 180 μmol) was dissolved in dioxane (1 mL), and dioxane hydrochloride solution (4 M, 1.35 mL) was added to the mixture. The reaction solution was stirred at 25° C. for 1 hour, concentrated under reduced pressure to obtain the hydrochloride of compound 30b.

MS-ESI calculated for [M+H]$^+$ 454 and 456, found 454 and 456.

Step 3

The hydrochloride of compound 30b (70.0 mg, 143 μmol) and compound 22b (30.4 mg, 214 μmol) were dissolved in dichloromethane (1 mL). Glacial acetic acid (8.56 mg, 143 μmol) was added to the mixture, and the reaction solution was stirred at 15° C. for 13 hours. Sodium triacetoxyborohydride (60.4 mg, 343 μmol) was added to the reaction solution, and the reaction solution was stirred at 15° C. for 1 hour. The pH was adjusted to about 9 using 10% sodium bicarbonate solution, and the reaction solution was diluted with water (100 mL), then extracted with dichloromethane (50 mL×3). The organic phases were combined, and the organic phases were washed with saturated brine (30 mL×3), dried over anhydrous sodium sulfate, and concentrated to obtain compound 30c.

MS-ESI calculated for [M+H]$^+$ 580 and 582, found 580 and 582.

Step 4

Compound 30c (60 mg, 248 μmol) was dissolved in anhydrous tetrahydrofuran (2 mL), and a solution of sodium hydroxide (16.5 mg, 413 μmol) in water (0.5 mL) was added to the mixture, and the reaction solution was stirred at 20° C. for 12 hours. The pH of the reaction solution was adjusted to about 5 with 1 N hydrochloric acid solution, and the mixture was concentrated under reduced pressure. The crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 43%-63%, 7 minutes} to obtain the hydrochloride of compound 30.

MS-ESI calculated for [M+H]$^+$ 552 and 554, found 552 and 554.

$^1$H NMR (400 MHz, CDCl$_3$) δ=8.37 (s, 1H), 8.12-8.03 (m, 2H), 7.98-7.78 (m, 1H), 7.50-7.36 (m, 1H), 7.01 (d, J=8.6 Hz, 1H), 4.81-4.65 (m, 1H), 4.32-2.79 (m, 10H), 2.60-2.08 (m, 4H), 1.75-1.42 (m, 2H), 1.46 (d, J=5.8 Hz, 6H).

Embodiment 31

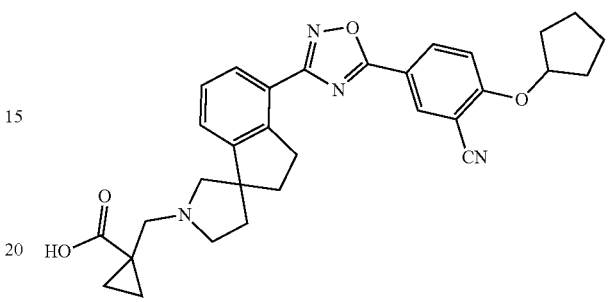

Compound 31

Synthetic route:

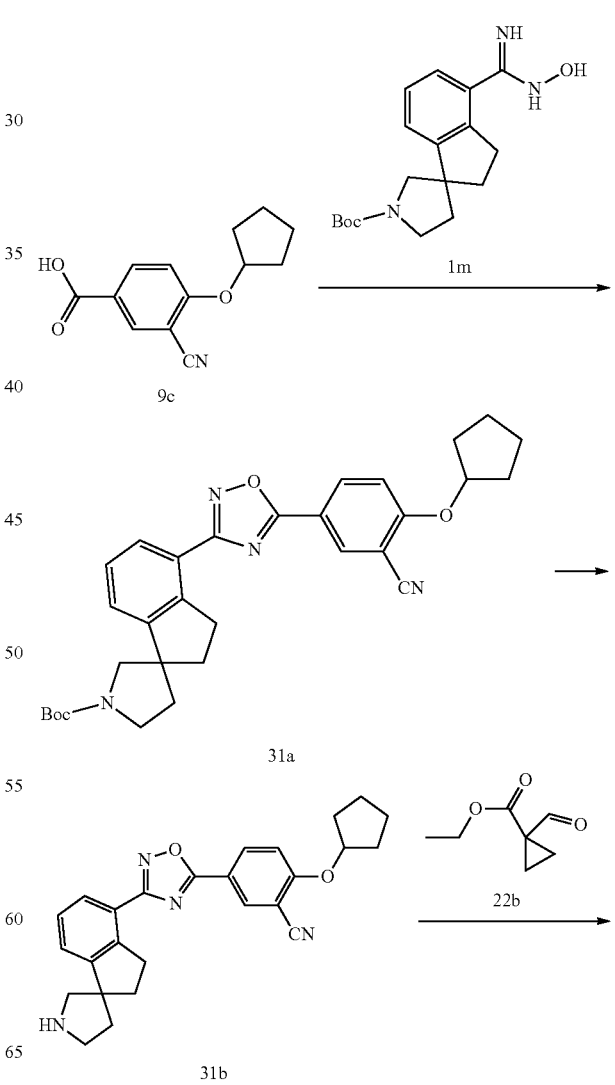

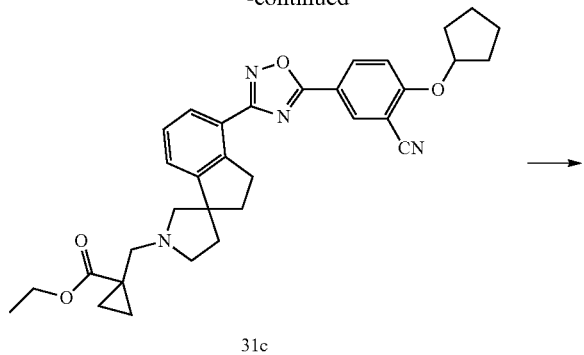

31c

Hydrochloride of compound 31

Step 1

Compound 9c (140 mg, 603 μmol) was dissolved in anhydrous N,N-dimethylformamide (3 mL), and 1-hydroxybenzotriazole (97.9 mg, 724 μmol) and 1-(3-dimethylaminopropyl)-3-ethylcarbodiimide hydrochloride (138 mg, 724 μmol) were added to the mixture. The reaction solution was stirred at 25° C. for 1 hour, and compound 1m (200 mg, 603 μmol) was added to the reaction solution. The reaction solution was stirred at 25° C. for 1 hour, and the reaction solution was further stirred at 80° C. for 12 hours. The reaction solution was concentrated under reduced pressure, and the reaction solution was added with water (100 mL), extracted with dichloromethane (50 mL×3). The organic phases were combined, and the combined organic phases were washed with saturated brine (30 mL×3), and dried over anhydrous sodium sulfate. The crude product was purified by thin-layer chromatography (1:1, petroleum ether/ethyl acetate, Rf=0.80) to obtain compound 31a.

MS-ESI calculated for [M+H−$^t$Bu]$^+$ 471, found 471.

Step 2

Compound 31a (300 mg, 570 μmol) was dissolved in dioxane (2 mL), and dioxane hydrochloride solution (4 M, 4.27 mL) was added to the mixture. The reaction solution was stirred at 25° C. for 1 hour, concentrated under reduced pressure to obtain the hydrochloride of compound 31b.

MS-ESI calculated for [M+H]$^+$ 427, found 427.

Step 3

The hydrochloride of compound 31b (200 mg, 431 μmol) and compound 22b (123 mg, 864 μmol) were dissolved in dichloromethane (2 mL). Glacial acetic acid (25.9 mg, 431 μmol) was added to the mixture, and the reaction solution was stirred at 15° C. for 13 hours. Sodium triacetoxyborohydride (183 mg, 864 μmol) was added to the reaction solution, and the reaction solution was stirred at 15° C. for 1 hour. The pH was adjusted to about 9 using 10% sodium bicarbonate solution, and the reaction solution was diluted with water (100 mL), then extracted with dichloromethane (50 mL×3). The organic phases were combined, and the organic phases were washed with saturated brine (30 mL×3), dried over anhydrous sodium sulfate, and concentrated to obtain compound 31c.

MS-ESI calculated for [M+H]$^+$ 553, found 553.

Step 4

Compound 31c (20 mg, 36.2 μmol) was dissolved in anhydrous dioxane (0.8 mL), and a solution of anhydrous lithium hydroxide (3.04 mg, 72.4 μmol) dissolved in water (0.2 mL) was added to the mixture, and the reaction solution was stirred at 28° C. for 2 hours. The pH of the reaction solution was adjusted to about 5, and the reaction solution was concentrated under reduced pressure. The crude product was purified by high performance liquid chromatography {hydrochloric acid condition, column type: Phenomenex luna C18 150*25 mm*10 μm; mobile phase: [water (0.05% HCl)-acetonitrile]; acetonitrile %: 29%-59%, 10 minutes} to obtain the hydrochloride of compound 31.

MS-ESI calculated for [M+H]$^+$ 525, found 525.

$^1$H NMR (400 MHz, CDCl$_3$) δ=8.42-8.28 (m, 2H), 8.07 (d, J=7.8 Hz, 1H), 7.49-7.38 (m, 1H), 7.14 (d, J=8.8 Hz, 1H), 5.04-4.95 (m, 1H), 3.53-3.19 (m, 6H), 2.49-0.73 (m, 18H).

Embodiment 32

Compound 32

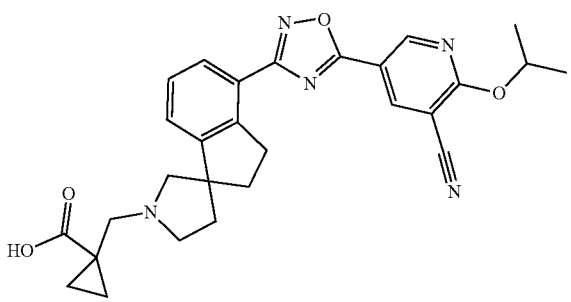

Synthetic route:

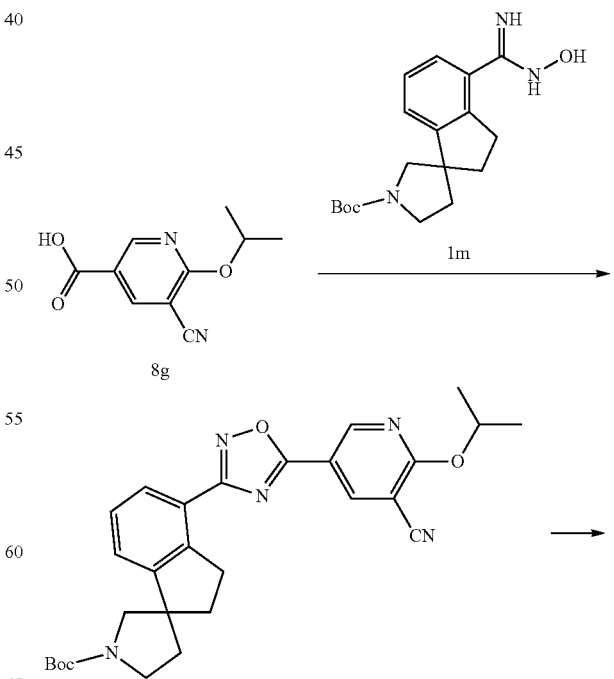

32a

-continued

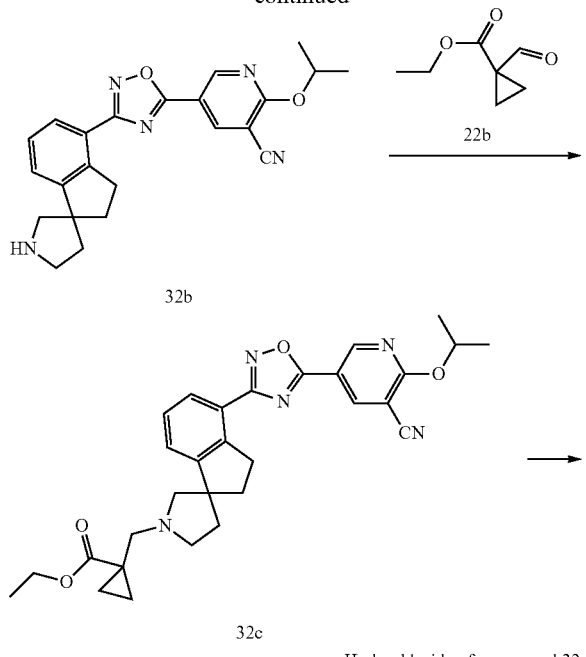

32b

32c

Hydrochloride of compound 32

Step 1

Compound 8g (790 mg, 3.83 mmol) was dissolved in anhydrous N,N-dimethylformamide (10 mL), and 1-hydroxybenzotriazole (621 mg, 4.60 mmol) and 1-(3-dimethylaminopropyl)-3-ethylcarbodiimide hydrochloride (881 mg, 4.60 mmol) were added to the mixture. The reaction solution was stirred at 25° C. for 1 hour, and compound 1m (1.27 g, 3.83 mmol) was added to the reaction solution. The reaction solution was stirred at 25° C. for 1 hour, and the reaction solution was further stirred at 80° C. for 8 hours. The reaction solution was added with 80 mL of water, extracted with ethyl acetate (60 mL×3). The organic phases were combined, and the organic phases were washed with saturated brine (60 mL×2), dried over anhydrous sodium sulfate, and concentrated to obtain compound 32a.

MS-ESI calculated for [M+H−$^t$Bu]$^+$ 446, found 446.

Step 2

Compound 32a (1.93 g, 2.74 mmol) was dissolved in ethyl acetate (30 mL), and hydrochloric acid/ethyl acetate (4 M, 6.85 mL) was added to the mixture. The reaction solution was stirred at 25° C. for 1 hour, concentrated under reduced pressure to obtain the hydrochloride of compound 32b.

MS-ESI calculated for [M+H]$^+$ 402, found 402.

Step 3

The hydrochloride of compound 32b (100 mg, 228 μmol) and compound 22b (48.7 mg, 343 μmol) were dissolved in dichloromethane (5 mL). Glacial acetic acid (13.7 mg, 228 μmol) was added to the mixture, and the reaction solution was stirred at 20° C. for 8 hours. Sodium triacetoxyborohydride (96.8 mg, 457 μmol) was added to the reaction solution, and the reaction solution was stirred at 20° C. for 10 hours. The solvent was removed under reduced pressure. 10% aqueous sodium bicarbonate (20 mL) solution was added to the residue, and the mixture was extracted with dichloromethane (30 mL×2). The organic phases were combined, and the organic phases were washed with water (30 mL) and saturated brine (30 mL), dried over anhydrous sodium sulfate, and concentrated to obtain compound 32c.

MS-ESI calculated for [M+H]$^+$ 528, found 528.

Step 4

Compound 32c (125 mg, 237 μmol) was dissolved in anhydrous tetrahydrofuran (6 mL), and a solution of sodium hydroxide (37.9 mg, 948 μmol) dissolved in methanol (3 mL) was added to the mixture, and the reaction solution was stirred at 20° C. for 12 hours. The pH of the reaction solution was adjusted to 5 with 12 N HCl solution, and the mixture was concentrated to remove the solvent. The crude product was purified by high performance liquid chromatography {hydrochloric acid condition, column type: 3_Phenomenex Luna C18 75*30 mm*3 μm; mobile phase: [water (0.05% HCl)-acetonitrile]; acetonitrile %: 43%-63%, 7 minutes} to obtain the hydrochloride of compound 32.

MS-ESI calculated for [M+H]$^+$ 500, found 500.

$^1$H NMR (400 MHz, CDCl$_3$) δ=9.16 (d, J=2.5 Hz, 1H), 8.64 (d, J=2.3 Hz, 1H), 8.10 (d, J=7.8 Hz, 1H), 7.52-7.42 (m, 1H), 7.28-7.25 (m, 1H), 5.63-5.54 (m, 1H), 3.68-3.20 (m, 6H), 2.63-1.55 (m, 8H), 1.49 (d, J=6.3 Hz, 6H), 1.41-1.19 (m, 2H).

Embodiment 33

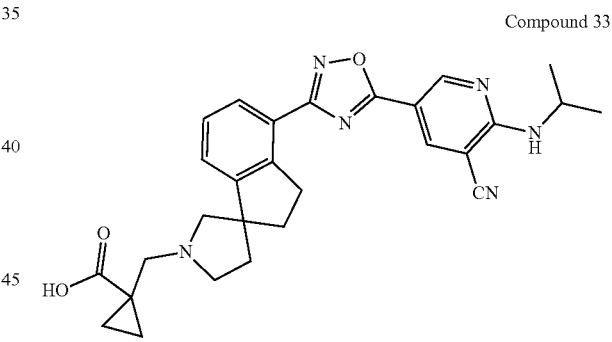

Compound 33

Synthetic route:

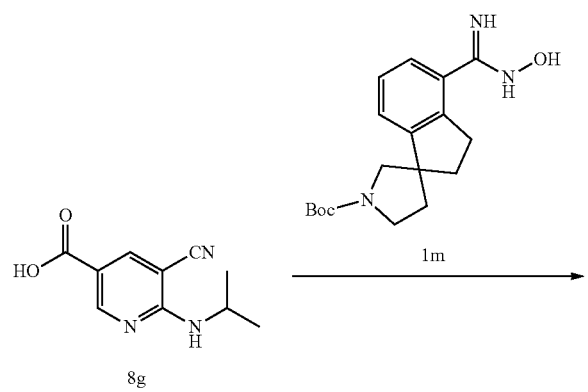

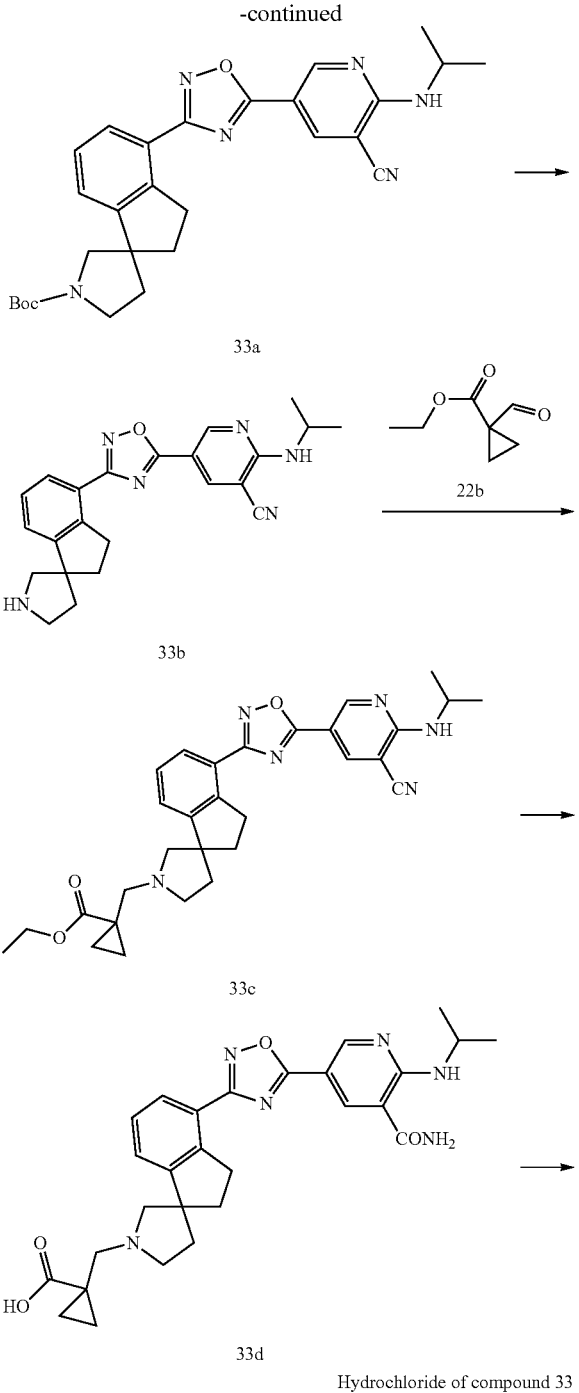

acetate (30 mL×2). The organic phases were combined, and the organic phases were washed with water (20 mL) and saturated brine (20 mL), and dried over anhydrous sodium sulfate. The crude product was subjected to silica gel column chromatography (2:1, petroleum ether/ethyl acetate) to obtain compound 33a.

MS-ESI calculated for [M+H−$^t$Bu]$^+$ 445, found 445.

Step 2

Compound 33a (208 mg, 415 mmol) was dissolved in ethyl acetate (2 mL), and hydrochloric acid/ethyl acetate (4 M, 0.52 mL) was added to the mixture. The reaction solution was stirred at 25° C. for 1 hour, the solvent was removed under reduced pressure, and the residue was dried to obtain the hydrochloride of compound 33b.

MS-ESI calculated for [M+H]$^+$ 401, found 401.

Step 3

The hydrochloride of compound 33b (50 mg, 0.11 μmol) and compound 22b (40.6 mg, 286 μmol) were dissolved in dichloromethane (5 mL). Glacial acetic acid (6.87 mg, 114 μmol) was added to the mixture, and the reaction solution was stirred at 25° C. for 8 hours. Sodium triacetoxyborohydride (48.5 mg, 228 μmol) was added to the reaction solution, and the reaction solution was stirred at 25° C. for 6 hours. The reaction solution was added with 10% aqueous sodium bicarbonate solution (10 mL), extracted with dichloromethane (10 mL×3). The organic phases were combined, and the organic phases were washed with water (20 mL) and saturated brine (20 mL), dried over anhydrous sodium sulfate and concentrated. Then the crude product was purified by thin-layer silica gel chromatography (0:1, petroleum ether/ethyl acetate) to obtain compound 33c.

MS-ESI calculated for [M+H]$^+$ 527, found 527.

Step 4

Compound 33c (53 mg, 0.10 mmol) was dissolved in anhydrous tetrahydrofuran (6 mL) and anhydrous methanol (3 mL), and a solution of lithium hydroxide monohydrate (12.6 mg, 301 μmol) dissolved in water (1.5 mL) was added to the mixture, and the reaction solution was stirred at 25° C. for 12 hours. The reaction solution was adjusted to pH=5 with 12 N HCl and concentrated under reduced pressure to obtain compound 33d.

MS-ESI calculated for [M+H]$^+$ 517, found 517.

Step 5

Compound 33d (51 mg, 99 μmol) was dissolved in anhydrous dichloromethane (3 mL), and then triethylamine (19.9 mg, 197 μmol) and trifluoroacetic anhydride (20.8 mg, 108 μmol) were added to the mixture. The reaction solution was stirred at 0° C. for 1 hour, and 1M HCl aqueous solution was added to the reaction solution to adjust to pH=5, and the mixture was concentrated under reduced pressure. The crude product was purified by high performance liquid chromatography {hydrochloric acid condition, column type: Boston Green ODS 150*30 mm*5 μm; mobile phase: [water (0.05% hydrochloric acid)-acetonitrile]; acetonitrile %: 32%-62%, 8 minutes} to obtain the hydrochloride of compound 33.

MS-ESI calculated for [M+H]$^+$ 499, found 499.

$^1$H NMR (400 MHz, CDCl$_3$) δ=11.86-11.55 (m, 1H), 9.08 (s, 1H), 8.40 (s, 1H), 8.05 (d, J=7.5 Hz, 1H), 7.92 (d, J=7.0 Hz, 1H), 7.48-7.37 (m, 1H), 5.64-5.48 (m, 1H), 4.58-4.44 (m, 1H), 4.31-3.84 (m, 2H), 3.65-3.10 (m, 6H), 2.60-2.07 (m, 4H), 1.86-1.48 (m, 4H), 1.35 (d, J=6.5 Hz, 6H).

Step 1

Compound 13d (150 mg, 731 μmol) was dissolved in anhydrous N,N-dimethylformamide (15 mL), and 1-hydroxybenzotriazole (118 mg, 877 μmol) and 1-(3-dimethylaminopropyl)-3-ethylcarbodiimide hydrochloride (168 mg, 877 μmol) were added to the mixture. The reaction solution was stirred at 25° C. for 1 hour, and compound 1m (242 mg, 730 μmol) was added to the reaction solution. The reaction solution was stirred at 25° C. for 2 hours, and the reaction solution was further stirred at 80° C. for 8 hours. The solvent was removed under reduced pressure, and the reaction solution was added with 20 mL of water, extracted with ethyl

Embodiment 34

Compound 34

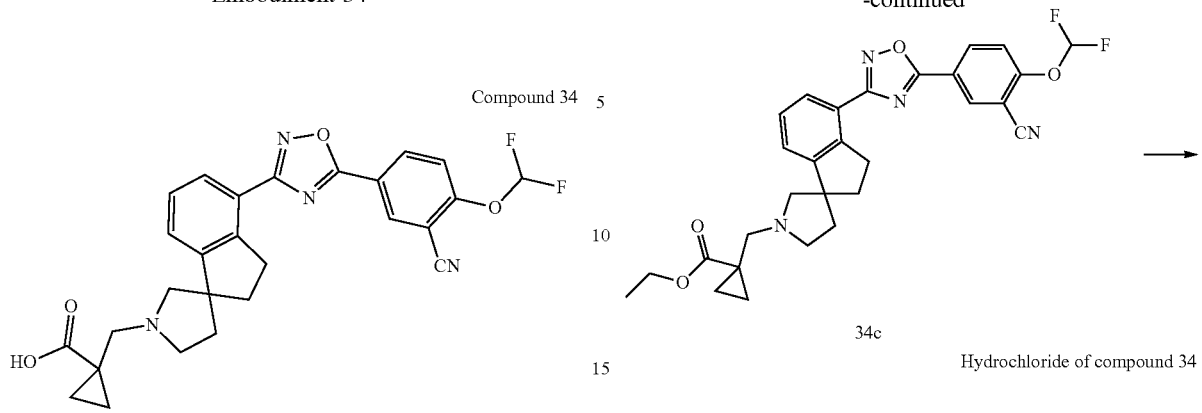

Synthetic route:

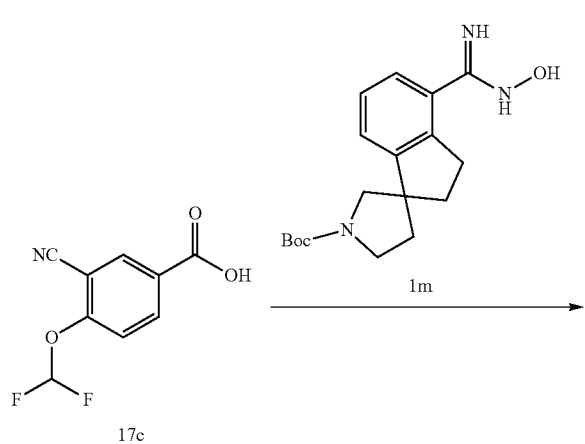

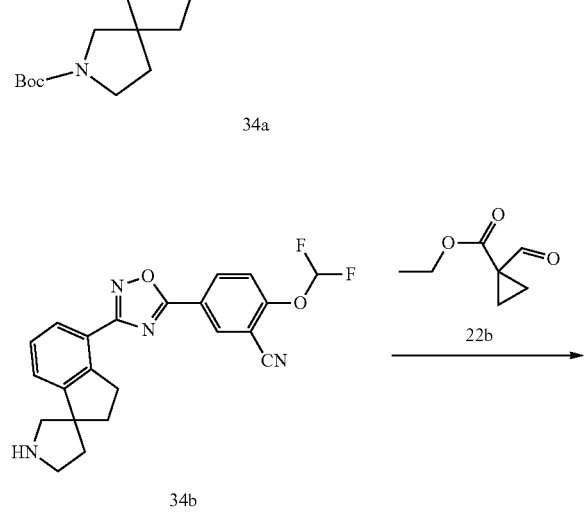

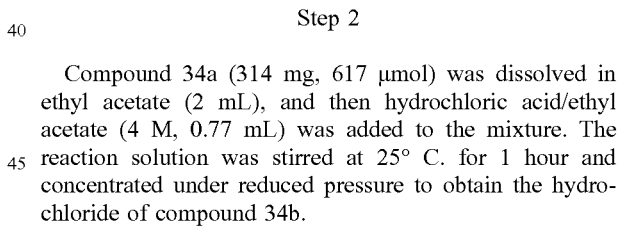

Hydrochloride of compound 34

Step 1

Compound 17c (100 mg, 469 μmol) was dissolved in anhydrous N,N-dimethylformamide (10 mL), and 1-hydroxybenzotriazole (76.1 mg, 563 μmol) and 1-(3-dimethylaminopropyl)-3-ethylcarbodiimide hydrochloride (107 mg, 563 μmol) were added to the mixture. The reaction solution was stirred at 25° C. for 1 hour, and compound 1m (155 mg, 469 μmol) was added to the reaction solution. The reaction solution was stirred at 25° C. for 2 hours, and the reaction solution was further stirred at 80° C. for 8 hours. The reaction solution was concentrated under reduced pressure, and the residue was diluted with 20 mL of water, extracted with ethyl acetate (30 mL×2). The organic phases were combined, and the organic phases were washed with water (20 mL) and saturated brine (20 mL), dried over anhydrous sodium sulfate, and concentrated to obtain compound 34a.

MS-ESI calculated for [M+H−$^t$Bu]$^+$ 453, found 453.

Step 2

Compound 34a (314 mg, 617 μmol) was dissolved in ethyl acetate (2 mL), and then hydrochloric acid/ethyl acetate (4 M, 0.77 mL) was added to the mixture. The reaction solution was stirred at 25° C. for 1 hour and concentrated under reduced pressure to obtain the hydrochloride of compound 34b.

MS-ESI calculated for [M+H]$^+$ 409, found 409.

Step 3

The hydrochloride of compound 34b (70 mg, 0.16 mmol) and compound 22b (44.7 mg, 314 μmol) were dissolved in dichloromethane (5 mL). Glacial acetic acid (9.5 mg, 0.16 mmol) was added to the reaction solution, and the reaction solution was stirred at 25° C. for 8 hours. Sodium triacetoxyborohydride (133 mg, 629 μmol) was added to the reaction solution, and the reaction solution was stirred at 25° C. for 6 hours. The reaction solution was added with 10% aqueous sodium bicarbonate solution (10 mL), extracted with dichloromethane (10 mL×3). The organic phases were combined, and the organic phases were washed with water (20 mL) and saturated brine (20 mL), dried over anhydrous sodium sulfate and concentrated. Then the crude product was purified by thin-layer silica gel chromatography (0:1, petroleum ether/ethyl acetate) to obtain compound 34c.

MS-ESI calculated for [M+H]$^+$ 535, found 535.

Step 4

Compound 34c (88 mg, 0.16 mmol) was dissolved in anhydrous tetrahydrofuran (10 mL), and then a solution of lithium hydroxide monohydrate (20.7 mg, 493 µmol) dissolved in water (2.5 mL) was added to the mixture, and the reaction solution was stirred at 25° C. for 12 hours. The reaction solution was adjusted to pH=5 with 12 N HCl, and concentrated under reduced pressure. The crude product was purified by high performance liquid chromatography {hydrochloric acid condition, column type: Venusil ASB Phenyl 150*30 mm*5 µm; mobile phase: [water (0.05% hydrochloric acid)-acetonitrile]; acetonitrile %: 42%-52%, 9 minutes} to obtain the hydrochloride of compound 34.

MS-ESI calculated for [M+H]$^+$ 507, found 507.

$^1$H NMR (400 MHz, CDCl$_3$) δ=12.11-11.84 (m, 1H), 8.53 (d, J=7.5 Hz, 1H), 8.43 (d, J=8.0 Hz, 1H), 8.14-8.05 (m, 1H), 8.04-7.92 (m, 1H), 7.60-7.53 (m, 1H), 7.50-7.42 (m, 1H), 6.79 (t, J=70.8 Hz, 1H), 4.36-3.83 (m, 2H), 3.65-3.18 (m, 6H), 2.62-2.21 (m, 4H), 1.75-1.56 (m, 4H).

Embodiment 35

Compound 35

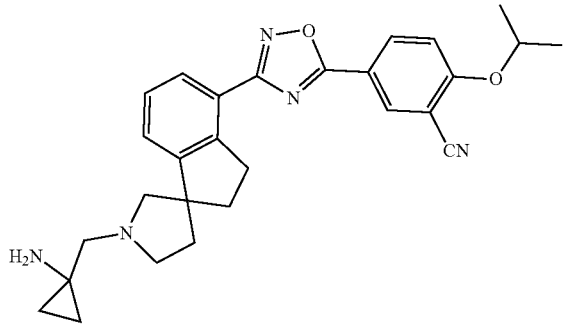

Synthetic route:

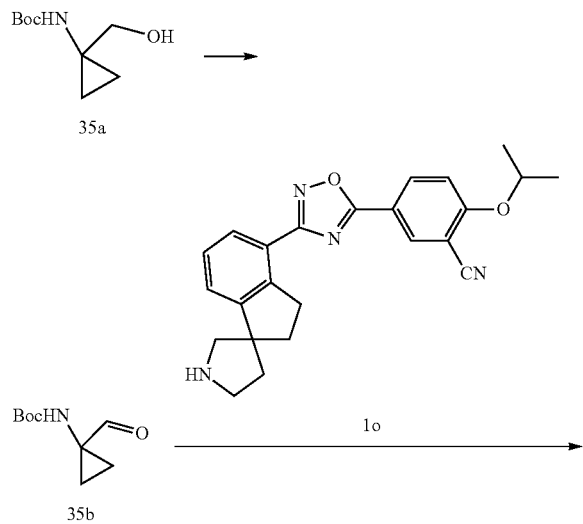

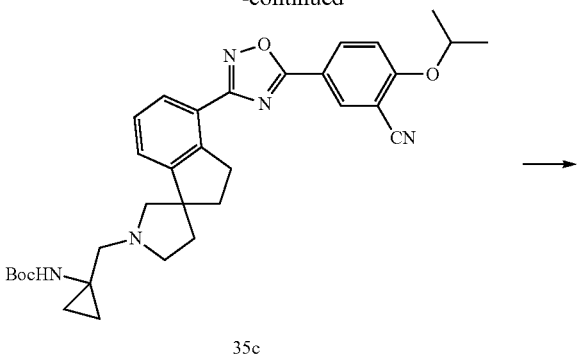

Hydrochloride of compound 35

Step 1

Compound 35a (50 mg, 0.27 mmol) was dissolved in anhydrous dichloromethane (5 mL), and then Dess-Martin periodinane (181 mg, 427 µmol) was added to the mixture. The reaction solution was stirred at 20° C. for 1 hour, and 10% aqueous sodium bicarbonate solution (10 mL) was added to the reaction solution. The mixture was extracted with dichloromethane (10 mL×3). The organic phases were combined, and the organic phases were washed with water (20 mL) and saturated brine (20 mL), dried over anhydrous sodium sulfate and concentrated under reduced pressure. Then the crude product was purified by thin-layer silica gel chromatography (2:1, petroleum ether/ethyl acetate) to obtain compound 35b.

$^1$H NMR (400 MHz, CDCl$_3$) δ=9.15 (s, 1H), 5.24 (s, 1H), 1.53-1.42 (m, 4H), 1.48 (s, 9H).

Step 2

The hydrochloride of compound 1o (100 mg, 228 µmol) and compound 35b (63.6 mg, 343 µmol) were dissolved in dichloromethane (10 mL). Glacial acetic acid (13.7 mg, 228 µmol) was added to the mixture, and the reaction solution was stirred at 25° C. for 8 hours. Sodium triacetoxyborohydride (194 mg, 915 µmol) was added to the reaction solution, and the reaction solution was stirred at 25° C. for 6 hours. The reaction solution was added with 10% aqueous sodium bicarbonate solution (10 mL), extracted with dichloromethane (10 mL×3). The organic phases were combined, and the organic phases were washed with water (20 mL) and saturated brine (20 mL), dried over anhydrous sodium sulfate and concentrated under reduced pressure. Then the crude product was purified by thin-layer silica gel chromatography (0:1, petroleum ether/ethyl acetate) to obtain compound 35c.

MS-ESI calculated for [M+H]$^+$ 570, found 570.

Step 3

Compound 35c (100 mg, 175 µmol) was dissolved in ethyl acetate (5 mL), and then hydrochloric acid/ethyl acetate (4M, 219 µL) was added to the mixture, and the reaction solution was stirred at 25° C. for 2 hours. The reaction solution was concentrated, and the crude product was purified by high performance liquid chromatography {hydrochloric acid conditions, column type: Boston Green ODS 150*30 mm*5 µm; mobile phase: [water (0.05% hydrochloric acid)-acetonitrile]; acetonitrile %: 17%-47%, 8 minutes} to obtain the hydrochloride of compound 35.

MS-ESI calculated for [M+H]$^+$ 470, found 470.

$^1$H NMR (400 MHz, DMSO-d$_6$) δ=8.78-8.66 (m, 1H), 8.63-8.54 (m, 1H), 8.41 (dd, J=9.0, 2.1 Hz, 1H), 8.08-7.98 (m, 1H), 7.61-7.47 (m, 2H), 5.05-4.92 (m, 1H), 4.38-3.08 (m, 8H), 2.65-1.84 (m, 8H), 1.39 (d, J=6.0 Hz, 6H).

Embodiment 36

Compound 36

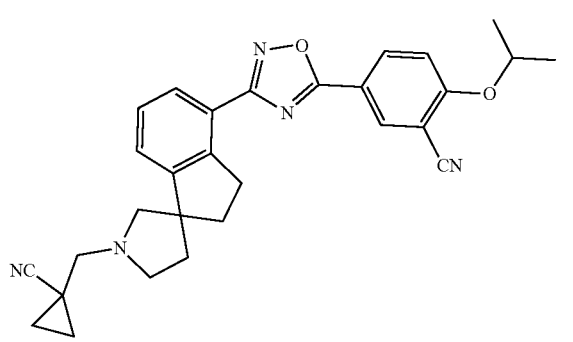

Synthetic route:

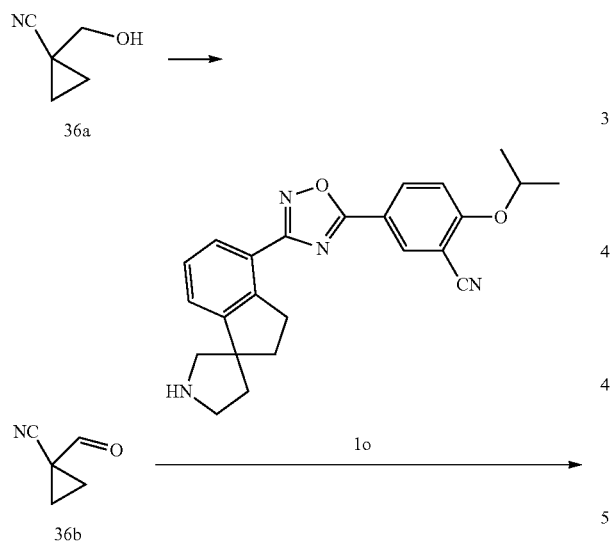

Step 1

Compound 36a (100 mg, 1.03 mmol) was dissolved in anhydrous dichloromethane (10 mL), and then Dess-Martin periodinane (699 mg, 1.65 mmol) was added to the mixture. The reaction solution was stirred at 20° C. for 1 hour, and 10% aqueous sodium bicarbonate solution (10 mL) was added to the reaction solution. The mixture was extracted with dichloromethane (10 mL×3). The organic phases were combined, and the organic phases were washed with water (20 mL) and saturated brine (20 mL), dried over anhydrous sodium sulfate and concentrated under reduced pressure.

Then the crude product was purified by thin-layer silica gel chromatography (1:1, petroleum ether/ethyl acetate) to obtain compound 36b.

$^1$H NMR (400 MHz, CDCl$_3$) δ=9.33 (s, 1H), 1.82-1.72 (m, 4H).

Step 2

Compound 1o (70 mg, 0.16 μmol) and compound 36b (22.8 mg, 240 μmol) were dissolved in dichloromethane (8 mL). Glacial acetic acid (1.92 mg, 32.0 μmol) was added to the reaction solution, and the reaction solution was stirred at 25° C. for 8 hours. Sodium triacetoxyborohydride (136 mg, 640 μmol) was added to the reaction solution, and the reaction solution was stirred at 25° C. for 6 hours. 10% aqueous sodium bicarbonate solution (10 mL) was added to the reaction solution, and the mixture was extracted with dichloromethane (10 mL×3). The organic phases were combined, and the organic phases were washed with water (20 mL) and saturated brine (20 mL), dried over sodium sulfate and concentrated under reduced pressure. Then the crude product was purified by high performance liquid chromatography {hydrochloric acid conditions, column type: Venusil ASB Phenyl 150*30 mm*5 μm; mobile phase: [water (0.05% hydrochloric acid)-acetonitrile]; acetonitrile %: 45%-55%, 9 minutes} to obtain the hydrochloride of compound 36.

MS-ESI calculated for [M+H]$^+$ 480, found 480.

Embodiment 37

Compound 37

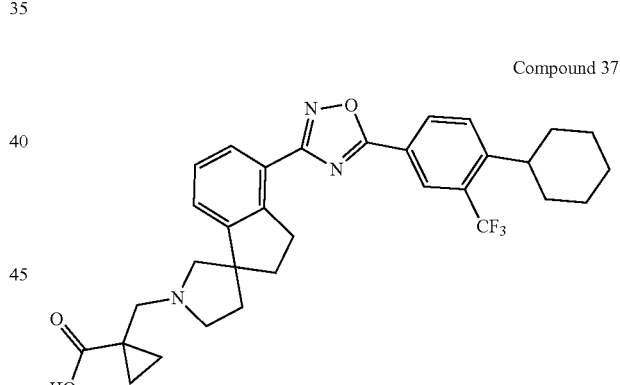

Synthetic route:

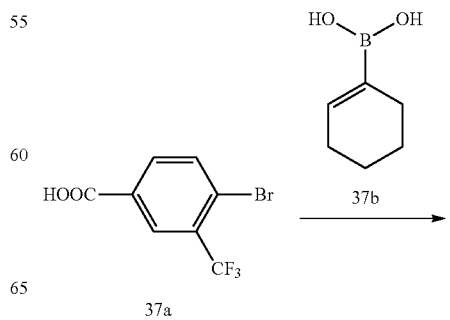

117
-continued

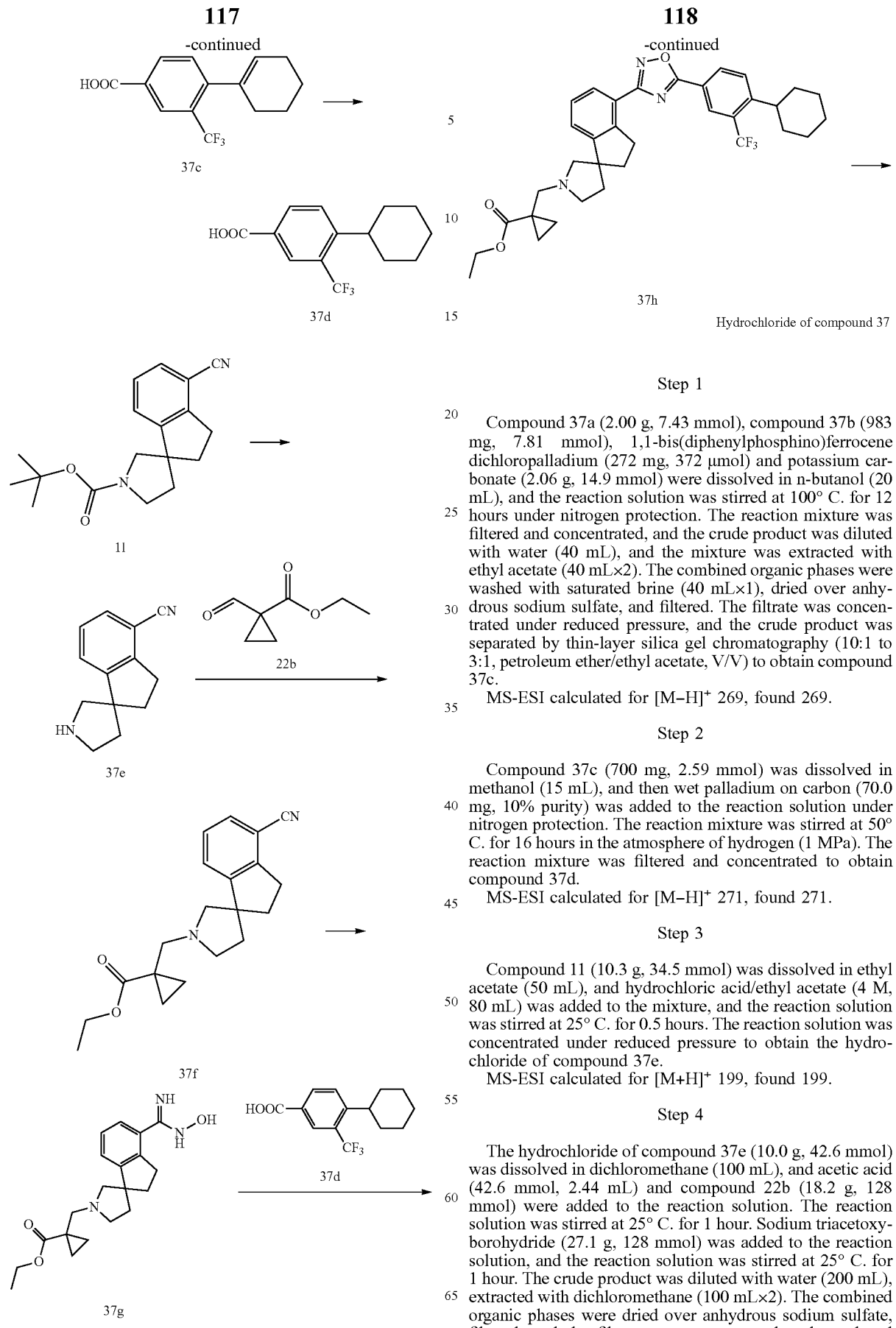

118
-continued

Hydrochloride of compound 37

Step 1

Compound 37a (2.00 g, 7.43 mmol), compound 37b (983 mg, 7.81 mmol), 1,1-bis(diphenylphosphino)ferrocene dichloropalladium (272 mg, 372 μmol) and potassium carbonate (2.06 g, 14.9 mmol) were dissolved in n-butanol (20 mL), and the reaction solution was stirred at 100° C. for 12 hours under nitrogen protection. The reaction mixture was filtered and concentrated, and the crude product was diluted with water (40 mL), and the mixture was extracted with ethyl acetate (40 mL×2). The combined organic phases were washed with saturated brine (40 mL×1), dried over anhydrous sodium sulfate, and filtered. The filtrate was concentrated under reduced pressure, and the crude product was separated by thin-layer silica gel chromatography (10:1 to 3:1, petroleum ether/ethyl acetate, V/V) to obtain compound 37c.

MS-ESI calculated for [M−H]$^+$ 269, found 269.

Step 2

Compound 37c (700 mg, 2.59 mmol) was dissolved in methanol (15 mL), and then wet palladium on carbon (70.0 mg, 10% purity) was added to the reaction solution under nitrogen protection. The reaction mixture was stirred at 50° C. for 16 hours in the atmosphere of hydrogen (1 MPa). The reaction mixture was filtered and concentrated to obtain compound 37d.

MS-ESI calculated for [M−H]$^+$ 271, found 271.

Step 3

Compound 11 (10.3 g, 34.5 mmol) was dissolved in ethyl acetate (50 mL), and hydrochloric acid/ethyl acetate (4 M, 80 mL) was added to the mixture, and the reaction solution was stirred at 25° C. for 0.5 hours. The reaction solution was concentrated under reduced pressure to obtain the hydrochloride of compound 37e.

MS-ESI calculated for [M+H]$^+$ 199, found 199.

Step 4

The hydrochloride of compound 37e (10.0 g, 42.6 mmol) was dissolved in dichloromethane (100 mL), and acetic acid (42.6 mmol, 2.44 mL) and compound 22b (18.2 g, 128 mmol) were added to the reaction solution. The reaction solution was stirred at 25° C. for 1 hour. Sodium triacetoxyborohydride (27.1 g, 128 mmol) was added to the reaction solution, and the reaction solution was stirred at 25° C. for 1 hour. The crude product was diluted with water (200 mL), extracted with dichloromethane (100 mL×2). The combined organic phases were dried over anhydrous sodium sulfate, filtered, and the filtrate was concentrated under reduced pressure. The crude product was separated by thin-layer silica gel chromatography (200:1 to 20:1, dichloromethane/methanol, V/V) to obtain compound 37f.

MS-ESI calculated for [M+H]$^+$ 325, found 325.

Step 5

Compound 37f (12.7 g, 39.2 mmol) was dissolved in anhydrous ethanol (150 mL), and hydroxylamine hydrochloride (8.16 g, 117 mmol) and triethylamine (16.4 mL, 117 mmol) were added to the mixture. The reaction solution was stirred at 80° C. for 5 hours. The reaction solution was concentrated under reduced pressure, and the crude product was purified by high performance liquid chromatography (chromatographic column: Phenomenex Synergi Max-RP 250×50 mm×10 μm; mobile phase: [water (0.1% TFA)-acetonitrile]; acetonitrile %: 1%-20%, 20 minutes) to obtain trifluoroacetate of compound 37g.

MS-ESI calculated for [M+H]$^+$ 358, found 358.

Step 6

Compound 37d (693 mg, 2.55 mmol) was dissolved in N,N-dimethylformamide (20 mL), and 1-hydroxybenzotriazole (413 mg, 3.05 mmol) and 1-ethyl-(3-dimethylaminopropyl)carbodiimide hydrochloride (586 mg, 3.05 mmol) were added to the mixture. The reaction solution was stirred at 20° C. for 1 hour, and the trifluoroacetate of compound 37g (1.20 g, 2.55 mmol) was added to the mixture. The reaction solution was stirred at 20° C. for 2 hours and then stirred at 80° C. for 8 hours. The reaction solution was diluted with water (100 mL), extracted with ethyl acetate (40 mL×2). The combined organic phases were dried over anhydrous sodium sulfate, filtered, and the filtrate was concentrated under reduced pressure. The crude product was separated by thin-layer silica gel chromatography (1:0 to 20:1, dichloromethane/methanol, V/V) to obtain compound 37h.

MS-ESI calculated for [M+H]$^+$ 594, found 594.

Step 7

Compound 37h (400 mg, 416 μmol) was dissolved in tetrahydrofuran (5 mL), methanol (5 mL) and water (2 mL), and lithium hydroxide monohydrate (52.4 mg, 1.25 mmol) was added thereto. The reaction solution was stirred at 25° C. for 12 hours. The reaction solution was concentrated under reduced pressure to remove the organic solvent, and the residue was diluted with water (30 mL), adjusted to pH=3 with 1 N aqueous hydrochloric acid solution, and extracted with ethyl acetate (30 mL×2). The combined organic phases were dried over anhydrous sodium sulfate, filtered and concentrated, and the crude product was purified by high performance liquid chromatography (chromatographic column: Phenomenex Gemini-NX C18 75×30 mm×3 μm; mobile phase: [water (0.225% FA)-acetonitrile]; acetonitrile %: 45%-75%, 7 minutes) to obtain the formate of compound 37.

MS-ESI calculated for [M+H]$^+$ 566, found 566.

$^1$H NMR (400 MHz, CD$_3$OD) δ=8.47-8.38 (m, 2H), 8.14-8.10 (m, 1H), 7.86 (d, J=8.2 Hz, 1H), 7.59 (d, J=7.2 Hz, 1H), 7.53-7.47 (m, 1H), 3.73-3.60 (m, 2H), 3.46-3.35 (m, 4H), 3.04 (t, J=11.4 Hz, 1H), 2.48-2.29 (m, 4H), 2.00-1.74 (m, 6H), 1.71-1.36 (m, 6H), 1.33-1.26 (m, 2H), 0.89-0.82 (m, 2H).

Embodiment 38

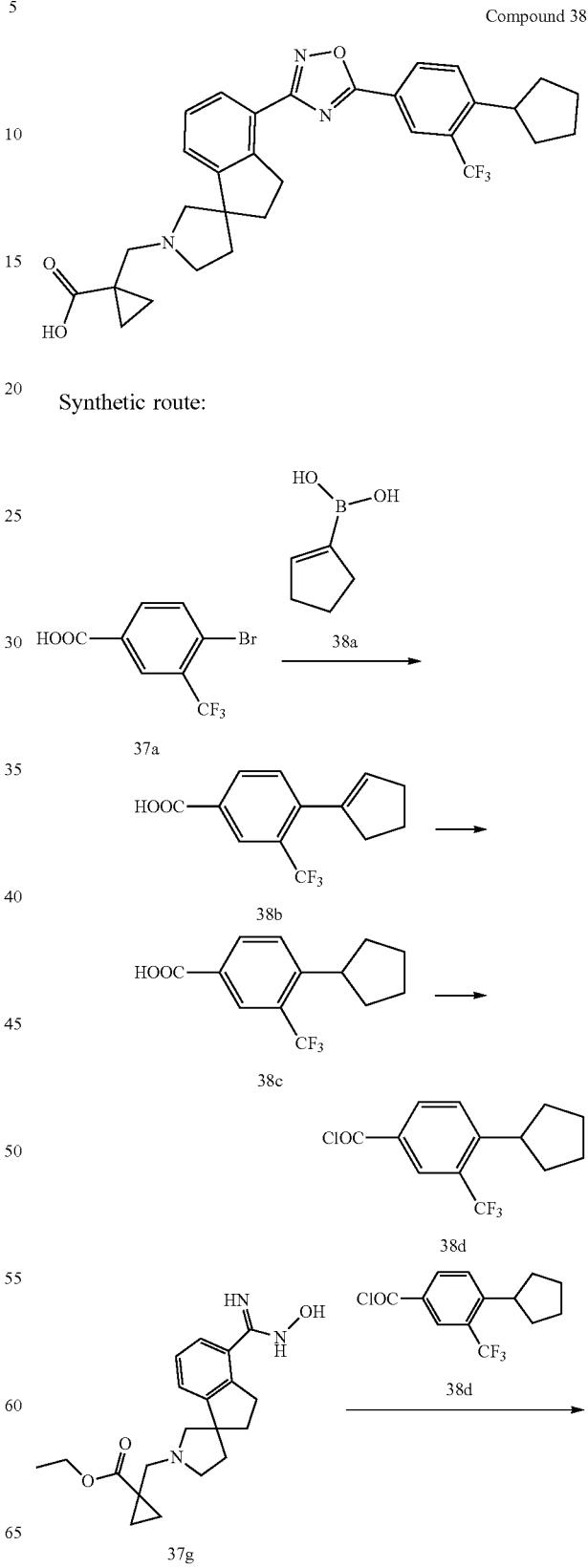

Synthetic route:

-continued

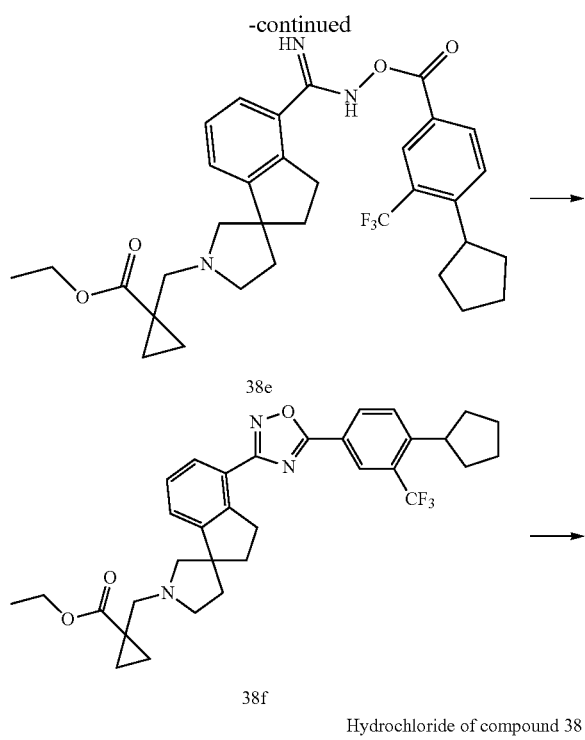

38e

38f

Hydrochloride of compound 38

Step 1

Compound 37a (2.00 g, 7.43 mmol), compound 38a (874 mg, 7.81 mmol), 1,1-bis(diphenylphosphino)ferrocene dichloropalladium (272 mg, 372 µmol) and potassium carbonate (2.05 g, 14.9 mmol) were dissolved in n-butanol (20 mL), and the reaction solution was stirred at 100° C. for 12 hours under nitrogen protection. The reaction mixture was filtered and concentrated, and the crude product was diluted with water (40 mL), and the mixture was extracted with ethyl acetate (40 mL×2). The combined organic phases were washed with saturated brine (40 mL×1), dried over anhydrous sodium sulfate, and filtered. The filtrate was concentrated under reduced pressure, and the crude product was separated by thin-layer silica gel chromatography (10:1 to 3:1, petroleum ether/ethyl acetate, V/V) to obtain compound 38b.

MS-ESI calculated for [M−H]⁺ 255, found 255.

Step 2

Compound 38b (700 mg, 2.73 mmol) was dissolved in methanol (15 mL), and then wet palladium on carbon (70.0 mg, 10% purity) was added to the reaction solution under nitrogen protection. The reaction mixture was stirred at 50° C. for 16 hours in the atmosphere of hydrogen (1 MPa). The reaction mixture was filtered and concentrated to obtain compound 38c.

MS-ESI calculated for [M−H]⁺ 257, found 257.

Step 3

Compound 38c (300 mg, 1.16 mmol) was dissolved in dichloromethane (6 mL), and oxalyl chloride (305 µL, 3.49 mmol) and N,N-dimethylformamide (8.49 mg, 116 µmol) were added to the reaction solution. The reaction solution was stirred at 25° C. for 0.5 hours, and the reaction solution was concentrated under reduced pressure to obtain compound 38d.

Step 4

Compound 38d (317 mg, 1.15 mmol) was dissolved in dichloromethane (8 mL), and triethylamine (1.91 mmol, 333 µL) and trifluoroacetate of compound 37g (300 mg, 636 µmol) were added to the reaction solution, and the reaction solution was stirred at 25° C. for 12 hours. The reaction solution was diluted with water (20 mL), extracted with dichloromethane (20 mL×2). The combined organic phases were dried over anhydrous sodium sulfate, filtered, and the filtrate was concentrated under reduced pressure to obtain compound 38e.

MS-ESI calculated for [M+H]⁺ 598, found 598.

Step 5

Compound 38e (522 mg, 873 µmol) was dissolved in acetonitrile (8 mL), and sodium hydroxide (34.9 mg, 873 µmol) was added to the reaction solution, and the reaction solution was stirred at 25° C. for 1 hour. The reaction solution was concentrated under reduced pressure, and the crude product was diluted with water (20 mL), extracted with ethyl acetate (20 mL×2). The combined organic phases were dried over anhydrous sodium sulfate, filtered, and the filtrate was concentrated under reduced pressure to obtain compound 38f.

MS-ESI calculated for [M+H]⁺ 580, found 580.

Step 6

Compound 38f (464 mg, 800 µmol) was dissolved in tetrahydrofuran (4 mL), methanol (4 mL) and water (2 mL), and lithium hydroxide monohydrate (101 mg, 2.40 mmol) was added thereto. The reaction solution was stirred at 25° C. for 12 hours. The reaction solution was concentrated under reduced pressure to remove the organic solvent, and the residue was diluted with water (30 mL), adjusted to pH=3 with 1 N aqueous hydrochloric acid solution, and extracted with ethyl acetate (30 mL×2). The combined organic phases were dried over anhydrous sodium sulfate, filtered and concentrated, and the crude product was purified by high performance liquid chromatography (chromatographic column: 3_Phenomenex Luna C18 75×30 mm×3 µm; mobile phase: [water (0.05% HCl)-acetonitrile]; acetonitrile %: 48%-68%, 6.5 minutes) to obtain the hydrochloride of compound 38.

MS-ESI calculated for [M+H]⁺ 552, found 552.

¹H NMR (400 MHz, CD₃OD) δ=8.46-8.39 (m, 2H), 8.17-8.11 (m, 1H), 7.87 (d, J=8.4 Hz, 1H), 7.61 (d, J=7.4 Hz, 1H), 7.54-7.48 (m, 1H), 3.97 (s, 2H), 3.70-3.37 (m, 7H), 2.58-2.24 (m, 4H), 2.22-2.10 (m, 2H), 2.04-1.91 (m, 2H), 1.86-1.68 (m, 4H), 1.52 (d, J=2.4 Hz, 2H), 1.20 (s, 2H).

Embodiment 39

Compound 39

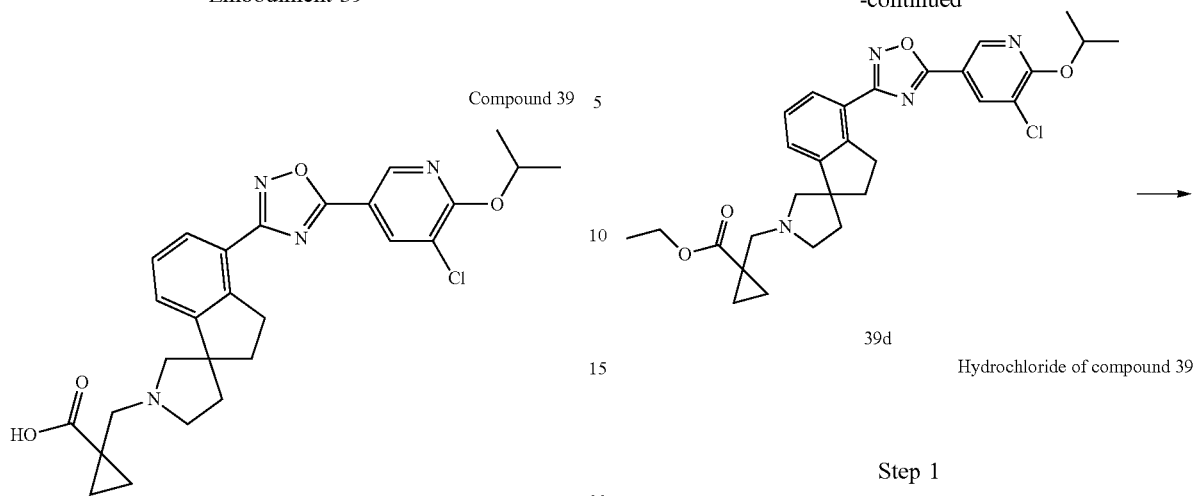

Synthetic route:

Step 1

Compound 39a (400 mg, 1.86 mmol) was dissolved in dichloromethane (6 mL), and oxalyl chloride (650 μL, 7.42 mmol) and N,N-dimethylformamide (27.1 mg, 371 μmol) were added to the reaction solution. The reaction solution was stirred at 25° C. for 0.5 hours, and the reaction solution was concentrated under reduced pressure to obtain compound 39b.

Step 2

The trifluoroacetate of compound 37g (550 mg, 1.17 mmol) and compound 39b (437 mg, 1.87 mmol) were dissolved in dichloromethane (10 mL), and N,N-diisopropylethylamine (3.50 mmol, 610 μL) was added to the reaction solution, and the reaction solution was stirred at 25° C. for 1 hour. The reaction solution was diluted with water (30 mL), extracted with dichloromethane (20 mL×2). The combined organic phases were dried over anhydrous sodium sulfate, filtered, and the filtrate was concentrated under reduced pressure to obtain compound 39c.

MS-ESI calculated for [M+H]$^+$ 555, found 555.

Step 3

Compound 39c (800 mg, 1.44 mmol) was dissolved in acetonitrile (15 mL), and sodium hydroxide (115 mg, 2.88 mmol) was added to the reaction solution, and the reaction solution was stirred at 25° C. for 1 hour. The reaction solution was concentrated under reduced pressure, and the crude product was diluted with water (20 mL), extracted with ethyl acetate (20 mL×2). The combined organic phases were dried over anhydrous sodium sulfate, filtered, and the filtrate was concentrated under reduced pressure to obtain compound 39d.

MS-ESI calculated for [M+H]$^+$ 537, found 537.

Step 4

Compound 39d (483 mg, 899 μmol) was dissolved in tetrahydrofuran (6 mL), methanol (3 mL) and water (3 mL), and lithium hydroxide monohydrate (113 mg, 2.70 mmol) was added thereto. The reaction solution was stirred at 25° C. for 12 hours. The reaction solution was concentrated under reduced pressure, and the crude product was separated by high performance liquid chromatography (chromatographic column: 3_Phenomenex Luna C18 75×30 mm×3 μm; mobile phase: 0.05% aqueous hydrochloric acid solution-acetonitrile; gradient: acetonitrile 39%-59%, 6.5 min) to obtain the hydrochloride of compound 39.

MS-ESI calculated for [M+H]⁺ 509, found 509.

¹H NMR (400 MHz, DMSO-d₆) δ=11.55-9.82 (m, 1H), 8.90 (d, J=2.2 Hz, 1H), 8.52 (d, J=2.2 Hz, 1H), 7.99 (d, J=7.4 Hz, 1H), 7.77 (d, J=7.6 Hz, 1H), 7.50 (t, J=7.6 Hz, 1H), 5.47-5.39 (m, 1H), 3.67-3.51 (m, 3H), 3.26-3.16 (m, 3H), 2.34 (s, 1H), 2.29-2.17 (m, 3H), 1.38 (d, J=6.2 Hz, 7H), 1.33-1.28 (m, 3H).

Embodiment 40

Compound 40

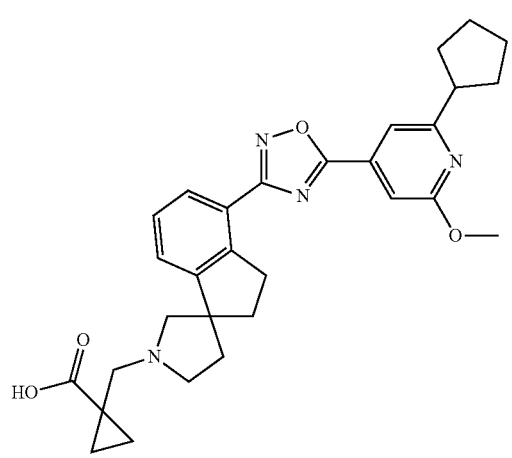

Synthetic route:

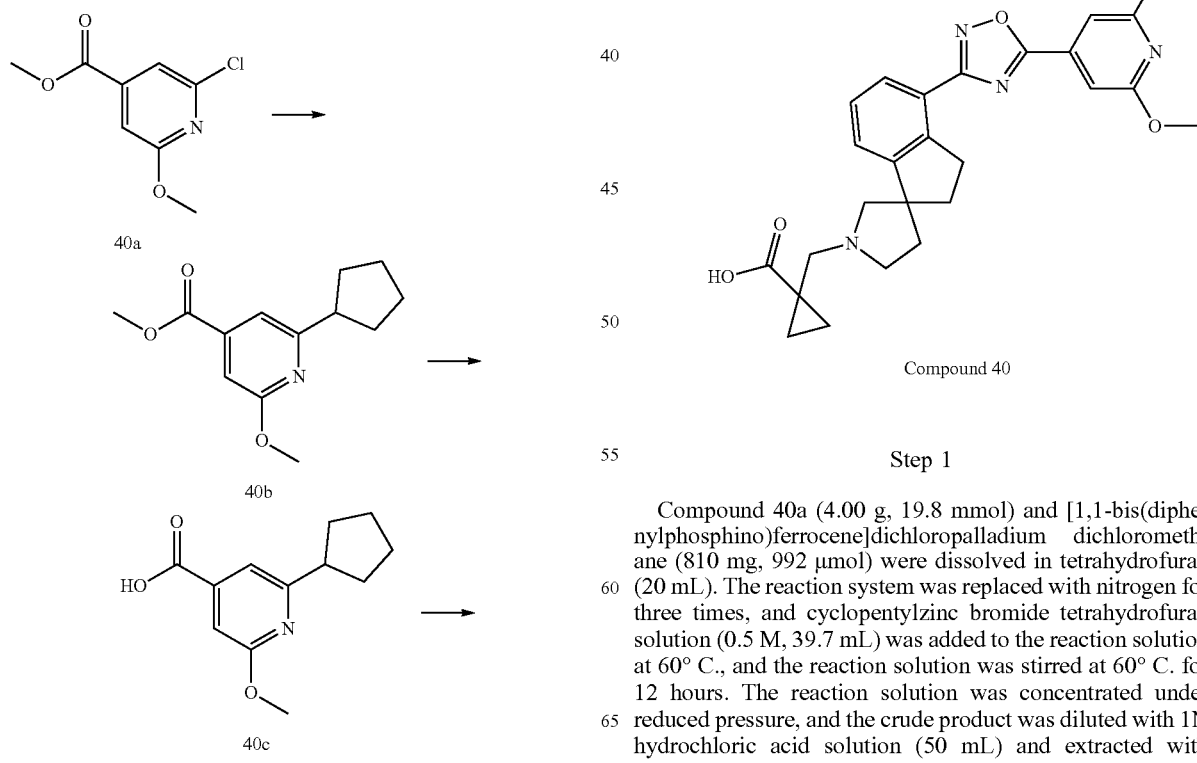

Step 1

Compound 40a (4.00 g, 19.8 mmol) and [1,1-bis(diphenylphosphino)ferrocene]dichloropalladium dichloromethane (810 mg, 992 μmol) were dissolved in tetrahydrofuran (20 mL). The reaction system was replaced with nitrogen for three times, and cyclopentylzinc bromide tetrahydrofuran solution (0.5 M, 39.7 mL) was added to the reaction solution at 60° C., and the reaction solution was stirred at 60° C. for 12 hours. The reaction solution was concentrated under reduced pressure, and the crude product was diluted with 1N hydrochloric acid solution (50 mL) and extracted with methyl tert-butyl ether (50 mL×3). The combined organic phases were washed with 1N hydrochloric acid solution (50 mL×1), dried over anhydrous sodium sulfate, filtered, and the filtrate was concentrated under reduced pressure. The crude product was separated by thin-layer silica gel chromatography (1:0, petroleum ether/ethyl acetate, V/V) to obtain compound 40b.

MS-ESI calculated for [M+H]$^+$ 236, found 236.

Step 2

Compound 40b (2.50 g, 10.6 mmol) was dissolved in ethanol (25 mL) and water (5 mL), and sodium hydroxide (1.27 g, 31.9 mmol) was added thereto, and the reaction solution was stirred at 90° C. for 0.5 hours. The reaction solution was concentrated under reduced pressure to remove the organic solvent, and the residue was diluted with water (100 mL), adjusted to pH=4 with 1 N aqueous hydrochloric acid solution, and extracted with dichloromethane (100 mL×2). The combined organic phases were dried over anhydrous sodium sulfate, filtered and concentrated, and the crude product was separated by thin-layer silica gel chromatography (10:1 to 2:1, petroleum ether/ethyl acetate, V/V) to obtain compound 40c.

MS-ESI calculated for [M+H]$^+$ 222, found 222.

Step 3

Compound 40c (200 mg, 904 μmol) was dissolved in dichloromethane (5 mL), and oxalyl chloride (237 μL, 2.71 mmol) and N,N-dimethylformamide (6.61 mg, 90.4 μmol) were added to the reaction solution. The reaction solution was stirred at 25° C. for 1 hour, and the reaction solution was concentrated under reduced pressure to obtain compound 40d.

Step 4

Compound 37g (200 mg, 560 μmol) and compound 40d (201 mg, 839 μmol) were dissolved in dichloromethane (6 mL), and N,N-diisopropylethylamine (839 μmol, 146 μL) was added to the reaction solution, and the reaction solution was stirred at 25° C. for 2 hours. The reaction solution was diluted with saturated aqueous sodium bicarbonate solution (50 mL), extracted with ethyl acetate (40 mL×3). The combined organic phases were dried over anhydrous sodium sulfate, filtered, and the filtrate was concentrated under reduced pressure. The crude product was separated by thin-layer chromatography (dichloromethane/methanol, 10/1, V/V) to obtain compound 40e.

MS-ESI calculated for [M+H]$^+$ 543, found 543.

Step 5

Compound 40e (68.0 mg, 125 μmol) was dissolved in tetrahydrofuran (3 mL) and methanol (3 mL), then 1M aqueous sodium hydroxide solution (4.26 mL) was added thereto, and the reaction solution was stirred at 50° C. for 3 hours. The reaction solution was cooled to 25° C., adjusted to pH=4-5 with 1 N aqueous hydrochloric acid solution, diluted with water (10 mL), and then concentrated under reduced pressure to remove the organic solvent. The aqueous phase was extracted with dichloromethane (40 mL×3), and the combined organic phases were dried over anhydrous sodium sulfate, filtered, and the filtrate was concentrated under reduced pressure. The crude product was separated by high performance liquid chromatography (chromatographic column: Phenomenex Gemini-NX C18 75×30 mm×3 μm; mobile phase: 10 mmol/L aqueous ammonium bicarbonate solution-acetonitrile; gradient: acetonitrile 44%-74%, 10 minutes) to obtain compound 40.

MS-ESI calculated for [M+H]$^+$ 515, found 515.

$^1$H NMR (400 MHz, CD$_3$OD) δ 8.11-8.15 (m, 1H), 7.60-7.62 (m, 1H), 7.49-7.54 (m, 2H), 7.30-7.31 (m, 1H), 4.00 (s, 3H), 3.40-3.54 (m, 7H), 2.37-2.40 (m, 5H), 2.09-2.11 (m, 2H), 1.90-1.93 (m, 5H), 1.87-1.89 (m, 2H), 1.44-1.46 (m, 2H), 1.07-1.08 (m, 2H).

Embodiment 43

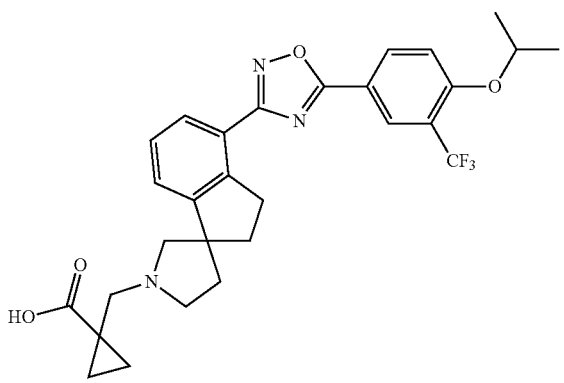

Compound 43

Synthetic route:

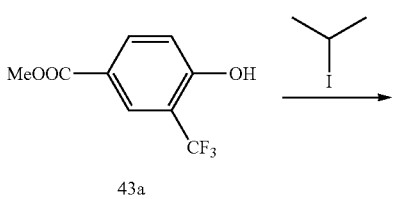

43a

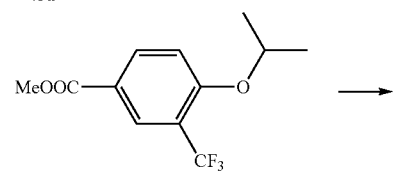

43b

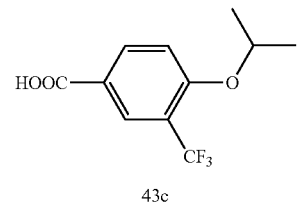

43c

-continued

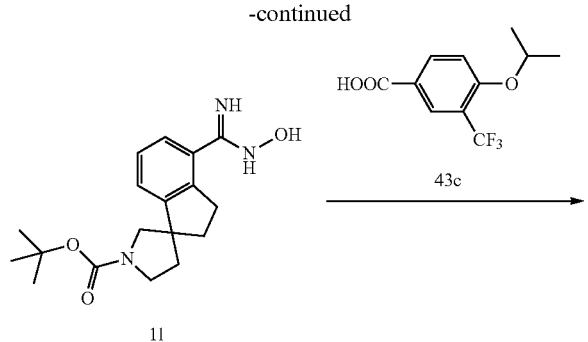

11

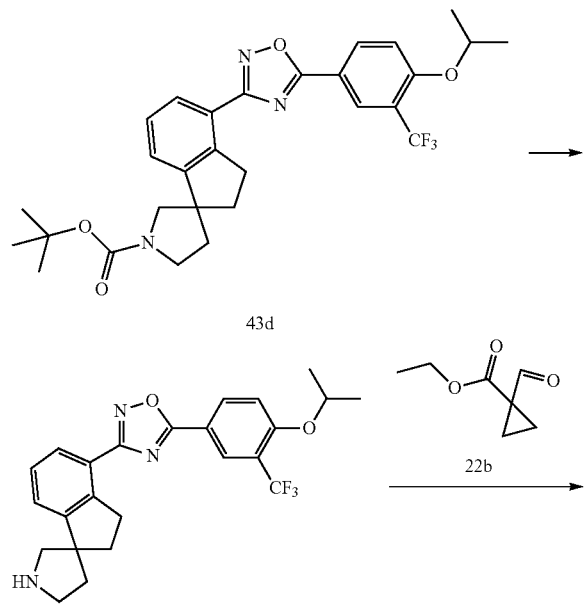

43d

43e

43f

Hydrochloride of compound 43

Step 1

Intermediate 43a (1000 mg, 5 mmol), iodoethylpropane (927 mg, 6 mmol) and silver carbonate (1250 mg, 5 mmol) were added to toluene (10 mL). The reaction solution was heated to 50° C. and reacted for 12 hours. The reaction solution was added to water (50 mL), extracted with ethyl acetate (30 mL×3), and the organic phases were combined, dried over anhydrous sodium sulfate, concentrated under reduced pressure and separated by silica gel column chromatography (petroleum ether/ethyl acetate, 100/1-5/1, V/V) to obtain intermediate 43b.

MS-ESI calculated for [M+H]$^+$ 263, found 263.

Step 2

Intermediate 43b (1260 mg, 5 mmol), lithium hydroxide hydrate (605 mg, 14 mmol) were added to tetrahydrofuran (12 mL) and water (3 mL). The reaction solution was reacted at room temperature for 12 hours. The reaction solution was added to water (20 mL), extracted with ethyl acetate (20 mL×3), and the organic phases were combined, dried over anhydrous sodium sulfate, and concentrated under reduced pressure to obtain intermediate 43c.

MS-ESI calculated for [M+H]$^+$ 249, found 249.

Step 3

Intermediate 11 (400 mg, 1 mmol), intermediate 43c (300 mg, 1 mmol), 1-hydroxybenzotriazole (196 mg, 1.5 mmol) and 1-(3-dimethylaminopropyl)-3-ethylcarbodiimide hydrochloride (278 mg, 1.5 mmol) were added to N,N-dimethylformamide (20 mL). The reaction solution was heated to 80° C. and reacted for 11 hours. The reaction solution was added to water (150 mL), extracted with ethyl acetate (40 mL×3), and the organic phases were combined, dried over anhydrous sodium sulfate, and concentrated under reduced pressure to obtain the crude product of compound 43d.

MS-ESI calculated for [M+Na]$^+$ 566, found 566.

Step 4

Compound 43d (815 mg, 1.5 mmol), 4M hydrochloric acid and ethyl acetate (1.87 mL) were added to ethyl acetate (6 mL), and the reaction solution was reacted at 25° C. for 1 hour. The reaction solution was concentrated under reduced pressure and separated by thin-layer silica gel chromatography (20:1, petroleum ether/ethyl acetate, V/V) to obtain the hydrochloride of intermediate 43e.

MS-ESI calculated for [M+H]$^+$ 444, found 444.

Step 5

The hydrochloride of intermediate 43e (250 mg, 564 μmol), intermediate 22b (240 mg, 1.7 mmol) and acetic acid (34 mg, 564 μmol) were added into dichloromethane (20 mL). The reaction solution was stirred at 25° C. for 1 hour, and then sodium triacetoxyborohydride (478 mg, 2.3 mmol) was added to the reaction solution, and the reaction solution was stirred at 25° C. for 13 hours. The reaction solution was added to 10% sodium bicarbonate solution (50 mL), extracted with dichloromethane (30 mL×3), and the organic phases were combined, dried over anhydrous sodium sulfate, concentrated under reduced pressure and separated by silica gel column chromatography (petroleum ether/ethyl acetate, 4/1-1/1, V/V) to obtain intermediate 43f.

MS-ESI calculated for [M+H]$^+$ 570, found 570.

Step 6

Compound 43f (100 mg, 176 μmol), lithium hydroxide hydrate (22 mg, 527 μmol) were added to tetrahydrofuran (10 mL) and water (2.5 mL), and the reaction solution was reacted at 25° C. for 12 hours. The reaction solution was concentrated under reduced pressure to obtain a crude product. The crude product was separated by high performance liquid chromatography (chromatographic column: Phenomenex Luna C18 75×30 mm×3 μm; mobile phase: 0.05% aqueous hydrochloric acid solution-acetonitrile; gradient: acetonitrile 38%-58%, 6.5 min) to obtain the hydrochloride of compound 43.

MS-ESI calculated for [M+H]$^+$ 542, found 542.

$^1$H NMR (400 MHz, CD$_3$OD) δ 8.42-8.33 (m, 2H), 8.10 (d, J=7.6 Hz, 1H), 7.62 (br s, 1H), 7.53-7.40 (m, 2H), 4.05-3.85 (m, 2H), 3.69-3.55 (m, 3H), 3.53-3.35 (m, 4H), 2.66 (s, 1H), 2.54-2.24 (m, 4H), 1.52 (br s, 2H), 1.42 (d, J=6.0 Hz, 6H), 1.30-1.21 (m, 2H).

Embodiment 44

Compound 44

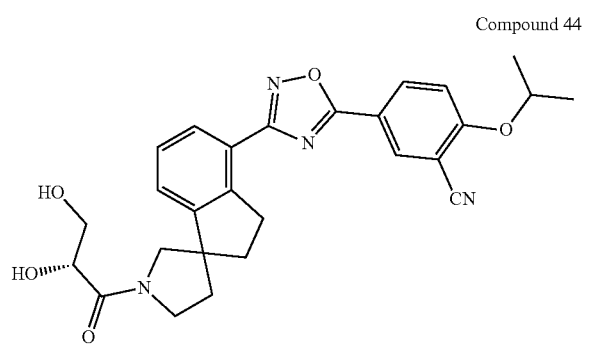 [SMILES: CC(C)Oc1ccc(-c2nc(-c3cccc4c3CCC43CCN(C(=O)[C@H](O)CO)C3)no2)cc1C#N]

Synthetic route:

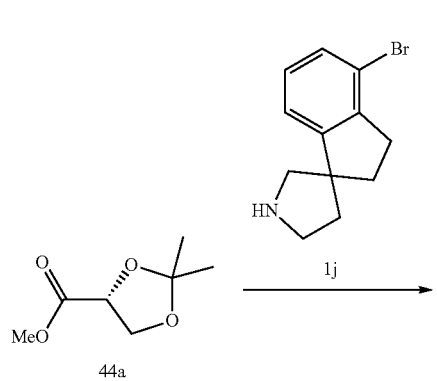

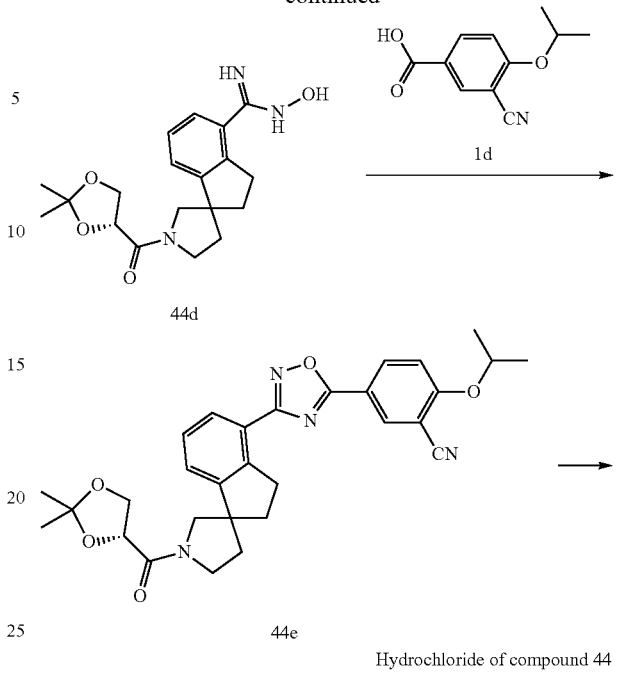

Hydrochloride of compound 44

Step 1

Intermediate 1j (3940 mg, 16 mmol) was added to intermediate 44a (3000 mg, 19 mmol). The reaction solution was heated to 25° C. and reacted for 60 hours. The reaction solution was concentrated under reduced pressure and separated by silica gel column chromatography (dichloromethane/methanol, 100/1 to 100/1, V/V) to obtain intermediate 44b.

MS-ESI calculated for [M+H]$^+$ 380, 382, found 380, 382.

Step 2

Compound 44b (1120 mg, 3 mmol) was dissolved in anhydrous N,N-dimethylformamide (25 mL), and zinc cyanide (660 mg, 5.6 mmol), tris(dibenzylideneacetone)dipalladium (81 mg, 88 μmol) and 2-di-tert-butylphosphino-2',4',6'-triisopropylbiphenyl (84 mg, 177 μmol) were added thereto, and the reaction system was replaced with nitrogen for three times. Under nitrogen protection, the reaction solution was stirred at 90° C. for 12 hours, and the reaction solution was concentrated after completion of the reaction. The residue was diluted with water (140 mL), extracted with ethyl acetate (50 mL×3). The combined organic phases were washed with saturated brine (100 mL), dried over anhydrous sodium sulfate, concentrated, and purified by silica gel column chromatography (petroleum ether/ethyl acetate, 1/0 to 0/1, V/V) to obtain intermediate 44c.

MS-ESI calculated for [M+H]$^+$ 327, found 327.

Step 3

Intermediate 44c (503 mg, 1.5 mmol), hydroxylamine hydrochloride (321 mg, 4.6 mmol) and triethylamine (468 mg, 4.6 mmol) were added to ethanol (10 mL). The reaction solution was reacted at 80° C. for 4 hours. The reaction solution was added to water (50 mL), extracted with ethyl acetate (60 mL×3), and the organic phases were combined, dried over anhydrous sodium sulfate, concentrated under reduced pressure and separated by thin-layer silica gel chromatography (20:1, petroleum ether/ethyl acetate, V/V) to obtain intermediate 44d.

MS-ESI calculated for [M+H]+ 360, found 360.

Step 4

Intermediate 44d (452 mg, 1 mmol), intermediate 1d (215 mg, 1 mmol), 1-hydroxybenzotriazole (170 mg, 1.3 mmol) and 1-(3-dimethylaminopropyl)-3-ethylcarbodiimide hydrochloride (241 mg, 1.3 mmol) were added to N—N dimethylformamide (30 mL). The reaction solution was heated to 80° C. and reacted for 11 hours. The reaction solution was added to water (120 mL), extracted with ethyl acetate (40 mL×2), and the organic phases were combined, dried over anhydrous sodium sulfate, and concentrated under reduced pressure to obtain the crude product of compound 44e.

MS-ESI calculated for [M+H]+ 529, found 529.

Step 5

Compound 44e (57 mg, 108 μmol) was added to acetic acid (149 mg, 2.5 mmol), and the reaction solution was reacted at 35° C. for 12 hours. The reaction solution was concentrated under reduced pressure to obtain a crude product. The crude product was separated by high performance liquid chromatography (chromatographic column: Phenomenex Luna C18 75×30 mm×3 μm; mobile phase: 0.05% aqueous hydrochloric acid solution-acetonitrile; gradient: acetonitrile 46%-66%, 6.5 min) to obtain the hydrochloride of compound 44.

MS-ESI calculated for [M+H]+ 489, found 489.

1H NMR (400 MHz, CD3OD) δ 8.36-8.27 (m, 2H), 8.00-7.91 (m, 1H), 7.48-7.29 (m, 3H), 4.96-4.88 (m, 2H), 4.63-4.42 (m, 1H), 4.04-3.51 (m, 7H), 2.33-1.98 (m, 4H), 1.44 (d, J=6.0 Hz, 6H).

Embodiment 45

Synthetic route:

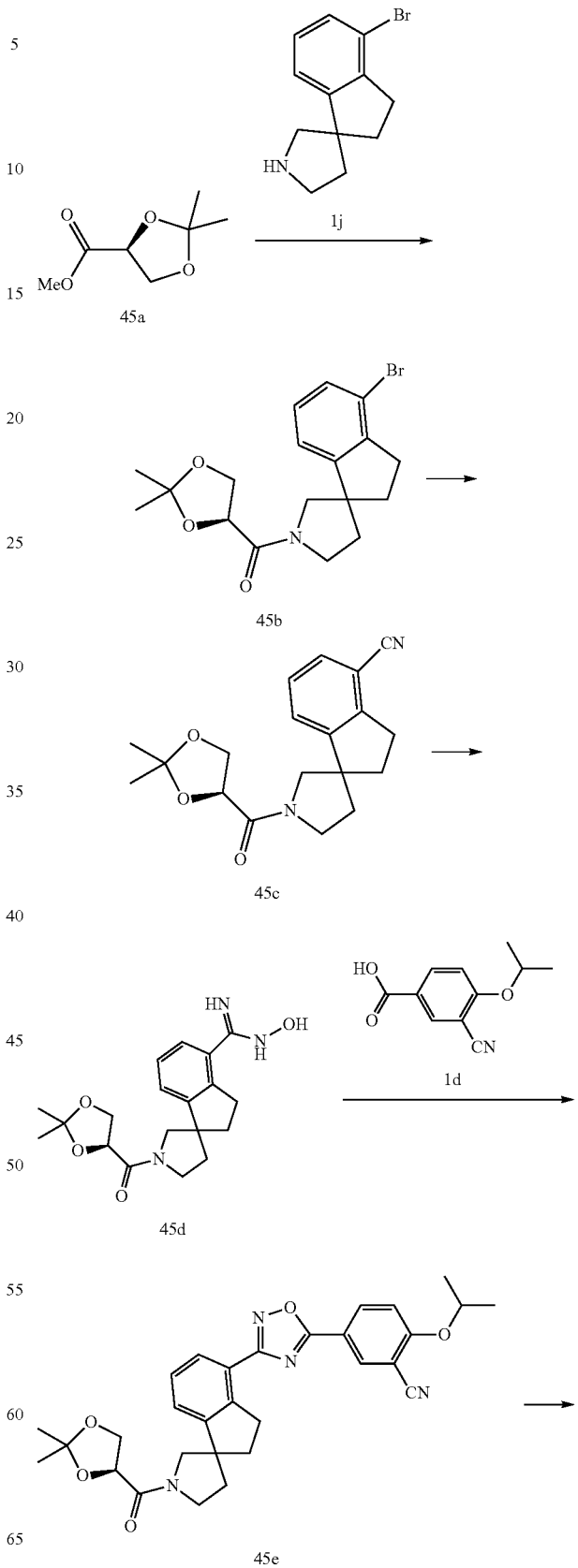

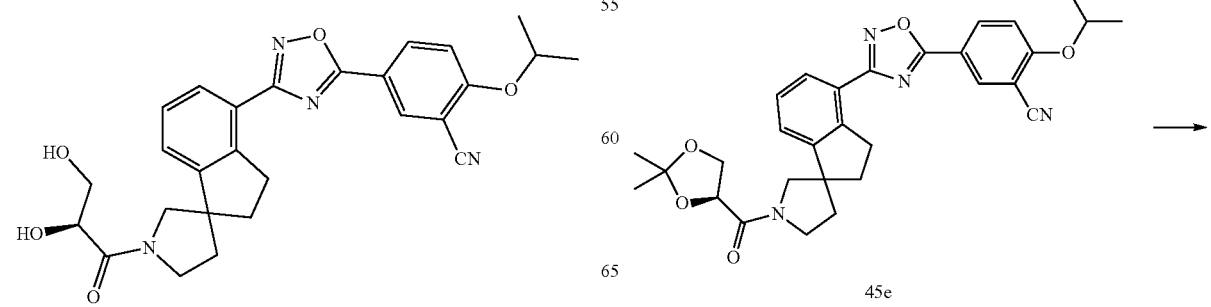

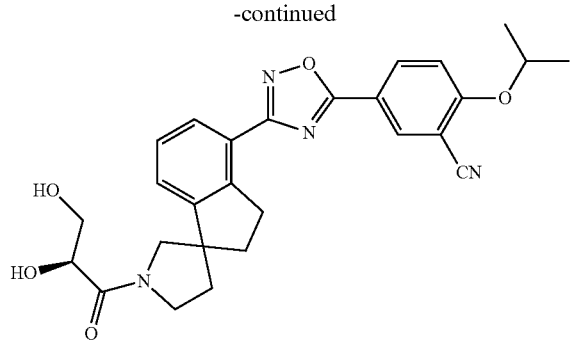

45

Step 1

Intermediate 1j (1500 mg, 5.2 mmol) was added to intermediate 45a (1140 mg, 7.1 mmol). The reaction solution was heated to 25° C. and reacted for 30 hours. The reaction solution was concentrated under reduced pressure and separated by silica gel column chromatography (dichloromethane/methanol, 100/1 to 5/1, V/V) to obtain intermediate 45b.

MS-ESI calculated for [M+H]$^+$ 380, 382, found 380, 382.

Step 2

Compound 45b (523 mg, 853 μmol) was dissolved in anhydrous N,N-dimethylformamide (6 mL), and zinc cyanide (242 mg, 2.1 mmol), tris(dibenzylideneacetone)dipalladium (38 mg, 41 μmol) and 2-di-tert-butylphosphino-2',4',6'-triisopropylbiphenyl (39 mg, 83 μmol) were added thereto, and the reaction system was replaced with nitrogen for three times. Under nitrogen protection, the reaction solution was stirred at 90° C. for 12 hours, and the reaction solution was concentrated after completion of the reaction. The residue was diluted with water (10 mL), extracted with ethyl acetate (20 mL×3). The combined organic phases were washed with saturated brine (30 mL), dried over anhydrous sodium sulfate, concentrated, and purified by silica gel column chromatography (petroleum ether/ethyl acetate, 5/1 to 1/1, V/V) to obtain intermediate 45c.

MS-ESI calculated for [M+H]$^+$ 327, found 327.

Step 3

Intermediate 45c (103 mg, 1.5 mmol), hydroxylamine hydrochloride (66 mg, 947 μmol) and triethylamine (96 mg, 947 μmol) were added to ethanol (4 mL). The reaction solution was reacted at 80° C. for 12 hours. The reaction solution was added to water (30 mL), extracted with ethyl acetate (20 mL×3), and the organic phases were combined, dried over anhydrous sodium sulfate, and concentrated under reduced pressure to obtain a crude product. The crude product was separated by thin-layer silica gel chromatography (20:1, dichloromethane/methanol, V/V) to obtain intermediate 45d.

MS-ESI calculated for [M+H]$^+$ 360, found 360.

Step 4

Intermediate 45d (98 mg, 215 μmol), intermediate 1d (44 mg, 215 μmol), 1-hydroxybenzotriazole (35 mg, 256 μmol) and 1-(3-dimethylaminopropyl)-3-ethylcarbodiimide hydrochloride (50 mg, 259 mmol) were added to N,N-dimethylformamide (10 mL). The reaction solution was heated to 80° C. and reacted for 11 hours. The reaction solution was added to water (50 mL), extracted with ethyl acetate (20 mL×3), and the organic phases were combined, dried over anhydrous sodium sulfate, and concentrated under reduced pressure to obtain the crude product of compound 45e.

MS-ESI calculated for [M+H]$^+$ 529, found 529.

Step 5

Compound 45e (70 mg, 132 μmol) was added to acetic acid (459 mg, 3.1 mmol), and the reaction solution was reacted at 35° C. for 12 hours. The reaction solution was concentrated under reduced pressure to obtain a crude product. The crude product was purified by thin-layer silica gel chromatography (20:1, dichloromethane/methanol, V/V) to obtain compound 45.

MS-ESI calculated for [M+H]$^+$ 489, found 489.

$^1$H NMR (400 MHz, CDCl$_3$) δ 8.44 (d, J=1.7 Hz, 1H), 8.38-8.32 (m, 1H), 8.14-8.07 (m, 1H), 7.45-7.38 (m, 1H), 7.35-7.30 (m, 1H), 7.14 (d, J=9.0 Hz, 1H), 4.87-4.75 (m, 1H), 4.47-4.29 (m, 1H), 3.92-3.68 (m, 6H), 3.41 (br t, J=7.2 Hz, 2H), 2.36-1.99 (m, 6H), 1.49 (d, J=6.1 Hz, 6H).

Embodiment 46

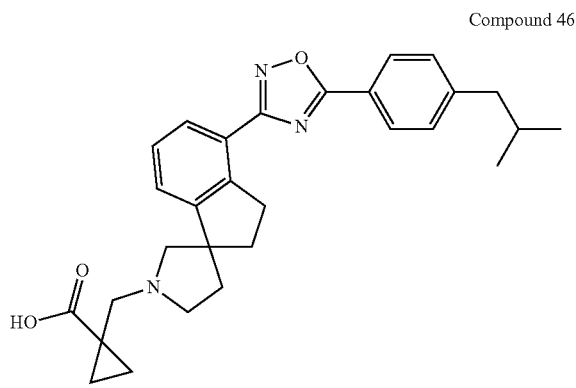 [SMILES: CC(C)Cc1ccc(-c2nc(-c3cccc4c3CCC43CCN(CC4(C(=O)O)CC4)C3)no2)cc1]

Compound 46

Synthetic route:

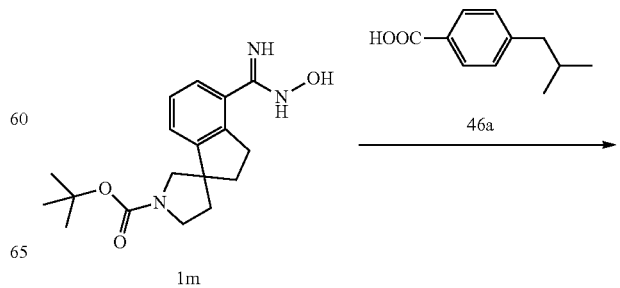

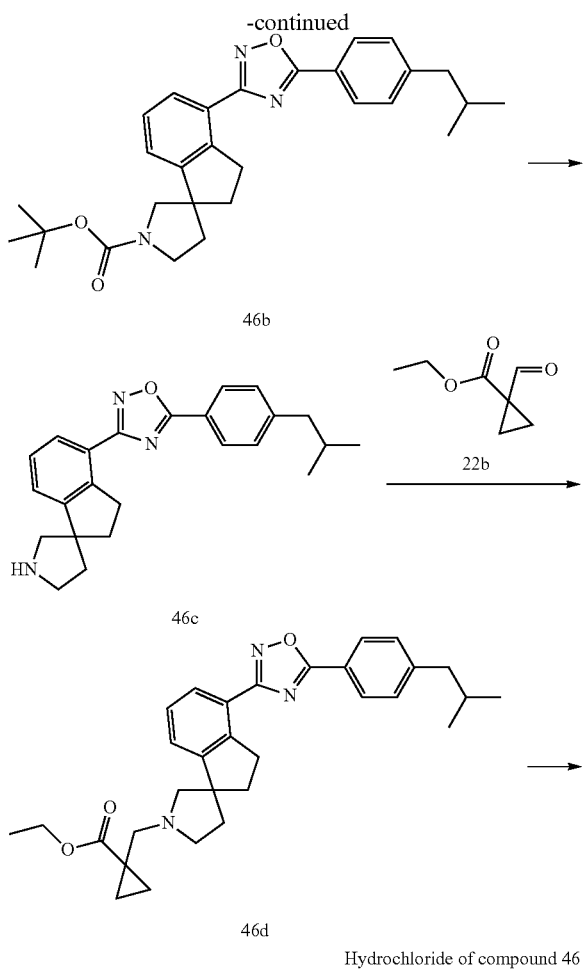

Hydrochloride of compound 46

Step 1

Intermediate 1m (300 mg, 905 μmol), intermediate 46a (161 mg, 905 μmol), 1-hydroxybenzotriazole (147 mg, 1.1 mmol) and 1-(3-dimethylaminopropyl)-3-ethylcarbodiimide hydrochloride (208 mg, 1.1 mmol) were added to N,N-dimethylformamide (10 mL). The reaction solution was heated to 80° C. and stirred for 11 hours. The reaction solution was added to water (20 mL), extracted with ethyl acetate (30 mL×2), and the organic phases were combined, dried over anhydrous sodium sulfate, concentrated under reduced pressure and subjected to silica gel column chromatography (petroleum ether/ethyl acetate, 100/1 to 10/1, V/V) to obtain intermediate 46b. MS-ESI calculated for [M+Na]$^+$ 496, found 496.

Step 2

Compound 46b (260 mg, 549 μmol), 4M hydrochloric acid and ethyl acetate (1 mL) were added to ethyl acetate (2 mL), and the reaction solution was reacted at 25° C. for 1 hour. The reaction solution was concentrated under reduced pressure and purified by thin-layer silica gel chromatography (20:1, dichloromethane/methanol) to obtain the hydrochloride of intermediate 46c.

MS-ESI calculated for [M+H]$^+$ 374, found 374.

Step 3

The hydrochloride of intermediate 46c (205 mg, 500 μmol), intermediate 22b (142 mg, 1 mmol) and acetic acid (30 mg, 500 μmol) were added to dichloromethane (15 mL), and the reaction solution was stirred at 25° C. for 1 hour. Sodium triacetoxyborohydride (424 mg, 2 mmol) was added to the reaction solution, and the reaction solution was stirred at 25° C. for 13 hours. The reaction solution was added with 10% sodium bicarbonate solution (20 mL), extracted with dichloromethane (20 mL×3), and the organic phases were combined, dried over anhydrous sodium sulfate, concentrated under reduced pressure and purified by thin-layer silica gel chromatography (0:1, petroleum ether/ethyl acetate, V/V) to obtain intermediate 46d.

MS-ESI calculated for [M+H]$^+$ 500, found 500.

Step 4

Compound 46d (138 mg, 276 μmol) and lithium hydroxide hydrate (12 mg, 276 μmol) were added to tetrahydrofuran (20 mL) and water (5 mL), and the reaction solution was reacted at 25° C. for 12 hours. The reaction solution was concentrated under reduced pressure to obtain a crude product, and the crude product was separated by high performance liquid chromatography (chromatographic column: Phenomenex Luna C18 75×30 mm×3 μm; mobile phase: 0.05% aqueous hydrochloric acid solution-acetonitrile; gradient: acetonitrile 46%-66%, 6.5 minutes) to obtain the hydrochloride of compound 46.

MS-ESI calculated for [M+H]$^+$ 472, found 472.

$^1$H NMR (400 MHz, CD$_3$OD) δ 8.17-8.03 (m, 3H), 7.62 (d, J=7.6 Hz, 1H), 7.49 (t, J=7.6 Hz, 1H), 7.42 (d, J=8.3 Hz, 2H), 7.03-7.00 (m, 1H), 3.69-3.54 (m, 3H), 3.41 (d, J=5.6 Hz, 2H), 2.66 (s, 2H), 2.61 (d, J=7.3 Hz, 2H), 2.46-2.29 (m, 2H), 2.55-2.24 (m, 1H), 2.01-1.89 (m, 1H), 1.56-1.48 (m, 1H), 1.51 (d, J=2.5 Hz, 1H), 1.54-1.45 (m, 1H), 1.36-1.26 (m, 1H), 1.22 (s, 2H), 0.95 (d, J=6.5 Hz, 6H).

Test Embodiment 1: In Vitro Evaluation of the Agonistic Activity of the Compounds of the Present Disclosure on S1PR1

Experimental objective: to detect the agonistic activity of compounds on S1PR1

I. Cell Treatment
1. A PathHunter cell line was thawed according to standard procedures;
2. the cells were inoculated in a 20 μL 384-well microplate and incubated at 37° C. for appropriate time.

II. Agonist
1. For agonist determination, cells were incubated with samples to be tested to induce a reaction;
2. a storage solution to be tested was 5-fold diluted into a buffer;
3. 5 μL of the 5-fold dilution was added to the cells and incubated at 37° C. for 90-180 minutes. The vehicle concentration was 1%.

III. Signal Detection
1. 12.5 μL or 15 μL of PathHunter detection reagent at a volume ratio of 50% was added at a time, and then incubated at room temperature for 1 hour to generate a detection signal;
2. the microplate was read with a PerkinElmer Envision™ instrument for chemiluminescent signal detection.

IV. Data Analysis
1. Activity analysis of the compound was carried out by using CBIS data analysis kit (ChemInnovation, CAA);
2. calculation formula:

% activity=100%×(average test sample RLU−average vehicle RLU)/(average maximum control ligand−average vehicle RLU)

Experimental results are shown in Table 1:

TABLE 1

S1PR1 agonistic activity test results

| Sample for test | S1PR1 agonistic activity, Emax |
|---|---|
| Compound 1 | 0.137 nM, 122% |
| Compound 3 | 0.129 nM, 88.6% |
| Compound 4 | 0.107 nM, 99.4% |
| Compound 5 | 0.0688 nM, 85.1% |
| Hydrochloride of compound 6 | 0.865 nM, 115% |
| Compound 7 | 0.123 nM, 90.7% |
| Compound 8 | 0.188 nM, 96.8% |
| Compound 9 | 2.15 nM, 75.8% |
| Compound 10 | 1.31 nM, 101% |
| Compound 11 | 1.78 nM, 84.6% |
| Compound 12 | 0.477 nM, 87.6% |
| Compound 13 | 10.7 nM, 77.8% |
| Compound 14 | 1.59 nM, 82.2% |
| Compound 15 | 2.20 nM, 98.9% |
| Compound 16 | 14.4 nM, 77.8% |
| Compound 17 | 8.59 nM, 80.8% |
| Compound 18 | 4.06 nM, 84.2% |
| Compound 19 | 3.25 nM, 77.8% |
| Compound 20 | 9.39 nM, 90.4% |
| Compound 21 | 21.7 nM, 70.8% |
| Hydrochloride of compound 22 | 0.0754 nM, 118% |
| Hydrochloride of compound 23 | 0.0353 nM, 68.3% |
| Hydrochloride of compound 24 | 4.99 nM, 87.1% |
| Hydrochloride of compound 25 | 11.5 nM, 82.1% |
| Hydrochloride of compound 26 | 4.47 nM, 73.8% |
| Hydrochloride of compound 27 | 9.78 nM, 63.4% |
| Hydrochloride of compound 28 | 1.32 nM, 77.7% |
| Hydrochloride of compound 37 | 0.047 nM, 94.1% |
| Hydrochloride of compound 38 | 0.041 nM, 100.3% |
| Hydrochloride of compound 39 | 3.46 nM, 144.2% |
| Compound 40 | 2.82 nM, 101.8% |
| Hydrochloride of compound 43 | 0.10 nM, 107.7% |
| Hydrochloride of compound 44 | 0.72 nM, 104.3% |
| Compound 45 | 0.29 nM, 125.5% |
| Hydrochloride of compound 46 | 5.76 nM, 104.8% |

Conclusion: the compounds of the present disclosure all have significant or even unexpected S1PR1 agonistic activity.

Test Embodiment 2: In Vitro Evaluation of the Agonistic Activity of the Compounds of the Present Disclosure on S1PR1

Experimental objective: to detect the agonistic activity of compounds on S1PR1
I. Cell Treatment
1. The cells U2OS-EDG1 (batch number: Invitrogen-K1520) were taken out from a liquid nitrogen tank and quickly thawed in a 37° C. water bath;
2. the cell suspension was aspirated into a 15 mL centrifuge tube, resuspended in 5 mL of pre-warmed culture medium, and centrifuged at 1000 rpm for 5 min;
3. the supernatant was discarded, 10 mL of culture medium was resuspended, transferred to a T75 culture flask, and cultured in a 37° C., 5% $CO_2$ incubator.
II. Agonist Assay
1. Compounds were diluted to working concentrations, and the compounds were 3-fold diluted by Echo 555 (manufacturer: Labcyte) to 10 concentrations, and then 200 nL of each concentration were transferred to cell plates, and centrifuged at 1000 rpm for 15 seconds;
2. the culture medium in the culture flask was aspirated, and 4 mL of Dulbecco's Phosphate Buffered Saline (DPBS, supplier: Coring, catalog number: 21-031-CVR, batch number: 03318006) was added thereto to wash off the residual serum, and 2 mL of trypsin was added thereto, and incubated in a 37° C. incubator for 2 minutes to digest the cells, and then 10 mL of seed plate culture medium was added to resuspend the cells, and 0.6 mL of the cell suspension was taken out for counting;
3. the cell density was adjusted with the seed plate culture medium to 1.88E+05 cells/mL, 40 μL was seeded per well (7500\well), and 40 μL of FreeStyle™ Expression culture medium was added around the cell plate, left to stand for 15 minutes at room temperature, and incubated at 37° C. with 5% $CO_2$ for 20 hours.
III. Signal Detection
1. LiveBLAzer™-FRET B/G Substrate (CCF4-AM) detection reagent was configured according to the instructions;
2. 8 μL of 6×Substrate Mixture was added to each well of the cell plate, centrifuged at 1000 rpm for 15 seconds, attached with a membrane, incubated at 23° C. for 2 hours, and detected by Envision chemiluminescence.
IV. Data Analysis
1. The original data was converted into % Effect by using the equation, and the value of $EC_{50}$ could be obtained by curve fitting with four parameters [obtained in the "log(agonist) vs. response—Variable slope" mode in GraphPad Prism];
2. calculation formula:

Ratio=(460 nm−blank)/(535 nm−blank)

% Effect=($Sample_{Ratio}$−Ave $LC_{Ratio}$)/(Ave $HC_{Ratio}$−Ave $LC_{Ratio}$)*100%

Experimental results are shown in Table 2:

TABLE 2

S1PR1 agonistic activity test results

| Sample for test | S1PR1 agonistic activity $EC_{50}$, Emax |
|---|---|
| Compound 22A | 0.15 nM, 84.2% |
| Compound 22B | 0.32 nM, 74.0% |
| Hydrochloride of compound 29 | 0.0211 nM, 91.5% |
| Hydrochloride of compound 30 | 0.132 nM, 103% |
| Hydrochloride of compound 31 | 0.456 nM, 101% |
| Hydrochloride of compound 32 | 1.45 nM, 95.9% |
| Hydrochloride of compound 33 | 10.2 nM, 99.9% |
| Hydrochloride of compound 34 | 6.07 nM, 94.9% |

Conclusion: the compounds of the present disclosure all have significant or even unexpected S1PR1 agonistic activity.

Test Embodiment 3: Pharmacokinetic Evaluation of Compound in Rats

Experimental objective: to test the pharmacokinetics of the compound in SD rats
Experimental Materials:
Sprague Dawley rat (male, 200-300 g, 7-9 weeks old, Shanghai SLAC)

Experimental Operation:

A standard protocol was used to test the pharmacokinetic characteristics of rodents after intravenous injection and oral administration of the compound. In the experiment, the candidate compound was prepared into a clear solution, and administrated to rats by single intravenous injection and oral administration. The vehicle for intravenous injection was a 5:95 DMSO and 10% hydroxypropyl cyclodextrin aqueous solution, and the vehicle for oral administration was a 0.5% w/v methylcellulose and 0.2% w/v tween 80 aqueous solution. Whole blood samples within 24 hours were collected, centrifuged at 3000 g for 15 minutes, and the supernatant was separated to obtain plasma samples. 4-fold volume of acetonitrile solution containing internal standard was added thereto to precipitate protein. The mixture was centrifuged, and the supernatant was taken, and an equal volume of water was added thereto. Then the mixture was centrifuged and the supernatant was taken for injection. The blood drug concentration was quantitatively analyzed by LC-MS/MS analysis method, and pharmacokinetic parameters, such as peak concentration, clearance rate, half-life, area under the drug-time curve and bioavailability, were calculated.

Experimental Results:

Test Embodiment 4: Pharmacokinetic Evaluation of Compound in Mice

Experimental objective: to test the pharmacokinetics of the compound in CD-1 mice Experimental Materials:

CD-1 mice (male, 20-40 g, 6-10 weeks old, Shanghai BK)

Experimental Operation:

The standard protocol was used to test the pharmacokinetic characteristics of rodents after intravenous injection and oral administration of the compound. In the experiment, the candidate compound was prepared into a clear solution or a suspension, and administrated to two mice by single intravenous injection and oral administration. The vehicle for intravenous injection was a 5:95 DMSO and 10% hydroxypropyl β-cyclodextrin aqueous solution, and the vehicle for oral administration was a 0.5% w/v methylcellulose and 0.2% w/v tween 80 aqueous solution. Whole blood samples within 24 hours were collected, centrifuged at 3200 g for 10 minutes, and the supernatant was separated to obtain plasma samples. 4-fold volume of acetonitrile solution containing internal standard was added thereto to precipitate protein. The mixture was centrifuged, and the supernatant was taken, and an equal volume of water was added thereto. Then the mixture was centrifuged and the supernatant was taken for injection. The blood drug concentration

TABLE 3

Pharmacokinetic test results

| Sample for test | Dosage of administration | Peak concentration $C_{max}$ (ng/mL) | Clearance rate CL (mL/min/kg) | Tissue distribution Vdss (L/kg) | Half-life $T_{1/2}$ (PO, h) | Area under the drug-time curve $AUC_{0-last}$ PO (nM·hr) | Bioavailability F(%) |
|---|---|---|---|---|---|---|---|
| Compound 1 | Intravenous injection (1.0 mg/kg) Oral administration (3.0 mg/kg) | 1135 | 5.97 | 2.66 | 4.91 | 11531 | 83.1 |
| Compound 22 | Intravenous injection (0.8 mg/kg) Oral administration (2.4 mg/kg) | 1770 | 3.44 | 1.60 | 4.67 | 16277 | 69.5 |
| Compound 40 | Intravenous injection (1.0 mg/kg) Oral administration (2.0 mg/kg) | 357 | 5.47 | 5.99 | 8.83 | 7138 | 63.9 |
| Compound 45 | Intravenous injection (1.0 mg/kg) Oral administration (2.0 mg/kg) | 1180 | 1.59 | 1.94 | 13.2 | 22888 | 59.2 |

Conclusion: the compounds of the present disclosure show good bioavailability, high area under the drug-time curve and low clearance rate in the pharmacokinetics of SD rats.

was quantitatively analyzed by LC-MS/MS analysis method, and pharmacokinetic parameters, such as peak concentration, clearance rate, half-life, area under the drug-time curve and bioavailability, were calculated.

Experimental Results:

TABLE 4

Pharmacokinetic test results

| Sample for test | Dosage of administration | Peak concentration $C_{max}$ (ng/mL) | Clearance rate CL (mL/min/kg) | Tissue distribution $V_{dss}$ (L/kg) | Half-life $T_{1/2}$ (PO, h) | Area under the drug-time curve $AUC_{0\text{-}last}$ PO (nM · hr) | Bioavailability F(%) |
|---|---|---|---|---|---|---|---|
| Compound 1 | Intravenous injection (0.5 mg/kg) Oral administration (2.0 mg/kg) | 615 | 18.2 | 2.17 | 3.61 | 2738 | 70.1 |
| Compound 8 | Intravenous injection (0.5 mg/kg) Oral administration (2.0 mg/kg) | 2280 | 3.58 | 0.816 | 2.90 | 16273 | 80.3 |
| Compound 22 | Intravenous injection (0.5 mg/kg) Oral administration (2.0 mg/kg) | 869 | 5.20 | 1.82 | 3.66 | 7882 | 62.5 |

Conclusion: the compounds of the present disclosure show good bioavailability, high area under the drug-time curve and low clearance rate in the pharmacokinetics of CD-1 mice.

Test Embodiment 5: Pharmacokinetic Evaluation of Compounds in Rats at Different Doses Experimental objective: to test the pharmacokinetics of the compounds in SD rats at different doses Experimental Materials:

Sprague Dawley rats (male, 200-300 g, 7-9 weeks old, Shanghai SLAC)

Experimental Operation:

A standard protocol was used to test the pharmacokinetic characteristics of the compounds in SD rats after oral administration. In the experiment, the candidate compound was prepared into a clear solution, and administered to rats by single oral administration. The vehicle for compound 1 was DMSO: 10% hydroxypropyl β-cyclodextrin aqueous solution=5:95. The vehicle for compounds 1A and 1B was 0.5% carboxymethyl cellulose +0.2% Tween 80. Whole blood samples of compounds 1, 1A and 1B within 48 hours were collected, centrifuged at 3000 g for 15 minutes, and the supernatant was separated to obtain plasma samples. 4-fold volume of acetonitrile solution containing internal standard was added thereto to precipitate protein. The mixture was centrifuged, and the supernatant was taken, and an equal volume of water was added thereto. Then the mixture was centrifuged and the supernatant was taken for injection. The blood drug concentration was quantitatively analyzed by LC-MS/MS analysis method, and pharmacokinetic parameters, such as peak concentration, peak time, half-life, area under the drug-time curve, were calculated.

Experimental results are shown in Table 5:

TABLE 5

Pharmacokinetic test results

| Sample for test | Peak concentration $C_{max}$ (nmol/L) | Peak time $T_{max}$ (h) | Half-life $T_{1/2}$ (PO, h) | Area under the drug-time curve $AUC_{0\text{-}last}$ PO (nM · hr) |
|---|---|---|---|---|
| Compound 22 (5 mg/kg) | 2405 | 5 | — | 32253 |
| Compound 22 (30 mg/kg) | 15300 | 2 | 8.24 | 256355 |
| Compound 22A (5 mg/kg) | 2505 | 2 | 5.69 | 26434 |
| Compound 22B (5 mg/kg) | 2935 | 3 | 6.7 | 32990 |

Note:
— represents uncertainty.

Conclusion: the systemic exposure increase of the compounds of the present disclosure at different doses in the pharmacokinetics of SD rats is in accordance with dose-related linear ratios; the compounds of the present disclosure all show high area under the drug-time curve and peak concentration in the pharmacokinetics of SD rats.

What is claimed is:

1. A compound represented by formula (P) or a pharmaceutically acceptable salt thereof,

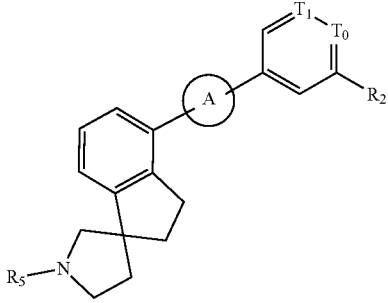
(P)

wherein,
$T_0$ is selected from CH-E-$R_3$ and N;
$T_1$ is selected from $CR_4$ and N;
E is absent, or is selected from O and NH;
ring A is selected from oxazolyl, 1,2,4-oxadiazolyl, thiazolyl, 1,3,4-thiadiazolyl, 1,2,4-thiadiazolyl, pyrimidinyl and pyrazinyl;
$R_2$ is selected from H, F, Cl, Br, CN, $C_{1-3}$ alkyl and $C_{1-3}$ alkoxy, and the $C_{1-3}$ alkyl and $C_{1-3}$ alkoxy are optionally substituted by 1, 2 or 3 $R_b$;
$R_3$ is selected from $C_{1-6}$ alkyl, cyclopentyl and cyclohexyl, and the $C_{1-6}$ alkyl, cyclopentyl and cyclohexyl are optionally substituted by 1, 2 or 3 $R_c$;
$R_4$ is selected from H and cyclopentyl;
$R_5$ is selected from

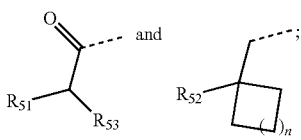

$R_{51}$ is selected from H, OH, $NH_2$, CN, COOH, $CH_2COOH$, $CH_2OH$, $C_{1-3}$ alkoxy and —$S(O)_2$—$C_{1-3}$ alkyl, and the $C_{1-3}$ alkoxy and $C_{1-3}$ alkyl are optionally substituted by 1, 2 or 3 $R_a$;
$R_{52}$ is selected from OH, CN, $NH_2$ and COOH;
$R_{53}$ is selected from H and OH;
$R_a$, $R_b$ and $R_c$ are each independently selected from F, Cl and Br;
n is selected from 0 and 1.

2. The compound or the pharmaceutically acceptable salt thereof according to claim 1, wherein, ring A is selected from

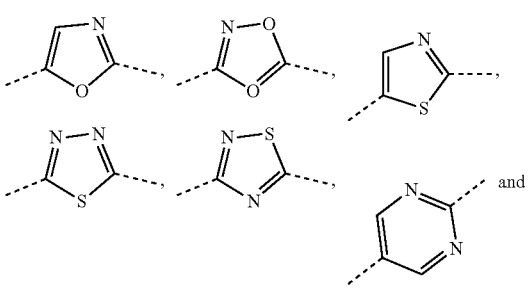

-continued

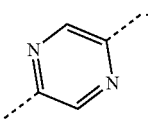

3. The compound or the pharmaceutically acceptable salt thereof according to claim 1, wherein, $R_2$ is selected from H, F, Cl, Br, CN, $CH_3$ and $OCH_3$, and the $CH_3$ and $OCH_3$ are optionally substituted by 1, 2 or 3 $R_b$.

4. The compound or the pharmaceutically acceptable salt thereof according to claim 3, wherein, $R_2$ is selected from H, Br, Cl, CN, $CHF_2$, $CF_3$ and $OCH_3$.

5. The compound or the pharmaceutically acceptable salt thereof according to claim 1, wherein, $R_3$ is selected from $C_{1-4}$ alkyl,

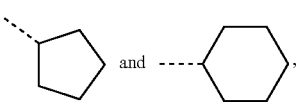

and the $C_{1-4}$ alkyl,

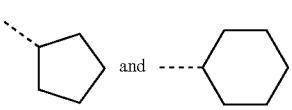

are optionally substituted by 1, 2 or 3 $R_c$.

6. The compound or the pharmaceutically acceptable salt thereof according to claim 5, wherein, $R_3$ is selected from $CH(CH_3)_2$, $CHF_2$, $CH_2CH(CH_3)_2$,

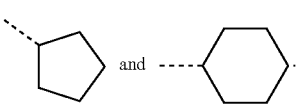

7. The compound or the pharmaceutically acceptable salt thereof according to claim 1, wherein, the structural moiety

is selected from

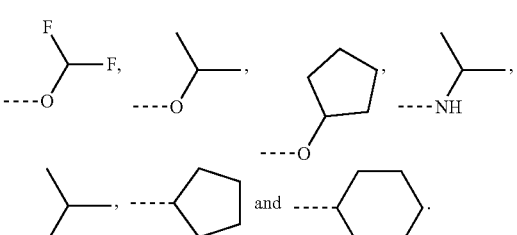

8. The compound or the pharmaceutically acceptable salt thereof according to claim 1, wherein, $R_{51}$ is selected from H, OH, NH$_2$, CN, COOH, CH$_2$COOH, CH$_2$OH, OCH$_3$ and —S(O)$_2$CH$_3$, and the OCH$_3$ and —S(O)$_2$CH$_3$ are optionally substituted by 1, 2 or 3 R$_a$.

9. The compound or the pharmaceutically acceptable salt thereof according to claim 8, wherein, R$_{51}$ is selected from OH, NH$_2$, CN, CH$_2$COOH, CH$_2$OH, OCH$_3$ and —S(O)$_2$CH$_3$.

10. The compound or the pharmaceutically acceptable salt thereof according to claim 1, wherein, the structural moiety

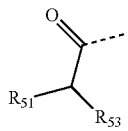

is selected from

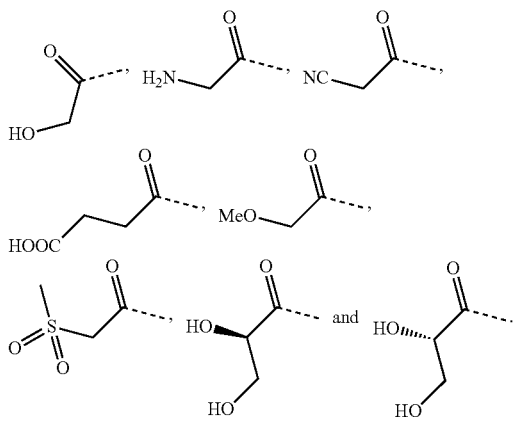

11. The compound or the pharmaceutically acceptable salt thereof according to claim 1, wherein, R$_{52}$ is selected from CN, NH$_2$ and COOH.

12. The compound or the pharmaceutically acceptable salt thereof according to claim 1, wherein, the structural moiety

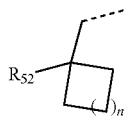

is selected from

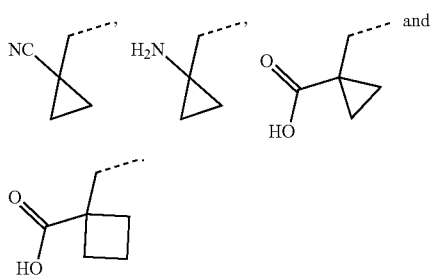

13. The compound or the pharmaceutically acceptable salt thereof according to claim 1, selecting from,

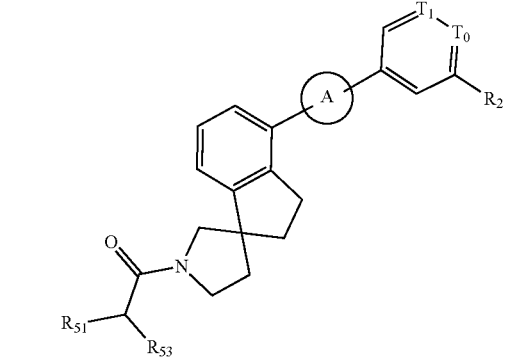
(P-1)

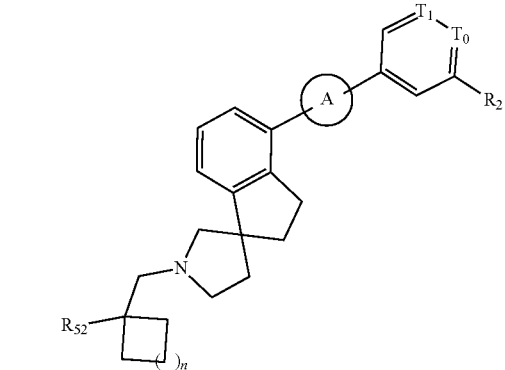
(P-2)

wherein, T$_0$, T$_1$, R$_{53}$, n, ring A, R$_2$, R$_{51}$ and R$_{52}$ are defined as above.

14. The compound or the pharmaceutically acceptable salt thereof according to claim 1, selecting from,

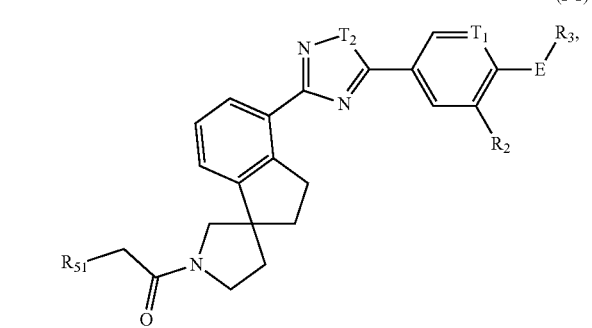
(I-1)

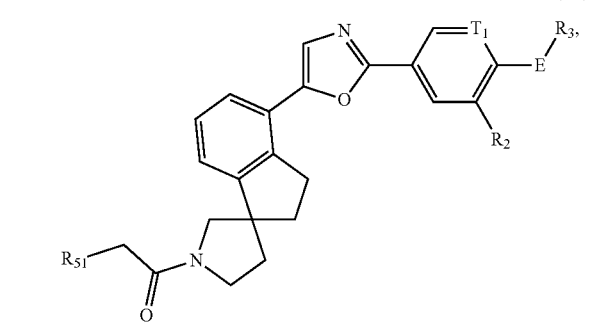
(I-2)

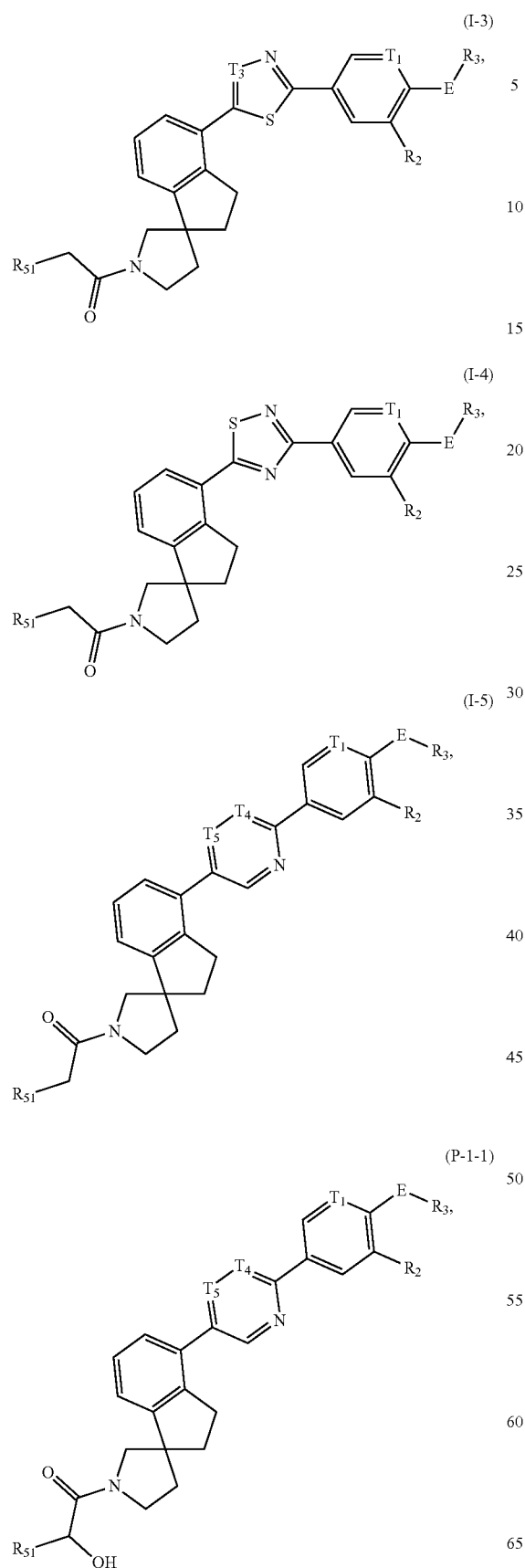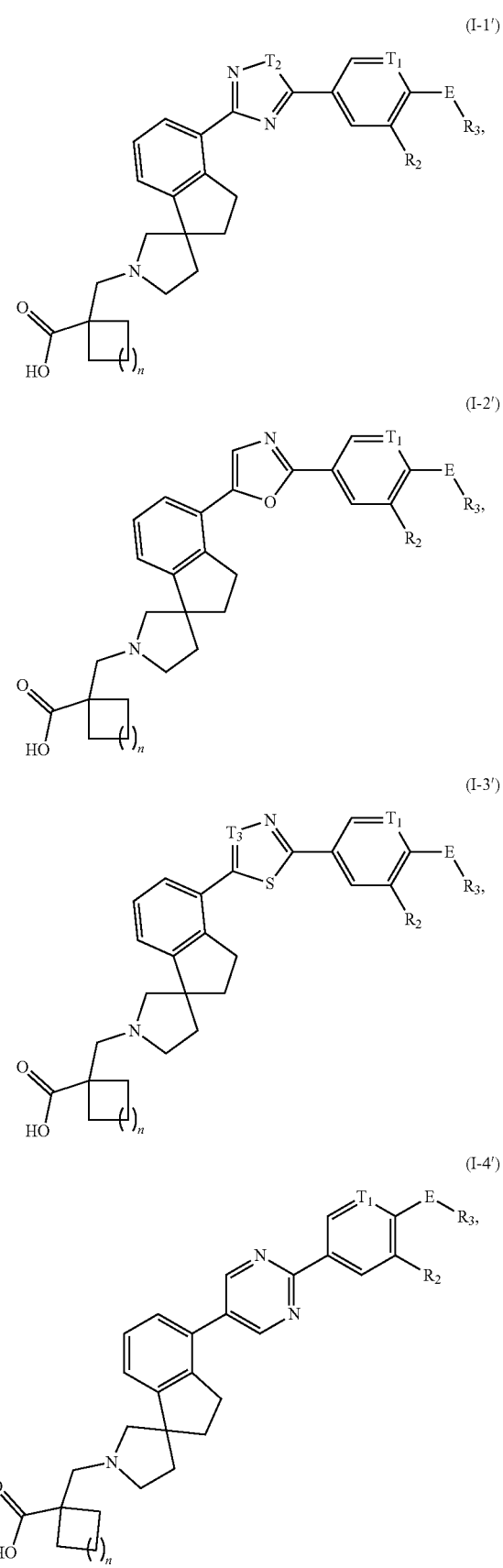

-continued
(II-1)
(II-2)
(P-2-1)
wherein,
R$_2$, R$_3$, T$_1$, E, n, T$_2$ and T$_3$ are defined as above;
T$_4$ is selected from CH and T$_5$ is selected from N, or T$_4$ is selected from N and T$_5$ is selected from CH.
15. A compound represented by the following formula or a pharmaceutically acceptable salt thereof, selected from:
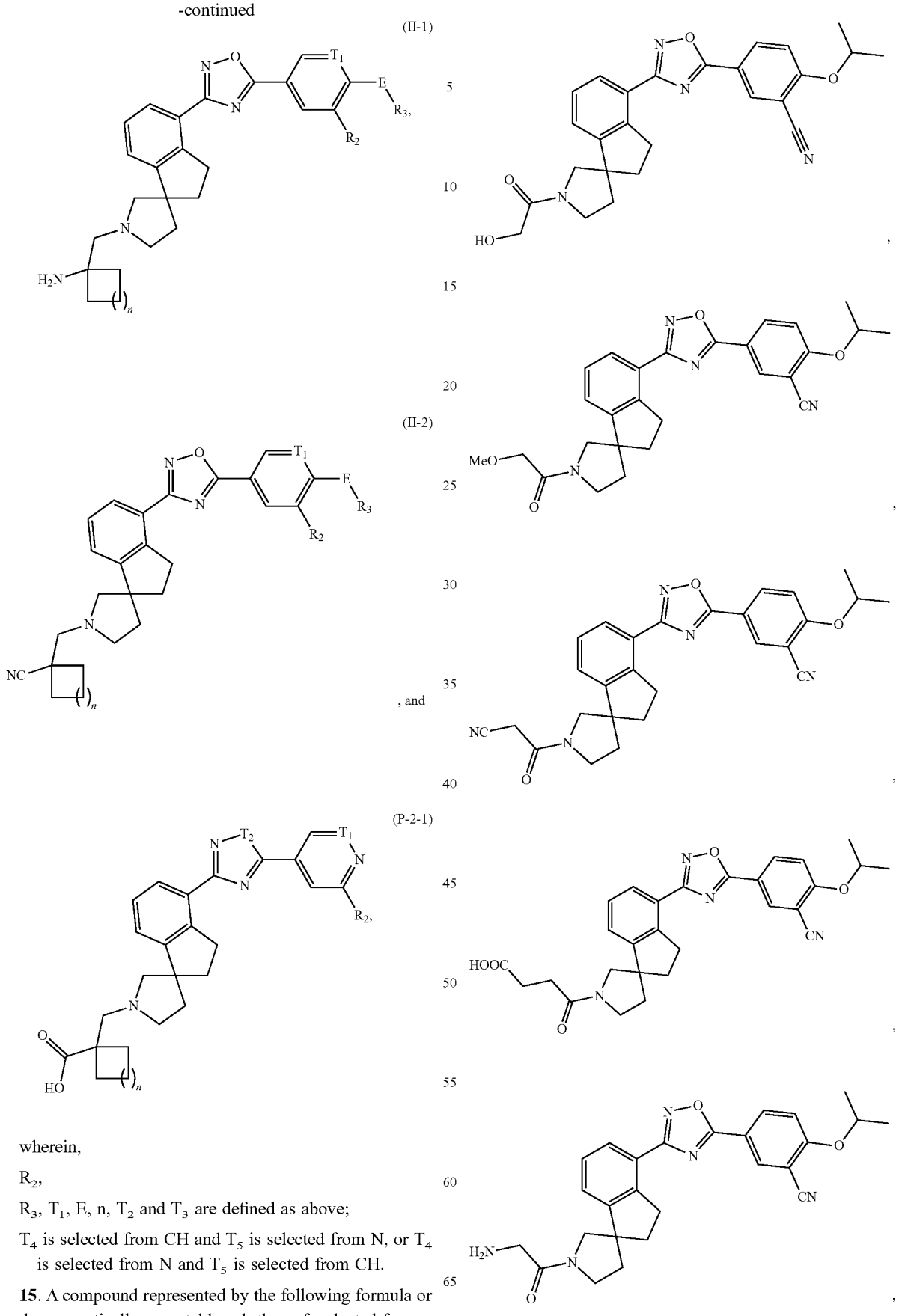

153
-continued
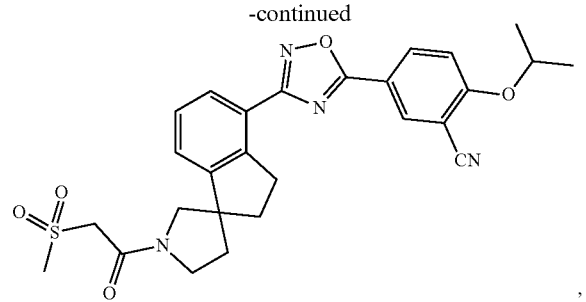
,
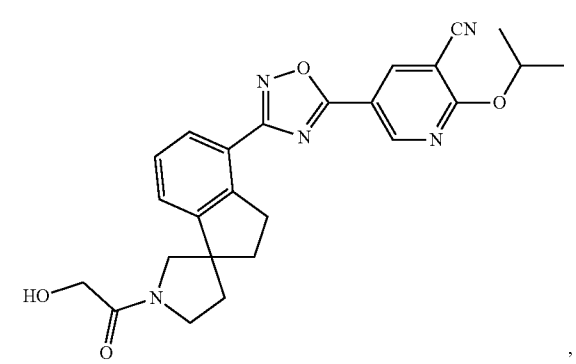
,
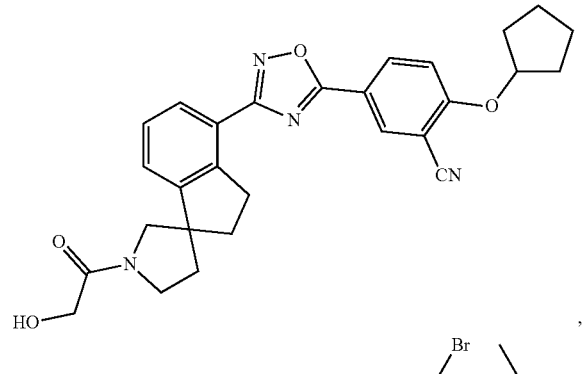
,
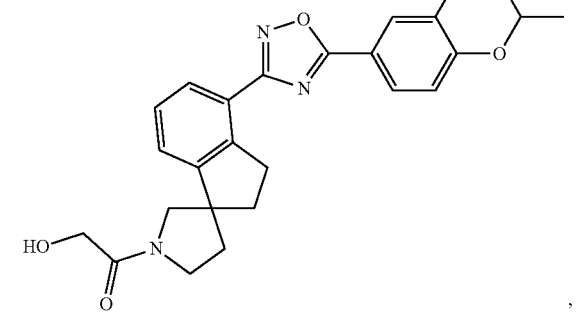
,
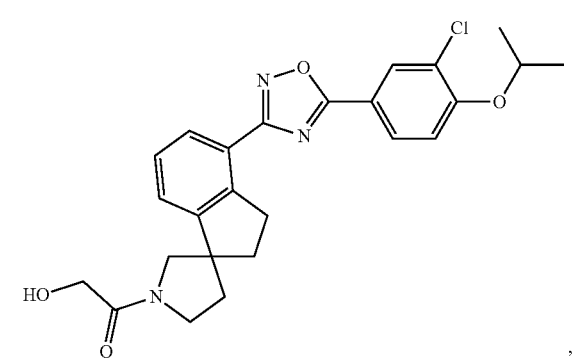
,
154
-continued
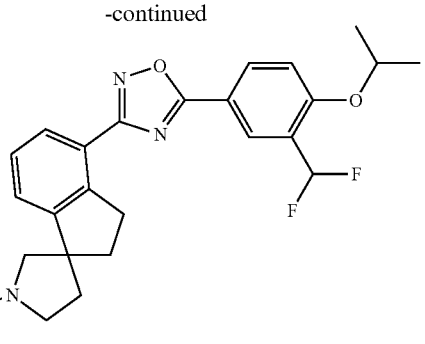
,
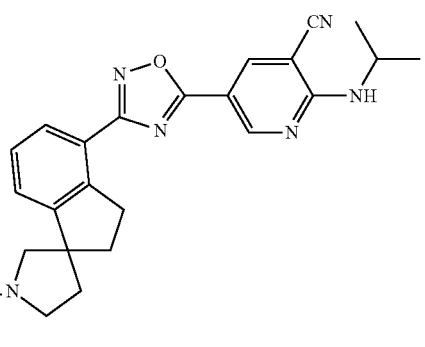
,
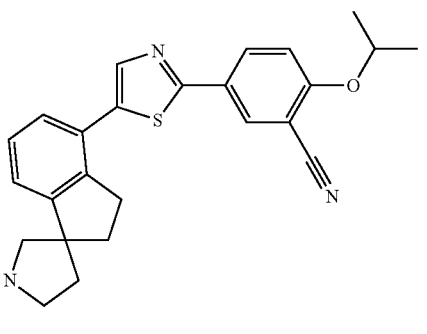
,
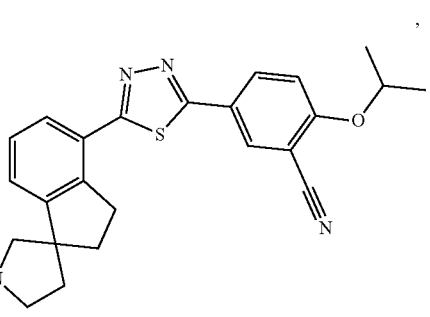
,
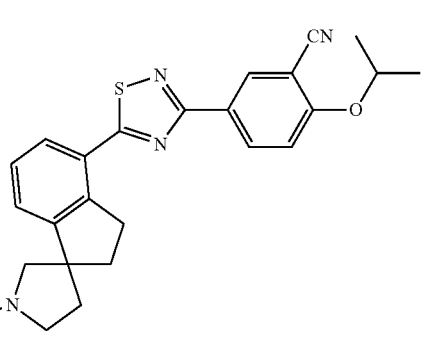
, 155
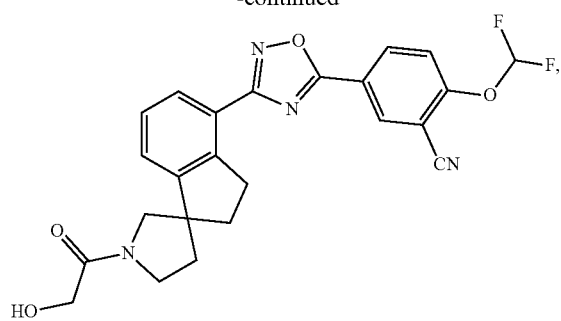
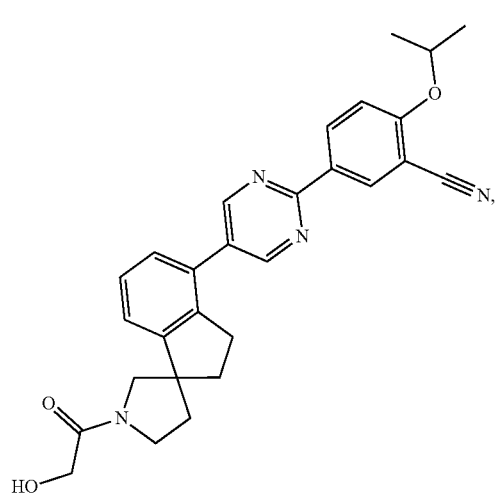
156
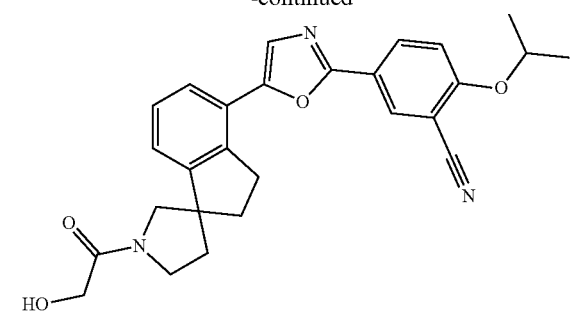
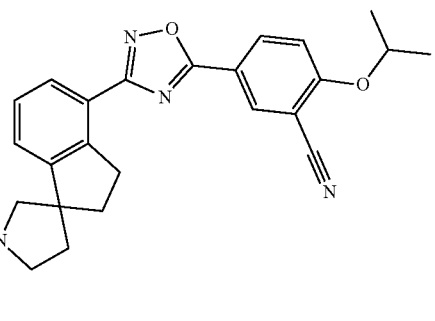
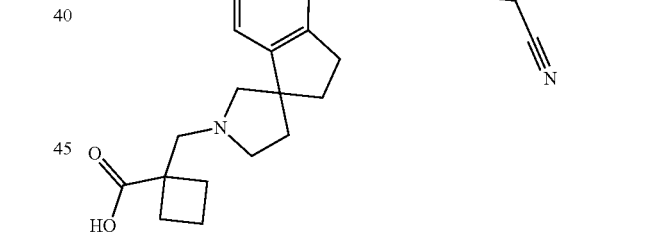
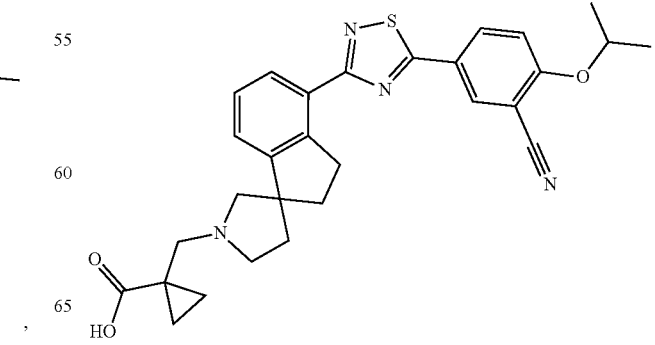

157
-continued
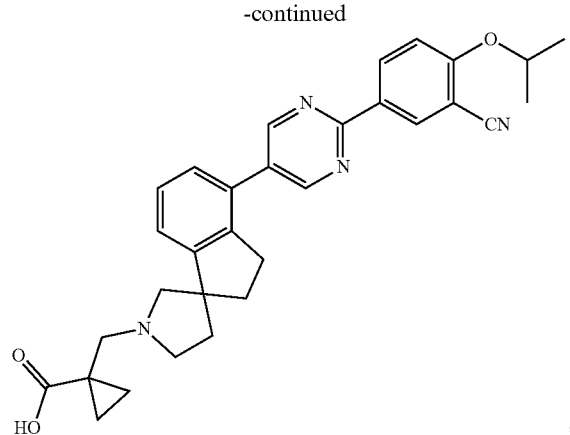
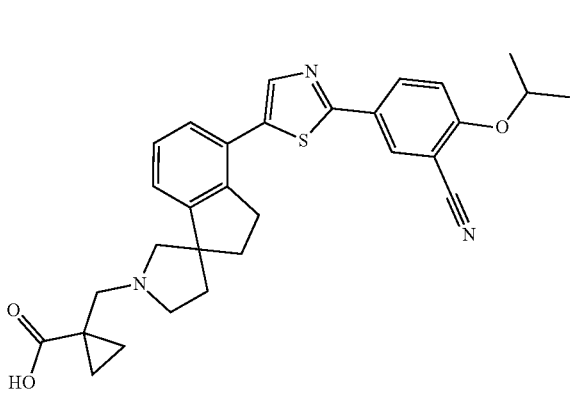
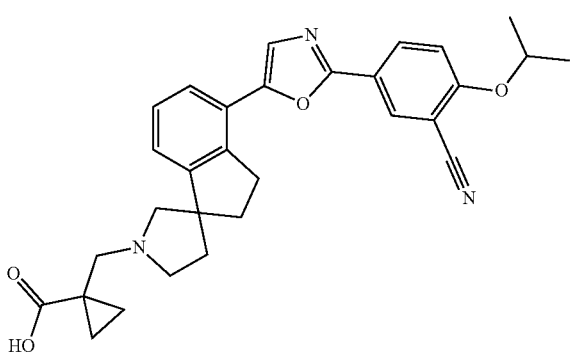
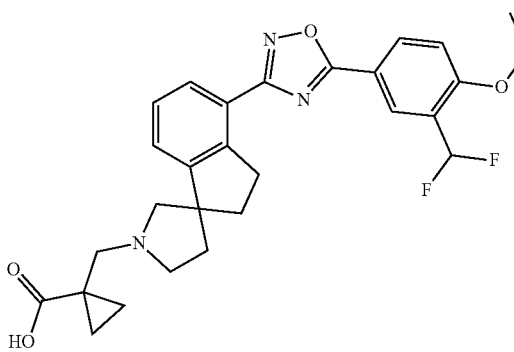
158
-continued
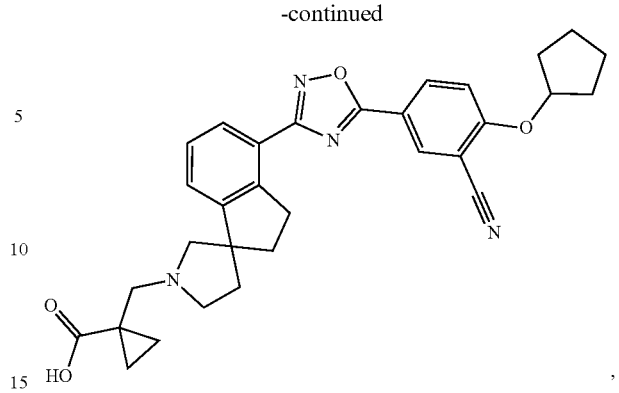
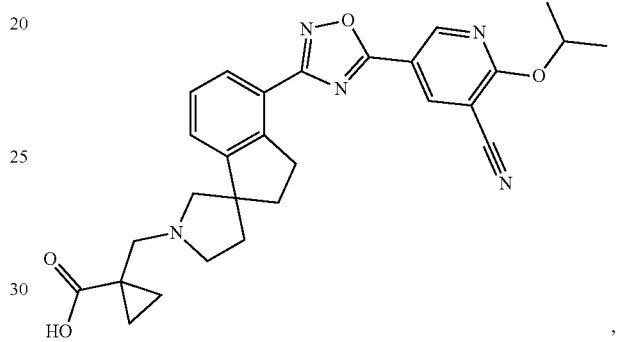
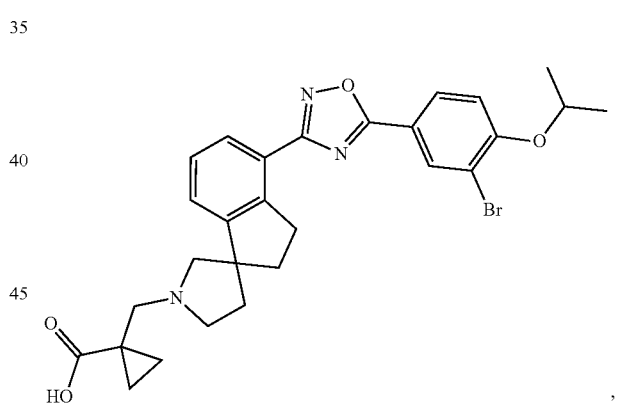
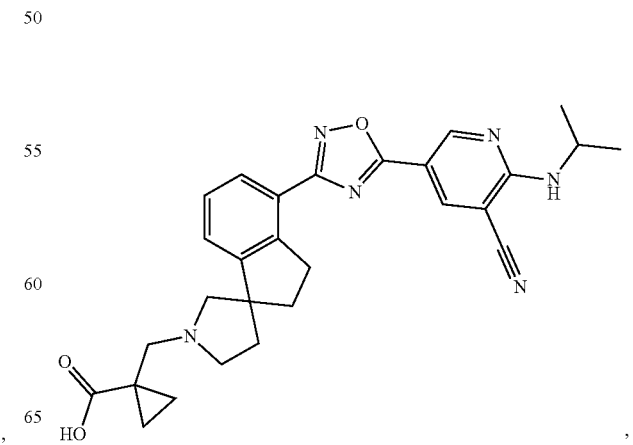

159
-continued
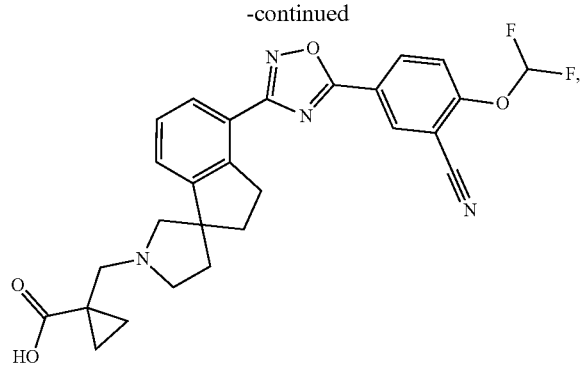
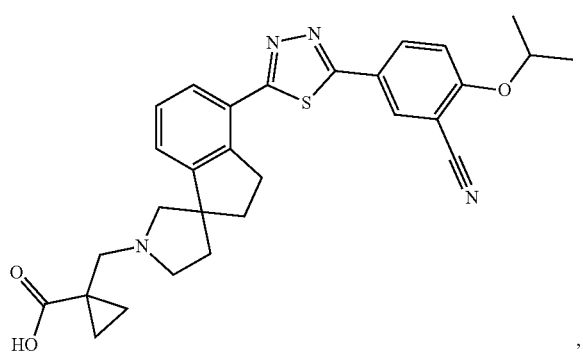
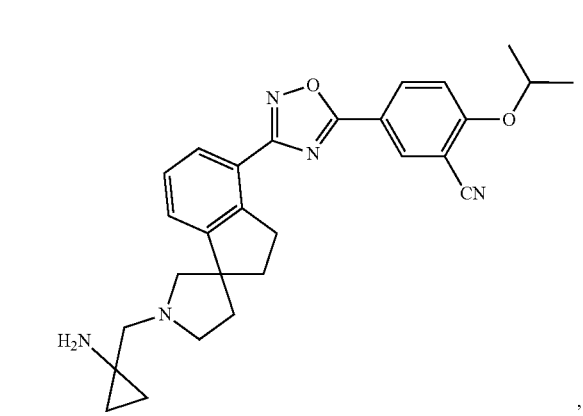
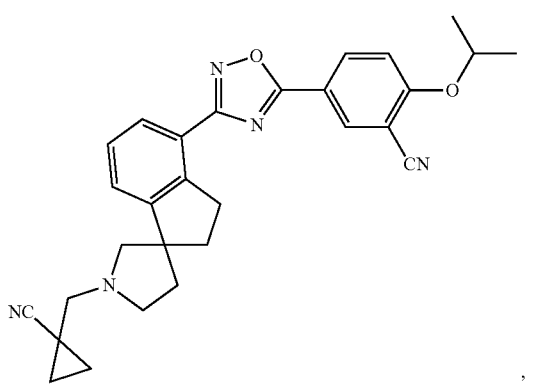
160
-continued
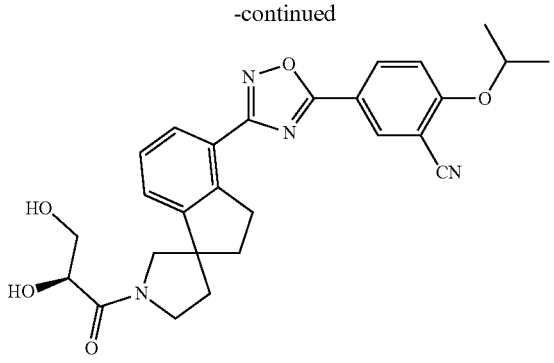
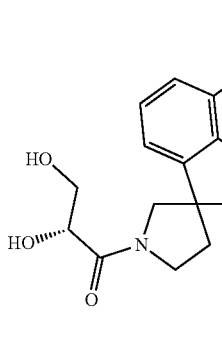
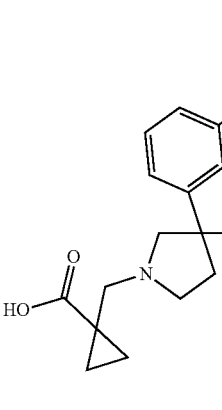
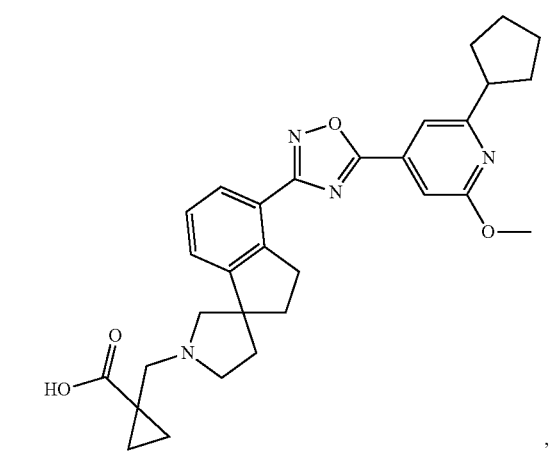

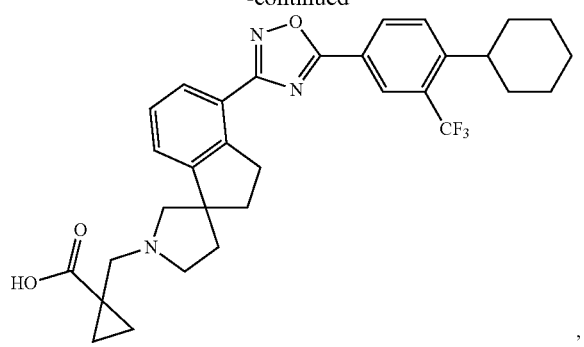
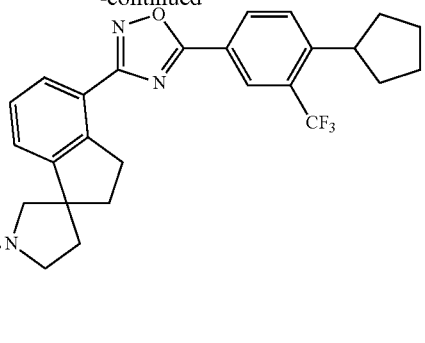
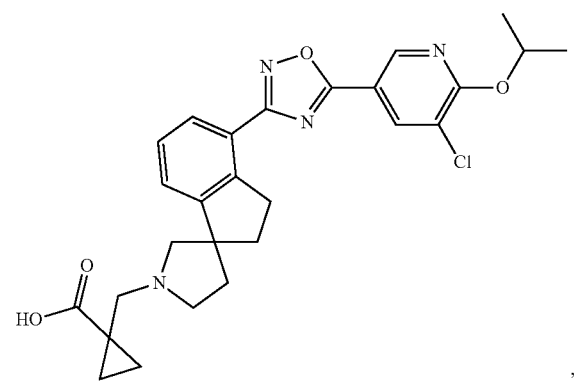
16. The compound or the pharmaceutically acceptable salt thereof according to claim 15, selecting from,
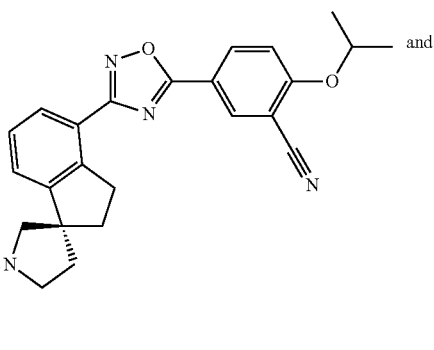
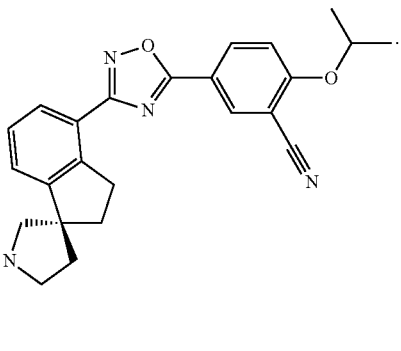
* * * * *